(12) United States Patent
Jung et al.

(10) Patent No.: US 10,308,650 B2
(45) Date of Patent: Jun. 4, 2019

(54) PESTICIDALLY ACTIVE TETRACYCLIC DERIVATIVES WITH SULFUR CONTAINING SUBSTITUENTS

(71) Applicant: Syngenta Participations AG, Basel (CH)

(72) Inventors: Pierre Joseph Marcel Jung, Stein (CH); Ottmar Franz Hueter, Stein (CH); Andrew Edmunds, Stein (CH); Michel Muehlebach, Stein (CH); Jerome Yves Cassayre, Stein (CH); Roger Graham Hall, Stein (CH); Andre Jeanguenat, Stein (CH)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

(21) Appl. No.: 15/534,734

(22) PCT Filed: Dec. 4, 2015

(86) PCT No.: PCT/EP2015/078609
§ 371 (c)(1),
(2) Date: Jun. 9, 2017

(87) PCT Pub. No.: WO2016/091731
PCT Pub. Date: Jun. 16, 2016

(65) Prior Publication Data
US 2017/0349581 A1    Dec. 7, 2017

(30) Foreign Application Priority Data

Dec. 11, 2014  (EP) .................................... 14197275
Jul. 30, 2015  (EP) .................................... 15179050

(51) Int. Cl.
*A01N 43/90*  (2006.01)
*C07D 471/04*  (2006.01)
*C07D 491/048*  (2006.01)

(52) U.S. Cl.
CPC .......... *C07D 471/04* (2013.01); *A01N 43/90* (2013.01); *C07D 491/048* (2013.01)

(58) Field of Classification Search
None
See application file for complete search history.

(56) References Cited

FOREIGN PATENT DOCUMENTS

| DE | 3225386 A1 | * | 1/1984 | .......... C07C 323/00 |
| DE | 3445299 A1 | * | 6/1986 | .......... C07D 471/04 |
| JP | 6323087 B2 | * | 5/2018 | |
| WO | 2012086848 A1 | | 6/2012 | |

OTHER PUBLICATIONS

Extended European Search Report for 14197275.2 dated Mar. 30, 2015.
International Search Report and Written Opinion for PCT/EP2015/078609, dated Mar. 16, 2016.

* cited by examiner

*Primary Examiner* — Alton N Pryor
(74) *Attorney, Agent, or Firm* — Toni-Junell Herbert; Dinsmore Shohl LLP

(57) ABSTRACT

Compounds of formula (I) wherein the substituents are as defined in claim 1, and the agrochemically acceptable salts, stereoisomers, enantiomers, tautomers and N-oxides of those compounds, can be used as insecticides and can be prepared in a manner known per se.

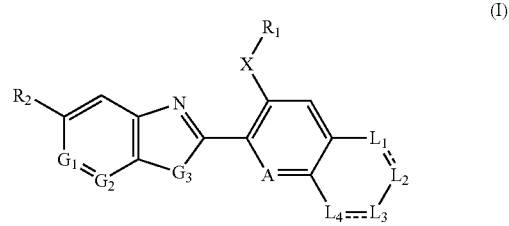

(I)

10 Claims, No Drawings

PESTICIDALLY ACTIVE TETRACYCLIC DERIVATIVES WITH SULFUR CONTAINING SUBSTITUENTS

RELATED APPLICATION INFORMATION

This application is a 371 of International Application No. PCT/EP2015/078609, filed 4 Dec. 2015, which claims priority to EP 14197275.2, filed 11 Dec. 2014, and EP 15179050.8, filed 30 Jul. 2015, the contents of which are incorporated herein by reference herein.

The present invention relates to pesticidally active, in particular insecticidally active tetracyclic derivatives containing sulfur substituents, to compositions comprising those compounds, and to their use for controlling animal pests (including arthropods and in particular insects or representatives of the order Acarina).

Heterocyclic compounds with pesticidal action are known and described, for example, in WO 2012/086848 and WO 2013/018928.

There have now been found novel pesticidally active tetracyclic derivatives with a sulfur containing bicyclic moiety.

The present invention accordingly relates to compounds of formula I,

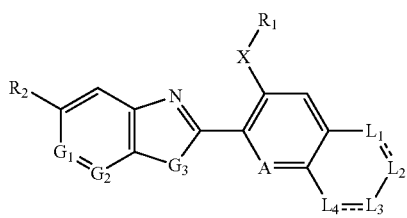

wherein

A represents CH or N;

X is S, SO or $SO_2$;

$R_1$ is $C_1$-$C_4$alkyl, $C_2$-$C_6$alkenyl, $C_2$-$C_6$haloalkenyl, $C_2$-$C_6$alkynyl, $C_1$-$C_4$haloalkyl, $C_3$-$C_6$cycloalkyl, $C_3$-$C_6$cycloalkyl-$C_1$-$C_4$alkyl; or is $C_3$-$C_6$cycloalkyl mono- or polysubstituted by substituents selected from the group consisting of halogen, cyano, $C_1$-$C_4$haloalkyl and $C_1$-$C_4$alkyl; or is $C_3$-$C_6$cycloalkyl-$C_1$-$C_4$alkyl mono- or polysubstituted by substituents selected from the group consisting of halogen, cyano, $C_1$-$C_4$ haloalkyl and $C_1$-$C_4$alkyl;

$R_2$ is hydrogen, halogen, $C_1$-$C_4$haloalkylsulfanyl, $C_1$-$C_4$haloalkylsulfinyl, $C_1$-$C_4$haloalkylsulfonyl, O($C_1$-$C_4$haloalkyl), —$SF_5$, —C(O)$C_1$-$C_4$haloalkyl, cyano, $C_1$-$C_6$haloalkyl or is $C_1$-$C_6$haloalkyl substituted by one or two substituents selected from the group consisting of hydroxyl, methoxy and cyano; or is $C_3$-$C_6$cycloalkyl which can be mono- or polysubstituted by substituents selected from the group consisting of halogen, cyano, $C_1$-$C_4$haloalkyl and $C_1$-$C_4$alkyl;

$G_1$ is N or $CR_4$;
$G_2$ is N or $CR_5$;
$G_3$ is O, S or $NR_6$;

$R_6$ is $C_1$-$C_4$alkyl which can be mono- or polysubstituted by substituents selected from the group consisting of halogen and $C_1$-$C_2$alkylsulfinyl;

$R_4$ and $R_5$, independently from each other, are hydrogen, halogen, cyano, nitro, $C_1$-$C_6$alkyl, $C_1$-$C_6$haloalkyl, or are $C_3$-$C_6$cycloalkyl which can be mono- or polysubstituted by $R_8$; or are $C_3$-$C_6$cycloalkyl-$C_1$-$C_4$alkyl which can be mono- or polysubstituted by $R_9$; or $R_4$ and $R_5$, independently from each other, are $C_2$-$C_6$alkenyl, $C_2$-$C_6$haloalkenyl, $C_2$-$C_6$alkynyl, $C_2$-$C_6$haloalkynyl, $C_1$-$C_6$haloalkoxy, $C_1$-$C_6$alkoxy, $C_1$-$C_6$alkylsulfanyl, $C_1$-$C_4$alkylsulfonyl, $C_1$-$C_6$alkylsulfinyl, $C_1$-$C_6$haloalkylsulfanyl, $C_1$-$C_4$haloalkylsulfonyl, $C_1$-$C_6$haloalkylsulfinyl or hydroxyl;

$R_8$ and $R_9$, independently from each other, are halogen, nitro, cyano, $C_1$-$C_4$haloalkoxy, $C_1$-$C_4$alkoxy, $C_1$-$C_4$alkyl or $C_1$-$C_4$haloalkyl;

$L_1$, $L_2$, $L_3$ and $L_4$ form together with the two carbon atoms to which $L_1$ and $L_4$ are attached, an aromatic, partially saturated carbocyclic or heterocyclic ring system; wherein $L_1$ is nitrogen, S(O)n, oxygen, N—$R_{10a}$ or $C(R_{10a})_m$;
$L_2$ is nitrogen, S(O)n, oxygen, N—$R_{10b}$ or $C(R_{10b})_m$;
$L_3$ is nitrogen, S(O)n, oxygen, N—$R_{10c}$, or $C(R_{10c})_m$;
$L_4$ is nitrogen, S(O)n, oxygen, a direct bond, N—$R_{10d}$ or $C(R_{10d})_m$; with the provisos that no more than 2 substituents selected from $L_1$, $L_2$, $L_3$ and $L_4$ can be oxygen or sulfur; and if two L groups are oxygen, they are not adjacent to each other; and no more than three L groups can be nitrogen;

n is 0 to 2;

m is 1 or 2;

$R_{10a}$, $R_{10b}$, $R_{10c}$, and $R_{10d}$, independently from each other, are hydrogen, halogen, nitro, cyano, amino, hydroxyl, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_6$alkoxy, $C_1$-$C_4$alkoxy $C_1$-$C_4$alkyl, $C_1$-$C_6$haloalkoxy, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, $C_2$-$C_6$alkylcarbonyl, $C_2$-$C_6$alkoxycarbonyl, $C_2$-$C_6$ haloalkylcarbonyl, $C_2$-$C_6$haloalkoxycarbonyl, ($C_1$-$C_6$alkyl)NH, ($C_1$-$C_6$alkyl)$_2$N, ($C_1$-$C_6$cycloalkyl)NH, ($C_1$-$C_6$cycloalkyl)$_2$N, $C_1$-$C_6$alkylcarbonylamino, $C_1$-$C_6$cycloalkylcarbonylamino or —$SF_5$; additionally one of $R_{10a}$, $R_{10b}$, $R_{10c}$ and $R_{10d}$ can be oxo; or $R_{10a}$, $R_{10b}$, $R_{10c}$, and $R_{10d}$, independently from each other, are $C_3$-$C_6$cycloalkyl mono- or polysubstituted by substituents selected from the group consisting of $C_1$-$C_4$ haloalkyl, $C_1$-$C_4$alkyl and cyano; or $R_{10a}$, $R_{10b}$, $R_{10c}$, and $R_{10d}$, independently from each other, are phenyl which can be mono- or polysubstituted by substituents selected from the group consisting of halogen, $C_1$-$C_4$ haloalkyl, $C_1$-$C_4$alkyl, $C_1$-$C_4$alkoxy and cyano; and agrochemically acceptable salts, stereoisomers, enantiomers, tautomers and N-oxides of those compounds.

Compounds of formula I which have at least one basic centre can form, for example, acid addition salts, for example with strong inorganic acids such as mineral acids, for example perchloric acid, sulfuric acid, nitric acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

m is 1 or 2 depending on the hybridization of the carbon atom.

If m is 2 in the definition $C(R_{10a})_m$, $R_{10a}$ can be the same or different; for example one $R_{10a}$ can be hydrogen and the other methyl. This is also valid for the definitions of $C(R_{10b})_m$, $C(R_{10c})_m$ and $C(R_{10d})_m$.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, nonyl, decyl and their branched isomers. Alkylsulfanyl, alkylsulfinyl, alkylsulfonyl, alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl.

Alkoxy is, for example, methoxy, ethoxy, propoxy, i-propoxy, n-butoxy, isobutoxy, sec-butoxy and tert-butoxy and also the isomeric pentyloxy and hexyloxy radicals.

Alkoxyalkyl groups preferably have a chain length of 1 to 6 carbon atoms.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkoxycarbonyl is for example methoxycarbonyl (which is $C_1$alkoxycarbonyl), ethoxycarbonyl, propoxycarbonyl, isopropoxycarbonyl, n-butoxycarbonyl, tert-butoxycarbonyl, n-pentoxycarbonyl or hexoxycarbonyl.

The cycloalkyl groups preferably have from 3 to 6 ring carbon atoms, for example cyclopropyl, cyclobutyl, cyclopentyl and cyclohexyl.

As used herein, the term "$C_2$-$C_6$alkynyl" refers to a straight or branched hydrocarbon chain radical group consisting solely of carbon and hydrogen atoms, containing at least one triple bond, having from two to six carbon atoms, and which is attached to the rest of the molecule by a single bond. The term "$C_2$-$C_4$ alkynyl" and "$C_2$-$C_3$alkynyl" are to be construed accordingly. Examples of $C_2$-$C_6$alkynyl include, but are not limited to, ethynyl, prop-1-ynyl, but-1-ynyl, but-2-ynyl.

As used herein, the term "$C_2$-$C_6$alkenyl" refers to a straight or branched hydrocarbon chain radical group consisting solely of carbon and hydrogen atoms, containing at least one double bond, having from two to six carbon atoms, and which is attached to the rest of the molecule by a single bond. The term "$C_2$-$C_4$ alkenyl" and "$C_2$-$C_3$alkenyl" are to be construed accordingly. Examples of $C_2$-$C_6$alkenyl include, but are not limited to, prop-1-enyl, but-1-enyl, but-2-enyl.

In the context of this invention "$L_1$, $L_2$, $L_3$ and $L_4$ form together with the two carbon atoms to which $L_1$ and $L_4$ are attached or to which $L_1$ and $L_3$ are attached when $L_4$ is bond, an aromatic or partially saturated carbocyclic ring system", the carbocyclic ring system is preferably a group having 5 to 6 ring carbon atoms which are unsaturated or partially saturated, for example, but are not limited to phenyl and cyclohexenyl.

In the context of this invention "$L_1$, $L_2$, $L_3$ and $L_4$ form together with the two carbon atoms to which $L_1$ and $L_4$ are attached or to which $L_1$ and $L_3$ are attached when $L_4$ is bond, an aromatic or partially saturated heterocyclic ring system", the heterocyclic ring system is preferably a group comprising 1 to 3 heteroatoms in the ring, which are unsaturated or partially saturated, for example, but are not limited to pyrrolyl; pyrazolyl; isoxazolyl; furanyl; thienyl; imidazolyl; oxazolyl; thiazolyl; isothiazolyl; triazolyl; oxadiazolyl; thiadiazolyl; tetrazolyl; furyl; pyridyl; pyrimidyl; pyrazinyl; pyridazinyl; triazinyl; pyranyl; pyrrolidinyl, piperidinyl; pyrrolidinyl-2-one; piperidinyl-2-one.

In the context of this invention "mono- to polysubstituted" in the definition of the substituents, means typically, depending on the chemical structure of the substituents, monosubstituted to seven-times substituted, preferably monosubstituted to five-times substituted, more preferably mono-, di- or tri-substituted.

An example for an aromatic or partially saturated carbocyclic or heterocyclic ring system wherein one of $R_{10a}$, $R_{10b}$, $R_{10c}$ or $R_{10d}$ can represent oxo, is the group $J_{15}$:

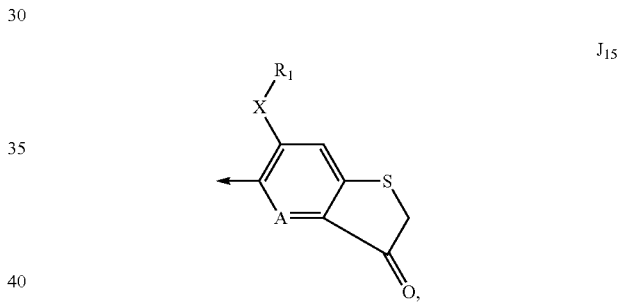

wherein X, $R_1$ and A are as defined under formula I above.

The compounds of formula I according to the invention also include hydrates which may be formed during the salt formation.

Compounds of formula I are preferred, wherein $R_1$ is $C_1$-$C_4$alkyl, $C_2$-$C_6$alkenyl, $C_2$-$C_6$haloalkenyl, $C_2$-$C_6$alkynyl, $C_1$-$C_4$haloalkyl, $C_3$-$C_6$cycloalkyl, $C_3$-$C_6$cycloalkyl-$C_1$-$C_4$alkyl; or is $C_3$-$C_6$cycloalkyl mono- or polysubstituted by substituents selected from the group consisting of halogen, cyano and $C_1$-$C_4$alkyl; or is $C_3$-$C_6$cycloalkyl-$C_1$-$C_4$alkyl mono- or polysubstituted by substituents selected from the group consisting of halogen, cyano and $C_1$-$C_4$alkyl;

$R_2$ is hydrogen, halogen, $C_1$-$C_4$haloalkylsulfanyl, $C_1$-$C_4$haloalkylsulfinyl, $C_1$-$C_4$haloalkylsulfonyl, $O(C_1$-$C_4$haloalkyl), —$SF_5$, —$C(O)C_1$-$C_4$haloalkyl, cyano, $C_1$-$C_6$haloalkyl or is $C_1$-$C_6$haloalkyl substituted by one or two substituents selected from the group consisting of hydroxyl, methoxy and cyano; or is $C_3$-$C_6$cycloalkyl which can be mono- or polysubstituted by substituents selected from the group consisting of halogen, cyano and $C_1$-$C_4$alkyl;

$G_1$ is N or $CR_4$;
$G_2$ is N or $CR_5$;
$G_3$ is O, S or $NR_6$;

$R_6$ is $C_1$-$C_4$alkyl which can be mono- or polysubstituted by substituents selected from the group consisting of halogen and $C_1$-$C_2$alkylsulfinyl;

$R_4$ and $R_5$, independently from each other, are hydrogen, halogen, cyano, nitro, $C_1$-$C_6$alkyl, $C_1$-$C_6$haloalkyl, or are $C_3$-$C_6$cycloalkyl which can be mono- or polysubstituted by $R_8$; or are $C_3$-$C_6$cycloalkyl-$C_1$-$C_4$alkyl which can be mono- or polysubstituted by $R_9$; or $R_4$ and $R_5$, independently from each other, are $C_2$-$C_6$alkenyl, $C_2$-$C_6$haloalkenyl, $C_2$-$C_6$alkynyl, $C_2$-$C_6$haloalkynyl, $C_1$-$C_6$haloalkoxy, $C_1$-$C_6$alkoxy, $C_1$-$C_6$alkylsulfanyl, $C_1$-$C_4$alkylsulfonyl, $C_1$-$C_6$alkylsulfinyl $C_1$-$C_6$haloalkylsulfanyl, $C_1$-$C_4$haloalkylsulfonyl, $C_1$-$C_6$haloalkylsulfinyl or hydroxyl;

$R_8$ and $R_9$, independently from each other, are halogen, nitro, cyano, $C_1$-$C_4$haloalkoxy, $C_1$-$C_4$alkoxy $C_1$-$C_4$alkyl or $C_1$-$C_4$haloalkyl; and $L_1$, $L_2$, $L_3$ and $L_4$ form together with the two carbon atoms to which $L_1$ and $L_4$ are attached, an aromatic or partially saturated carbocyclic or heterocyclic ring system; wherein
$L_1$ is nitrogen, sulfur, oxygen or C—$R_{10a}$;
$L_2$ is nitrogen, sulfur, oxygen or C—$R_{10b}$;
$L_3$ is nitrogen, sulfur, oxygen or C—$R_{10c}$;
$L_4$ is nitrogen, sulfur, oxygen, a direct bond or C—$R_{10d}$;
with the provisos that no more than 2 substituents selected from $L_1$, $L_2$, $L_3$ and $L_4$ can be oxygen or sulfur; and if two L groups are oxygen, they are not adjacent to each other;

$R_{10a}$, $R_{10b}$, $R_{10c}$, and $R_{10d}$, independently from each other, are hydrogen, halogen, nitro, cyano, hydroxyl, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_6$alkoxy, $C_1$-$C_6$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, $C_2$-$C_4$alkylcarbonyl, $C_2$-$C_6$alkoxycarbonyl or —$SF_5$; additionally one of $R_{10a}$, $R_{10b}$, $R_{10c}$ and $R_{10d}$ can be oxo; and agrochemically acceptable salts, stereoisomers, enantiomers, tautomers and N-oxides of those compounds.

A preferred group of compounds of formula I is represented by the compounds of formula I-1

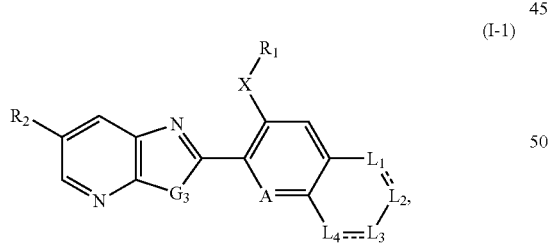
(I-1)

wherein the substituents X, A, $R_1$, $R_2$, $R_6$, $G_3$, $L_1$, $L_2$, $L_3$ and $L_4$ are as defined under formula I above.

Embodiment (A1)

Preferred are compounds of formula I-1, wherein
A is C—H or N;
$R_1$ is $C_1$-$C_4$alkyl, $C_3$-$C_6$cycloalkyl-$C_1$-$C_4$alkyl or $C_3$-$C_6$cycloalkyl;
$R_2$ is halogen, $C_1$-$C_4$haloalkylsulfanyl, $C_1$-$C_4$haloalkylsulfinyl, $C_1$-$C_4$haloalkylsulfonyl, $C_1$-$C_4$haloalkoxy, $C_1$-$C_4$haloalkyl, cyano or is $C_3$-$C_6$cycloalkyl which can be mono- or polysubstituted by substituents selected from the group consisting of halogen, cyano and $C_1$-$C_4$alkyl;

X and $G_3$ is as defined under formula I above;

$L_1$, $L_2$, $L_3$ and $L_4$ are as defined under formula I above; and $R_{10a}$, $R_{10b}$, $R_{10c}$, and $R_{10d}$, independently from each other, are hydrogen, halogen, nitro, cyano, hydroxyl, $C_1$-$C_6$alkyl, $C_2$-$C_6$alkenyl, $C_2$-$C_6$alkynyl, $C_3$-$C_6$cycloalkyl, $C_3$-$C_6$cycloalkyl-$C_1$-$C_4$ cycloalkyl, $C_1$-$C_6$haloalkyl, $C_2$-$C_6$haloalkenyl, $C_2$-$C_6$haloalkynyl, $C_3$-$C_6$halocycloalkyl, $C_3$-$C_6$cyclohaloalkyl-$C_1$-$C_4$ cycloalkyl, $C_1$-$C_6$alkoxy, $C_1$-$C_6$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, $C_2$-$C_4$alkylcarbonyl, $C_2$-$C_6$alkoxycarbonyl, —$SF_5$; additionally one of $R_{10a}$, $R_{10b}$, $R_{10c}$ and $R_{10d}$ can be oxo.

Embodiment (A2)

Further preferred are compounds of formula I-1a

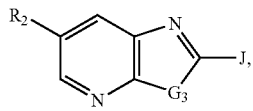
(I-1a)

wherein J is selected from the group consisting of

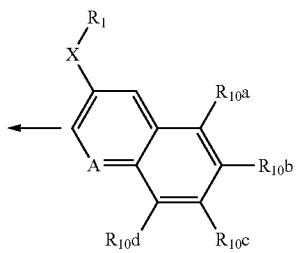
$J_1$

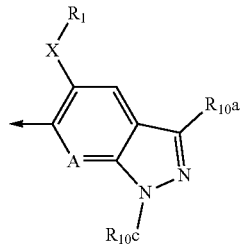
$J_2$

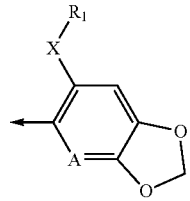
$J_3$

-continued

J4

J5

J6

J7

J8

J9

-continued

J10

J11

J12

J13

J14

J15

J16

-continued

J17 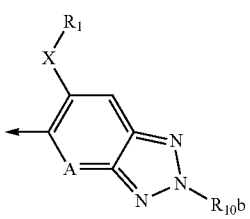

J18 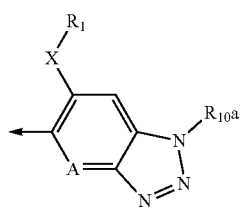

J19 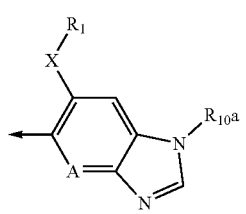

J20 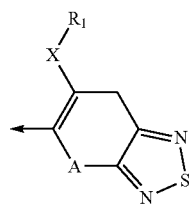

J21 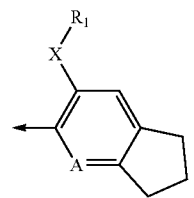

J22 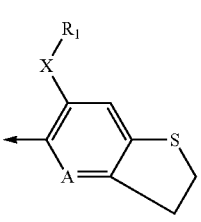

J23 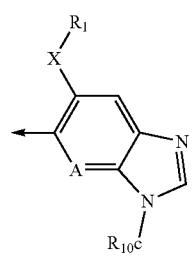

-continued

J24 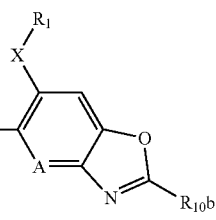

J25 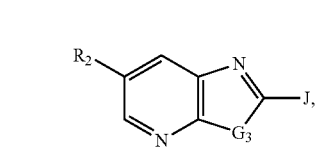

J26 and A, $G_3$, $R_1$, $R_2$, X, $R_{10a}$, $R_{10b}$, $R_{10c}$, $R_{10d}$, are as defined under Embodiment (A1).

Embodiment (A3)

Further preferred are compounds of formula I-1a $$\text{(I-1a)}$$

wherein J is as defined under Embodiment (A2) above and

A is C—H or N;

$R_1$ is $C_1$-$C_4$alkyl, $C_3$-$C_6$cycloalkyl-$C_1$-$C_4$alkyl or $C_3$-$C_6$cycloalkyl;

$R_2$ is halogen, $C_1$-$C_4$haloalkylsulfanyl, $C_1$-$C_4$haloalkylsulfinyl, $C_1$-$C_4$haloalkylsulfonyl, $C_1$-$C_4$haloalkoxy, $C_1$-$C_4$haloalkyl, cyano or $C_3$-$C_6$cycloalkyl;

X and $G_3$ is as defined under formula I above; and $R_{10a}$, $R_{10b}$, $R_{10c}$, and $R_{10d}$, independently from each other, are hydrogen, halogen, nitro, cyano, hydroxyl, $C_1$-$C_6$alkyl, $C_2$-$C_6$alkenyl, $C_2$-$C_6$alkynyl, $C_3$-$C_6$cycloalkyl, $C_3$-$C_6$cycloalkyl-$C_1$-$C_4$ cycloalkyl, $C_1$-$C_6$haloalkyl, $C_2$-$C_6$haloalkenyl, $C_2$-$C_6$haloalkynyl, $C_3$-$C_6$halocycloalkyl, $C_3$-$C_6$cyclohaloalkyl-$C_1$-$C_4$ cycloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl or $C_1$-$C_4$haloalkylsulfonyl.

Embodiment (A4)

Further preferred are compounds of formula I-1a

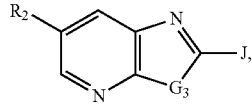
(I-1a)

wherein J is as defined under Embodiment (A2) above and

A is C—H or N;
$R_1$ is $C_1$-$C_4$alkyl;
$R_2$ is $C_1$-$C_4$haloalkylsulfanyl, $C_1$-$C_4$haloalkylsulfinyl, $C_1$-$C_4$haloalkylsulfonyl, $C_1$-$C_4$haloalkoxy or $C_1$-$C_4$haloalkyl;
X is as defined under formula I above; and
$G_3$ is N—$R_6$, wherein $R_6$ is as defined under formula I above; and
$R_{10a}$, $R_{10b}$, $R_{10c}$, and $R_{10d}$, independently from each other, are hydrogen, halogen, nitro, cyano, hydroxyl, $C_1$-$C_6$alkyl, $C_2$-$C_6$alkenyl, $C_2$-$C_6$alkynyl, $C_3$-$C_6$cycloalkyl, $C_3$-$C_6$cycloalkyl-$C_1$-$C_4$ cycloalkyl, $C_1$-$C_6$haloalkyl, $C_2$-$C_6$haloalkenyl, $C_2$-$C_6$haloalkynyl, $C_3$-$C_6$halocycloalkyl, $C_3$-$C_6$cyclohaloalkyl-$C_1$-$C_4$ cycloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl or $C_1$-$C_4$haloalkylsulfonyl.

Embodiment (A5)

Further preferred are compounds of formula I-1a

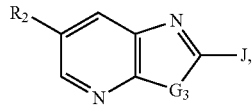
(I-1a)

wherein J is as defined under Embodiment (A2) above and

A is C—H or N;
$R_1$ is $C_1$-$C_4$ alkyl;
$R_2$ is —$OCF_3$, —$SCF_3$, —$S(O)CF_3$, —$S(O)_2CF_3$ or $CF_3$;
X is as defined under formula I above; and
$G_3$ is N—$R_6$, wherein $R_6$ is as defined under formula I above; and
$R_{10a}$, $R_{10b}$, $R_{10c}$, and $R_{10d}$, independently from each other, are hydrogen, halogen, cyano, $C_1$-$C_6$alkyl, $C_2$-$C_6$alkenyl, $C_2$-$C_6$alkynyl, $C_1$-$C_6$haloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl or $C_1$-$C_4$haloalkylsulfonyl.

Embodiment (A6)

Further preferred are compounds of formula I-1a

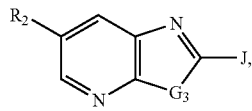
(I-1a)

wherein J is as defined under Embodiment (A2) above and

A is C—H or N;
$R_1$ is ethyl;
$R_2$ is $CF_3$;
X is as defined under formula I above; and
$G_3$ is N—$R_6$, wherein $R_6$ is as defined under formula I above; and
$R_{10a}$, $R_{10b}$, $R_{10c}$, and $R_{10d}$, independently from each other, are hydrogen, Br, Cl, I, F, cyano, methyl, ethyl, isopropyl, propyl, trifluoromethyl, $CF_3CH_2$—, $CH_3O$, —$SCF_3$, —$S(O)CF_3$ or —$S(O)_2CF_3$.

Embodiment (A7)

Further preferred are compounds of formula I-1a

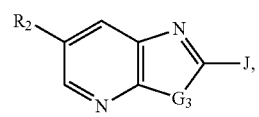
(I-1a)

wherein J is as defined under Embodiment (A2) above and

A is C—H or N;
$R_1$ is ethyl;
$R_2$ is $CF_3$;
X is as defined under formula I above;
$G_3$ is N—$R_6$, wherein $R_6$ is as defined under formula I above; and
$R_{10a}$, $R_{10b}$, $R_{10c}$, and $R_{10d}$, independently from each other, are hydrogen, Br, Cl, I, F, cyano, methyl, or $CF_3$.

Embodiment (A8)

Further preferred are compounds of formula I-1a

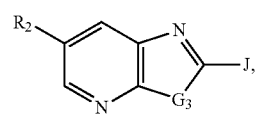
(I-1a)

wherein J is as defined under Embodiment (A2) and

A is C—H or N;
$R_1$ is ethyl;
$R_2$ is $CF_3$;
X is as defined under formula I above;
$G_3$ is N—$R_6$, $R_6$ is as defined under formula I above;
$R_{10a}$, $R_{10b}$, $R_{10c}$, and $R_{10d}$, independently from each other, are hydrogen in all groups J except $J_2$; and
$R_{10a}$, $R_{10b}$ and $R_{10d}$, independently from each other, are hydrogen in $J_2$ and $R_{10c}$ is methyl in $J_2$.

In all of the preferred embodiments of formula I-1 above, X is preferably S or $SO_2$ and, independently from the definition of X, $R_6$ is methyl.

A further preferred group of compounds of formula I is represented by the compounds of formula I-2

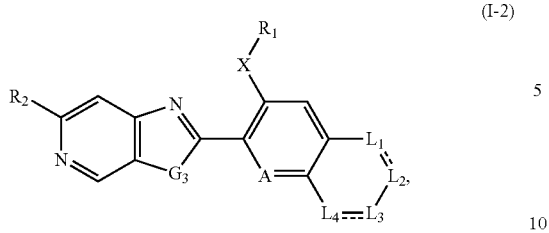
(I-2)

wherein the substituents X, A, $R_1$, $R_2$, $R_6$, $G_3$, $L_1$, $L_2$, $L_3$ and $L_4$ are as defined under formula I above.

Embodiment (B1)

Preferred are compounds of formula I-2, wherein
A is C—H or N;
$R_1$ is $C_1$-$C_4$alkyl, $C_3$-$C_6$cycloalkyl-$C_1$-$C_4$alkyl or $C_3$-$C_6$cycloalkyl;
$R_2$ is halogen, $C_1$-$C_4$haloalkylsulfanyl, $C_1$-$C_4$haloalkylsulfinyl, $C_1$-$C_4$haloalkylsulfonyl, $C_1$-$C_4$haloalkoxy, $C_1$-$C_4$haloalkyl, cyano or is $C_3$-$C_6$cycloalkyl which can be mono- or polysubstituted by substituents selected from the group consisting of halogen, cyano and $C_1$-$C_4$alkyl;
X and $G_3$ is as defined under formula I above;
$L_1$, $L_2$, $L_3$ and $L_4$ are as defined under formula I above; and
$R_{10a}$, $R_{10b}$, $R_{10c}$, and $R_{10d}$, independently from each other, are hydrogen, halogen, nitro, cyano, hydroxyl, $C_1$-$C_6$alkyl, $C_2$-$C_6$alkenyl, $C_2$-$C_6$alkynyl, $C_3$-$C_6$cycloalkyl, $C_3$-$C_6$cycloalkyl-$C_1$-$C_4$ cycloalkyl, $C_1$-$C_6$haloalkyl, $C_2$-$C_6$haloalkenyl, $C_2$-$C_6$haloalkynyl, $C_3$-$C_6$halocycloalkyl, $C_3$-$C_6$cyclohaloalkyl-$C_1$-$C_4$ cycloalkyl, $C_1$-$C_6$alkoxy, $C_1$-$C_6$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, $C_2$-$C_4$alkylcarbonyl, $C_2$-$C_6$alkoxycarbonyl, —$SF_5$; additionally one of $R_{10a}$, $R_{10b}$, $R_{10c}$ and $R_{10d}$ can be oxo.

Embodiment (B2)

Further preferred are compounds of formula I-2a

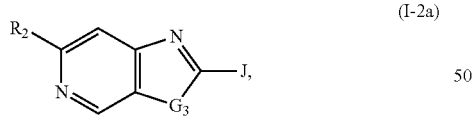
(I-2a)

wherein J is selected from the group consisting of

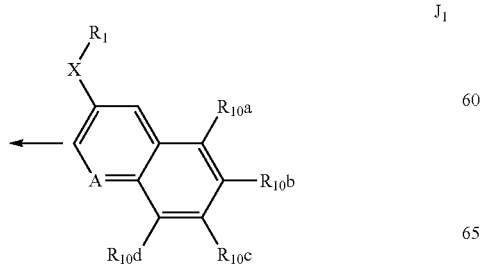
$J_1$

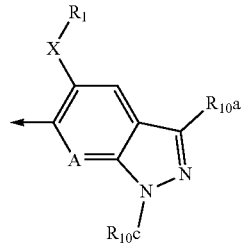
$J_2$

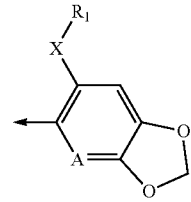
$J_3$

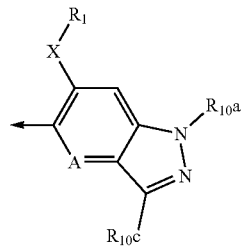
$J_4$

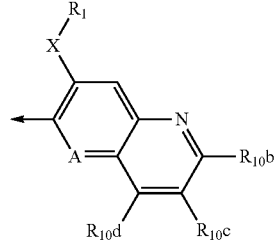
$J_5$

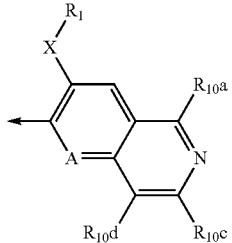
$J_6$

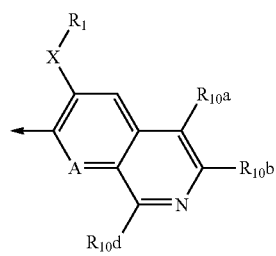
$J_7$

-continued
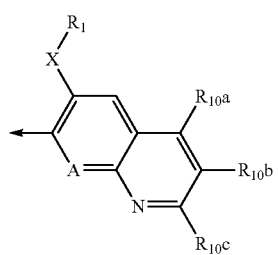
J8
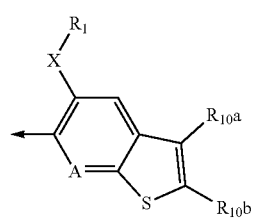
J9
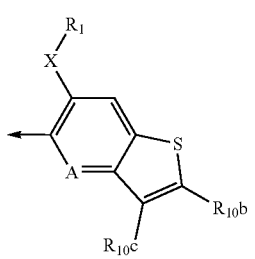
J10
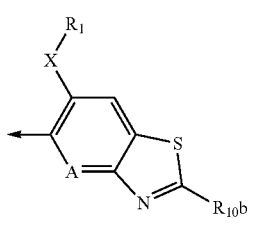
J11
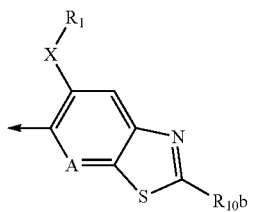
J12
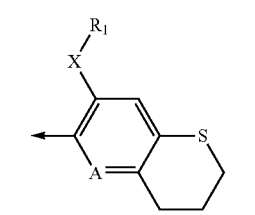
J13
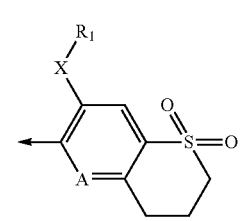
J14
-continued
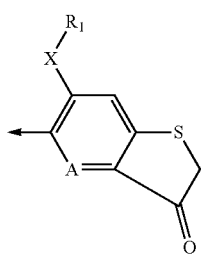
J15
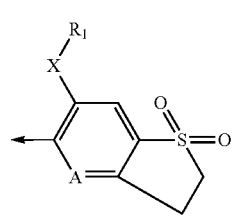
J16
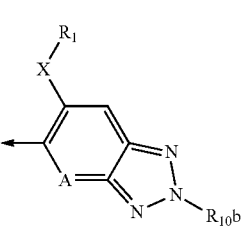
J17
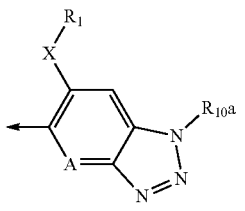
J18
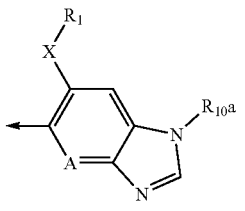
J19
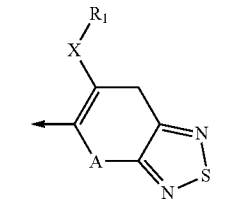
J20
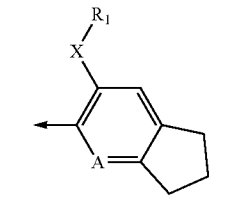
J21

-continued

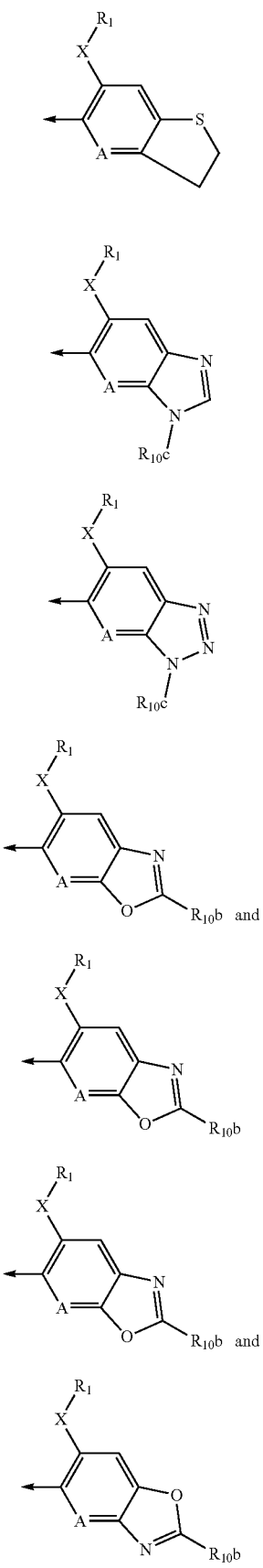

and A, G$_3$, R$_1$, R$_2$, X, R$_{10a}$, R$_{10b}$, R$_{10c}$, R$_{10d}$, are as defined under Embodiment (B1).

Embodiment (B3)

Further preferred are compounds of formula I-2a

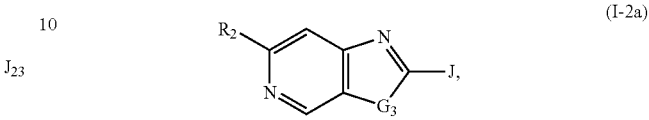

(I-2a)

wherein J is as defined under Embodiment (B2) and

A is C—H or N;

R$_1$ is C$_1$-C$_4$alkyl, C$_3$-C$_6$cycloalkyl-C$_1$-C$_4$alkyl or C$_3$-C$_6$cycloalkyl;

R$_2$ is halogen, C$_1$-C$_4$haloalkylsulfanyl, C$_1$-C$_4$haloalkylsulfinyl, C$_1$-C$_4$haloalkylsulfonyl, C$_1$-C$_4$haloalkoxy, C$_1$-C$_4$haloalkyl, cyano or C$_3$-C$_6$cycloalkyl;

X and G$_3$ is as defined under formula I above; and

R$_{10a}$, R$_{10b}$, R$_{10c}$, and R$_{10d}$, independently from each other, are hydrogen, halogen, nitro, cyano, hydroxyl, C$_1$-C$_6$alkyl, C$_2$-C$_6$alkenyl, C$_2$-C$_6$alkynyl, C$_3$-C$_6$cycloalkyl, C$_3$-C$_6$cycloalkyl-C$_1$-C$_4$ cycloalkyl, C$_1$-C$_6$haloalkyl, C$_2$-C$_6$haloalkenyl, C$_2$-C$_6$haloalkynyl, C$_3$-C$_6$halocycloalkyl, C$_3$-C$_6$cyclohaloalkyl-C$_1$-C$_4$ cycloalkyl, C$_1$-C$_4$alkoxy, C$_1$-C$_4$haloalkoxy, C$_1$-C$_4$alkylthio, C$_1$-C$_4$alkylsulfinyl, C$_1$-C$_4$alkylsulfonyl, C$_1$-C$_4$haloalkylthio, C$_1$-C$_4$haloalkylsulfinyl or C$_1$-C$_4$haloalkylsulfonyl.

Embodiment (B4)

Further preferred are compounds of formula I-2a

(I-2a)

wherein J is as defined under Embodiment (B2) and

A is C—H or N;

R$_1$ is C$_1$-C$_4$alkyl;

R$_2$ is C$_1$-C$_4$haloalkylsulfanyl, C$_1$-C$_4$haloalkylsulfinyl, C$_1$-C$_4$haloalkylsulfonyl, C$_1$-C$_4$haloalkoxy or C$_1$-C$_4$haloalkyl;

X is as defined under formula I above; and

G$_3$ is N—R$_6$, wherein R$_6$ is as defined under formula I above; and

R$_{10a}$, R$_{10b}$, R$_{10c}$, and R$_{10d}$, independently from each other, are hydrogen, halogen, nitro, cyano, hydroxyl, C$_1$-C$_6$alkyl, C$_2$-C$_6$alkenyl, C$_2$-C$_6$alkynyl, C$_3$-C$_6$cycloalkyl, C$_3$-C$_6$cycloalkyl-C$_1$-C$_4$ cycloalkyl, C$_1$-C$_6$haloalkyl, C$_2$-C$_6$haloalkenyl, C$_2$-C$_6$haloalkynyl, C$_3$-C$_6$halocycloalkyl, C$_3$-C$_6$cyclohaloalkyl-C$_1$-C$_4$ cycloalkyl, C$_1$-C$_4$alkoxy, C$_1$-C$_4$haloalkoxy, C$_1$-C$_4$alkylthio, C$_1$-C$_4$alkylsulfinyl, C$_1$-C$_4$alkylsulfonyl, C$_1$-C$_4$haloalkylthio, C$_1$-C$_4$haloalkylsulfinyl or C$_1$-C$_4$haloalkylsulfonyl.

Embodiment (B5)

Further preferred are compounds of formula I-2a

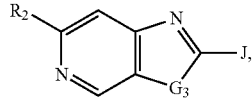
(I-2a)

wherein J is as defined under Embodiment (B2) and
A is C—H or N;
$R_1$ is $C_1$-$C_4$ alkyl;
$R_2$ is —$OCF_3$, —$SCF_3$, —$S(O)CF_3$, —$S(O)_2CF_3$ or $CF_3$;
X is as defined under formula I above; and
$G_3$ is N—$R_6$, wherein $R_6$ is as defined under formula I above; and
$R_{10a}$, $R_{10b}$, $R_{10c}$, and $R_{10d}$, independently from each other, are hydrogen, halogen, cyano, $C_1$-$C_6$alkyl, $C_2$-$C_6$alkenyl, $C_2$-$C_6$alkynyl, $C_1$-$C_6$haloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl or $C_1$-$C_4$haloalkylsulfonyl.

Embodiment (B6)

Further preferred are compounds of formula I-2a

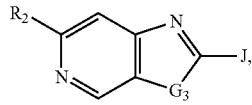
(I-2a)

wherein J is as defined under Embodiment (B2) and
A is C—H or N;
$R_1$ is ethyl;
$R_2$ is $CF_3$;
X is as defined under formula I above; and
$G_3$ is N—$R_6$, wherein $R_6$ is as defined under formula I above; and
$R_{10a}$, $R_{10b}$, $R_{10c}$, and $R_{10d}$, independently from each other, are hydrogen, Br, Cl, I, F, cyano, methyl, ethyl, isopropyl, propyl, $CF_3$, $CF_3CH_2$—, $CH_3O$, —$SCF_3$, —$S(O)CF_3$ or —$S(O)_2CF_3$.

Embodiment (B7)

Further preferred are compounds of formula I-2a

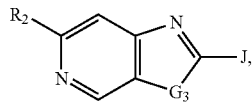
(I-2a)

wherein J is as defined under Embodiment (B2) and
A is C—H or N;
$R_1$ is ethyl;
$R_2$ is $CF_3$;
X is as defined under formula I above; and
$G_3$ is N—$R_6$, wherein $R_6$ is as defined under formula I above; and $R_{10a}$, $R_{10b}$, $R_{10c}$, and $R_{10d}$, independently from each other, are hydrogen, Br, Cl, I, F, cyano, methyl, or $CF_3$.

Embodiment (B8)

Further preferred are compounds of formula I-2a

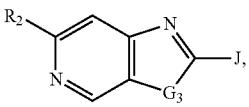
(I-2a)

wherein J is as defined under Embodiment (B2) and
A is C—H or N;
$R_1$ is ethyl;
$R_2$ is $CF_3$;
X is as defined under formula I above;
$G_3$ is N—$R_6$, $R_6$ is as defined under formula I above;
$R_{10a}$, $R_{10b}$, $R_{10c}$, and $R_{10d}$, independently from each other, are hydrogen in all groups J except $J_2$; and
$R_{10a}$, $R_{10b}$, and $R_{10d}$, independently from each other, are hydrogen in $J_2$ and $R_{10c}$ is methyl in $J_2$.

In all of the preferred embodiments of formula I-2 above, X is preferably S or $SO_2$ and independently from the definition of X, $R_6$ is methyl.

A further preferred group of compounds of formula I is represented by the compounds of formula I-3

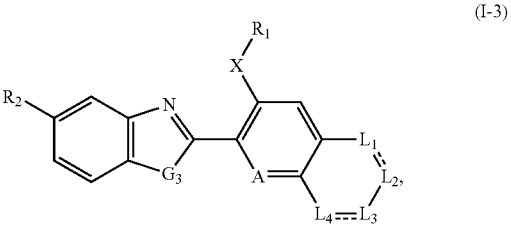
(I-3)

wherein the substituents X, A, $R_1$, $R_2$, $R_6$, $G_3$, $L_1$, $L_2$, $L_3$ and $L_4$ are as defined under formula I above.

Embodiment (C1)

Preferred are compounds of formula I-3, wherein
A is C—H or N;
$R_1$ is $C_1$-$C_4$alkyl, $C_3$-$C_6$Cycloalkyl-$C_1$-$C_4$alkyl or $C_3$-$C_6$Cycloalkyl;
$R_2$ is halogen, $C_1$-$C_4$haloalkylsulfanyl, $C_1$-$C_4$haloalkylsulfinyl, $C_1$-$C_4$haloalkylsulfonyl, $C_1$-$C_4$haloalkoxy, $C_1$-$C_4$haloalkyl, cyano or is $C_3$-$C_6$cycloalkyl which can be mono- or polysubstituted by substituents selected from the group consisting of halogen, cyano and $C_1$-$C_4$alkyl;
X and $G_3$ is as defined under formula I above;
$L_1$, $L_2$, $L_3$ and $L_4$ are as defined under formula I above; and
$R_{10a}$, $R_{10b}$, $R_{10c}$, and $R_{10d}$, independently from each other, are hydrogen, halogen, nitro, cyano, hydroxyl, $C_1$-$C_6$alkyl, $C_2$-$C_6$alkenyl, $C_2$-$C_6$alkynyl, $C_3$-$C_6$cycloalkyl, $C_3$-$C_6$cycloalkyl-$C_1$-$C_4$ cycloalkyl, $C_1$-$C_6$haloalkyl, $C_2$-$C_6$haloalkenyl, $C_2$-$C_6$haloalkynyl, $C_3$-$C_6$halocycloalkyl, $C_3$-$C_6$cyclohaloalkyl-$C_1$-$C_4$ cycloalkyl, $C_1$-$C_6$alkoxy, $C_1$-$C_6$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, $C_2$-$C_4$alkylcarbonyl, $C_2$-$C_6$alkoxycarbonyl, —$SF_5$; additionally one of $R_{10a}$, $R_{10b}$, $R_{10c}$ and $R_{10d}$ can be oxo.
Embodiment (C2)
Further preferred are compounds of formula I-3a
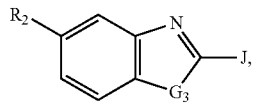
(I-3a)
wherein J is selected from the group consisting of
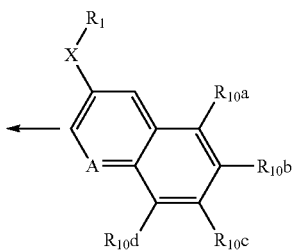
$J_1$
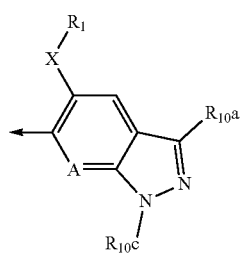
$J_2$
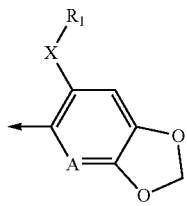
$J_3$
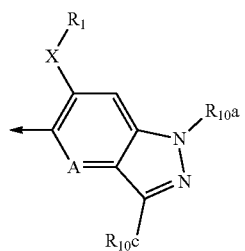
$J_4$
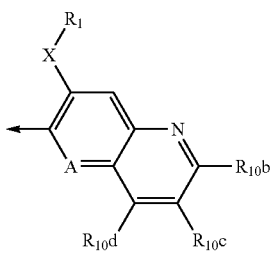
$J_5$
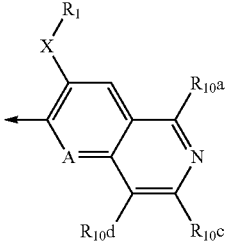
$J_6$
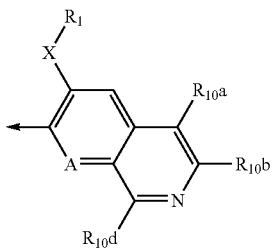
$J_7$
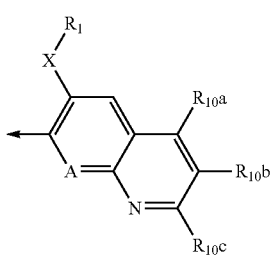
$J_8$
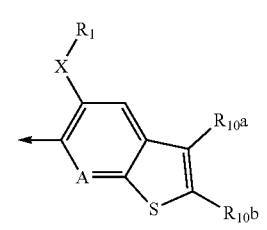
$J_9$
$J_{10}$ -continued
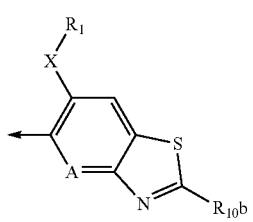
J₁₁
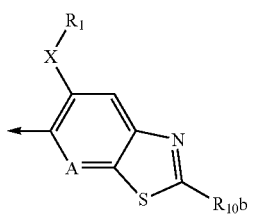
J₁₂
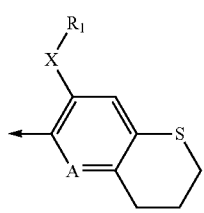
J₁₃
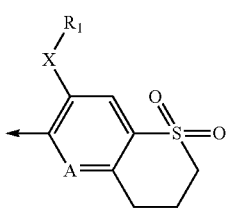
J₁₄
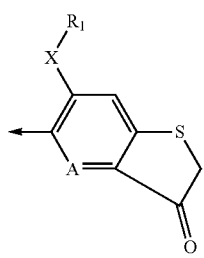
J₁₅
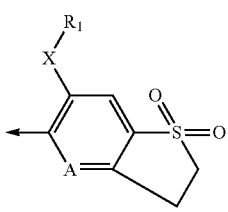
J₁₆
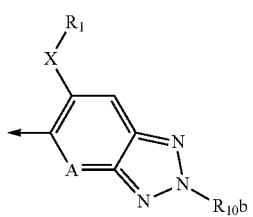
J₁₇
-continued
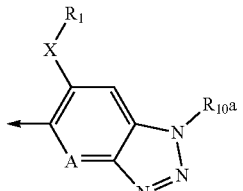
J₁₈
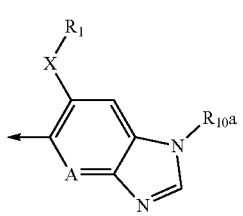
J₁₉
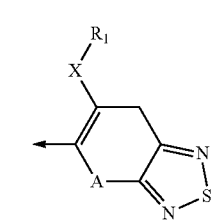
J₂₀
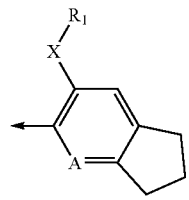
J₂₁
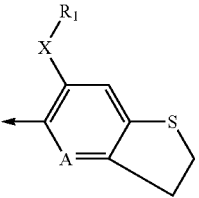
J₂₂
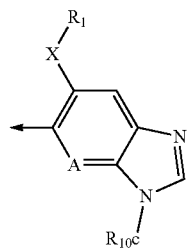
J₂₃
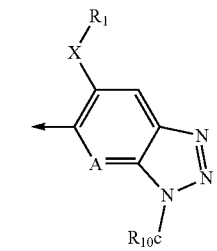
J₂₄

-continued

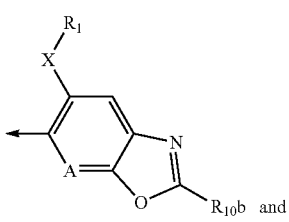

J$_{25}$

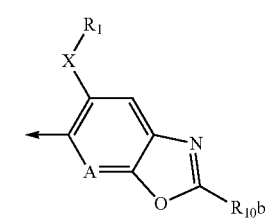

J$_{26}$

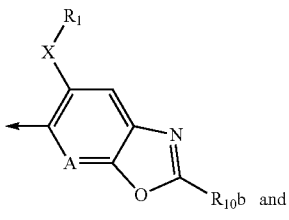

J$_{25}$

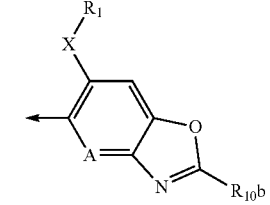

J$_{26}$ and A, G$_3$, R$_1$, R$_2$, X, R$_{10a}$, R$_{10b}$, R$_{10c}$, R$_{10d}$, are as defined under Embodiment (C1).

Embodiment (C3)

Further preferred are compounds of formula I-3a

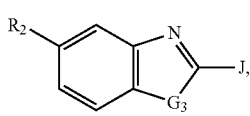
(I-3a)

wherein J is as defined under Embodiment (C2) and
A is C—H or N;
R$_1$ is C$_1$-C$_4$alkyl, C$_3$-C$_6$cycloalkyl-C$_1$-C$_4$alkyl or C$_3$-C$_6$cycloalkyl;
R$_2$ is halogen, C$_1$-C$_4$haloalkylsulfanyl, C$_1$-C$_4$haloalkylsulfinyl, C$_1$-C$_4$haloalkylsulfonyl, C$_1$-C$_4$haloalkoxy, C$_1$-C$_4$haloalkyl, cyano or C$_3$-C$_6$cycloalkyl;
X and G$_3$ is as defined under formula I above; and
R$_{10a}$, R$_{10b}$, R$_{10c}$, and R$_{10d}$, independently from each other, are hydrogen, halogen, nitro, cyano, hydroxyl, C$_1$-C$_6$alkyl, C$_2$-C$_6$alkenyl, C$_2$-C$_6$alkynyl, C$_3$-C$_6$cycloalkyl, C$_3$-C$_6$cycloalkyl-C$_1$-C$_4$ cycloalkyl, C$_1$-C$_6$haloalkyl, C$_2$-C$_6$haloalkenyl, C$_2$-C$_6$haloalkynyl, C$_3$-C$_6$halocycloalkyl, C$_3$-C$_6$cyclohaloalkyl-C$_1$-C$_4$ cycloalkyl, C$_1$-C$_4$alkoxy, C$_1$-C$_4$haloalkoxy, C$_1$-C$_4$alkylthio, C$_1$-C$_4$alkylsulfinyl, C$_1$-C$_4$alkylsulfonyl, C$_1$-C$_4$haloalkylthio, C$_1$-C$_4$haloalkylsulfinyl or C$_1$-C$_4$haloalkylsulfonyl.

Embodiment (C4)

Further preferred are compounds of formula I-3a

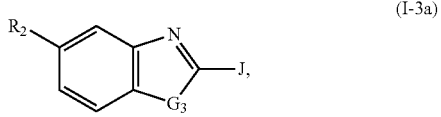
(I-3a)

wherein J is as defined under Embodiment (C2) and
A is C—H or N;
R$_1$ is C$_1$-C$_4$alkyl;
R$_2$ is C$_1$-C$_4$haloalkylsulfanyl, C$_1$-C$_4$haloalkylsulfinyl, C$_1$-C$_4$haloalkylsulfonyl, C$_1$-C$_4$haloalkoxy or C$_1$-C$_4$haloalkyl;
X is as defined under formula I above; and
G$_3$ is N—R$_6$, wherein R$_6$ is as defined under formula I above; and
R$_{10a}$, R$_{10b}$, R$_{10c}$, and R$_{10d}$, independently from each other, are hydrogen, halogen, nitro, cyano, hydroxyl, C$_1$-C$_6$alkyl, C$_2$-C$_6$alkenyl, C$_2$-C$_6$alkynyl, C$_3$-C$_6$cycloalkyl, C$_3$-C$_6$cycloalkyl-C$_1$-C$_4$ cycloalkyl, C$_1$-C$_6$haloalkyl, C$_2$-C$_6$haloalkenyl, C$_2$-C$_6$haloalkynyl, C$_3$-C$_6$halocycloalkyl, C$_3$-C$_6$cyclohaloalkyl-C$_1$-C$_4$ cycloalkyl, C$_1$-C$_4$alkoxy, C$_1$-C$_4$haloalkoxy, C$_1$-C$_4$alkylthio, C$_1$-C$_4$alkylsulfinyl, C$_1$-C$_4$alkylsulfonyl, C$_1$-C$_4$haloalkylthio, C$_1$-C$_4$haloalkylsulfinyl or C$_1$-C$_4$haloalkylsulfonyl.

Embodiment (C5)

Further preferred are compounds of formula I-3a

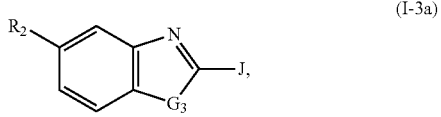
(I-3a)

wherein J is as defined under Embodiment (C2) and
A is C—H or N;
R$_1$ is C$_1$-C$_4$ alkyl;
R$_2$ is —OCF$_3$, —SCF$_3$, —S(O)CF$_3$, —S(O)$_2$CF$_3$ or CF$_3$;
X is as defined under formula I above; and
G$_3$ is N—R$_6$, wherein R$_6$ is as defined under formula I above; and
R$_{10a}$, R$_{10b}$, R$_{10c}$, and R$_{10d}$, independently from each other, are hydrogen, halogen, cyano, C$_1$-C$_6$alkyl, C$_2$-C$_6$alkenyl, C$_2$-C$_6$alkynyl, C$_1$-C$_6$haloalkyl, C$_1$-C$_4$alkoxy, C$_1$-C$_4$haloalkoxy, C$_1$-C$_4$alkylthio, C$_1$-C$_4$alkylsulfinyl, C$_1$-C$_4$alkylsulfonyl, C$_1$-C$_4$haloalkylthio, C$_1$-C$_4$haloalkylsulfinyl or C$_1$-C$_4$haloalkylsulfonyl.

Embodiment (C6)

Further preferred are compounds of formula I-3a (I-3a)

wherein J is as defined under Embodiment (C2) and

A is C—H or N;

$R_1$ is ethyl;

$R_2$ is $CF_3$;

X is as defined under formula I above; and $G_3$ is N—$R_6$, wherein $R_6$ is as defined under formula I above; and $R_{10a}$, $R_{10b}$, $R_{10c}$, and $R_{10d}$, independently from each other, are hydrogen, Br, Cl, I, F, cyano, methyl, ethyl, isopropyl, propyl, $CF_3$, $CF_3CH_2$—, $CH_3O$, —$SCF_3$, —$S(O)CF_3$ or —$S(O)_2CF_3$.

Embodiment (C7)

Further preferred are compounds of formula I-3a

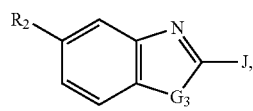
(I-3a)

wherein J is as defined under Embodiment (C2) and

A is C—H or N;

$R_1$ is ethyl;

$R_2$ is $CF_3$;

X is as defined under formula I above;

$G_3$ is N—$R_6$, wherein $R_6$ is as defined under formula I above; and $R_{10a}$, $R_{10b}$, $R_{10c}$, and $R_{10d}$, independently from each other, are hydrogen, Br, Cl, I, F, cyano, methyl, or $CF_3$.

Embodiment (C8)

Further preferred are compounds of formula I-3a

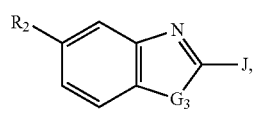
(I-3a)

wherein J is as defined under Embodiment (C2) and

A is C—H or N;

$R_1$ is ethyl;

$R_2$ is $CF_3$;

X is as defined under formula I above;

$G_3$ is N—$R_6$, $R_6$ is as defined under formula I above;

$R_{10a}$, $R_{10b}$, $R_{10c}$, and $R_{10d}$, independently from each other, are hydrogen in all groups J except $J_2$; and $R_{10a}$, $R_{10b}$, and $R_{10d}$, independently from each other, are hydrogen in $J_2$ and $R_{10c}$ is methyl in $J_2$.

In all of the preferred embodiments of formula I-3 above, X is preferably S or $SO_2$ and independently from the definition of X, $R_6$ is methyl.

A further preferred group of compounds of formula I is represented by the compounds of formula I-4

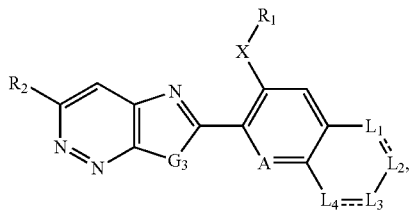
(I-4)

wherein the substituents X, A, $R_1$, $R_2$, $R_6$, $G_3$, $L_1$, $L_2$, $L_3$ and $L_4$ are as defined under formula I above.

Embodiment (D1)

Preferred are compounds of formula I-4, wherein

A is C—H or N;

$R_1$ is $C_1$-$C_4$alkyl, $C_3$-$C_6$Cycloalkyl-$C_1$-$C_4$alkyl or $C_3$-$C_6$Cycloalkyl;

$R_2$ is halogen, $C_1$-$C_4$haloalkylsulfanyl, $C_1$-$C_4$haloalkylsulfinyl, $C_1$-$C_4$haloalkylsulfonyl, $C_1$-$C_4$haloalkoxy, $C_1$-$C_4$haloalkyl, cyano or is $C_3$-$C_6$cycloalkyl which can be mono- or polysubstituted by substituents selected from the group consisting of halogen, cyano and $C_1$-$C_4$alkyl;

X and $G_3$ is as defined under formula I above;

$L_1$, $L_2$, $L_3$ and $L_4$ are as defined under formula I above; and $R_{10a}$, $R_{10b}$, $R_{10c}$, and $R_{10d}$, independently from each other, are hydrogen, halogen, nitro, cyano, hydroxyl, $C_1$-$C_6$alkyl, $C_2$-$C_6$alkenyl, $C_2$-$C_6$alkynyl, $C_3$-$C_6$cycloalkyl, $C_3$-$C_6$cycloalkyl-$C_1$-$C_4$ cycloalkyl, $C_1$-$C_6$haloalkyl, $C_2$-$C_6$haloalkenyl, $C_2$-$C_6$haloalkynyl, $C_3$-$C_6$halocycloalkyl, $C_3$-$C_6$cyclohaloalkyl-$C_1$-$C_4$ cycloalkyl, $C_1$-$C_6$alkoxy, $C_1$-$C_6$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, $C_2$-$C_4$alkylcarbonyl, $C_2$-$C_6$alkoxycarbonyl, —$SF_5$; additionally one of $R_{10a}$, $R_{10b}$, $R_{10c}$ and $R_{10d}$ can be oxo.

Embodiment (D2)

Further preferred are compounds of formula I-4a

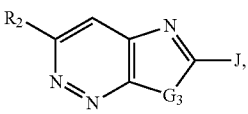
(I-4a)

wherein J is selected from the group consisting of

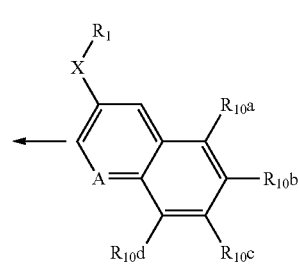
$J_1$

-continued
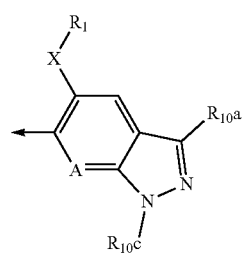
J₂
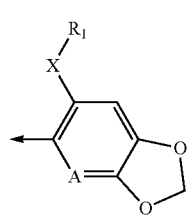
J₃
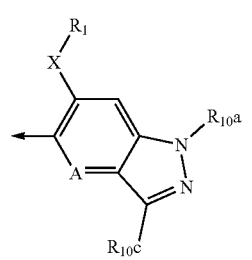
J₄
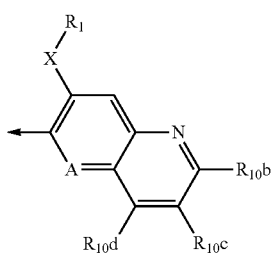
J₅
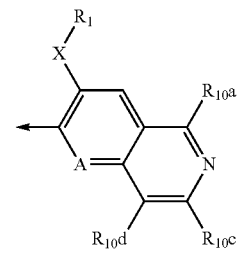
J₆
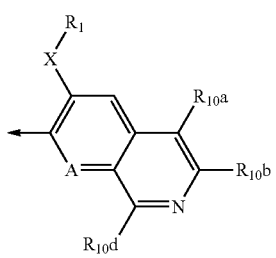
J₇
-continued
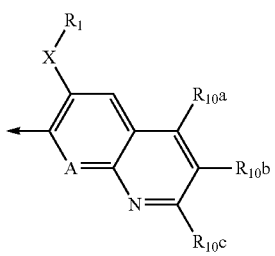
J₈
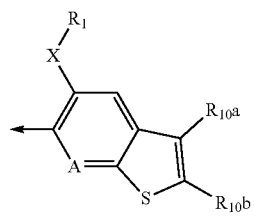
J₉
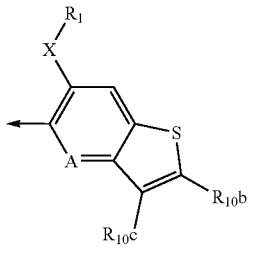
J₁₀
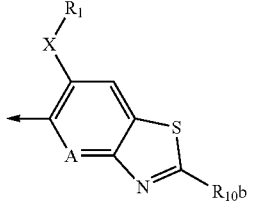
J₁₁
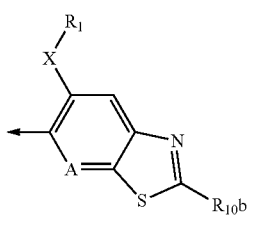
J₁₂
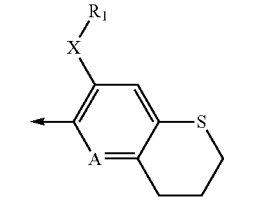
J₁₃
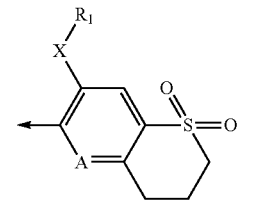
J₁₄

-continued
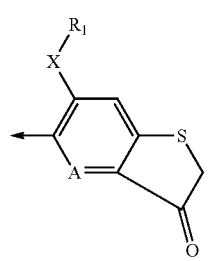
J15
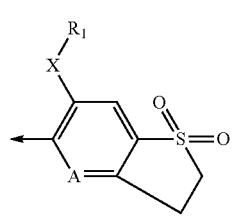
J16
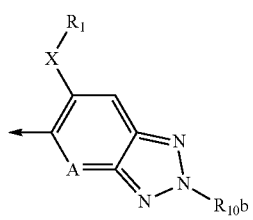
J17
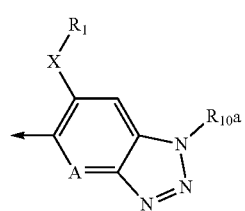
J18
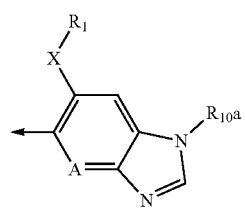
J19
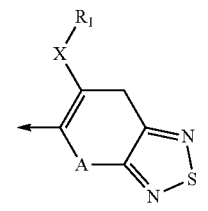
J20
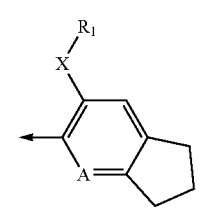
J21
-continued
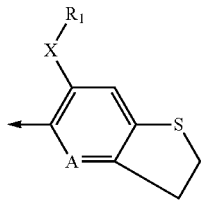
J22
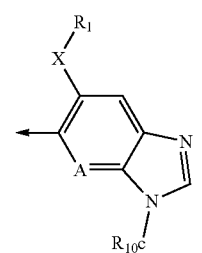
J23
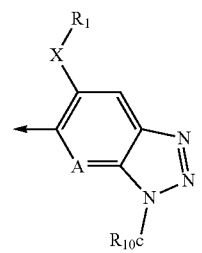
J24
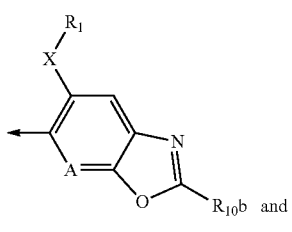
J25
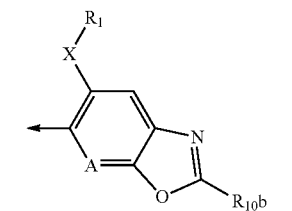 and
J26
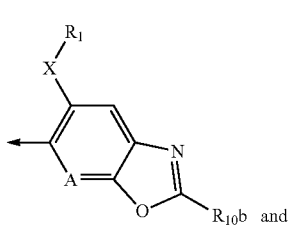
J25
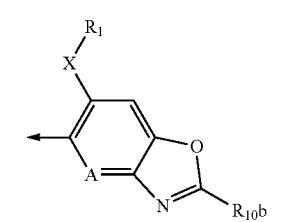 and
J26 and A, $G_3$, $R_1$, $R_2$, X, $R_{10a}$, $R_{10b}$, $R_{10c}$, $R_{10d}$, are as defined under Embodiment (D1).

Embodiment (D3)

Further preferred are compounds of formula I-4a

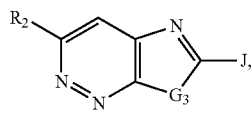

(I-4a)

wherein J is as defined under Embodiment (D2) and
A is C—H or N;
$R_1$ is $C_1$-$C_4$alkyl, $C_3$-$C_6$cycloalkyl-$C_1$-$C_4$alkyl or $C_3$-$C_6$cycloalkyl;
$R_2$ is halogen, $C_1$-$C_4$haloalkylsulfanyl, $C_1$-$C_4$haloalkylsulfinyl, $C_1$-$C_4$haloalkylsulfonyl, $C_1$-$C_4$haloalkoxy, $C_1$-$C_4$haloalkyl, cyano or $C_3$-$C_6$cycloalkyl;
X and $G_3$ is as defined under formula I above; and
$R_{10a}$, $R_{10b}$, $R_{10c}$, and $R_{10d}$, independently from each other, are hydrogen, halogen, nitro, cyano, hydroxyl, $C_1$-$C_6$alkyl, $C_2$-$C_6$alkenyl, $C_2$-$C_6$alkynyl, $C_3$-$C_6$cycloalkyl, $C_3$-$C_6$cycloalkyl-$C_1$-$C_4$ cycloalkyl, $C_1$-$C_6$haloalkyl, $C_2$-$C_6$haloalkenyl, $C_2$-$C_6$haloalkynyl, $C_3$-$C_6$halocycloalkyl, $C_3$-$C_6$cyclohaloalkyl-$C_1$-$C_4$ cycloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl or $C_1$-$C_4$haloalkylsulfonyl.

Embodiment (4)

Further preferred are compounds of formula I-4a

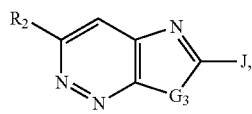

(I-4a)

wherein J is as defined under Embodiment (D2) and
A is C—H or N;
$R_1$ is $C_1$-$C_4$alkyl;
$R_2$ is $C_1$-$C_4$haloalkylsulfanyl, $C_1$-$C_4$haloalkylsulfinyl, $C_1$-$C_4$haloalkylsulfonyl, $C_1$-$C_4$haloalkoxy or $C_1$-$C_4$haloalkyl;
X is as defined under formula I above; and
$G_3$ is N—$R_6$, wherein $R_6$ is as defined under formula I above; and
$R_{10a}$, $R_{10b}$, $R_{10c}$, and $R_{10d}$, independently from each other, are hydrogen, halogen, nitro, cyano, hydroxyl, $C_1$-$C_6$alkyl, $C_2$-$C_6$alkenyl, $C_2$-$C_6$alkynyl, $C_3$-$C_6$cycloalkyl, $C_3$-$C_6$cycloalkyl-$C_1$-$C_4$ cycloalkyl, $C_1$-$C_6$haloalkyl, $C_2$-$C_6$haloalkenyl, $C_2$-$C_6$haloalkynyl, $C_3$-$C_6$halocycloalkyl, $C_3$-$C_6$cyclohaloalkyl-$C_1$-$C_4$ cycloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl or $C_1$-$C_4$haloalkylsulfonyl.

Embodiment (D5)

Further preferred are compounds of formula I-4a

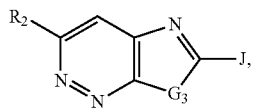

(I-4a)

wherein J is as defined under Embodiment (D2) and
A is C—H or N;
$R_1$ is $C_1$-$C_4$ alkyl;
$R_2$ is —$OCF_3$, —$SCF_3$, —$S(O)CF_3$, —$S(O)_2CF_3$ or $CF_3$;
X is as defined under formula I above; and
$G_3$ is N—$R_6$, wherein $R_6$ is as defined under formula I above; and
$R_{10a}$, $R_{10b}$, $R_{10c}$, and $R_{10d}$, independently from each other, are hydrogen, halogen, cyano, $C_1$-$C_6$alkyl, $C_2$-$C_6$alkenyl, $C_2$-$C_6$alkynyl, $C_1$-$C_6$haloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl or $C_1$-$C_4$haloalkylsulfonyl.

Embodiment (D6)

Further preferred are compounds of formula I-4a

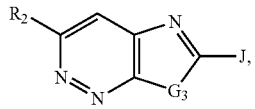

(I-4a)

wherein J is as defined under Embodiment (D2) and
A is C—H or N;
$R_1$ is ethyl;
$R_2$ is $CF_3$;
X is as defined under formula I above; and
$G_3$ is N—$R_6$, wherein $R_6$ is as defined under formula I above; and
$R_{10a}$, $R_{10b}$, $R_{10c}$, and $R_{10d}$, independently from each other, are hydrogen, Br, Cl, I, F, cyano, methyl, ethyl, isopropyl, propyl, $CF_3$, $CF_3CH_2$—, $CH_3O$, —$SCF_3$, —$S(O)CF_3$ or —$S(O)_2CF_3$.

Embodiment (D7)

Further preferred are compounds of formula I-4a

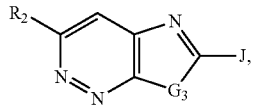

(I-4a)

wherein J is as defined under Embodiment (D2) and
A is C—H or N;
$R_1$ is ethyl;
$R_2$ is $CF_3$;
X is as defined under formula I above;
$G_3$ is N—$R_6$, wherein $R_6$ is as defined under formula I above; and $R_{10a}$, $R_{10b}$, $R_{10c}$, and $R_{10d}$, independently from each other, are hydrogen, Br, Cl, I, F, cyano, methyl, or $CF_3$.

Embodiment (D8)

Further preferred are compounds of formula I-4a

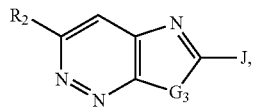
(I-4a)

wherein J is as defined under Embodiment (D2) and
A is C—H or N;
$R_1$ is ethyl;
$R_2$ is $CF_3$;
X is as defined under formula I above;
$G_3$ is N—$R_6$, $R_6$ is as defined under formula I above;
$R_{10a}$, $R_{10b}$, $R_{10c}$, and $R_{10d}$, independently from each other, are hydrogen in all groups J except $J_2$; and
$R_{10a}$, $R_{10b}$, and $R_{10d}$, independently from each other, are hydrogen in $J_2$ and $R_{10c}$ is methyl in $J_2$.

In all of the preferred embodiments of formula I-4 above, X is preferably S or $SO_2$ and independently from the definition of X, $R_6$ is methyl.

In all of the preferred embodiments A2-A8, B2-B8, C2-C8 and D2-D8, J is preferably $J_1$, $J_2$, $J_3$, $J_4$, $J_5$, $J_6$, $J_{12}$, $J_{17}$, $J_{18}$, $J_{24}$, $J_{19}$, $J_{20}$ or $J_{23}$, in particular J is $J_1$.

Further preferred compounds of formula I are represented by the compounds of formula I-5a

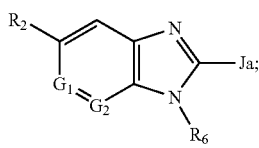
(I-5a)

wherein
$G_1$ is N or CH;
$G_2$ is N or CH;
$R_2$ is $C_1$-$C_4$haloalkyl;
A is N or CH;
$R_6$ is $C_1$-$C_4$alkyl;
X is S or $SO_2$;
$R_1$ is $C_1$-$C_4$alkyl; and
Ja is selected from the group consisting of

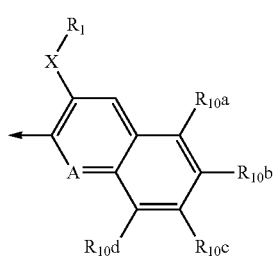
$J_{1a}$

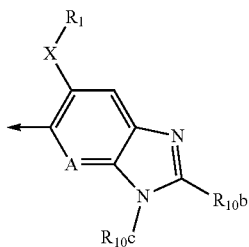
$J_{23a}$

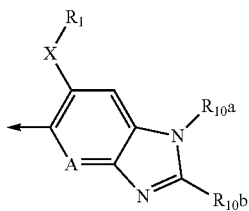
$J_{23b}$

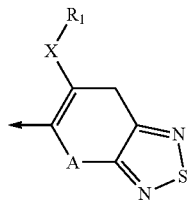
$J_{20}$

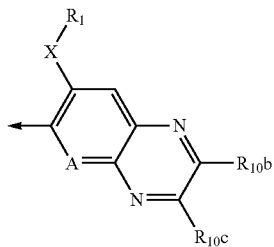
$J_{1b}$

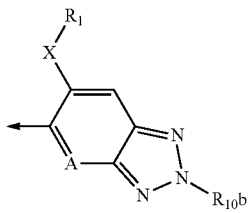
$J_{17}$

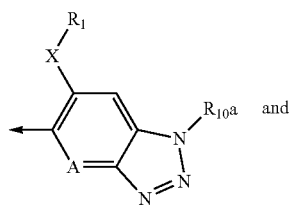
$J_{18}$ and

-continued

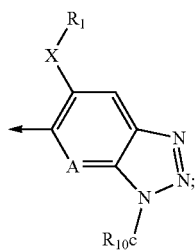
J<sub>24</sub> and $R_{10a}$, $R_{10b}$, $R_{10c}$, and $R_{10d}$, independently from each other, are hydrogen, halogen, cyano, cyclopropyl, $C_1$-$C_4$ alkyl or $C_1$-$C_4$ haloalkyl.

In especially preferred compounds of formula I

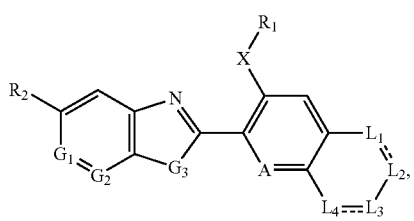
(I)

$R_1$ is $C_1$-$C_4$alkyl;
$R_2$ is $C_1$-$C_4$haloalkyl;
X is S or $SO_2$;
A is CH or N;
$G_1$ is CH or N;
$G_2$ is CH or N;
$G_3$ is N($C_1$-$C_4$alkyl);
$L_1$, $L_2$, $L_3$ and $L_4$ form together with the two carbon atoms to which $L_1$ and $L_4$ are attached, an aromatic or partially saturated carbocyclic or heterocyclic ring system; wherein
$L_1$ is CH, NH, N—$C_1$-$C_4$alkyl or S;
$L_2$ is CH, C($C_1$-$C_4$alkyl), C($C_1$-$C_4$haloalkyl), N or S;
$L_3$ is CH, N or N—$C_1$-$C_4$alkyl; and
$L_4$ is absent or N;
with the proviso that no more than three L groups can be nitrogen.

In especially preferred compounds of formula I-5a

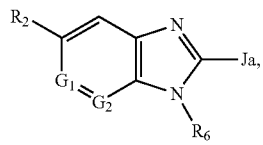
(I-5a)

$G_1$ is N or CH;
$G_2$ is N or CH;
$R_2$ is $C_1$-$C_4$haloalkyl, $C_1$-$C_4$haloalkylsulfanyl or $C_1$-$C_4$haloalkylsulfinyl;
A is N or CH;
$R_6$ is $C_1$-$C_4$alkyl;
X is S or $SO_2$;
$R_1$ is $C_1$-$C_4$alkyl; and Ja is selected from the group consisting of

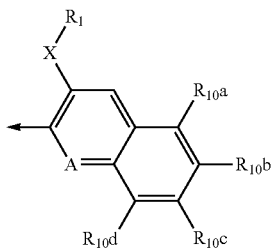
J<sub>1a</sub>

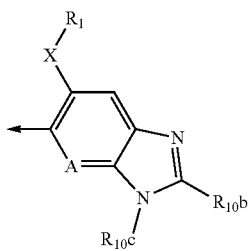
J<sub>23a</sub>

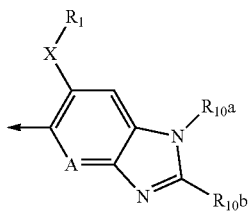
J<sub>23b</sub>

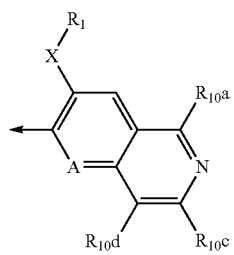
J<sub>6</sub>

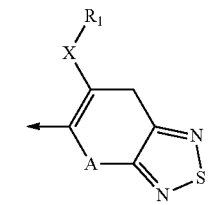
J<sub>20</sub>

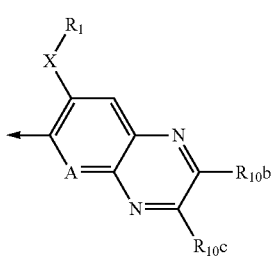
J<sub>1b</sub>

-continued

J$_{12}$
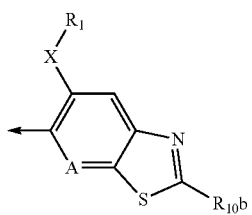

J$_{17}$
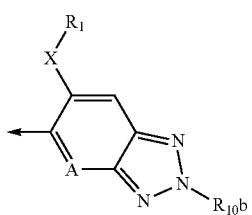

J$_{18}$
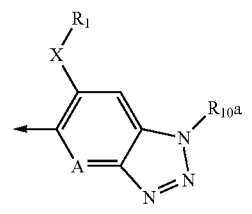

J$_{24}$
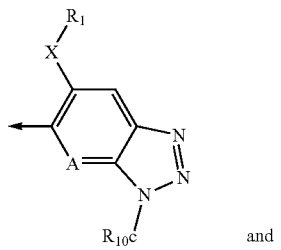

and

J$_{27}$
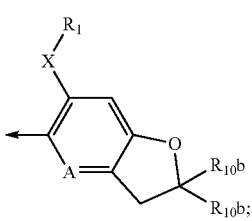

in particular from J$_{1a}$, J$_{23a}$, J$_{23b}$, J$_6$, J$_{20}$, J$_{1b}$, J$_{12}$, J$_{17}$, J$_{18}$, and J$_{24}$, most preferred J$_{1a}$, J$_{23a}$, J$_{23b}$, J$_6$, J$_{20}$, J$_{12}$, J$_{17}$, J$_{18}$, and J$_{24}$;

wherein R$_{10a}$; R$_{10b}$, R$_{10c}$, and R$_{10d}$; independently from each other, are selected from the group consisting of hydrogen, halogen, cyano cyclopropyl, C$_1$-C$_4$ alkyl and C$_1$-C$_4$ haloalkyl.

The process according to the invention for preparing compounds of formula (I) is carried out by methods known to those skilled in the art, or described for example in WO 2009/131237, WO 2011/043404, WO 2011/040629, WO 2010/125985, WO 2012/086848, WO 2013/018928, WO 2013/191113, WO 2013/180193 and WO 2013/180194, and involves reaction of a compound of formula II,

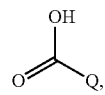
(II)

wherein Q is the group

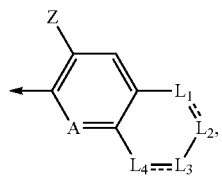
(Q)

wherein Z is X—R$_1$ or a leaving group, for example a halogen, and wherein X, R$_1$, L$_1$, L$_2$, L$_3$, L$_4$ and A are as described under formula I above, and wherein the arrow in the radical Q shows the point of attachment to the carbon atom of the carboxyl group in the compound of formula II, with a compound of formula III,

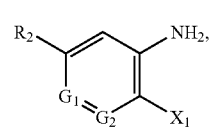
(III)

wherein R$_6$, R$_2$, G$_1$ and G$_2$ are as described under formula I above and wherein X$_1$ is OH, SH or NH—R$_6$, in the presence of a dehydrating agent, such as for example polyphosphoric acid at temperature between 150° C. to 250° C., to yield compounds of formula Ia, wherein the substituents are as described above and under formula I.

Such processes are well known and have been described for example in WO 2008/128968 or WO 2006/003440. The process is summarized in scheme 1 for compounds of formula Ia:

Scheme 1

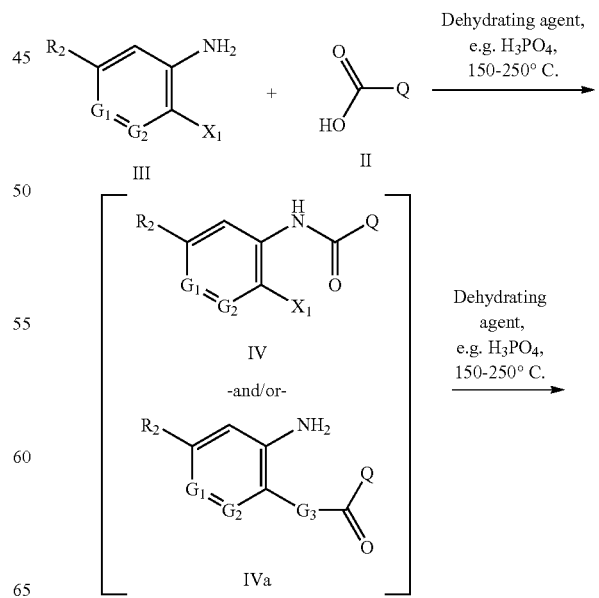

-continued

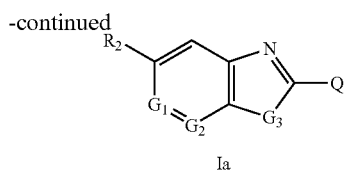

Ia

As can be seen in scheme 1, the formation of compounds of formula Ia, wherein $R_2$, $G_1$, $G_2$ and $G_3$ are as described in compounds of formula I, occurs through the intermediacy of a compound of formula IV (and/or its position isomer Iva). Intermediate IV or intermediate IVa may form as a pure entity, or intermediates IV and IVa may arise as a mixture of regioisomeric acylation products. It is in many cases advantageous to thus prepare compounds of formula (I) through such intermediates IV/IVa, which may be isolated and optionally purified. This is illustrated for compounds of formula Ia in scheme 2:

compounds of formula II with, for example, 1-ethyl-3-(3-dimethylaminopropyl)carbodiimide EDC or dicyclohexyl carbodiimide DCC will generate an activated species IIa, wherein $X_{00}$ is $X_{01}$ or $X_{02}$ respectively, in an inert solvent, such as pyridine or tetrahydrofuran THF, optionally in the presence of a base, such as triethylamine, at temperatures between 25-180° C.; followed by ii) treatment of the activated species IIa with a compound of formula III (or a salt thereof), wherein $R_6$, $R_2$, $G_1$ and $G_2$ are as described under formula I above, optionally in the presence of a base, such as triethylamine or pyridine, in an inert solvents such as dichloromethane, tetrahydrofuran, dioxane or toluene, at temperatures between 0 and 80° C., to form the compounds of formula IV and/or IVa (or a mixture thereof).

Compounds of formula IV and/or IVa (or a mixture thereof) may further be converted into compounds of formula Ia, wherein Q is as defined above, and wherein $R_6$, $R_2$, Scheme 2

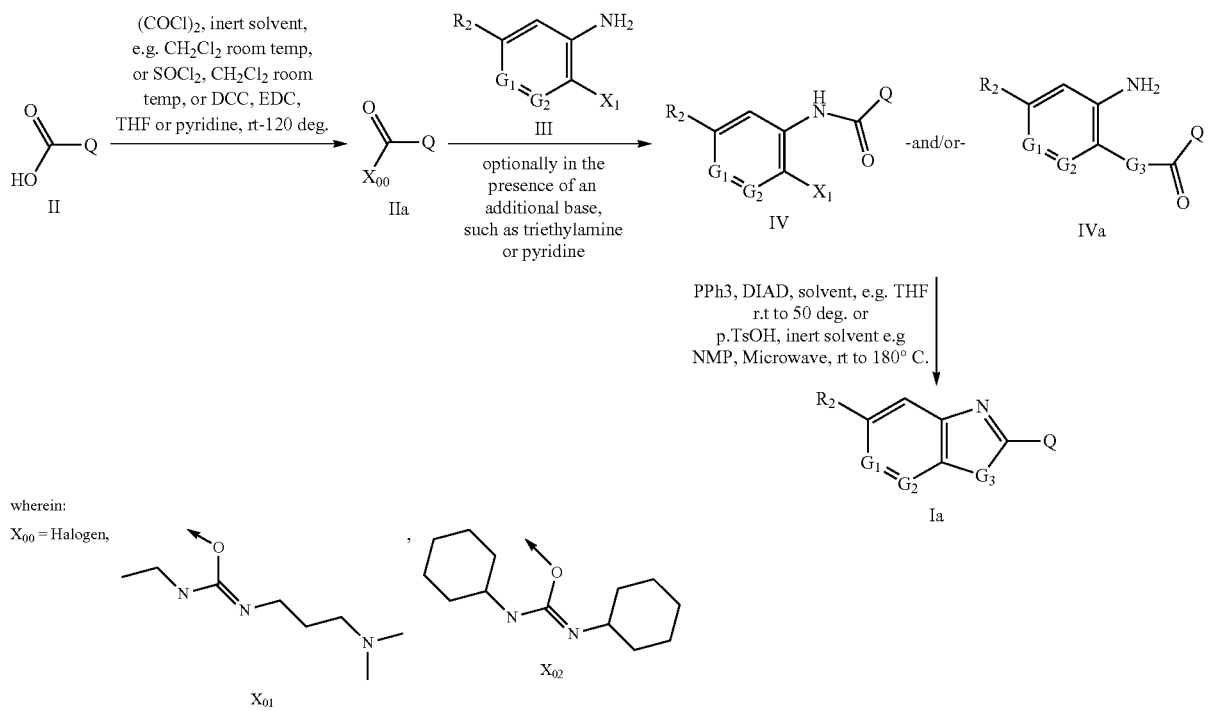

Compounds of the formula IV and/or IVa (or a mixture thereof), or a salt thereof, wherein Q is as defined above, and wherein $R_6$, $R_2$, $G_1$, $G_2$ and $G_3$ are as described under formula I above and $X_1$ are as described before, may be prepared by i) activation of compound of formula II, wherein Q is as defined above, by methods known to those skilled in the art and described in, for example, Tetrahedron, 2005, 61 (46), 10827-10852, to form an activated species IIa, wherein Q is as defined above and wherein $X_{00}$ is halogen, preferably chlorine. For example, compounds IIa where $X_{00}$ is halogen, preferably chlorine, are formed by treatment of II with, for example, oxalyl chloride $(COCl)_2$ or thionyl chloride $SOCl_2$ in the presence of catalytic quantities of N,N-dimethylformamide DMF in inert solvents such as methylene chloride $CH_2Cl_2$ or tetrahydrofuran THF at temperatures between 20 to 100° C., preferably 25° C. Alternatively, treatment of $G_1$, $G_2$ and $G_3$ are as described under formula I above, by dehydration, eg. by heating the compounds IV and/or IVa (or a mixture thereof) in the presence of an acid catalyst, such as for example methane sulfonic acid, or para-toluene sulfonic acid TsOH, in an inert solvent such as N-methyl pyrrolidine NMP at temperatures between 25-180° C., preferably 100-170° C., optionally under microwave conditions. Such processes have been described previously, for example, in WO 2010/125985.

Compounds of formula Ia, wherein Q is as defined above, and wherein Z is a leaving group, for example halogen, preferably fluorine or chlorine, and wherein $R_6$, $R_2$, $G_1$, $G_3$ and $G_2$ are as described under formula I above, can be reacted with compounds of formula V $$R_1-SH \qquad (V),$$

or a salt thereof, wherein $R_1$ is as defined in formula I, optionally in the presence of a suitable base, such as alkali metal carbonates, for example sodium carbonate and potassium carbonate, or alkali metal hydrides such as sodium hydride, or alkali metal hydroxides such as sodium hydroxide and potassium hydroxide, in an inert solvent at temperatures preferably between 25-120° C., to generate compounds of formula Ib, wherein $R_1$ is as described under formula I above, and in which $R_6$, A, $R_2$, $L_1$, $L_2$, $L_3$, $L_4$, $G_1$, $G_2$ and $G_3$ are as described under formula I above. Examples of solvent to be used include ethers such as THF, ethylene glycol dimethyl ether, tert-butylmethyl ether, and 1,4-dioxane, aromatic hydrocarbons such as toluene and xylene, nitriles such as acetonitrile or polar aprotic solvents such as N,N-dimethylformamide, N,N-dimethylacetamide, N-methyl-2-pyrrolidone or dimethyl sulfoxide. Similar chemistry has been previously described, as for example in WO2013/018928. Examples of salts of the compound of formula V include compounds of the formula Va $R_1$—S-M     (Va), wherein $R_1$ is as defined above and wherein M is, for example, sodium or potassium. This is illustrated for compounds of formula Ib in scheme 3:

Scheme 3

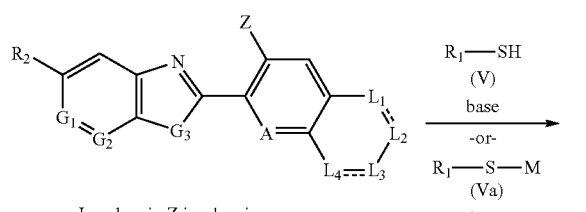

Ia, wherein Z is a leaving group
(for example a halogen)

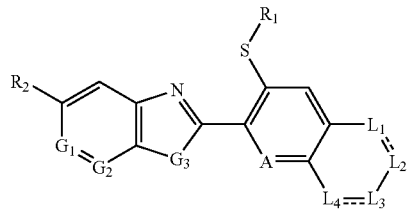

Ib, that is a compound of formula I
wherein X is a sulfur (a sulfide)

Alternatively, this reaction can be carried out in the presence of a palladium catalyst, such as tris(dibenzylideneacetone)dipalladium(0), in the presence of a phosphor ligand, such as xanthphos, in an inert solvent, for example, xylene at temperatures between 100-160° C., preferably 140° C., as described by Perrio et al. in Tetrahedron 2005, 61, 5253-5259.

The subgroup of compounds of formula I, wherein X is SO (sulfoxide) and/or $SO_2$ (sulfone), may be obtained by means of an oxidation reaction of the corresponding sulfide compounds of formula I, wherein X is S (i.e. a compound of formula Ib above), involving reagents such as, for example, m-chloroperoxybenzoic acid (mCPBA), hydrogen peroxide, oxone, sodium periodate, sodium hypochlorite or tert-butyl hypochlorite amongst other oxidants. The oxidation reaction is generally conducted in the presence of a solvent. Examples of the solvent to be used in the reaction include aliphatic halogenated hydrocarbons such as dichloromethane and chloroform; alcohols such as methanol and ethanol; acetic acid; water; and mixtures thereof. The amount of the oxidant to be used in the reaction is generally 1 to 3 moles, preferably 1 to 1.2 moles, relative to 1 mole of the sulfide compounds Ib to produce the sulfoxide compounds I (wherein X=SO), and preferably 2 to 2.2 moles of oxidant, relative to 1 mole of the sulfide compounds Ib to produce the sulfone compounds I (wherein X=$SO_2$). Such oxidation reactions are disclosed, for example, in WO 2013/018928.

More specifically, Compounds of formula VIa, wherein Z is X—$R_1$ or a leaving group, for example halogen, and wherein X, $R_1$, $R_2$, $R_6$ and A are as described under formula I above, wherein $G_1$ is N, $G_3$ is N—$R_6$, $G_2$ is C—H and $X_1$ is $NHR_6$, may be prepared by reaction between compounds of formula II respectively IIa, wherein Z is X—$R_1$ or a leaving group, for example halogen, and wherein X, $R_1$ and A are as described under formula I above, and in which $X_{00}$ is as described above, and compounds of formula IIIa, wherein $R_6$ and $R_2$ are as described under formula I above, under similar conditions as for the preparation of compounds of formula Ia from compounds of formula II/IIa and III described above (see scheme 1 and 2). This is illustrated for compounds of formula VIa in scheme 4:

Scheme 4

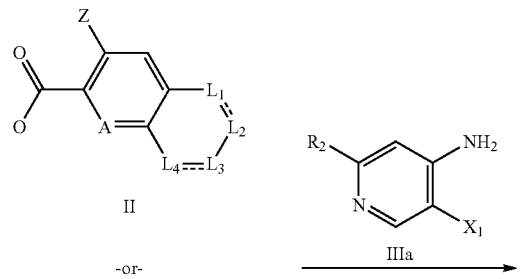

II

-or-

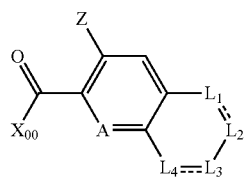

IIa

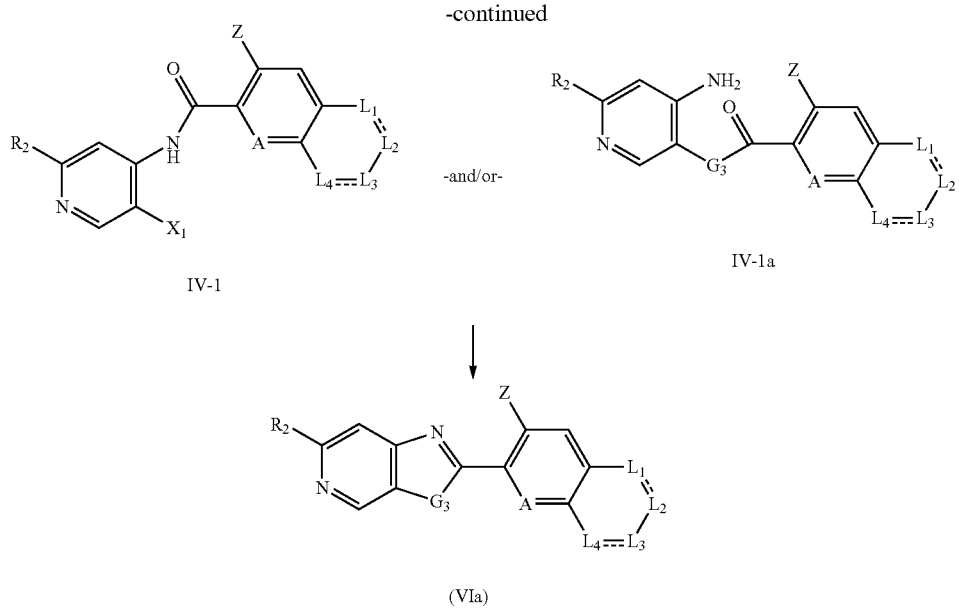

IV-1

-and/or-

IV-1a (VIa)

Analogeusly to descriptions in schemes 1 and 2, the formation of compounds of formula VIa occurs through the intermediacy of compounds of formula IV-1 and/or IV-1a (or a mixture thereof), or salts thereof, which optionally may be isolated and purified.

Compounds of the formula IIIa, wherein $R_6$, and $R_2$ are as described under formula I above, may be prepared from diamino compounds of formula VII, wherein $R_2$ is as described under formula I above, by means of a direct alkylation with $R_6$—$X_{LG}$, wherein $R_6$ is as described under formula I above and wherein $X_{LG}$ is a leaving group, such as halogen, preferably iodine, bromine or chlorine, in presence of a base, such as sodium carbonate, potassium carbonate or cesium carbonate, or sodium hydride, in an appropriate solvent such as for example N,N-dimethylformamide, N,N-dimethylacetamide or acetonitrile (scheme 5).

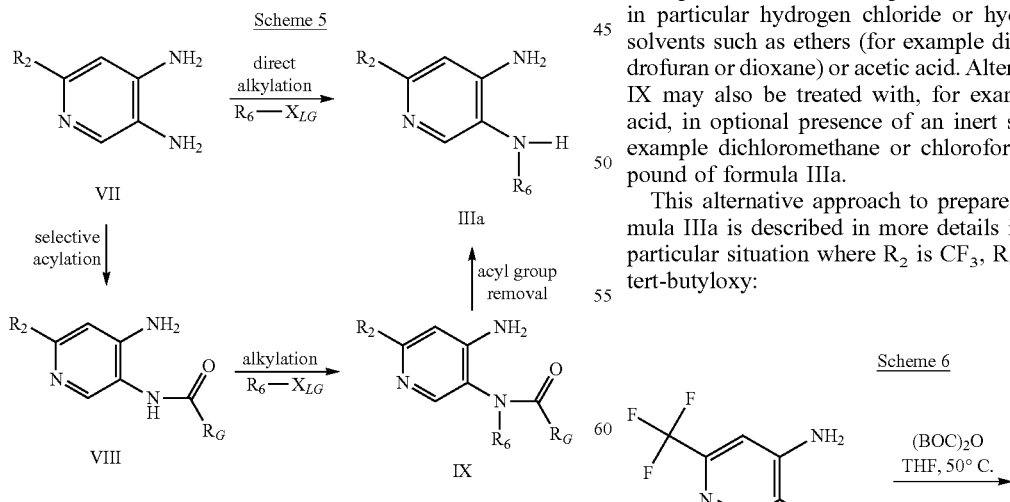

Scheme 5

Alternatively, the sequence to prepare compounds of formula IIIa from compounds of formula VII, may involve i. a selective acylation of compound VII to form a compound of formula VIII, wherein $R_2$ is as described under formula I above and wherein the acylation agent is for example di-tert-butyl dicarbonate (leading to compound VIII wherein $R_G$ is tert-butyloxy), in an ether solvent, such as for example, tetrahydrofuran or dioxane; ii. alkylation of compound VIII with $R_6$—$X_{LG}$, wherein $R_6$ is as described under formula I above and wherein $X_{LG}$ is a leaving group, such as halogen, preferably iodine, bromine or chlorine, in presence of a base, such as sodium carbonate, potassium carbonate or cesium carbonate, or sodium hydride, in an appropriate solvent such as for example N,N-dimethylformamide, N,N-dimethylacetamide or acetonitrile, to generate a compound of formula IX, wherein $R_6$ and $R_2$ are as described under formula I above and wherein $R_G$ is for example tert-butyloxy; and finally iii. deacylation of compound IX to form the compound of formula IIIa, wherein $R_6$, and $R_2$ are as described under formula I above. When $R_G$ is for example tert-butyloxy, conditions for the acyl group removal include, for example, treatment of compound IX with hydrogen halide, in particular hydrogen chloride or hydrogen bromide, in solvents such as ethers (for example diethyl ether, tetrahydrofuran or dioxane) or acetic acid. Alternatively, compound IX may also be treated with, for example, trifluoroacetic acid, in optional presence of an inert solvent, such as for example dichloromethane or chloroform, to form a compound of formula IIIa.

This alternative approach to prepare compounds of formula IIIa is described in more details in scheme 6 for the particular situation where $R_2$ is $CF_3$, $R_6$ is $CH_3$, and $R_G$ is tert-butyloxy:

Scheme 6 prepared as described in U.S. Pat. No. 7,767,687

-continued

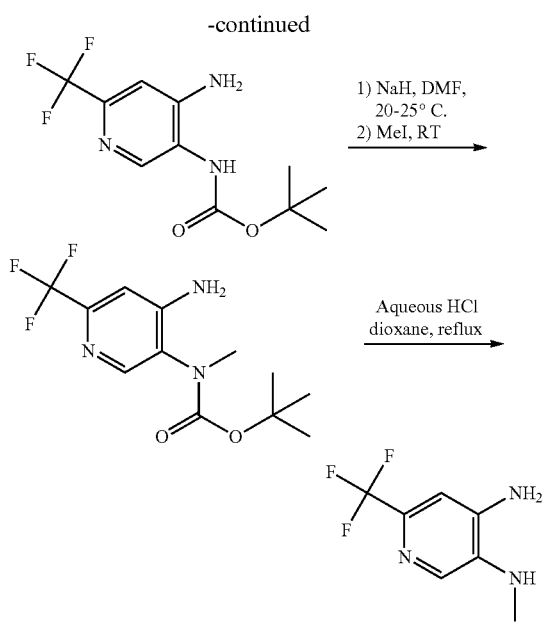

Common abbreviations
(BOC)₂O = di-tert-butyl dicarbonate; THF = tetrahydrofuran; NaH = sodium hydride; DMF = N,N-dimethylformamide; MeI = methyl iodide; RT = room temperature; HCl = hydrogen chloride.

Diamino compounds of formula (VII) are either known, commercially available or may be made by methods known to a person skilled in the art, for example in analogy to a preparation method described in U.S. Pat. No. 7,767,687.

Diamino compounds of formula IIIb and IIIc, Where in $X_1$ is OH, SH or NH—$R_6$ Scheme 7

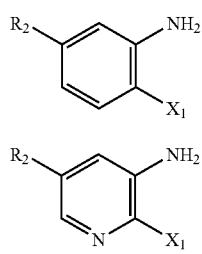

are either known, commercially available or may be made by methods known to a person skilled in the art.

Compounds of formula II,

Scheme 8

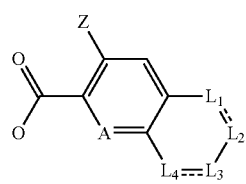

wherein Z is X—$R_1$ or a leaving group or a group that could be transformed in leaving group such as, for example halogen, amine or nitro, and wherein X, $R_1$, $L_1$, $L_2$, $L_3$, $L_4$ and A are as described under formula I above, may be either known, commercially available or may be made by methods known to a person skilled in the art.

Compounds of formula IIc, wherein Q is as defined above, and wherein Z is a leaving group, for example halogen, preferably fluorine, chlorine, and wherein A, $L_1$, $L_2$, $L_3$ and $L_4$ are as described under formula I above, and wherein R is alkyl or hydrogen can be reacted with compounds of formula V $$R_1\text{—SH} \quad (V),$$

or a salt thereof, wherein $R_1$ is as defined in formula I, optionally in the presence of a suitable base, such as alkali metal carbonates, for example sodium carbonate and potassium carbonate, or alkali metal hydrides such as sodium hydride, or alkali metal hydroxides such as sodium hydroxide and potassium hydroxide, in an inert solvent at temperatures preferably between 25-120° C., to generate compounds of formula IId, wherein R is alkyl or hydrogen, $R_1$ is as described under formula I above, and in which A, $L_1$, $L_2$, $L_3$ and $L_4$ are as described under formula I above. Examples of solvent to be used include ethers such as THF, ethylene glycol dimethyl ether, tert-butylmethyl ether, and 1,4-dioxane, aromatic hydrocarbons such as toluene and xylene, nitriles such as acetonitrile or polar aprotic solvents such as N,N-dimethylformamide, N,N-dimethylacetamide, N-methyl-2-pyrrolidone or dimethyl sulfoxide. Examples of salts of the compound of formula V include compounds of the formula Va $$R_1\text{—S-M} \quad (Va),$$

wherein $R_1$ is as defined above and wherein M is, for example, sodium or potassium. This is illustrated for compounds of formula IId in scheme 9:

Scheme 9

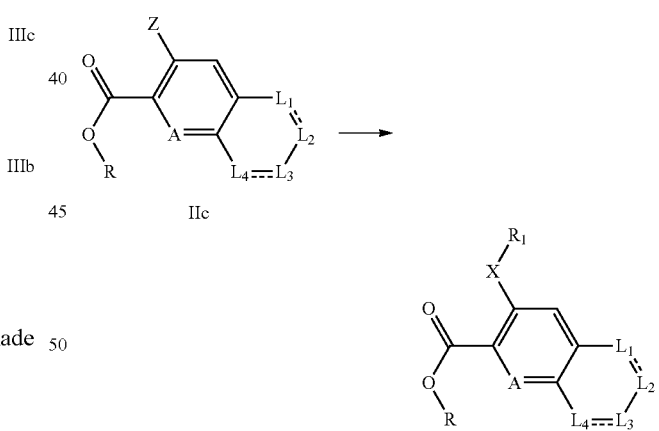

Alternatively, compounds of formula IIc, wherein Z is a amine and wherein A, $L_1$, $L_2$, $L_3$ and $L_4$ are as described under formula I above, and wherein R is alkyl or hydrogen can be transformed to compounds of formula IId via diazotation and reaction with dialkyldisulfide. This transformation is well known and could be made by methods known to a person skilled in the art (see for example: Synthetic Communications, 31 (12), 1857-1861; 2001 or Organic & Biomolecular Chemistry, 6 (4), 745-761; 2008). Compounds of formula IIc, wherein Z is a amine and wherein A, $L_1$, $L_2$, $L_3$ and $L_4$ are as described under formula I above, and wherein R is alkyl or hydrogen can be transformed to compounds of formula IIe via diazotation and reaction with sodium sulphide, followed by reduction. This transformation is well known and could be made by methods known to a person skilled in the art (see for example: US 20040116734 or Chemische Berichte, 120 (7), 1151-73; 1987). Alkylation of compound IIe with $R_1$—$X_{LG}$, wherein $R_1$ is as described under formula I above and wherein $X_{LG}$ is a leaving group, such as halogen, preferably iodine, bromine or chlorine, in presence of a base, such as sodium carbonate, potassium carbonate or cesium carbonate, or sodium hydride, in a appropriate solvent such as for example N,N-dimethylformamide, N,N-dimethylacetamide or acetonitrile, to generate a compound of formula IId, wherein $R_1$ is as described under formula I above. See scheme 10.

Scheme 10

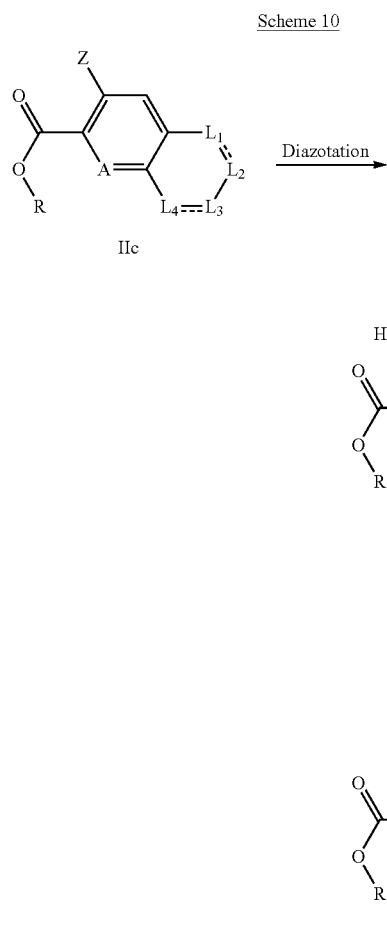

Compound of formula (ii) may be prepared by reaction of a compound of formula (IId), wherein R is alkyl via hydrolysis. For instance, in the case where R is methyl or ethyl, the hydrolysis can be done with water and a base, such as potassium hydroxide or lithium hydroxide, in the absence or in the presence of a solvent, such as, for instance, tetrahydrofuran or methanol. In the case where R is, for example, tert-butyl, the hydrolysis is done in the presence of acid, such as trifluoroacetic acid or hydrochloric acid. The reaction is carried out at a temperature of from −120° C. to +130° C., preferably from −100° C. to 100° C. See scheme 11.

Scheme 11

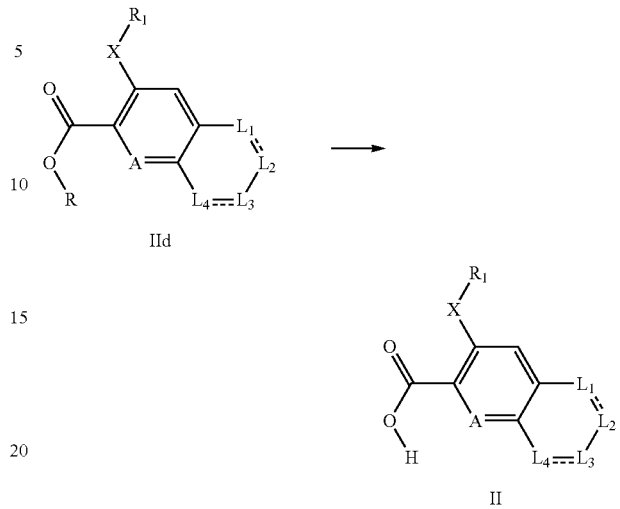

Alternatively, compound of formula II may be prepared by reaction of a compound of formula (X) wherein Z is a leaving group as nitro or halogen such as fluorine and wherein A, $L_1$, $L_2$, $L_3$ and $L_4$ are as described under formula I above by reaction of a compound of formula V or Va

to give compounds of formula Xd or a salt thereof, wherein $R_1$ is as defined in formula I, optionally in the presence of a suitable base, such as alkali metal carbonates, for example sodium carbonate and potassium carbonate, or alkali metal hydrides such as sodium hydride, or alkali metal hydroxides such as sodium hydroxide and potassium hydroxide, in an inert solvent at temperatures preferably between 25-120° C., to generate compounds of formula XIIb, wherein $R_1$ is as described under formula I above, and in which A, $L_1$, $L_2$, $L_3$ and $L_4$ are as described under formula I above. Examples of solvent to be used include ethers such as THF, ethylene glycol dimethyl ether, tert-butylmethyl ether, and 1,4-dioxane, aromatic hydrocarbons such as toluene and xylene, nitriles such as acetonitrile or polar aprotic solvents such as N,N-dimethylformamide, N,N-dimethylacetamide, N-methyl-2-pyrrolidone or dimethyl sulfoxide.

Examples of salts of the compound of formula V include compounds of the formula Va

wherein $R_1$ is as defined above and wherein M is, for example, sodium or potassium. Compounds of formula II may be prepared by hydrolysis of the cyano of compound of formula Xd in acidic or basic conditions. This transformation is well known and could be made by methods known to a person skilled in the art (see for example: Comprehensive Organic Transformations: A Guide to Functional Group Preparations. Edited by Richard C. Larock 1989 p 993, VCH publishers).

This is illustrated for compounds of formula II in scheme 12.

Scheme 12

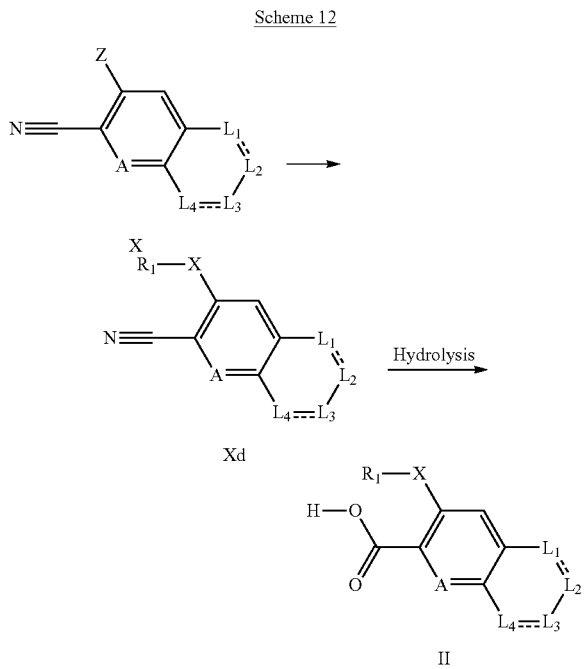

Compounds of formula X are either known, commercially available or may be made by methods known to a person skilled in the art.

Alternatively, compound of formula IIc, where in R is Hydrogen, may be prepared by reaction of a compound of formula (XI) where in Z is a leaving group as nitro or halogen such as fluorine and wherein A, $L_1$, $L_2$, $L_3$ and $L_4$ are as described under formula I above by oxidation in presence of a oxidant such as oxygen, hydrogen peroxide or an metal oxide such as chromium trioxide with or without acid such as sulphuric acid with or without metal catalyst. This transformation is well known and could be made by methods known to a person skilled in the art (see for example: Comprehensive Organic Transformations: A Guide to Functional Group Preparations. Edited by Richard C. Larock 1989 p 823, VCH publishers). This is illustrated for compounds of formula II in scheme 13.

Scheme 13

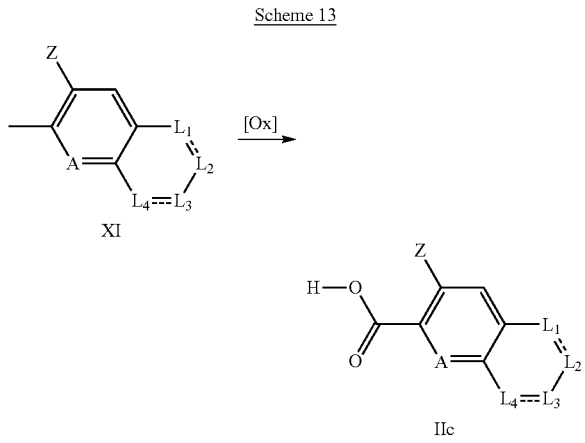

Compounds of formula XI are either known, commercially available or may be made by methods known to a person skilled in the art.

Compound of formula IIc, wherein R is $C_1$-$C_6$ Alkyl, A, $L_1$, $L_2$, $L_3$ and $L_4$ are as described under formula I above and Z is $NH_2$, may be prepared by reaction of a compound of formula (XII) with a compound of formula XIII wherein, for example $X_{00}$ is an halogen such as, for example, bromide and R is $C_1$-$C_6$ alkyl such as, for example, ethyl. these reactions are known to a person skilled in the art and are, for example described in Tetrahedron 60 (2004) 2937-2942. This is illustrated for compounds of formula IIc in scheme 14.

Scheme 14

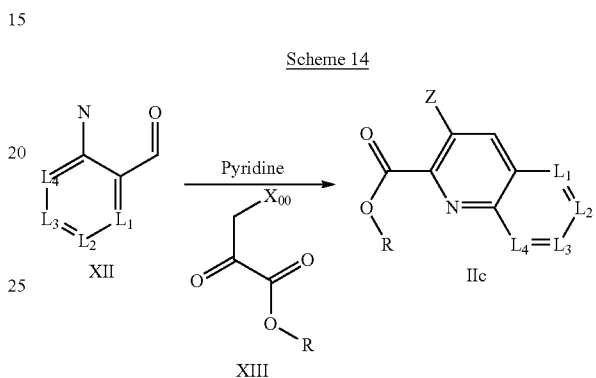

Alternatively synthesis of compounds of formula I (benzimidazoles ($J_{19}$ and $J_{23}$) wherein: $L_1$=N or $NR_{10a}$, $L_2$=C—$R_{10b}$, $L_3$=N or N—$R_{10c}$, $L_4$=bond; benzothiadiazoles ($J_{20}$): $L_1$=N, $L_2$=S, $L_3$=N, $L_4$=bond; benzothiazoles ($J_{12}$): $L_1$=N, $L_2$=C—$R_{10b}$, $L_3$=S, $L_4$=bond; benzotriazoles ($J_{18}$, $J_{17}$ and $J_{24}$): $L_1$=N or N—$R_{10a}$, $L_2$=N or N—$R_{10b}$, $L_3$=N or N—$R_{10c}$, $L_4$=bond; benzoxazoles ($J_{25}$): $L_1$=N, $L_2$=C—$R_{10b}$, $L_3$=O, $L_4$=bond can be made via cyclisation of intermediates of formulae XVI or XVII as depicted in scheme 15.

The synthesis of cyclic compounds as described in the scheme 16 is very well known and could be made by methods known to a person skilled in the art by analogy of what was described previously in literature. For example, for the synthesis of benzimidazoles starting from the intermediate type XVII see Monatshefte fuer Chemie 2011, 142 (1), 87-91; Organic Preparations and Procedures International 2013, 45 (1), 57-65; Organic Preparations and Procedures International 2013, 45 (2), 162-167; Tetrahedron Letters 2007 48 (18), 3251-3254; or starting from the intermediate type XVI, see for example Journal of Organic Chemistry 2011, 76 (23), 9577-9583 or Tetrahedron 2013, 69 (6), 1717-1719. In general manner, see for review on the preparation of benzimidazoles: The Chemistry of Heterocyclic Compounds; Weissberger, A., Taylor, E. C., Eds.; Wiley-VCH: New York, N.Y., 1981; Vol. 40, pp 6-60.

For example, for the synthesis of benzothiadiazoles starting from the intermediate type XVII see Tetrahedron 2005, 61 (46), 10975-10982. See for a more general review on the preparation and properties of benzimidazoles: Eur. J. Org. Chem. 2013, 228-255.

For example, for the synthesis of benzotriazoles starting from the intermediate type XVII see for example, Bioorganic & Medicinal Chemistry 2010, 18 (24), 8457-8462, using cyclocondensation as described in scheme 15 (e.g. AcOH, $NaNO_2$). For a more general review on the preparation of benzotriazoles, see, for example, Journal Chem. Pharm. Res., 2011, 3 (6) p 375-381.

For example, for the synthesis of benzothiazoles starting from the intermediate type XVI see for example, Journal of Combinatorial Chemistry 2009, 11 (6), 1047-1049; Chemistry—A European Journal 2012, 18 (16), 4840-4843, S4840/1-S4840/35; or WO13066729. In addition, synthesis of benzothiazoles are well known and could be made easily by methods known to a person skilled in the art via other type of intermediates see, for example, Journal of Current Pharmaceutical Research 2010; 3 (1): 13-23.

Scheme 15: Alternative Preparation of compounds of formula I

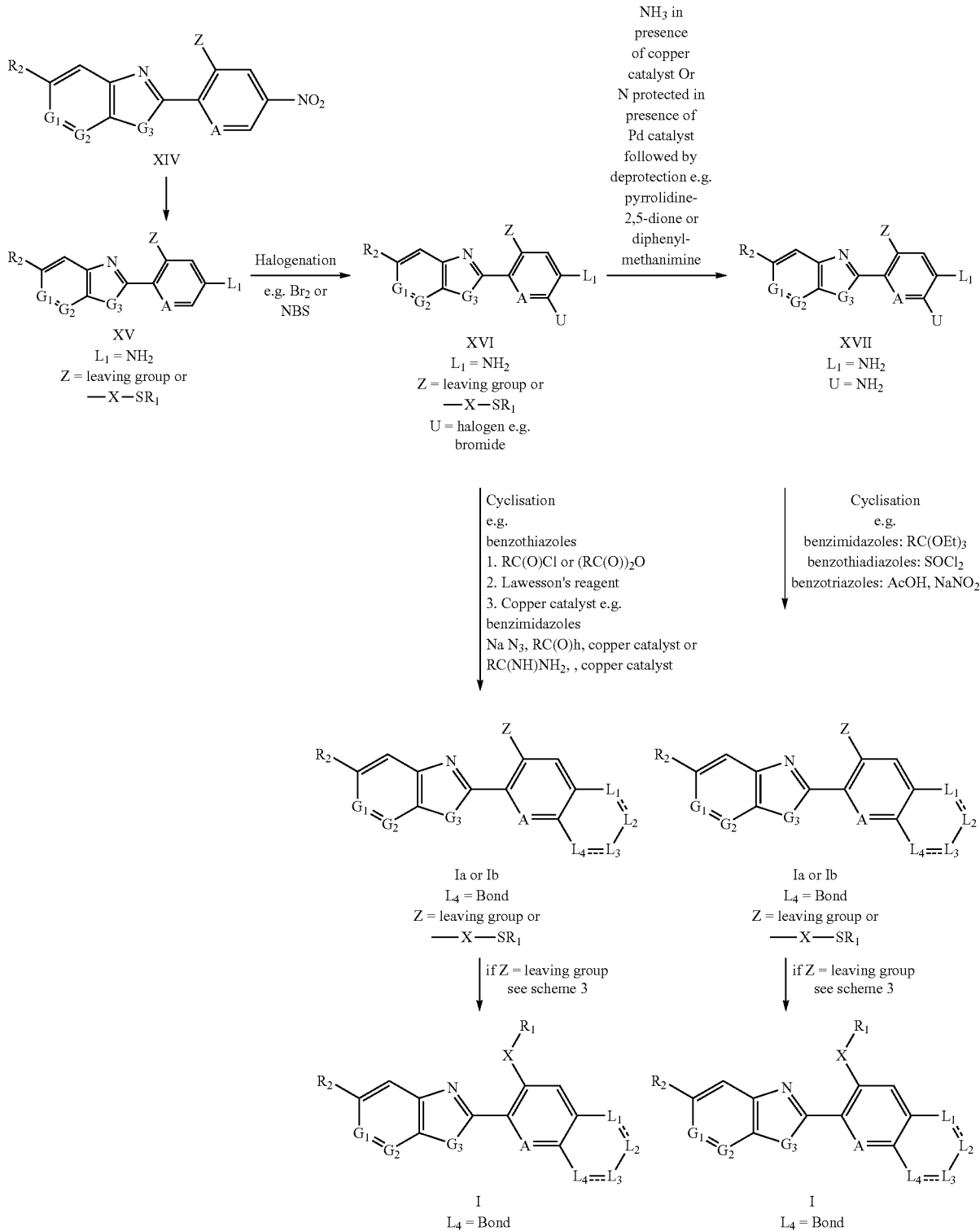

Compounds of formula XIV may be prepared by identical reaction described in scheme 1 to 6 wherein L1 is $NO_2$ or compounds of formula XV may be prepared by identical reaction described in scheme 1 to 6 wherein $L_1$ is a protected nitrogen, for example $L_1$ could be pyrrolidine-2,5-dione followed by deprotection, for example with hydrazine.

Compounds of formula Ia, Ib, and I containing an N—H as $L_1$, $L_2$ or $L_3$ could react with a alkylation agent such as methyl iodide in presence of a base, such as potassium carbonate or sodium hydride, to give compounds of formula Ia, Ib, and I wherein $L_1$, $L_2$ or $L_3$ is an N—$CH_3$.

The same type of process described in the general references used in the explanation of scheme 15 could be used, for example, on intermediate XI, II, IIc, IId, X, Xd.

Compounds of Formula I wherein $G_3$ is O or S can be prepared, as described in scheme 1 and scheme 2, by reaction of a compound of formula III, wherein $X_1$ is SH or OH with a compound of formula II.

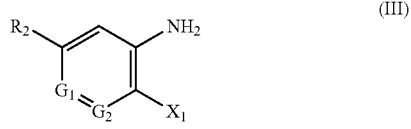

(III)

All of these methods are known to those skilled in the art or described for example in WO 2011/040629 or WO 2009131237, WO 2011088990, WO2011049222 or *Inorg. Chimica Acta,* 358 (9), 2701-2710; 2005. The methods used for the synthesis of this type of heterocycles are well known to those skilled in the art, for review or information around the synthesis of these type of structure via (XVI) or via other types of intermediates, see, for example, RSC Advances (2014), 4 (104), 60176-60208, Pure and Applied Chemistry (2008), 80 (4), 707-715, Chemical Science Review and Letters (2014), 2 (6), 408-414, Tetrahedron Letters 55 (2014) 5515-5520 (and cited references), Tetrahedron (2015), 71 (4), 700-708 (and cited references), Heterocycles (2014), 89 (6), 1441-1453 (and cited references), Heterocycles (1994) 38, 1001, Asian Journal of chemistry (2004) 16, No 3-4, p 1241-1260 or Chin. J. Org. Chem. 2014, Vol. 34, No 6, 1048-1060.

Compounds of formula XXa wherein $X_1$ is OH can be produced from compounds of formula XVIII by treatment with a base, for example alkaline earth metal bases in water, NMP, DMF, 2-Imidazolidinone, or mixtures thereof at temperatures between 50-100° C. Reduction of the produced XIX by methods known to those skilled in the art, for example with a metal in acidic medium, for example Fe in acetic acid or hydrochloric acid. Such reductions of $NO_2$ groups have been described for example in Org. Synth.; Coll. Vol. 5: 346, 1973 to leads to compounds of formula XIIa. Similar reactions are well known to those skilled in the art and have been described, for example in Organic Letters, 10 (14), 3025-3028; 2008 or Bioorganic & Medicinal Chemistry Letters, 16 (8), 2293-2298; 2006. The chemistry is summarized in scheme 16.

Scheme 16:

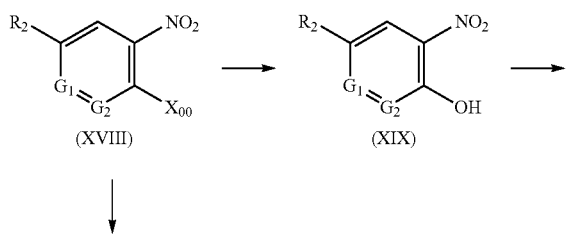

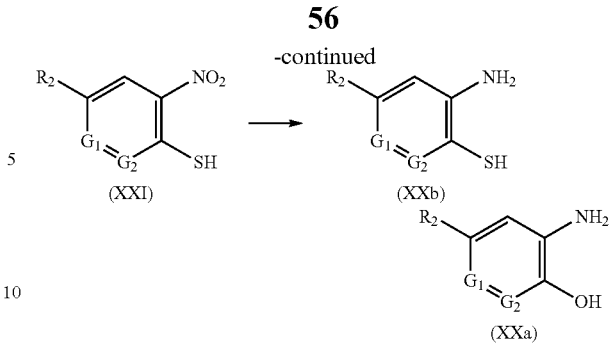

Alternatively, Compounds of formula XIX can be produced from compounds of formula XXII via nitration reaction. Similar reactions are well known to those skilled in the art and have been described, for example in WO-2011049222 or WO-2011049220 (scheme 17).

Scheme 17:

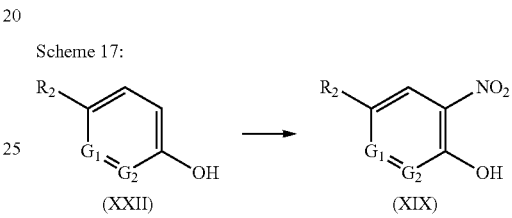

The compound of formula XXI can be produced by reacting a compound of formula XVII with a sulfating agent. Examples of the sulfating agent to be used in the reaction include sodium sulfide, sodium sulfide 9-hydrate, and thiourea. The reaction may be conducted in the presence of a base. Examples of the base to be used in the reaction include inorganic bases such as potassium carbonate, cesium carbonate, and tripotassium phosphate; and organic bases, for example triethylamine. The reaction is generally conducted in the presence of a solvent. Examples of the solvent to be used in the reaction include water; alcohols such as methanol and ethanol; ethers such as THF, ethylene glycol dimethyl ether, tert-butylmethyl ether, and 1,4-dioxane; aromatic hydrocarbons such as toluene and xylene; nitriles such as acetonitrile; aprotic polar solvents such as DMF, NMP, and DMSO; carboxylic acids such as acetic acid; and mixtures thereof. Similar reactions have been described in the literature (see, for example: ChemMedChem, 4 (6), 935-938; 2009, Bioorganic & Medicinal Chemistry, 16 (23), 9948-9956; 2008 or Journal of Heterocyclic Chemistry, 38 (5), 1153-1166; 2001). Reduction of the nitro group in compound XXI by methods known to those skilled in the art, for example with a metal in acidic medium, for example Fe in acetic acid or hydrochloric acid. Such reductions of $NO_2$ groups have been described for example in Org. Synth.; Coll. Vol. 5: 346, 1973, leads to compounds of formula XXb. The chemistry is summarized in scheme 16.

Preparation of Quinoxalines derivatives analogues (J1 b): The compound of formula Ia or Ib wherein $R_2$, $G_1$, $G_2$ and $G_3$ are as defined in formula I, L1 and L2 are nitrogen, $L_2$ and $L_3$ are, respectively C—$R_{10b}$ and C—$R_{10c}$, and Z is a leaving group or X—$R_1$, can be produced by reacting a compound of formula XVII (for example, prepared as describe in scheme 15) with Glyoxal analogues (XXIII) and transformed in compound of formula I (if Z is a leaving group) via the conditions described, for example in scheme 3. Such transformation is well known to those skilled in the art and have been described, for example in Journal of Heterocyclic Chemistry, 51 (5), 1504-1508; 2014, Synthesis, 45 (11), 1546-1552; 2013 and cited references. This is illustrated for compounds of formula I in scheme 19.

Scheme 19:

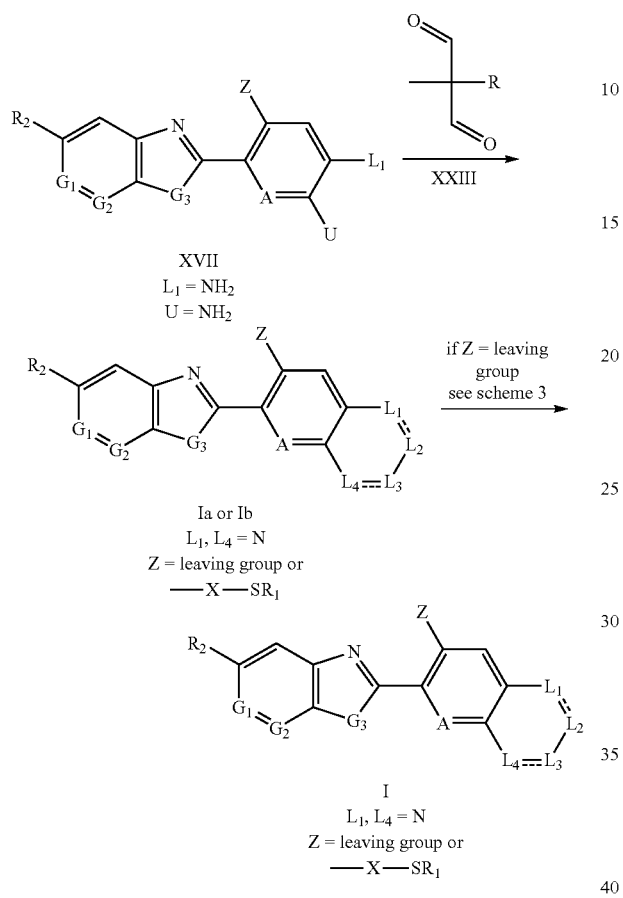

Preparation of benzofuran derivatives analogues (e.g. J27): The compound of formula I wherein A, $R_2$, $G_1$, $G_2$ and $G_3$ are as defined in formula I, L1 is oxygen, $L_2$ and $L_3$ are, respectively $C(R_{10b})_m$ and $C(R_{10c})_m$, and Z is a leaving group or X—$R_1$, can be produced by:
1. reacting compounds of formula XXIV with an allyl analogues such as compound of formula XXV in presence of a base such as, for example, potassium carbonate in a solvent such as, for example, acetone, acetonitrile or dimethylformamide or a mixture of solvent such as, dimethylformamide and acetone, in presence or not of a catalyst such as sodium iodine. The formation of the ester XXVI is analogues to transformation well known by a person skilled in the art and could be done in conditions described, for example in Organic Letters, 17 (12), 3118-3121; 2015; Tetrahedron, 2004, 60, 7973-7981 or Protective groups in organic synthesis (third edition, Theodora W. Greene, Peter G. M. Wuts 1999) p 262.
2. then via Claisen rearrangement of compounds of formula XXVI under heating conditions. This reaction and the conditions to realize it are well known to person skilled in the art, see for example Strategic Applications of Named Reactions in Organic Synthesis by Kurti, Laszlo; Czako, Barbara; Editors; 2005, page 88.
3. and by cyclisation of compounds of formula XXVII under acidic condition such as acid formic. Such transformation (Intramolecular Hydroalkoxylation) is well known to those skilled in the art and have been described, see for example, Angewandte Chemie, International Edition, 54 (13), 4014-4017; 2015 and cited references; ChemCatChem, 5 (11), 3309-3315; 2013; Chemistry—A European Journal, 16 (11), 3403-3422, S3403/1-S3403/38; 2010 and cited references; Journal of Organic Chemistry, 76 (22), 9353-9361; 2011.

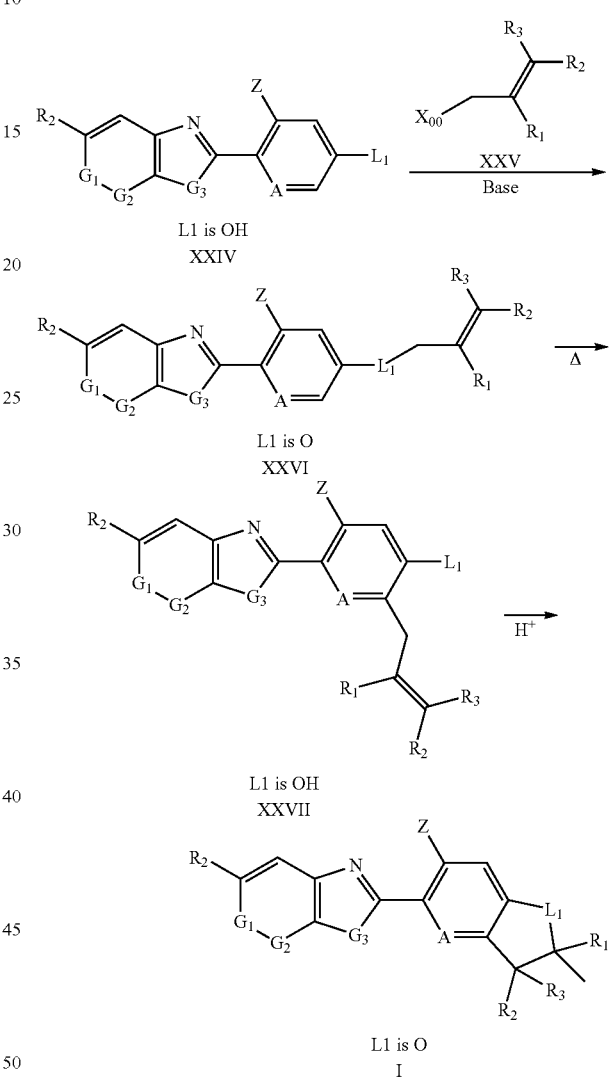

Preparation of compounds of formula XXIV could be made, to person skilled in the art, by the use of protocols described previously in this patent or with procedures described in WO 2015000715, US 20140018373 (WO 2012086848) or US 20140194290 (WO 2013018928).

For preparing all other compounds of the formula (I) functionalized according to the definitions of formula III and II, there are a large number of suitable known standard methods, for example alkylation, halogenation, acylation, amidation, oximation, oxidation and reduction, the choice of the preparation methods which are suitable depending on the properties (reactivity) of the substituents in the intermediates.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula I can be converted in a manner known per se into another compound of formula I by replacing one or more substituents of the starting compound of formula I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties, can be obtained in free form or in the form of salts.

The compounds of formula I and, where appropriate, the tautomer's thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and herein below, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from *J. Med. Chem.* 1989, 32, 2561 or WO 2000/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the following Tables 1 to 4 below can be prepared according to the methods described above. The examples which follow are intended to illustrate the invention and show preferred compounds of formula I. "Ph" represents the phenyl group.

Table 1: This table discloses the 128 compounds of the formula I-1a:

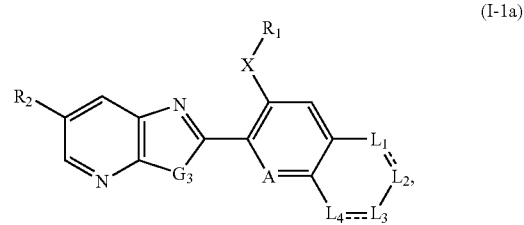

(I-1a)

TABLE 1

$G_3$ is N—$R_6$

| Comp. No. | X | $R_1$ | A | $R_2$ | $R_6$ | $L_1$ | $L_2$ | $L_3$ | $L_4$ |
|---|---|---|---|---|---|---|---|---|---|
| 1.001 | S | —CH$_2$CH$_3$ | C—H | CF$_3$ | CH$_3$ | CH | CH | CH | CH |
| 1.002 | SO | —CH$_2$CH$_3$ | C—H | CF$_3$ | CH$_3$ | CH | CH | CH | CH |
| 1.003 | SO$_2$ | —CH$_2$CH$_3$ | C—H | CF$_3$ | CH$_3$ | CH | CH | CH | CH |
| 1.004 | S | —CH$_2$CH$_3$ | N | CF$_3$ | CH$_3$ | CH | CH | CH | CH |
| 1.005 | SO | —CH$_2$CH$_3$ | N | CF$_3$ | CH$_3$ | CH | CH | CH | CH |
| 1.006 | SO$_2$ | —CH$_2$CH$_3$ | N | CF$_3$ | CH$_3$ | CH | CH | CH | CH |
| 1.007 | S | —CH$_2$CH$_3$ | C—H | CF$_3$ | CH$_3$ | O | CH$_2$ | O | bond |
| 1.008 | SO$_2$ | —CH$_2$CH$_3$ | C—H | CF$_3$ | CH$_3$ | O | CH$_2$ | O | bond |
| 1.009 | S | —CH$_2$CH$_3$ | C—H | CF$_3$ | CH$_3$ | CH | N | N—CH$_3$ | bond |
| 1.010 | SO$_2$ | —CH$_2$CH$_3$ | C—H | CF$_3$ | CH$_3$ | CH | N | N—CH$_3$ | bond |
| 1.011 | S | —CH$_2$CH$_3$ | C—H | CF$_3$ | CH$_3$ | CH | N—CH$_3$ | N | bond |
| 1.012 | SO$_2$ | —CH$_2$CH$_3$ | C—H | CF$_3$ | CH$_3$ | CH | N—CH$_3$ | N | bond |
| 1.013 | S | —CH$_2$CH$_3$ | N | CF$_3$ | CH$_3$ | CH | N | N—CH$_3$ | bond |
| 1.014 | SO$_2$ | —CH$_2$CH$_3$ | N | CF$_3$ | CH$_3$ | CH | N | N—CH$_3$ | bond |
| 1.015 | S | —CH$_2$CH$_3$ | N | CF$_3$ | CH$_3$ | CH | N—CH$_3$ | N | bond |
| 1.016 | SO$_2$ | —CH$_2$CH$_3$ | N | CF$_3$ | CH$_3$ | CH | N—CH$_3$ | N | bond |
| 1.017 | S | —CH$_2$CH$_3$ | C—H | CF$_3$ | CH$_3$ | N | CH | CH | CH |
| 1.018 | SO$_2$ | —CH$_2$CH$_3$ | C—H | CF$_3$ | CH$_3$ | N | CH | CH | CH |
| 1.019 | S | —CH$_2$CH$_3$ | N | CF$_3$ | CH$_3$ | N | CH | CH | CH |
| 1.020 | SO$_2$ | —CH$_2$CH$_3$ | N | CF$_3$ | CH$_3$ | N | CH | CH | CH |
| 1.021 | S | —CH$_2$CH$_3$ | C—H | CF$_3$ | CH$_3$ | CH | N | CH | CH |
| 1.022 | SO$_2$ | —CH$_2$CH$_3$ | C—H | CF$_3$ | CH$_3$ | CH | N | CH | CH |
| 1.023 | S | —CH$_2$CH$_3$ | N | CF$_3$ | CH$_3$ | CH | N | CH | CH |
| 1.024 | SO$_2$ | —CH$_2$CH$_3$ | N | CF$_3$ | CH$_3$ | CH | N | CH | CH |
| 1.025 | S | —CH$_2$CH$_3$ | C—H | CF$_3$ | CH$_3$ | N—CH$_3$ | N | CH | Bond |
| 1.026 | SO$_2$ | —CH$_2$CH$_3$ | C—H | CF$_3$ | CH$_3$ | N—CH$_3$ | N | CH | Bond |
| 1.027 | S | —CH$_2$CH$_3$ | N | CF$_3$ | CH$_3$ | N—CH$_3$ | N | CH | Bond |
| 1.028 | SO$_2$ | —CH$_2$CH$_3$ | N | CF$_3$ | CH$_3$ | N—CH$_3$ | N | CH | Bond |
| 1.029 | S | —CH$_2$CH$_3$ | C—H | CF$_3$ | CH$_3$ | N | N—CH$_3$ | CH | Bond |
| 1.030 | SO$_2$ | —CH$_2$CH$_3$ | C—H | CF$_3$ | CH$_3$ | N | N—CH$_3$ | CH | Bond |
| 1.031 | S | —CH$_2$CH$_3$ | N | CF$_3$ | CH$_3$ | N | N—CH$_3$ | CH | Bond |
| 1.032 | SO$_2$ | —CH$_2$CH$_3$ | N | CF$_3$ | CH$_3$ | N | N—CH$_3$ | CH | Bond |
| 1.033 | S | —CH$_2$CH$_3$ | C—H | CF$_3$ | CH$_3$ | N | N—H | CH | Bond |
| 1.034 | SO$_2$ | —CH$_2$CH$_3$ | C—H | CF$_3$ | CH$_3$ | N | N—H | CH | Bond |
| 1.035 | S | —CH$_2$CH$_3$ | N | CF$_3$ | CH$_3$ | N | N—H | CH | Bond |
| 1.036 | SO$_2$ | —CH$_2$CH$_3$ | N | CF$_3$ | CH$_3$ | N | N—H | CH | Bond |
| 1.037 | S | —CH$_2$CH$_3$ | C—H | CF$_3$ | CH$_3$ | CH | N | N—H | bond |
| 1.038 | SO$_2$ | —CH$_2$CH$_3$ | C—H | CF$_3$ | CH$_3$ | CH | N | N—H | bond |
| 1.039 | S | —CH$_2$CH$_3$ | N | CF$_3$ | CH$_3$ | CH | N | N—H | bond |
| 1.040 | SO$_2$ | —CH$_2$CH$_3$ | N | CF$_3$ | CH$_3$ | CH | N | N—H | bond |
| 1.041 | S | —CH$_2$CH$_3$ | C—H | CF$_3$ | CH$_3$ | N | S | N | bond |
| 1.042 | SO$_2$ | —CH$_2$CH$_3$ | C—H | CF$_3$ | CH$_3$ | N | S | N | bond |
| 1.043 | S | —CH$_2$CH$_3$ | N | CF$_3$ | CH$_3$ | N | S | N | bond |
| 1.044 | SO$_2$ | —CH$_2$CH$_3$ | N | CF$_3$ | CH$_3$ | N | S | N | bond |
| 1.045 | S | —CH$_2$CH$_3$ | C—H | CF$_3$ | CH$_3$ | N | NH | N | bond |
| 1.046 | SO$_2$ | —CH$_2$CH$_3$ | C—H | CF$_3$ | CH$_3$ | N | NH | N | bond |
| 1.047 | S | —CH$_2$CH$_3$ | N | CF$_3$ | CH$_3$ | N | NH | N | bond |
| 1.048 | SO$_2$ | —CH$_2$CH$_3$ | N | CF$_3$ | CH$_3$ | N | NH | N | bond |
| 1.049 | S | —CH$_2$CH$_3$ | C—H | CF$_3$ | CH$_3$ | N | N—CH$_3$ | N | bond |
| 1.050 | SO$_2$ | —CH$_2$CH$_3$ | C—H | CF$_3$ | CH$_3$ | N | N—CH$_3$ | N | bond |
| 1.051 | S | —CH$_2$CH$_3$ | N | CF$_3$ | CH$_3$ | N | N—CH$_3$ | N | bond |
| 1.052 | SO$_2$ | —CH$_2$CH$_3$ | N | CF$_3$ | CH$_3$ | N | N—CH$_3$ | N | bond |
| 1.053 | S | —CH$_2$CH$_3$ | C—H | CF$_3$ | CH$_3$ | N | N | N—CH$_3$ | bond |
| 1.054 | SO$_2$ | —CH$_2$CH$_3$ | C—H | CF$_3$ | CH$_3$ | N | N | N—CH$_3$ | bond |
| 1.055 | S | —CH$_2$CH$_3$ | N | CF$_3$ | CH$_3$ | N | N | N—CH$_3$ | bond |
| 1.056 | SO$_2$ | —CH$_2$CH$_3$ | N | CF$_3$ | CH$_3$ | N | N | N—CH$_3$ | bond |
| 1.057 | S | —CH$_2$CH$_3$ | C—H | CF$_3$ | CH$_3$ | N—CH$_3$ | N | N | bond |
| 1.058 | SO$_2$ | —CH$_2$CH$_3$ | C—H | CF$_3$ | CH$_3$ | N—CH$_3$ | N | N | bond |
| 1.059 | S | —CH$_2$CH$_3$ | N | CF$_3$ | CH$_3$ | N—CH$_3$ | N | N | bond |
| 1.060 | SO$_2$ | —CH$_2$CH$_3$ | N | CF$_3$ | CH$_3$ | N—CH$_3$ | N | N | bond |

TABLE 1-continued

| | | | | | $G_3$ is N—$R_6$ | | | | |
|---|---|---|---|---|---|---|---|---|---|
| Comp. No. | X | $R_1$ | A | $R_2$ | $R_6$ | $L_1$ | $L_2$ | $L_3$ | $L_4$ |
| 1.061 | S | —CH$_2$CH$_3$ | C—H | CF$_3$ | CH$_3$ | CH | C—CF3 | CH | CH |
| 1.062 | SO$_2$ | —CH$_2$CH$_3$ | C—H | CF$_3$ | CH$_3$ | CH | C—CF$_3$ | CH | CH |
| 1.063 | S | —CH$_2$CH$_3$ | N | CF$_3$ | CH$_3$ | CH | C—CF$_3$ | CH | CH |
| 1.064 | SO$_2$ | —CH$_2$CH$_3$ | N | CF$_3$ | CH$_3$ | CH | C—CF$_3$ | CH | CH |
| 1.065 | S | —CH$_2$CH$_3$ | C—H | CF$_3$ | CH$_3$ | CH | C—F | CH | CH |
| 1.066 | SO$_2$ | —CH$_2$CH$_3$ | C—H | CF$_3$ | CH$_3$ | CH | C—F | CH | CH |
| 1.067 | S | —CH$_2$CH$_3$ | N | CF$_3$ | CH$_3$ | CH | C—F | CH | CH |
| 1.068 | SO$_2$ | —CH$_2$CH$_3$ | N | CF$_3$ | CH$_3$ | CH | C—F | CH | CH |
| 1.069 | S | —CH$_2$CH$_3$ | C—H | CF$_3$ | CH$_3$ | N | C—H | S | bond |
| 1.070 | SO$_2$ | —CH$_2$CH$_3$ | C—H | CF$_3$ | CH$_3$ | N | C—H | S | bond |
| 1.071 | S | —CH$_2$CH$_3$ | N | CF$_3$ | CH$_3$ | N | C—H | S | bond |
| 1.072 | SO$_2$ | —CH$_2$CH$_3$ | N | CF$_3$ | CH$_3$ | N | C—H | S | bond |
| 1.073 | S | —CH$_2$CH$_3$ | C—H | CF$_3$ | CH$_3$ | N | C—CH$_3$ | S | bond |
| 1.074 | SO$_2$ | —CH$_2$CH$_3$ | C—H | CF$_3$ | CH$_3$ | N | C—CH$_3$ | S | bond |
| 1.075 | S | —CH$_2$CH$_3$ | N | CF$_3$ | CH$_3$ | N | C—CH$_3$ | S | bond |
| 1.076 | SO$_2$ | —CH$_2$CH$_3$ | N | CF$_3$ | CH$_3$ | N | C—CH$_3$ | S | bond |
| 1.077 | S | —CH$_2$CH$_3$ | C—H | CF$_3$ | CH$_3$ | N | C—CF$_3$ | S | bond |
| 1.078 | SO$_2$ | —CH$_2$CH$_3$ | C—H | CF$_3$ | CH$_3$ | N | C—CF$_3$ | S | bond |
| 1.079 | S | —CH$_2$CH$_3$ | N | CF$_3$ | CH$_3$ | N | C—CF$_3$ | S | bond |
| 1.080 | SO$_2$ | —CH$_2$CH$_3$ | N | CF$_3$ | CH$_3$ | N | C—CF$_3$ | S | bond |
| 1.081 | S | —CH$_2$CH$_3$ | C—H | CF$_3$ | CH$_3$ | S | C—H | N | bond |
| 1.082 | SO$_2$ | —CH$_2$CH$_3$ | C—H | CF$_3$ | CH$_3$ | S | C—H | N | bond |
| 1.083 | S | —CH$_2$CH$_3$ | N | CF$_3$ | CH$_3$ | S | C—H | N | bond |
| 1.084 | SO$_2$ | —CH$_2$CH$_3$ | N | CF$_3$ | CH$_3$ | S | C—H | N | bond |
| 1.085 | S | —CH$_2$CH$_3$ | C—H | CF$_3$ | CH$_3$ | S | C—CH$_3$ | N | bond |
| 1.086 | SO$_2$ | —CH$_2$CH$_3$ | C—H | CF$_3$ | CH$_3$ | S | C—CH$_3$ | N | bond |
| 1.087 | S | —CH$_2$CH$_3$ | N | CF$_3$ | CH$_3$ | S | C—CH$_3$ | N | bond |
| 1.088 | SO$_2$ | —CH$_2$CH$_3$ | N | CF$_3$ | CH$_3$ | S | C—CH$_3$ | N | bond |
| 1.089 | S | —CH$_2$CH$_3$ | C—H | CF$_3$ | CH$_3$ | S | C—CF$_3$ | N | bond |
| 1.090 | SO$_2$ | —CH$_2$CH$_3$ | C—H | CF$_3$ | CH$_3$ | S | C—CF$_3$ | N | bond |
| 1.091 | S | —CH$_2$CH$_3$ | N | CF$_3$ | CH$_3$ | S | C—CF$_3$ | N | bond |
| 1.092 | SO$_2$ | —CH$_2$CH$_3$ | N | CF$_3$ | CH$_3$ | S | C—CF$_3$ | N | bond |
| 1.093 | S | —CH$_2$CH$_3$ | C—H | CF$_3$ | CH$_3$ | N—H | C—CF$_3$ | N | bond |
| 1.094 | SO$_2$ | —CH$_2$CH$_3$ | C—H | CF$_3$ | CH$_3$ | N—H | C—CF$_3$ | N | bond |
| 1.095 | S | —CH$_2$CH$_3$ | N | CF$_3$ | CH$_3$ | N—H | C—CF$_3$ | N | bond |
| 1.096 | SO$_2$ | —CH$_2$CH$_3$ | N | CF$_3$ | CH$_3$ | N—H | C—CF$_3$ | N | bond |
| 1.097 | S | —CH$_2$CH$_3$ | C—H | CF$_3$ | CH$_3$ | N—H | C—CH$_3$ | N | bond |
| 1.098 | SO$_2$ | —CH$_2$CH$_3$ | C—H | CF$_3$ | CH$_3$ | N—H | C—CH$_3$ | N | bond |
| 1.099 | S | —CH$_2$CH$_3$ | N | CF$_3$ | CH$_3$ | N—H | C—CH$_3$ | N | bond |
| 1.100 | SO$_2$ | —CH$_2$CH$_3$ | N | CF$_3$ | CH$_3$ | N—H | C—CH$_3$ | N | bond |
| 1.101 | S | —CH$_2$CH$_3$ | C—H | CF$_3$ | CH$_3$ | N—H | CH | N | bond |
| 1.102 | SO$_2$ | —CH$_2$CH$_3$ | C—H | CF$_3$ | CH$_3$ | N—H | CH | N | bond |
| 1.103 | S | —CH$_2$CH$_3$ | N | CF$_3$ | CH$_3$ | N—H | CH | N | bond |
| 1.104 | SO$_2$ | —CH$_2$CH$_3$ | N | CF$_3$ | CH$_3$ | N—H | CH | N | bond |
| 1.105 | S | —CH$_2$CH$_3$ | C—H | CF$_3$ | CH$_3$ | N—CH$_3$ | CH | N | bond |
| 1.106 | SO$_2$ | —CH$_2$CH$_3$ | C—H | CF$_3$ | CH$_3$ | N—CH$_3$ | CH | N | bond |
| 1.107 | S | —CH$_2$CH$_3$ | N | CF$_3$ | CH$_3$ | N—CH$_3$ | CH | N | bond |
| 1.108 | SO$_2$ | —CH$_2$CH$_3$ | N | CF$_3$ | CH$_3$ | N—CH$_3$ | CH | N | bond |
| 1.109 | S | —CH$_2$CH$_3$ | C—H | CF$_3$ | CH$_3$ | N—CH$_3$ | C—CH$_3$ | N | bond |
| 1.110 | SO$_2$ | —CH$_2$CH$_3$ | C—H | CF$_3$ | CH$_3$ | N—CH$_3$ | C—CH$_3$ | N | bond |
| 1.111 | S | —CH$_2$CH$_3$ | N | CF$_3$ | CH$_3$ | N—CH$_3$ | C—CH$_3$ | N | bond |
| 1.112 | SO$_2$ | —CH$_2$CH$_3$ | N | CF$_3$ | CH$_3$ | N—CH$_3$ | C—CH$_3$ | N | bond |
| 1.113 | S | —CH$_2$CH$_3$ | C—H | CF$_3$ | CH$_3$ | N—CH$_3$ | C—CF$_3$ | N | bond |
| 1.114 | SO$_2$ | —CH$_2$CH$_3$ | C—H | CF$_3$ | CH$_3$ | N—CH$_3$ | C—CF$_3$ | N | bond |
| 1.115 | S | —CH$_2$CH$_3$ | N | CF$_3$ | CH$_3$ | N—CH$_3$ | C—CF$_3$ | N | bond |
| 1.116 | SO$_2$ | —CH$_2$CH$_3$ | N | CF$_3$ | CH$_3$ | N—CH$_3$ | C—CF$_3$ | N | bond |
| 1.117 | S | —CH$_2$CH$_3$ | C—H | CF$_3$ | CH$_3$ | N | CH | N—CH$_3$ | bond |
| 1.118 | SO$_2$ | —CH$_2$CH$_3$ | C—H | CF$_3$ | CH$_3$ | N | CH | N—CH$_3$ | bond |
| 1.119 | S | —CH$_2$CH$_3$ | N | CF$_3$ | CH$_3$ | N | CH | N—CH$_3$ | bond |
| 1.120 | SO$_2$ | —CH$_2$CH$_3$ | N | CF$_3$ | CH$_3$ | N | CH | N—CH$_3$ | bond |
| 1.121 | S | —CH$_2$CH$_3$ | C—H | CF$_3$ | CH$_3$ | N | C—CH$_3$ | N—CH$_3$ | bond |
| 1.122 | SO$_2$ | —CH$_2$CH$_3$ | C—H | CF$_3$ | CH$_3$ | N | C—CH$_3$ | N—CH$_3$ | bond |
| 1.123 | S | —CH$_2$CH$_3$ | N | CF$_3$ | CH$_3$ | N | C—CH$_3$ | N—CH$_3$ | bond |
| 1.124 | SO$_2$ | —CH$_2$CH$_3$ | N | CF$_3$ | CH$_3$ | N | C—CH$_3$ | N—CH$_3$ | bond |
| 1.125 | S | —CH$_2$CH$_3$ | C—H | CF$_3$ | CH$_3$ | N | C—CF$_3$ | N—CH$_3$ | bond |
| 1.126 | SO$_2$ | —CH$_2$CH$_3$ | C—H | CF$_3$ | CH$_3$ | N | C—CF$_3$ | N—CH$_3$ | bond |
| 1.127 | S | —CH$_2$CH$_3$ | N | CF$_3$ | CH$_3$ | N | C—CF$_3$ | N—CH$_3$ | bond |
| 1.128 | SO$_2$ | —CH$_2$CH$_3$ | N | CF$_3$ | CH$_3$ | N | C—CF$_3$ | N—CH$_3$ | bond | and the N-oxides or tautomers of the compounds of Table 1.

Table 2: This table discloses the 128 compounds of the formula I-1b:

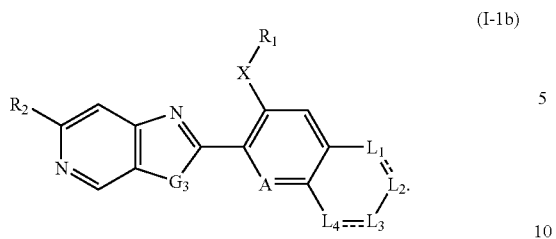

(I-1b)

TABLE 2

G₃ is N—R₆

| Comp. No. | X | $R_1$ | A | $R_2$ | $R_6$ | $L_1$ | $L_2$ | $L_3$ | $L_4$ |
|---|---|---|---|---|---|---|---|---|---|
| 2.001 | S | —CH₂CH₃ | C—H | CF₃ | CH₃ | CH | CH | CH | CH |
| 2.002 | SO | —CH₂CH₃ | C—H | CF₃ | CH₃ | CH | CH | CH | CH |
| 2.003 | SO₂ | —CH₂CH₃ | C—H | CF₃ | CH₃ | CH | CH | CH | CH |
| 2.004 | S | —CH₂CH₃ | N | CF₃ | CH₃ | CH | CH | CH | CH |
| 2.005 | SO | —CH₂CH₃ | N | CF₃ | CH₃ | CH | CH | CH | CH |
| 2.006 | SO₂ | —CH₂CH₃ | N | CF₃ | CH₃ | CH | CH | CH | CH |
| 2.007 | S | —CH₂CH₃ | C—H | CF₃ | CH₃ | O | CH₂ | O | bond |
| 2.008 | SO₂ | —CH₂CH₃ | C—H | CF₃ | CH₃ | O | CH₂ | O | bond |
| 2.009 | S | —CH₂CH₃ | C—H | CF₃ | CH₃ | CH | N | N—CH₃ | bond |
| 2.010 | SO₂ | —CH₂CH₃ | C—H | CF₃ | CH₃ | CH | N | N—CH₃ | bond |
| 2.011 | S | —CH₂CH₃ | C—H | CF₃ | CH₃ | CH | N—CH₃ | N | bond |
| 2.012 | SO₂ | —CH₂CH₃ | C—H | CF₃ | CH₃ | CH | N—CH₃ | N | bond |
| 2.013 | S | —CH₂CH₃ | N | CF₃ | CH₃ | CH | N | N—CH₃ | bond |
| 2.014 | SO₂ | —CH₂CH₃ | N | CF₃ | CH₃ | CH | N | N—CH₃ | bond |
| 2.015 | S | —CH₂CH₃ | N | CF₃ | CH₃ | CH | N—CH₃ | N | bond |
| 2.016 | SO₂ | —CH₂CH₃ | N | CF₃ | CH₃ | CH | N—CH₃ | N | bond |
| 2.017 | S | —CH₂CH₃ | C—H | CF₃ | CH₃ | N | CH | CH | CH |
| 2.018 | SO₂ | —CH₂CH₃ | C—H | CF₃ | CH₃ | N | CH | CH | CH |
| 2.019 | S | —CH₂CH₃ | N | CF₃ | CH₃ | N | CH | CH | CH |
| 2.020 | SO₂ | —CH₂CH₃ | N | CF₃ | CH₃ | N | CH | CH | CH |
| 2.021 | S | —CH₂CH₃ | C—H | CF₃ | CH₃ | CH | N | CH | CH |
| 2.022 | SO₂ | —CH₂CH₃ | C—H | CF₃ | CH₃ | CH | N | CH | CH |
| 2.023 | S | —CH₂CH₃ | N | CF₃ | CH₃ | CH | N | CH | CH |
| 2.024 | SO₂ | —CH₂CH₃ | N | CF₃ | CH₃ | CH | N | CH | CH |
| 2.025 | S | —CH₂CH₃ | C—H | CF₃ | CH₃ | N—CH₃ | N | CH | bond |
| 2.026 | SO₂ | —CH₂CH₃ | C—H | CF₃ | CH₃ | N—CH₃ | N | CH | bond |
| 2.027 | S | —CH₂CH₃ | N | CF₃ | CH₃ | N—CH₃ | N | CH | bond |
| 2.028 | SO₂ | —CH₂CH₃ | N | CF₃ | CH₃ | N—CH₃ | N | CH | bond |
| 2.029 | S | —CH₂CH₃ | C—H | CF₃ | CH₃ | N | N—CH₃ | CH | bond |
| 2.030 | SO₂ | —CH₂CH₃ | C—H | CF₃ | CH₃ | N | N—CH₃ | CH | bond |
| 2.031 | S | —CH₂CH₃ | N | CF₃ | CH₃ | N | N—CH₃ | CH | bond |
| 2.032 | SO₂ | —CH₂CH₃ | N | CF₃ | CH₃ | N | N—CH₃ | CH | bond |
| 2.033 | S | —CH₂CH₃ | C—H | CF₃ | CH₃ | N | N—H | CH | bond |
| 2.034 | SO₂ | —CH₂CH₃ | C—H | CF₃ | CH₃ | N | N—H | CH | bond |
| 2.035 | S | —CH₂CH₃ | N | CF₃ | CH₃ | N | N—H | CH | bond |
| 2.036 | SO₂ | —CH₂CH₃ | N | CF₃ | CH₃ | N | N—H | CH | bond |
| 2.037 | S | —CH₂CH₃ | C—H | CF₃ | CH₃ | CH | N | N—H | bond |
| 2.038 | SO₂ | —CH₂CH₃ | C—H | CF₃ | CH₃ | CH | N | N—H | bond |
| 2.039 | S | —CH₂CH₃ | N | CF₃ | CH₃ | CH | N | N—H | bond |
| 2.040 | SO₂ | —CH₂CH₃ | N | CF₃ | CH₃ | CH | N | N—H | bond |
| 2.041 | S | —CH₂CH₃ | C—H | CF₃ | CH₃ | N | S | N | bond |
| 2.042 | SO₂ | —CH₂CH₃ | C—H | CF₃ | CH₃ | N | S | N | bond |
| 2.043 | S | —CH₂CH₃ | N | CF₃ | CH₃ | N | S | N | bond |
| 2.044 | SO₂ | —CH₂CH₃ | N | CF₃ | CH₃ | N | S | N | bond |
| 2.045 | S | —CH₂CH₃ | C—H | CF₃ | CH₃ | N | NH | N | bond |
| 2.046 | SO₂ | —CH₂CH₃ | C—H | CF₃ | CH₃ | N | NH | N | bond |
| 2.047 | S | —CH₂CH₃ | N | CF₃ | CH₃ | N | NH | N | bond |
| 2.048 | SO₂ | —CH₂CH₃ | N | CF₃ | CH₃ | N | NH | N | bond |
| 2.049 | S | —CH₂CH₃ | C—H | CF₃ | CH₃ | N | N—CH₃ | N | bond |
| 2.050 | SO₂ | —CH₂CH₃ | C—H | CF₃ | CH₃ | N | N—CH₃ | N | bond |
| 2.051 | S | —CH₂CH₃ | N | CF₃ | CH₃ | N | N—CH₃ | N | bond |
| 2.052 | SO₂ | —CH₂CH₃ | N | CF₃ | CH₃ | N | N—CH₃ | N | bond |
| 2.053 | S | —CH₂CH₃ | C—H | CF₃ | CH₃ | N | N | N—CH₃ | bond |
| 2.054 | SO₂ | —CH₂CH₃ | C—H | CF₃ | CH₃ | N | N | N—CH₃ | bond |
| 2.055 | S | —CH₂CH₃ | N | CF₃ | CH₃ | N | N | N—CH₃ | bond |
| 2.056 | SO₂ | —CH₂CH₃ | N | CF₃ | CH₃ | N | N | N—CH₃ | bond |
| 2.057 | S | —CH₂CH₃ | C—H | CF₃ | CH₃ | N—CH₃ | N | N | bond |
| 2.058 | SO₂ | —CH₂CH₃ | C—H | CF₃ | CH₃ | N—CH₃ | N | N | bond |
| 2.059 | S | —CH₂CH₃ | N | CF₃ | CH₃ | N—CH₃ | N | N | bond |
| 2.060 | SO₂ | —CH₂CH₃ | N | CF₃ | CH₃ | N—CH₃ | N | N | bond |

TABLE 2-continued

G$_3$ is N—R$_6$

| Comp. No. | X | R$_1$ | A | R$_2$ | R$_6$ | L$_1$ | L$_2$ | L$_3$ | L$_4$ |
|---|---|---|---|---|---|---|---|---|---|
| 2.061 | S | —CH$_2$CH$_3$ | C—H | CF$_3$ | CH$_3$ | CH | C—CF$_3$ | CH | CH |
| 2.062 | SO$_2$ | —CH$_2$CH$_3$ | C—H | CF$_3$ | CH$_3$ | CH | C—CF$_3$ | CH | CH |
| 2.063 | S | —CH$_2$CH$_3$ | N | CF$_3$ | CH$_3$ | CH | C—CF$_3$ | CH | CH |
| 2.064 | SO$_2$ | —CH$_2$CH$_3$ | N | CF$_3$ | CH$_3$ | CH | C—CF$_3$ | CH | CH |
| 2.065 | S | —CH$_2$CH$_3$ | C—H | CF$_3$ | CH$_3$ | CH | C—F | CH | CH |
| 2.066 | SO$_2$ | —CH$_2$CH$_3$ | C—H | CF$_3$ | CH$_3$ | CH | C—F | CH | CH |
| 2.067 | S | —CH$_2$CH$_3$ | N | CF$_3$ | CH$_3$ | CH | C—F | CH | CH |
| 2.068 | SO$_2$ | —CH$_2$CH$_3$ | N | CF$_3$ | CH$_3$ | CH | C—F | CH | CH |
| 2.069 | S | —CH$_2$CH$_3$ | C—H | CF$_3$ | CH$_3$ | N | C—H | S | bond |
| 2.070 | SO$_2$ | —CH$_2$CH$_3$ | C—H | CF$_3$ | CH$_3$ | N | C—H | S | bond |
| 2.071 | S | —CH$_2$CH$_3$ | N | CF$_3$ | CH$_3$ | N | C—H | S | bond |
| 2.072 | SO$_2$ | —CH$_2$CH$_3$ | N | CF$_3$ | CH$_3$ | N | C—H | S | bond |
| 2.073 | S | —CH$_2$CH$_3$ | C—H | CF$_3$ | CH$_3$ | N | C—CH$_3$ | S | bond |
| 2.074 | SO$_2$ | —CH$_2$CH$_3$ | C—H | CF$_3$ | CH$_3$ | N | C—CH$_3$ | S | bond |
| 2.075 | S | —CH$_2$CH$_3$ | N | CF$_3$ | CH$_3$ | N | C—CH$_3$ | S | bond |
| 2.076 | SO$_2$ | —CH$_2$CH$_3$ | N | CF$_3$ | CH$_3$ | N | C—CH$_3$ | S | bond |
| 2.077 | S | —CH$_2$CH$_3$ | C—H | CF$_3$ | CH$_3$ | N | C—CF$_3$ | S | bond |
| 2.078 | SO$_2$ | —CH$_2$CH$_3$ | C—H | CF$_3$ | CH$_3$ | N | C—CF$_3$ | S | bond |
| 2.079 | S | —CH$_2$CH$_3$ | N | CF$_3$ | CH$_3$ | N | C—CF$_3$ | S | bond |
| 2.080 | SO$_2$ | —CH$_2$CH$_3$ | N | CF$_3$ | CH$_3$ | N | C—CF$_3$ | S | bond |
| 2.081 | S | —CH$_2$CH$_3$ | C—H | CF$_3$ | CH$_3$ | S | C—H | N | bond |
| 2.082 | SO$_2$ | —CH$_2$CH$_3$ | C—H | CF$_3$ | CH$_3$ | S | C—H | N | bond |
| 2.083 | S | —CH$_2$CH$_3$ | N | CF$_3$ | CH$_3$ | S | C—H | N | bond |
| 2.084 | SO$_2$ | —CH$_2$CH$_3$ | N | CF$_3$ | CH$_3$ | S | C—H | N | bond |
| 2.085 | S | —CH$_2$CH$_3$ | C—H | CF$_3$ | CH$_3$ | S | C—CH$_3$ | N | bond |
| 2.086 | SO$_2$ | —CH$_2$CH$_3$ | C—H | CF$_3$ | CH$_3$ | S | C—CH$_3$ | N | bond |
| 2.087 | S | —CH$_2$CH$_3$ | N | CF$_3$ | CH$_3$ | S | C—CH$_3$ | N | bond |
| 2.088 | SO$_2$ | —CH$_2$CH$_3$ | N | CF$_3$ | CH$_3$ | S | C—CH$_3$ | N | bond |
| 2.089 | S | —CH$_2$CH$_3$ | C—H | CF$_3$ | CH$_3$ | S | C—CF$_3$ | N | bond |
| 2.090 | SO$_2$ | —CH$_2$CH$_3$ | C—H | CF$_3$ | CH$_3$ | S | C—CF$_3$ | N | bond |
| 2.091 | S | —CH$_2$CH$_3$ | N | CF$_3$ | CH$_3$ | S | C—CF$_3$ | N | bond |
| 2.092 | SO$_2$ | —CH$_2$CH$_3$ | N | CF$_3$ | CH$_3$ | S | C—CF$_3$ | N | bond |
| 2.093 | S | —CH$_2$CH$_3$ | C—H | CF$_3$ | CH$_3$ | N—H | C—CF$_3$ | N | bond |
| 2.094 | SO$_2$ | —CH$_2$CH$_3$ | C—H | CF$_3$ | CH$_3$ | N—H | C—CF$_3$ | N | bond |
| 2.095 | S | —CH$_2$CH$_3$ | N | CF$_3$ | CH$_3$ | N—H | C—CF$_3$ | N | bond |
| 2.096 | SO$_2$ | —CH$_2$CH$_3$ | N | CF$_3$ | CH$_3$ | N—H | C—CF$_3$ | N | bond |
| 2.097 | S | —CH$_2$CH$_3$ | C—H | CF$_3$ | CH$_3$ | N—H | C—CH$_3$ | N | bond |
| 2.098 | SO$_2$ | —CH$_2$CH$_3$ | C—H | CF$_3$ | CH$_3$ | N—H | C—CH$_3$ | N | bond |
| 2.099 | S | —CH$_2$CH$_3$ | N | CF$_3$ | CH$_3$ | N—H | C—CH$_3$ | N | bond |
| 2.100 | SO$_2$ | —CH$_2$CH$_3$ | N | CF$_3$ | CH$_3$ | N—H | C—CH$_3$ | N | bond |
| 2.101 | S | —CH$_2$CH$_3$ | C—H | CF$_3$ | CH$_3$ | N—H | CH | N | bond |
| 2.102 | SO$_2$ | —CH$_2$CH$_3$ | C—H | CF$_3$ | CH$_3$ | N—H | CH | N | bond |
| 2.103 | S | —CH$_2$CH$_3$ | N | CF$_3$ | CH$_3$ | N—H | CH | N | bond |
| 2.104 | SO$_2$ | —CH$_2$CH$_3$ | N | CF$_3$ | CH$_3$ | N—H | CH | N | bond |
| 2.105 | S | —CH$_2$CH$_3$ | C—H | CF$_3$ | CH$_3$ | N—CH$_3$ | CH | N | bond |
| 2.106 | SO$_2$ | —CH$_2$CH$_3$ | C—H | CF$_3$ | CH$_3$ | N—CH$_3$ | CH | N | bond |
| 2.107 | S | —CH$_2$CH$_3$ | N | CF$_3$ | CH$_3$ | N—CH$_3$ | CH | N | bond |
| 2.108 | SO$_2$ | —CH$_2$CH$_3$ | N | CF$_3$ | CH$_3$ | N—CH$_3$ | CH | N | bond |
| 2.109 | S | —CH$_2$CH$_3$ | C—H | CF$_3$ | CH$_3$ | N—CH$_3$ | C—CH$_3$ | N | bond |
| 2.110 | SO$_2$ | —CH$_2$CH$_3$ | C—H | CF$_3$ | CH$_3$ | N—CH$_3$ | C—CH$_3$ | N | bond |
| 2.111 | S | —CH$_2$CH$_3$ | N | CF$_3$ | CH$_3$ | N—CH$_3$ | C—CH$_3$ | N | bond |
| 2.112 | SO$_2$ | —CH$_2$CH$_3$ | N | CF$_3$ | CH$_3$ | N—CH$_3$ | C—CH$_3$ | N | bond |
| 2.113 | S | —CH$_2$CH$_3$ | C—H | CF$_3$ | CH$_3$ | N—CH$_3$ | C—CF$_3$ | N | bond |
| 2.114 | SO$_2$ | —CH$_2$CH$_3$ | C—H | CF$_3$ | CH$_3$ | N—CH$_3$ | C—CF$_3$ | N | bond |
| 2.115 | S | —CH$_2$CH$_3$ | N | CF$_3$ | CH$_3$ | N—CH$_3$ | C—CF$_3$ | N | bond |
| 2.116 | SO$_2$ | —CH$_2$CH$_3$ | N | CF$_3$ | CH$_3$ | N—CH$_3$ | C—CF$_3$ | N | bond |
| 2.117 | S | —CH$_2$CH$_3$ | C—H | CF$_3$ | CH$_3$ | N | CH | N—CH$_3$ | bond |
| 2.118 | SO$_2$ | —CH$_2$CH$_3$ | C—H | CF$_3$ | CH$_3$ | N | CH | N—CH$_3$ | bond |
| 2.119 | S | —CH$_2$CH$_3$ | N | CF$_3$ | CH$_3$ | N | CH | N—CH$_3$ | bond |
| 2.120 | SO$_2$ | —CH$_2$CH$_3$ | N | CF$_3$ | CH$_3$ | N | CH | N—CH$_3$ | bond |
| 2.121 | S | —CH$_2$CH$_3$ | C—H | CF$_3$ | CH$_3$ | N | C—CH$_3$ | N—CH$_3$ | bond |
| 2.122 | SO$_2$ | —CH$_2$CH$_3$ | C—H | CF$_3$ | CH$_3$ | N | C—CH$_3$ | N—CH$_3$ | bond |
| 2.123 | S | —CH$_2$CH$_3$ | N | CF$_3$ | CH$_3$ | N | C—CH$_3$ | N—CH$_3$ | bond |
| 2.124 | SO$_2$ | —CH$_2$CH$_3$ | N | CF$_3$ | CH$_3$ | N | C—CH$_3$ | N—CH$_3$ | bond |
| 2.125 | S | —CH$_2$CH$_3$ | C—H | CF$_3$ | CH$_3$ | N | C—CF$_3$ | N—CH$_3$ | bond |
| 2.126 | SO$_2$ | —CH$_2$CH$_3$ | C—H | CF$_3$ | CH$_3$ | N | C—CF$_3$ | N—CH$_3$ | bond |
| 2.127 | S | —CH$_2$CH$_3$ | N | CF$_3$ | CH$_3$ | N | C—CF$_3$ | N—CH$_3$ | bond |
| 2.128 | SO$_2$ | —CH$_2$CH$_3$ | N | CF$_3$ | CH$_3$ | N | C—CF$_3$ | N—CH$_3$ | bond | and the N-oxides and tautomers of the compounds of Table 2.

Table 3: This table discloses the 128 compounds of the formula I-1c:

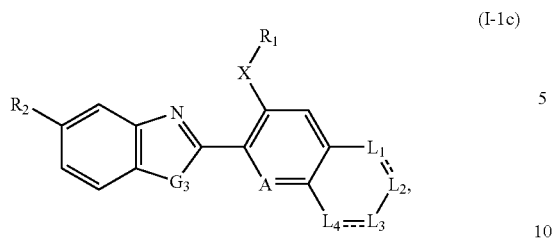

(I-1c)

TABLE 3

G₃ is N—R₆

| Comp. No. | X | $R_1$ | A | $R_2$ | $R_6$ | $L_1$ | $L_2$ | $L_3$ | $L_4$ |
|---|---|---|---|---|---|---|---|---|---|
| 3.001 | S | —CH₂CH₃ | C—H | CF₃ | CH₃ | CH | CH | CH | CH |
| 3.002 | SO | —CH₂CH₃ | C—H | CF₃ | CH₃ | CH | CH | CH | CH |
| 3.003 | SO₂ | —CH₂CH₃ | C—H | CF₃ | CH₃ | CH | CH | CH | CH |
| 3.004 | S | —CH₂CH₃ | N | CF₃ | CH₃ | CH | CH | CH | CH |
| 3.005 | SO | —CH₂CH₃ | N | CF₃ | CH₃ | CH | CH | CH | CH |
| 3.006 | SO₂ | —CH₂CH₃ | N | CF₃ | CH₃ | CH | CH | CH | CH |
| 3.007 | S | —CH₂CH₃ | C—H | CF₃ | CH₃ | O | CH₂ | O | bond |
| 3.008 | SO₂ | —CH₂CH₃ | C—H | CF₃ | CH₃ | O | CH₂ | O | bond |
| 3.009 | S | —CH₂CH₃ | C—H | CF₃ | CH₃ | CH | N | N—CH₃ | bond |
| 3.010 | SO₂ | —CH₂CH₃ | C—H | CF₃ | CH₃ | CH | N | N—CH₃ | bond |
| 3.011 | S | —CH₂CH₃ | C—H | CF₃ | CH₃ | CH | N—CH₃ | N | bond |
| 3.012 | SO₂ | —CH₂CH₃ | C—H | CF₃ | CH₃ | CH | N—CH₃ | N | bond |
| 3.013 | S | —CH₂CH₃ | N | CF₃ | CH₃ | CH | N | N—CH₃ | bond |
| 3.014 | SO₂ | —CH₂CH₃ | N | CF₃ | CH₃ | CH | N | N—CH₃ | bond |
| 3.015 | S | —CH₂CH₃ | N | CF₃ | CH₃ | CH | N—CH₃ | N | bond |
| 3.016 | SO₂ | —CH₂CH₃ | N | CF₃ | CH₃ | CH | N—CH₃ | N | bond |
| 3.017 | S | —CH₂CH₃ | C—H | CF₃ | CH₃ | N | CH | CH | CH |
| 3.018 | SO₂ | —CH₂CH₃ | C—H | CF₃ | CH₃ | N | CH | CH | CH |
| 3.019 | S | —CH₂CH₃ | N | CF₃ | CH₃ | N | CH | CH | CH |
| 3.020 | SO₂ | —CH₂CH₃ | N | CF₃ | CH₃ | N | CH | CH | CH |
| 3.021 | S | —CH₂CH₃ | C—H | CF₃ | CH₃ | CH | N | CH | CH |
| 3.022 | SO₂ | —CH₂CH₃ | C—H | CF₃ | CH₃ | CH | N | CH | CH |
| 3.023 | S | —CH₂CH₃ | N | CF₃ | CH₃ | CH | N | CH | CH |
| 3.024 | SO₂ | —CH₂CH₃ | N | CF₃ | CH₃ | CH | N | CH | CH |
| 3.025 | S | —CH₂CH₃ | C—H | CF₃ | CH₃ | N—CH₃ | N | CH | bond |
| 3.026 | SO₂ | —CH₂CH₃ | C—H | CF₃ | CH₃ | N—CH₃ | N | CH | bond |
| 3.027 | S | —CH₂CH₃ | N | CF₃ | CH₃ | N—CH₃ | N | CH | bond |
| 3.028 | SO₂ | —CH₂CH₃ | N | CF₃ | CH₃ | N—CH₃ | N | CH | bond |
| 3.029 | S | —CH₂CH₃ | C—H | CF₃ | CH₃ | N | N—CH₃ | CH | bond |
| 3.030 | SO₂ | —CH₂CH₃ | C—H | CF₃ | CH₃ | N | N—CH₃ | CH | bond |
| 3.031 | S | —CH₂CH₃ | N | CF₃ | CH₃ | N | N—CH₃ | CH | bond |
| 3.032 | SO₂ | —CH₂CH₃ | N | CF₃ | CH₃ | N | N—CH₃ | CH | bond |
| 3.033 | S | —CH₂CH₃ | C—H | CF₃ | CH₃ | N | N—H | CH | bond |
| 3.034 | SO₂ | —CH₂CH₃ | C—H | CF₃ | CH₃ | N | N—H | CH | bond |
| 3.035 | S | —CH₂CH₃ | N | CF₃ | CH₃ | N | N—H | CH | bond |
| 3.036 | SO₂ | —CH₂CH₃ | N | CF₃ | CH₃ | N | N—H | CH | bond |
| 3.037 | S | —CH₂CH₃ | C—H | CF₃ | CH₃ | CH | N | N—H | bond |
| 3.038 | SO₂ | —CH₂CH₃ | C—H | CF₃ | CH₃ | CH | N | N—H | bond |
| 3.039 | S | —CH₂CH₃ | N | CF₃ | CH₃ | CH | N | N—H | bond |
| 3.040 | SO₂ | —CH₂CH₃ | N | CF₃ | CH₃ | CH | N | N—H | bond |
| 3.041 | S | —CH₂CH₃ | C—H | CF₃ | CH₃ | N | S | N | bond |
| 3.042 | SO₂ | —CH₂CH₃ | C—H | CF₃ | CH₃ | N | S | N | bond |
| 3.043 | S | —CH₂CH₃ | N | CF₃ | CH₃ | N | S | N | bond |
| 3.044 | SO₂ | —CH₂CH₃ | N | CF₃ | CH₃ | N | S | N | bond |
| 3.045 | S | —CH₂CH₃ | C—H | CF₃ | CH₃ | N | NH | N | bond |
| 3.046 | SO₂ | —CH₂CH₃ | C—H | CF₃ | CH₃ | N | NH | N | bond |
| 3.047 | S | —CH₂CH₃ | N | CF₃ | CH₃ | N | NH | N | bond |
| 3.048 | SO₂ | —CH₂CH₃ | N | CF₃ | CH₃ | N | NH | N | bond |
| 3.049 | S | —CH₂CH₃ | C—H | CF₃ | CH₃ | N | N—CH₃ | N | bond |
| 3.050 | SO₂ | —CH₂CH₃ | C—H | CF₃ | CH₃ | N | N—CH₃ | N | bond |
| 3.051 | S | —CH₂CH₃ | N | CF₃ | CH₃ | N | N—CH₃ | N | bond |
| 3.052 | SO₂ | —CH₂CH₃ | N | CF₃ | CH₃ | N | N—CH₃ | N | bond |
| 3.053 | S | —CH₂CH₃ | C—H | CF₃ | CH₃ | N | N | N—CH₃ | bond |
| 3.054 | SO₂ | —CH₂CH₃ | C—H | CF₃ | CH₃ | N | N | N—CH₃ | bond |
| 3.055 | S | —CH₂CH₃ | N | CF₃ | CH₃ | N | N | N—CH₃ | bond |
| 3.056 | SO₂ | —CH₂CH₃ | N | CF₃ | CH₃ | N | N | N—CH₃ | bond |
| 3.057 | S | —CH₂CH₃ | C—H | CF₃ | CH₃ | N—CH₃ | N | N | bond |
| 3.058 | SO₂ | —CH₂CH₃ | C—H | CF₃ | CH₃ | N—CH₃ | N | N | bond |
| 3.059 | S | —CH₂CH₃ | N | CF₃ | CH₃ | N—CH₃ | N | N | bond |
| 3.060 | SO₂ | —CH₂CH₃ | N | CF₃ | CH₃ | N—CH₃ | N | N | bond |

TABLE 3-continued

| | | | | | G$_3$ is N—R$_6$ | | | |
|---|---|---|---|---|---|---|---|---|
| Comp. No. | X | R$_1$ | A | R$_2$ | R$_6$ | L$_1$ | L$_2$ | L$_3$ | L$_4$ |
| 3.061 | S | —CH$_2$CH$_3$ | C—H | CF$_3$ | CH$_3$ | CH | C—CF$_3$ | CH | CH |
| 3.062 | SO$_2$ | —CH$_2$CH$_3$ | C—H | CF$_3$ | CH$_3$ | CH | C—CF$_3$ | CH | CH |
| 3.063 | S | —CH$_2$CH$_3$ | N | CF$_3$ | CH$_3$ | CH | C—CF$_3$ | CH | CH |
| 3.064 | SO$_2$ | —CH$_2$CH$_3$ | N | CF$_3$ | CH$_3$ | CH | C—CF$_3$ | CH | CH |
| 3.065 | S | —CH$_2$CH$_3$ | C—H | CF$_3$ | CH$_3$ | CH | C—F | CH | CH |
| 3.066 | SO$_2$ | —CH$_2$CH$_3$ | C—H | CF$_3$ | CH$_3$ | CH | C—F | CH | CH |
| 3.067 | S | —CH$_2$CH$_3$ | N | CF$_3$ | CH$_3$ | CH | C—F | CH | CH |
| 3.068 | SO$_2$ | —CH$_2$CH$_3$ | N | CF$_3$ | CH$_3$ | CH | C—F | CH | CH |
| 3.069 | S | —CH$_2$CH$_3$ | C—H | CF$_3$ | CH$_3$ | N | C—H | S | bond |
| 3.070 | SO$_2$ | —CH$_2$CH$_3$ | C—H | CF$_3$ | CH$_3$ | N | C—H | S | bond |
| 3.071 | S | —CH$_2$CH$_3$ | N | CF$_3$ | CH$_3$ | N | C—H | S | bond |
| 3.072 | SO$_2$ | —CH$_2$CH$_3$ | N | CF$_3$ | CH$_3$ | N | C—H | S | bond |
| 3.073 | S | —CH$_2$CH$_3$ | C—H | CF$_3$ | CH$_3$ | N | C—CH$_3$ | S | bond |
| 3.074 | SO$_2$ | —CH$_2$CH$_3$ | C—H | CF$_3$ | CH$_3$ | N | C—CH$_3$ | S | bond |
| 3.075 | S | —CH$_2$CH$_3$ | N | CF$_3$ | CH$_3$ | N | C—CH$_3$ | S | bond |
| 3.076 | SO$_2$ | —CH$_2$CH$_3$ | N | CF$_3$ | CH$_3$ | N | C—CH$_3$ | S | bond |
| 3.077 | S | —CH$_2$CH$_3$ | C—H | CF$_3$ | CH$_3$ | N | C—CF$_3$ | S | bond |
| 3.078 | SO$_2$ | —CH$_2$CH$_3$ | C—H | CF$_3$ | CH$_3$ | N | C—CF$_3$ | S | bond |
| 3.079 | S | —CH$_2$CH$_3$ | N | CF$_3$ | CH$_3$ | N | C—CF$_3$ | S | bond |
| 3.080 | SO$_2$ | —CH$_2$CH$_3$ | N | CF$_3$ | CH$_3$ | N | C—CF$_3$ | S | bond |
| 3.081 | S | —CH$_2$CH$_3$ | C—H | CF$_3$ | CH$_3$ | S | C—H | N | bond |
| 3.082 | SO$_2$ | —CH$_2$CH$_3$ | C—H | CF$_3$ | CH$_3$ | S | C—H | N | bond |
| 3.083 | S | —CH$_2$CH$_3$ | N | CF$_3$ | CH$_3$ | S | C—H | N | bond |
| 3.084 | SO$_2$ | —CH$_2$CH$_3$ | N | CF$_3$ | CH$_3$ | S | C—H | N | bond |
| 3.085 | S | —CH$_2$CH$_3$ | C—H | CF$_3$ | CH$_3$ | S | C—CH$_3$ | N | bond |
| 3.086 | SO$_2$ | —CH$_2$CH$_3$ | C—H | CF$_3$ | CH$_3$ | S | C—CH$_3$ | N | bond |
| 3.087 | S | —CH$_2$CH$_3$ | N | CF$_3$ | CH$_3$ | S | C—CH$_3$ | N | bond |
| 3.088 | SO$_2$ | —CH$_2$CH$_3$ | N | CF$_3$ | CH$_3$ | S | C—CH$_3$ | N | bond |
| 3.089 | S | —CH$_2$CH$_3$ | C—H | CF$_3$ | CH$_3$ | S | C—CF$_3$ | N | bond |
| 3.090 | SO$_2$ | —CH$_2$CH$_3$ | C—H | CF$_3$ | CH$_3$ | S | C—CF$_3$ | N | bond |
| 3.091 | S | —CH$_2$CH$_3$ | N | CF$_3$ | CH$_3$ | S | C—CF$_3$ | N | bond |
| 3.092 | SO$_2$ | —CH$_2$CH$_3$ | N | CF$_3$ | CH$_3$ | S | C—CF$_3$ | N | bond |
| 3.093 | S | —CH$_2$CH$_3$ | C—H | CF$_3$ | CH$_3$ | N—H | C—CF$_3$ | N | bond |
| 3.094 | SO$_2$ | —CH$_2$CH$_3$ | C—H | CF$_3$ | CH$_3$ | N—H | C—CF$_3$ | N | bond |
| 3.095 | S | —CH$_2$CH$_3$ | N | CF$_3$ | CH$_3$ | N—H | C—CF$_3$ | N | bond |
| 3.096 | SO$_2$ | —CH$_2$CH$_3$ | N | CF$_3$ | CH$_3$ | N—H | C—CF$_3$ | N | bond |
| 3.097 | S | —CH$_2$CH$_3$ | C—H | CF$_3$ | CH$_3$ | N—H | C—CH$_3$ | N | bond |
| 3.098 | SO$_2$ | —CH$_2$CH$_3$ | C—H | CF$_3$ | CH$_3$ | N—H | C—CH$_3$ | N | bond |
| 3.099 | S | —CH$_2$CH$_3$ | N | CF$_3$ | CH$_3$ | N—H | C—CH$_3$ | N | bond |
| 3.100 | SO$_2$ | —CH$_2$CH$_3$ | N | CF$_3$ | CH$_3$ | N—H | C—CH$_3$ | N | bond |
| 3.101 | S | —CH$_2$CH$_3$ | C—H | CF$_3$ | CH$_3$ | N—H | CH | N | bond |
| 3.102 | SO$_2$ | —CH$_2$CH$_3$ | C—H | CF$_3$ | CH$_3$ | N—H | CH | N | bond |
| 3.103 | S | —CH$_2$CH$_3$ | N | CF$_3$ | CH$_3$ | N—H | CH | N | bond |
| 3.104 | SO$_2$ | —CH$_2$CH$_3$ | N | CF$_3$ | CH$_3$ | N—H | CH | N | bond |
| 3.105 | S | —CH$_2$CH$_3$ | C—H | CF$_3$ | CH$_3$ | N—CH$_3$ | CH | N | bond |
| 3.106 | SO$_2$ | —CH$_2$CH$_3$ | C—H | CF$_3$ | CH$_3$ | N—CH$_3$ | CH | N | bond |
| 3.107 | S | —CH$_2$CH$_3$ | N | CF$_3$ | CH$_3$ | N—CH$_3$ | CH | N | bond |
| 3.108 | SO$_2$ | —CH$_2$CH$_3$ | N | CF$_3$ | CH$_3$ | N—CH$_3$ | CH | N | bond |
| 3.109 | S | —CH$_2$CH$_3$ | C—H | CF$_3$ | CH$_3$ | N—CH$_3$ | C—CH$_3$ | N | bond |
| 3.110 | SO$_2$ | —CH$_2$CH$_3$ | C—H | CF$_3$ | CH$_3$ | N—CH$_3$ | C—CH$_3$ | N | bond |
| 3.111 | S | —CH$_2$CH$_3$ | N | CF$_3$ | CH$_3$ | N—CH$_3$ | C—CH$_3$ | N | bond |
| 3.112 | SO$_2$ | —CH$_2$CH$_3$ | N | CF$_3$ | CH$_3$ | N—CH$_3$ | C—CH$_3$ | N | bond |
| 3.113 | S | —CH$_2$CH$_3$ | C—H | CF$_3$ | CH$_3$ | N—CH$_3$ | C—CF$_3$ | N | bond |
| 3.114 | SO$_2$ | —CH$_2$CH$_3$ | C—H | CF$_3$ | CH$_3$ | N—CH$_3$ | C—CF$_3$ | N | bond |
| 3.115 | S | —CH$_2$CH$_3$ | N | CF$_3$ | CH$_3$ | N—CH$_3$ | C—CF$_3$ | N | bond |
| 3.116 | SO$_2$ | —CH$_2$CH$_3$ | N | CF$_3$ | CH$_3$ | N—CH$_3$ | C—CF$_3$ | N | bond |
| 3.117 | S | —CH$_2$CH$_3$ | C—H | CF$_3$ | CH$_3$ | N | CH | N—CH$_3$ | bond |
| 3.118 | SO$_2$ | —CH$_2$CH$_3$ | C—H | CF$_3$ | CH$_3$ | N | CH | N—CH$_3$ | bond |
| 3.119 | S | —CH$_2$CH$_3$ | N | CF$_3$ | CH$_3$ | N | CH | N—CH$_3$ | bond |
| 3.120 | SO$_2$ | —CH$_2$CH$_3$ | N | CF$_3$ | CH$_3$ | N | CH | N—CH$_3$ | bond |
| 3.121 | S | —CH$_2$CH$_3$ | C—H | CF$_3$ | CH$_3$ | N | C—CH$_3$ | N—CH$_3$ | bond |
| 3.122 | SO$_2$ | —CH$_2$CH$_3$ | C—H | CF$_3$ | CH$_3$ | N | C—CH$_3$ | N—CH$_3$ | bond |
| 3.123 | S | —CH$_2$CH$_3$ | N | CF$_3$ | CH$_3$ | N | C—CH$_3$ | N—CH$_3$ | bond |
| 3.124 | SO$_2$ | —CH$_2$CH$_3$ | N | CF$_3$ | CH$_3$ | N | C—CH$_3$ | N—CH$_3$ | bond |
| 3.125 | S | —CH$_2$CH$_3$ | C—H | CF$_3$ | CH$_3$ | N | C—CF$_3$ | N—CH$_3$ | bond |
| 3.126 | SO$_2$ | —CH$_2$CH$_3$ | C—H | CF$_3$ | CH$_3$ | N | C—CF$_3$ | N—CH$_3$ | bond |
| 3.127 | S | —CH$_2$CH$_3$ | N | CF$_3$ | CH$_3$ | N | C—CF$_3$ | N—CH$_3$ | bond |
| 3.128 | SO$_2$ | —CH$_2$CH$_3$ | N | CF$_3$ | CH$_3$ | N | C—CF$_3$ | N—CH$_3$ | bond | and the N-oxides and tautomers of the compounds of Table 3.

Table 4: This table discloses the 128 compounds of the formula I-1d:

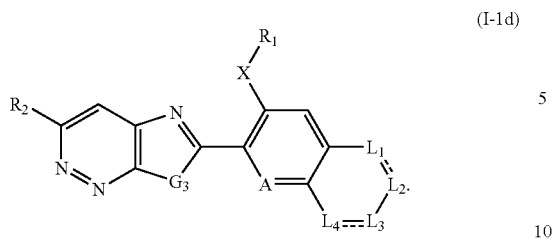

(I-1d)

TABLE 4

G$_3$ is N—R$_6$

| Comp. No. | X | R$_1$ | A | R$_2$ | R$_6$ | L$_1$ | L$_2$ | L$_3$ | L$_4$ |
|---|---|---|---|---|---|---|---|---|---|
| 4.001 | S | —CH$_2$CH$_3$ | C—H | CF$_3$ | CH$_3$ | CH | CH | CH | CH |
| 4.002 | SO | —CH$_2$CH$_3$ | C—H | CF$_3$ | CH$_3$ | CH | CH | CH | CH |
| 4.003 | SO$_2$ | —CH$_2$CH$_3$ | C—H | CF$_3$ | CH$_3$ | CH | CH | CH | CH |
| 4.004 | S | —CH$_2$CH$_3$ | N | CF$_3$ | CH$_3$ | CH | CH | CH | CH |
| 4.005 | SO | —CH$_2$CH$_3$ | N | CF$_3$ | CH$_3$ | CH | CH | CH | CH |
| 4.006 | SO$_2$ | —CH$_2$CH$_3$ | N | CF$_3$ | CH$_3$ | CH | CH | CH | CH |
| 4.007 | S | —CH$_2$CH$_3$ | C—H | CF$_3$ | CH$_3$ | O | CH$_2$ | O | bond |
| 4.008 | SO$_2$ | —CH$_2$CH$_3$ | C—H | CF$_3$ | CH$_3$ | O | CH$_2$ | O | bond |
| 4.009 | S | —CH$_2$CH$_3$ | C—H | CF$_3$ | CH$_3$ | CH | N | N—CH$_3$ | bond |
| 4.010 | SO$_2$ | —CH$_2$CH$_3$ | C—H | CF$_3$ | CH$_3$ | CH | N | N—CH$_3$ | bond |
| 4.011 | S | —CH$_2$CH$_3$ | C—H | CF$_3$ | CH$_3$ | CH | N—CH$_3$ | N | bond |
| 4.012 | SO$_2$ | —CH$_2$CH$_3$ | C—H | CF$_3$ | CH$_3$ | CH | N—CH$_3$ | N | bond |
| 4.013 | S | —CH$_2$CH$_3$ | N | CF$_3$ | CH$_3$ | CH | N | N—CH$_3$ | bond |
| 4.014 | SO$_2$ | —CH$_2$CH$_3$ | N | CF$_3$ | CH$_3$ | CH | N | N—CH$_3$ | bond |
| 4.015 | S | —CH$_2$CH$_3$ | N | CF$_3$ | CH$_3$ | CH | N—CH$_3$ | N | bond |
| 4.016 | SO$_2$ | —CH$_2$CH$_3$ | N | CF$_3$ | CH$_3$ | CH | N—CH$_3$ | N | bond |
| 4.017 | S | —CH$_2$CH$_3$ | C—H | CF$_3$ | CH$_3$ | N | CH | CH | CH |
| 4.018 | SO$_2$ | —CH$_2$CH$_3$ | C—H | CF$_3$ | CH$_3$ | N | CH | CH | CH |
| 4.019 | S | —CH$_2$CH$_3$ | N | CF$_3$ | CH$_3$ | N | CH | CH | CH |
| 4.020 | SO$_2$ | —CH$_2$CH$_3$ | N | CF$_3$ | CH$_3$ | N | CH | CH | CH |
| 4.021 | S | —CH$_2$CH$_3$ | C—H | CF$_3$ | CH$_3$ | CH | N | CH | CH |
| 4.022 | SO$_2$ | —CH$_2$CH$_3$ | C—H | CF$_3$ | CH$_3$ | CH | N | CH | CH |
| 4.023 | S | —CH$_2$CH$_3$ | N | CF$_3$ | CH$_3$ | CH | N | CH | CH |
| 4.024 | SO$_2$ | —CH$_2$CH$_3$ | N | CF$_3$ | CH$_3$ | CH | N | CH | CH |
| 4.025 | S | —CH$_2$CH$_3$ | C—H | CF$_3$ | CH$_3$ | N—CH$_3$ | N | CH | bond |
| 4.026 | SO$_2$ | —CH$_2$CH$_3$ | C—H | CF$_3$ | CH$_3$ | N—CH$_3$ | N | CH | bond |
| 4.027 | S | —CH$_2$CH$_3$ | N | CF$_3$ | CH$_3$ | N—CH$_3$ | N | CH | bond |
| 4.028 | SO$_2$ | —CH$_2$CH$_3$ | N | CF$_3$ | CH$_3$ | N—CH$_3$ | N | CH | bond |
| 4.029 | S | —CH$_2$CH$_3$ | C—H | CF$_3$ | CH$_3$ | N | N—CH$_3$ | CH | bond |
| 4.030 | SO$_2$ | —CH$_2$CH$_3$ | C—H | CF$_3$ | CH$_3$ | N | N—CH$_3$ | CH | bond |
| 4.031 | S | —CH$_2$CH$_3$ | N | CF$_3$ | CH$_3$ | N | N—CH$_3$ | CH | bond |
| 4.032 | SO$_2$ | —CH$_2$CH$_3$ | N | CF$_3$ | CH$_3$ | N | N—CH$_3$ | CH | bond |
| 4.033 | S | —CH$_2$CH$_3$ | C—H | CF$_3$ | CH$_3$ | N | N—H | CH | bond |
| 4.034 | SO$_2$ | —CH$_2$CH$_3$ | C—H | CF$_3$ | CH$_3$ | N | N—H | CH | bond |
| 4.035 | S | —CH$_2$CH$_3$ | N | CF$_3$ | CH$_3$ | N | N—H | CH | bond |
| 4.036 | SO$_2$ | —CH$_2$CH$_3$ | N | CF$_3$ | CH$_3$ | N | N—H | CH | Bond |
| 4.037 | S | —CH$_2$CH$_3$ | C—H | CF$_3$ | CH$_3$ | CH | N | N—H | bond |
| 4.038 | SO$_2$ | —CH$_2$CH$_3$ | C—H | CF$_3$ | CH$_3$ | CH | N | N—H | bond |
| 4.039 | S | —CH$_2$CH$_3$ | N | CF$_3$ | CH$_3$ | CH | N | N—H | bond |
| 4.040 | SO$_2$ | —CH$_2$CH$_3$ | N | CF$_3$ | CH$_3$ | CH | N | N—H | bond |
| 4.041 | S | —CH$_2$CH$_3$ | C—H | CF$_3$ | CH$_3$ | N | S | N | bond |
| 4.042 | SO$_2$ | —CH$_2$CH$_3$ | C—H | CF$_3$ | CH$_3$ | N | S | N | bond |
| 4.043 | S | —CH$_2$CH$_3$ | N | CF$_3$ | CH$_3$ | N | S | N | bond |
| 4.044 | SO$_2$ | —CH$_2$CH$_3$ | N | CF$_3$ | CH$_3$ | N | S | N | bond |
| 4.045 | S | —CH$_2$CH$_3$ | C—H | CF$_3$ | CH$_3$ | N | NH | N | bond |
| 4.046 | SO$_2$ | —CH$_2$CH$_3$ | C—H | CF$_3$ | CH$_3$ | N | NH | N | bond |
| 4.047 | S | —CH$_2$CH$_3$ | N | CF$_3$ | CH$_3$ | N | NH | N | bond |
| 4.048 | SO$_2$ | —CH$_2$CH$_3$ | N | CF$_3$ | CH$_3$ | N | NH | N | bond |
| 4.049 | S | —CH$_2$CH$_3$ | C—H | CF$_3$ | CH$_3$ | N | N—CH$_3$ | N | bond |
| 4.050 | SO$_2$ | —CH$_2$CH$_3$ | C—H | CF$_3$ | CH$_3$ | N | N—CH$_3$ | N | bond |
| 4.051 | S | —CH$_2$CH$_3$ | N | CF$_3$ | CH$_3$ | N | N—CH$_3$ | N | bond |
| 4.052 | SO$_2$ | —CH$_2$CH$_3$ | N | CF$_3$ | CH$_3$ | N | N—CH$_3$ | N | bond |
| 4.053 | S | —CH$_2$CH$_3$ | C—H | CF$_3$ | CH$_3$ | N | N | N—CH$_3$ | bond |
| 4.054 | SO$_2$ | —CH$_2$CH$_3$ | C—H | CF$_3$ | CH$_3$ | N | N | N—CH$_3$ | bond |
| 4.055 | S | —CH$_2$CH$_3$ | N | CF$_3$ | CH$_3$ | N | N | N—CH$_3$ | bond |
| 4.056 | SO$_2$ | —CH$_2$CH$_3$ | N | CF$_3$ | CH$_3$ | N | N | N—CH$_3$ | bond |
| 4.057 | S | —CH$_2$CH$_3$ | C—H | CF$_3$ | CH$_3$ | N—CH$_3$ | N | N | bond |
| 4.058 | SO$_2$ | —CH$_2$CH$_3$ | C—H | CF$_3$ | CH$_3$ | N—CH$_3$ | N | N | bond |
| 4.059 | S | —CH$_2$CH$_3$ | N | CF$_3$ | CH$_3$ | N—CH$_3$ | N | N | bond |
| 4.060 | SO$_2$ | —CH$_2$CH$_3$ | N | CF$_3$ | CH$_3$ | N—CH$_3$ | N | N | bond |

TABLE 4-continued

G₃ is N—R₆

| Comp. No. | X | $R_1$ | A | $R_2$ | $R_6$ | $L_1$ | $L_2$ | $L_3$ | $L_4$ |
|---|---|---|---|---|---|---|---|---|---|
| 4.061 | S | —CH₂CH₃ | C—H | CF₃ | CH₃ | CH | C—CF₃ | CH | CH |
| 4.062 | SO₂ | —CH₂CH₃ | C—H | CF₃ | CH₃ | CH | C—CF₃ | CH | CH |
| 4.063 | S | —CH₂CH₃ | N | CF₃ | CH₃ | CH | C—CF₃ | CH | CH |
| 4.064 | SO₂ | —CH₂CH₃ | N | CF₃ | CH₃ | CH | C—CF₃ | CH | CH |
| 4.065 | S | —CH₂CH₃ | C—H | CF₃ | CH₃ | CH | C—F | CH | CH |
| 4.066 | SO₂ | —CH₂CH₃ | C—H | CF₃ | CH₃ | CH | C—F | CH | CH |
| 4.067 | S | —CH₂CH₃ | N | CF₃ | CH₃ | CH | C—F | CH | CH |
| 4.068 | SO₂ | —CH₂CH₃ | N | CF₃ | CH₃ | CH | C—F | CH | CH |
| 4.069 | S | —CH₂CH₃ | C—H | CF₃ | CH₃ | N | C—H | S | bond |
| 4.070 | SO₂ | —CH₂CH₃ | C—H | CF₃ | CH₃ | N | C—H | S | bond |
| 4.071 | S | —CH₂CH₃ | N | CF₃ | CH₃ | N | C—H | S | bond |
| 4.072 | SO₂ | —CH₂CH₃ | N | CF₃ | CH₃ | N | C—H | S | bond |
| 4.073 | S | —CH₂CH₃ | C—H | CF₃ | CH₃ | N | C—CH₃ | S | bond |
| 4.074 | SO₂ | —CH₂CH₃ | C—H | CF₃ | CH₃ | N | C—CH₃ | S | bond |
| 4.075 | S | —CH₂CH₃ | N | CF₃ | CH₃ | N | C—CH₃ | S | bond |
| 4.076 | SO₂ | —CH₂CH₃ | N | CF₃ | CH₃ | N | C—CH₃ | S | bond |
| 4.077 | S | —CH₂CH₃ | C—H | CF₃ | CH₃ | N | C—CF₃ | S | bond |
| 4.078 | SO₂ | —CH₂CH₃ | C—H | CF₃ | CH₃ | N | C—CF₃ | S | bond |
| 4.079 | S | —CH₂CH₃ | N | CF₃ | CH₃ | N | C—CF₃ | S | bond |
| 4.080 | SO₂ | —CH₂CH₃ | N | CF₃ | CH₃ | N | C—CF₃ | S | bond |
| 4.081 | S | —CH₂CH₃ | C—H | CF₃ | CH₃ | S | C—H | N | bond |
| 4.082 | SO₂ | —CH₂CH₃ | C—H | CF₃ | CH₃ | S | C—H | N | bond |
| 4.083 | S | —CH₂CH₃ | N | CF₃ | CH₃ | S | C—H | N | bond |
| 4.084 | SO₂ | —CH₂CH₃ | N | CF₃ | CH₃ | S | C—H | N | bond |
| 4.085 | S | —CH₂CH₃ | C—H | CF₃ | CH₃ | S | C—CH₃ | N | bond |
| 4.086 | SO₂ | —CH₂CH₃ | C—H | CF₃ | CH₃ | S | C—CH₃ | N | bond |
| 4.087 | S | —CH₂CH₃ | N | CF₃ | CH₃ | S | C—CH₃ | N | bond |
| 4.088 | SO₂ | —CH₂CH₃ | N | CF₃ | CH₃ | S | C—CH₃ | N | bond |
| 4.089 | S | —CH₂CH₃ | C—H | CF₃ | CH₃ | S | C—CF₃ | N | bond |
| 4.090 | SO₂ | —CH₂CH₃ | C—H | CF₃ | CH₃ | S | C—CF₃ | N | bond |
| 4.091 | S | —CH₂CH₃ | N | CF₃ | CH₃ | S | C—CF₃ | N | bond |
| 4.092 | SO₂ | —CH₂CH₃ | N | CF₃ | CH₃ | S | C—CF₃ | N | bond |
| 4.093 | S | —CH₂CH₃ | C—H | CF₃ | CH₃ | N—H | C—CF₃ | N | bond |
| 4.094 | SO₂ | —CH₂CH₃ | C—H | CF₃ | CH₃ | N—H | C—CF₃ | N | bond |
| 4.095 | S | —CH₂CH₃ | N | CF₃ | CH₃ | N—H | C—CF₃ | N | bond |
| 4.096 | SO₂ | —CH₂CH₃ | N | CF₃ | CH₃ | N—H | C—CF₃ | N | bond |
| 4.097 | S | —CH₂CH₃ | C—H | CF₃ | CH₃ | N—H | C—CH₃ | N | bond |
| 4.098 | SO₂ | —CH₂CH₃ | C—H | CF₃ | CH₃ | N—H | C—CH₃ | N | bond |
| 4.099 | S | —CH₂CH₃ | N | CF₃ | CH₃ | N—H | C—CH₃ | N | bond |
| 4.100 | SO₂ | —CH₂CH₃ | N | CF₃ | CH₃ | N—H | C—CH₃ | N | bond |
| 4.101 | S | —CH₂CH₃ | C—H | CF₃ | CH₃ | N—H | CH | N | bond |
| 4.102 | SO₂ | —CH₂CH₃ | C—H | CF₃ | CH₃ | N—H | CH | N | bond |
| 4.103 | S | —CH₂CH₃ | N | CF₃ | CH₃ | N—H | CH | N | bond |
| 4.104 | SO₂ | —CH₂CH₃ | N | CF₃ | CH₃ | N—H | CH | N | bond |
| 4.105 | S | —CH₂CH₃ | C—H | CF₃ | CH₃ | N—CH₃ | CH | N | bond |
| 4.106 | SO₂ | —CH₂CH₃ | C—H | CF₃ | CH₃ | N—CH₃ | CH | N | bond |
| 4.107 | S | —CH₂CH₃ | N | CF₃ | CH₃ | N—CH₃ | CH | N | bond |
| 4.108 | SO₂ | —CH₂CH₃ | N | CF₃ | CH₃ | N—CH₃ | CH | N | bond |
| 4.109 | S | —CH₂CH₃ | C—H | CF₃ | CH₃ | N—CH₃ | C—CH₃ | N | bond |
| 4.110 | SO₂ | —CH₂CH₃ | C—H | CF₃ | CH₃ | N—CH₃ | C—CH₃ | N | bond |
| 4.111 | S | —CH₂CH₃ | N | CF₃ | CH₃ | N—CH₃ | C—CH₃ | N | bond |
| 4.112 | SO₂ | —CH₂CH₃ | N | CF₃ | CH₃ | N—CH₃ | C—CH₃ | N | bond |
| 4.113 | S | —CH₂CH₃ | C—H | CF₃ | CH₃ | N—CH₃ | C—CF₃ | N | bond |
| 4.114 | SO₂ | —CH₂CH₃ | C—H | CF₃ | CH₃ | N—CH₃ | C—CF₃ | N | bond |
| 4.115 | S | —CH₂CH₃ | N | CF₃ | CH₃ | N—CH₃ | C—CF₃ | N | bond |
| 4.116 | SO₂ | —CH₂CH₃ | N | CF₃ | CH₃ | N—CH₃ | C—CF₃ | N | bond |
| 4.117 | S | —CH₂CH₃ | C—H | CF₃ | CH₃ | N | CH | N—CH₃ | bond |
| 4.118 | SO₂ | —CH₂CH₃ | C—H | CF₃ | CH₃ | N | CH | N—CH₃ | bond |
| 4.119 | S | —CH₂CH₃ | N | CF₃ | CH₃ | N | CH | N—CH₃ | bond |
| 4.120 | SO₂ | —CH₂CH₃ | N | CF₃ | CH₃ | N | CH | N—CH₃ | bond |
| 4.121 | S | —CH₂CH₃ | C—H | CF₃ | CH₃ | N | C—CH₃ | N—CH₃ | bond |
| 4.122 | SO₂ | —CH₂CH₃ | C—H | CF₃ | CH₃ | N | C—CH₃ | N—CH₃ | bond |
| 4.123 | S | —CH₂CH₃ | N | CF₃ | CH₃ | N | C—CH₃ | N—CH₃ | bond |
| 4.124 | SO₂ | —CH₂CH₃ | N | CF₃ | CH₃ | N | C—CH₃ | N—CH₃ | bond |
| 4.125 | S | —CH₂CH₃ | C—H | CF₃ | CH₃ | N | C—CF₃ | N—CH₃ | bond |
| 4.126 | SO₂ | —CH₂CH₃ | C—H | CF₃ | CH₃ | N | C—CF₃ | N—CH₃ | bond |
| 4.127 | S | —CH₂CH₃ | N | CF₃ | CH₃ | N | C—CF₃ | N—CH₃ | bond |
| 4.128 | SO₂ | —CH₂CH₃ | N | CF₃ | CH₃ | N | C—CF₃ | N—CH₃ | bond | and the N-oxides and tautomers of the compounds of Table 4.

The compounds of formula I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i. e. in destruction of the pests, which takes place either immediately or only after some time has elapsed, for example during ecdysis, or indirectly, for example in a reduced oviposition and/or hatching rate.

Examples of the abovementioned animal pests are:

from the order Acarina, for example,

*Acalitus* spp, *Aculus* spp, *Acaricalus* spp, *Aceria* spp, *Acarus siro*, *Amblyomma* spp., *Argas* spp., *Boophilus* spp., *Brevipalpus* spp., *Bryobia* spp, *Calipitrimerus* spp., *Chorioptes* spp., *Dermanyssus gallinae*, *Dermatophagoides* spp., *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.; from the order Coleoptera, for example,

*Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp., *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp, *Phlyctinus* spp., *Popillia* spp., *Psylliodes* spp., *Rhyssomatus aubtilis*, *Rhizopertha* spp., *Scarabeidae*, *Sitophilus* spp., *Sitotroga* spp., *Somaticus* spp, *Sphenophorus* spp, *Sternechus subsignatus*, *Tenebrio* spp., *Tribolium* spp. and *Trogoderma* spp.;

from the order Diptera, for example,

*Aedes* spp., *Anopheles* spp, *Antherigona soccata*, *Bactrocea oleae*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *Tannia* spp. and *Tipula* spp.;

from the order Hemiptera, for example,

*Acanthocoris scabrator*, *Acrosternum* spp, *Adelphocoris lineolatus*, *Amblypelta nitida*, *Bathycoelia thalassina*, *Blissus* spp, *Cimex*spp., *Clavigralla tomentosicollis*, *Creontiades* spp, *Distantiella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilellus*, *Leptocorisa* spp., *Lygus* spp, *Margarodes* spp., *Murgantia histrionic*, *Neomegalotomus* spp, *Nesidiocoris tenuis*, *Nezara* spp., *Nysius simulans*, *Oebalus insularis*, *Piesma* spp, *Piezodorus* spp., *Rhodnius* spp., *Sahlbergella singularis*, *Scaptocoris castanea*, *Scotino-phara* spp., *Thyanta* spp, *Triatoma* spp., *Vatiga illudens*;

*Acyrthosium pisum*, *Adalges* spp, *Agalliana ensigera*, *Agonoscena targionii*, *Aleurodicus* spp, *Aleurocanthus* spp, *Aleurolobus barodensis*, *Aleurothrixus floccosus*, *Aleyrodes brassicae*, *Amarasca biguttula*, *Amritodus atkinsoni*, *Aonidiella* spp., *Aphididae*, *Aphis* spp., *Aspidiotus* spp., *Aulacorthum solani*, *Bactericera cockerelli*, *Bemisia* spp, *Brachycaudus* spp, *Brevicoryne brassicae*, *Cacopsylla* spp, *Cavariella aegopodii Scop.*, *Ceroplaster* spp., *Chrysomphalus aonidium*, *Chrysomphalus dictyospermi*, *Cicadella* spp, *Cofana spectra*, *Cryptomyzus* spp, *Cicadulina* spp, *Coccus hesperidum*, *Dalbulus maidis*, *Dialeurodes* spp, *Diaphorina citri*, *Diuraphis noxia*, *Dysaphis* spp, *Empoasca* spp., *Eriosoma larigerum*, *Erythroneura* spp., *Gascardia* spp., *Glycaspis brimblecombei*, *Hyadaphis pseudobrassicae*, *Hyalopterus* spp, *Hyperomyzus pallidus*, *Idioscopus clypealis*, *Jacobiasca lybica*, *Laodelphax* spp., *Lecanium corni*, *Lepidosaphes* spp., *Lopaphis erysimi*, *Lyogenys maidis*, *Macrosiphum* spp., *Mahanarva* spp, *Metcalfa pruinosa*, *Metopolophium dirhodum*, *Myndus crudus*, *Myzus* spp., *Neotoxoptera* sp, *Nephotettix* spp., *Nilaparvata* spp., *Nippolachnus piri Mats*, *Odonaspis ruthae*, *Oregma lanigera Zehnter*, *Parabemisia myricae*, *Paratrioza cockerelli*, *Parlatoria* spp., *Pemphigus* spp., *Peregrinus maidis*, *Perkinsiella* spp, *Phorodon humuli*, *Phylloxera* spp, *Planococcus* spp., *Pseudaulacaspis* spp., *Pseudococcus* spp., *Pseudatomoscelis seriatus*, *Psylla* spp., *Pulvinaria aethiopica*, *Quadraspidiotus* spp., *Quesada gigas*, *Recilia dorsalis*, *Rhopalosiphum* spp., *Saissetia* spp., *Scaphoideus* spp., *Schizaphis* spp., *Sitobion* spp., *Sogatella furcifera*, *Spissistilus festinus*, *Tarophagus Proserpina*, *Toxoptera* spp., *Trialeurodes* spp., *Tridiscus sporoboli*, *Trionymus* spp, *Trioza erytreae*, *Unaspis citri*, *Zygina flammigera*, *Zyginidia scutellaris*;

from the order Hymenoptera, for example,

*Acromyrmex*, *Arge* spp, *Atta* spp., *Cephus* spp., *Diprion* spp., *Diprionidae*, *Gilpinia polytoma*, *Hoplocampa* spp., *Lasius* spp., *Monomorium pharaonis*, *Neodiprion* spp., *Pogonomyrmex* spp, *Slenopsis invicta*, *Solenopsis* spp. and *Vespa* spp.;

from the order Isoptera, for example,

*Coptotermes* spp, *Corniternes cumulans*, *Incisitermes* spp, *Macrotermes* spp, *Mastotermes* spp, *Microtermes* spp, *Reticulitermes* spp.; *Solenopsis geminate* from the order Lepidoptera, for example,

*Acleris* spp., *Adoxophyes* spp., *Aegeria* spp., *Agrotis* spp., *Alabama argillaceae*, *Amylois* spp., *Anticarsia gemmatalis*, *Archips* spp., *Argyresthia* spp, *Argyrotaenia* spp., *Autographa* spp., *Bucculatrix thurberiella*, *Busseola fusca*, *Cadra cautella*, *Carposina nipponensis*, *Chilo* spp., *Choristoneura* spp., *Chrysoteuchia topiaria*, *Clysia ambiguella*, *Cnaphalocrocis* spp., *Cnephasia* spp., *Cochylis* spp., *Coleophora* spp., *Colias lesbia*, *Cosmophila flava*, *Crambus* spp, *Crocidolomia binotalis*, *Cryptophlebia leucotreta*, *Cydalima perspectalis*, *Cydia* spp., *Diaphania perspectalis*, *Diatraea* spp., *Diparopsis castanea*, *Earias* spp., *Eldana saccharina*, *Ephestia* spp., *Epinotia* spp, *Estigmene acrea*, *Etiella zinckinella*, *Eucosma* spp., *Eupoecilia ambiguella*, *Euproctis* spp., *Euxoa* spp., *Feltia jaculiferia*, *Grapholita* spp., *Hedya nubiferana*, *Heliothis* spp., *Hellula undalis*, *Herpetogramma* spp, *Hyphantria cunea*, *Keiferia lycopersicella*, *Lasmopalpus lignosellus*, *Leucoptera scitella*, *Lithocollethis* spp., *Lobesia botrana*, *Loxostege bifidalis*, *Lymantria* spp., *Lyonetia* spp., *Malacosoma* spp., *Mamestra brassicae*, *Manduca sexta*, *Mythimna* spp, *Noctua* spp, *Operophtera* spp., *Orniodes indica*, *Ostrinia nubilalis*, *Pammene* spp., *Pandemis* spp., *Panolis flammea*, *Papaipema nebris*, *Pectinophora gossypiela*, *Perileucoptera coffeella*, *Pseudaletia unipuncta*, *Phthorimaea operculella*, *Pieris rapae*, *Pieris* spp., *Plutella*

*xylostella, Prays* spp., *Pseudoplusia* spp, *Rachiplusia nu, Richia albicosta, Scirpophaga* spp., *Sesamia* spp., *Sparganothis* spp., *Spodoptera* spp., *Sylepta derogate, Synanthedon* spp., *Thaumetopoea* spp., *Tortrix* spp., *Trichoplusia ni, Tuta absoluta,* and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae, Locusta* spp., *Neocurtilla hexadactyla, Periplaneta* spp., *Scapteriscus* spp, and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis;* from the order Thysanoptera, for example,

*Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp;

from the order Thysanura, for example, *Lepisma saccharina.*

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family and latex plants.

The compositions and/or methods of the present invention may be also used on any ornamental and/or vegetable crops, including flowers, shrubs, broad-leaved trees and evergreens.

For example the invention may be used on any of the following ornamental species: *Ageratum* spp., *Alonsoa* spp., *Anemone* spp., *Anisodontea capsenisis, Anthemis* spp., *Antirrhinum* spp., *Aster* spp., *Begonia* spp. (e.g. *B. elatior, B. semperflorens, B. tubereux*), *Bougainvillea* spp., *Brachycome* spp., *Brassica* spp. (ornamental), *Calceolaria* spp., *Capsicum annuum, Catharanthus roseus, Canna* spp., *Centaurea* spp., *Chrysanthemum* spp., *Cineraria* spp. (*C. maritime*), *Coreopsis* spp., *Crassula coccinea, Cuphea ignea, Dahlia* spp., *Delphinium* spp., *Dicentra spectabilis, Dorotheantus* spp., *Eustoma grandiflorum, Forsythia* spp., *Fuchsia* spp., *Geranium gnaphalium, Gerbera* spp., *Gomphrena globosa, Heliotropium* spp., *Helianthus* spp., *Hibiscus* spp., *Hortensia* spp., *Hydrangea* spp., *Hypoestes phyllostachya, Impatiens* spp. (*I. Walleriana*), *Iresines* spp., *Kalanchoe* spp., *Lantana camara, Lavatera trimestris, Leonotis leonurus, Lilium* spp., *Mesembryanthemum* spp., *Mimulus* spp., *Monarda* spp., *Nemesia* spp., *Tagetes* spp., *Dianthus* spp. (carnation), *Canna* spp., *Oxalis* spp., *Bellis* spp., *Pelargonium* spp. (*P. peltatum, P. Zonale*), *Viola* spp. (pansy), *Petunia* spp., *Phlox* spp., *Plecthranthus* spp., *Poinsettia* spp., *Parthenocissus* spp. (*P. quinquefolia, P. tricuspidata*), *Primula* spp., *Ranunculus* spp., *Rhododendron* spp., *Rosa* spp. (rose), *Rudbeckia* spp., *Saintpaulia* spp., *Salvia* spp., *Scaevola aemola, Schizanthus wisetonensis, Sedum* spp., *Solanum* spp., *Surfinia* spp., *Tagetes* spp., *Nicotinia* spp., *Verbena* spp., *Zinnia* spp. and other bedding plants.

For example the invention may be used on any of the following vegetable species: *Allium* spp. (*A. sativum, A. cepa, A. oschaninii, A. Porrum, A. ascalonicum, A. fistulosum*), *Anthriscus cerefolium, Apium graveolus, Asparagus officinalis, Beta vulgarus, Brassica* spp. (*B. Oleracea, B. Pekinensis, B. rapa*), *Capsicum annuum, Cicer arietinum, Cichorium endivia, Cichorum* spp. (*C. intybus, C. endivia*), *Citrillus lanatus, Cucumis* spp. (*C. sativus, C. melo*), *Cucurbita* spp. (*C. pepo, C. maxima*), *Cyanara* spp. (*C. scolymus, C. cardunculus*), *Daucus carota, Foeniculum vulgare, Hypericum* spp., *Lactuca sativa, Lycopersicon* spp. (*L. esculentum, L. lycopersicum*), *Mentha* spp., *Ocimum basilicum, Petroselinum crispum, Phaseolus* spp. (*P. vulgaris, P. coccineus*), *Pisum sativum, Raphanus sativus, Rheum rhaponticum, Rosemarinus* spp., *Salvia* spp., *Scorzonera hispanica, Solanum melongena, Spinacea oleracea, Valerianella* spp. (*V. locusta, V. eriocarpa*) and *Vicia faba.*

Preferred ornamental species include African violet, *Begonia, Dahlia, Gerbera, Hydrangea, Verbena, Rosa, Kalanchoe, Poinsettia, Aster, Centaurea, Coreopsis, Delphinium, Monarda, Phlox, Rudbeckia, Sedum, Petunia, Viola, Impatiens, Geranium, Chrysanthemum, Ranunculus, Fuchsia, Salvia, Hortensia,* rosemary, sage, St. Johnswort, mint, sweet pepper, tomato and cucumber.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatos) and *Chilo supressalis* (preferably in rice).

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla, Meloidogyne incognita, Meloidogyne javanica, Meloidogyne arenaria* and other *Meloidogyne* species; cyst-forming nematodes, *Globodera rostochiensis* and other *Globodera* species; *Heterodera avenae, Heterodera glycines, Heterodera schachtii, Heterodera trifolii,* and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus, Pratylenchus penetrans, Pratylenchus curvitatus, Pratylenchus goodeyi* and other *Pra-*

*tylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

The compounds of the invention may also have activity against the molluscs. Examples of which include, for example, Ampullariidae; Arion (*A. ater, A. circumscriptus, A. hortensis, A. rufus*); Bradybaenidae (*Bradybaena fruticum*); Cepaea (*C. hortensis, C. Nemoralis*); ochlodina; Deroceras (*D. agrestis, D. empiricorum, D. laeve, D. reticulatum*); Discus (*D. rotundatus*); Euomphalia; Galba (*G. trunculata*); Helicelia (*H. itala, H. obvia*); Helicidae Helicigona arbustorum); Helicodiscus; Helix (*H. aperta*); Limax (*L. cinereoniger, L. flavus, L. marginatus, L. maximus, L. tenellus*); Lymnaea; Milax (*M. gagates, M. marginatus, M. sowerbyi*); Opeas; Pomacea (*P. canaticulata*); Vallonia and Zanitoides.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins.

Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cry1-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt1 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt1 1 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch). The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Crops may also be modified for enhanced resistance to fungal (for example *Fusarium*, Anthracnose, or *Phytophthora*), bacterial (for example *Pseudomonas*) or viral (for example potato leafroll virus, tomato spotted wilt virus, cucumber mosaic virus) pathogens.

Crops also include those that have enhanced resistance to nematodes, such as the soybean cyst nematode.

Crops that are tolerance to abiotic stress include those that have enhanced tolerance to drought, high salt, high temperature, chill, frost, or light radiation, for example through expression of NF—YB or other proteins known in the art.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and store ambients and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents. A further object of the invention is therefore a substrate selected from nonwoven and fabric material comprising a composition which contains a compound of formula I.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO 2006/128870, EP 1724392, WO2005113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables A and B:

TABLE A

Examples of exotic woodborers of economic importance.

| Family | Species | Host or Crop Infested |
|---|---|---|
| Buprestidae | *Agrilus planipennis* | Ash |
| Cerambycidae | *Anoplura glabripennis* | Hardwoods |
| Scolytidae | *Xylosandrus crassiusculus* | Hardwoods |
| | *X. mutilatus* | Hardwoods |
| | *Tomicus piniperda* | Conifers |

TABLE B

Examples of native woodborers of economic importance.

| Family | Species | Host or Crop Infested |
|---|---|---|
| Buprestidae | *Agrilus anxius* | Birch |
| | *Agrilus politus* | Willow, Maple |
| | *Agrilus sayi* | Bayberry, Sweetfern |
| | *Agrilus vittaticolllis* | Apple, Pear, Cranberry, Serviceberry, Hawthorn |
| | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
| | *Texania campestris* | Basswood, Beech, Maple, Oak, Sycamore, Willow, Yellow-poplar |
| Cerambycidae | *Goes pulverulentus* | Beech, Elm, Nuttall, Willow, Black oak, Cherrybark oak, Water oak, Sycamore |
| | *Goes tigrinus* | Oak |
| | *Neoclytus acuminatus* | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
| | *Neoptychodes trilineatus* | Fig, Alder, Mulberry, Willow, Netleaf hackberry |
| | *Oberea ocellata* | Sumac, Apple, Peach, Plum, Pear, Currant, Blackberry |
| | *Oberea tripunctata* | Dogwood, Viburnum, Elm, Sourwood, Blueberry, Rhododendron, Azalea, Laurel, Poplar, Willow, Mulberry |
| | *Oncideres cingulata* | Hickory, Pecan, Persimmon, Elm, Sourwood, Basswood, Honeylocust, Dogwood, Eucalyptus, Oak, Hackberry, Maple, Fruit trees |
| | *Saperda calcarata* | Poplar |
| | *Strophiona nitens* | Chestnut, Oak, Hickory, Walnut, Beech, Maple |
| Scolytidae | *Corthylus columbianus* | Maple, Oak, Yellow-poplar, Beech, Boxelder, Sycamore, Birch, Basswood, Chestnut, Elm |
| | *Dendroctonus frontalis* | Pine |
| | *Dlyocoetes betulae* | Birch, Sweetgum, Wild cherry, Beech, Pear |
| | *Monarthrum fasciatum* | Oak, Maple, Birch, Chestnut, Sweetgum, Blackgum, Poplar, Hickory, Mimosa, Apple, Peach, Pine |
| | *Phloeotribus liminaris* | Peach, Cherry, Plum, Black cherry, Elm, Mulberry, Mountain-ash |
| | *Pseudopityophthorus pruinosus* | Oak, American beech, Black cherry, Chickasaw plum, Chestnut, Maple, Hickory, Hornbeam, Hophornbeam |
| Sesiidae | *Paranthrene simulans* | Oak, American chestnut |
| | *Sannina uroceriformis* | Persimmon |
| | *Synanthedon exitiosa* | Peach, Plum, Nectarine, Cherry, Apricot, Almond, Black cherry |
| | *Synanthedon pictipes* | Peach, Plum, Cherry, Beach, Black Cherry |
| | *Synanthedon rubrofascia* | Tupelo |
| | *Synanthedon scitula* | Dogwood, Pecan, Hickory, Oak, Chestnut, Beech, Birch, Black cherry, Elm, Mountain-ash, Viburnum, Willow, Apple, Loquat, Ninebark, Bayberry |
| | *Vitacea polistiformis* | Grape |

The present invention may be also used to control any insect pests that may be present in turfgrass, including for example beetles, caterpillars, fire ants, ground pearls, millipedes, sow bugs, mites, mole crickets, scales, mealybugs ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as *Cyclocephala* spp. (e.g. masked chafer, *C. lurida*), *Rhizotrogus* spp. (e.g. European chafer, *R. majalis*), *Cotinus* spp. (e.g. Green June beetle, *C. nitida*), *Popillia* spp. (e.g. Japanese beetle, *P. japonica*), *Phyllophaga* spp. (e.g. May/June beetle), *Ataenius* spp. (e.g. Black turfgrass ataenius, *A. spretulus*), *Maladera* spp. (e.g. Asiatic garden beetle, *M. castanea*) and *Tomarus* spp.), ground pearls (*Margarodes* spp.), mole crickets (tawny, southern, and short-winged; *Scapteriscus* spp., *Gryllotalpa africana*) and leatherjackets (European crane fly, *Tipula* spp.).

The present invention may also be used to control insect pests of turfgrass that are thatch dwelling, including armyworms (such as fall armyworm *Spodoptera frugiperda*, and common armyworm *Pseudaletia unipuncta*), cutworms, billbugs (*Sphenophorus* spp., such as *S. venatus verstitus* and *S. parvulus*), and sod webworms (such as *Crambus* spp. and the tropical sod webworm, *Herpetogramma phaeopteralis*).

The present invention may also be used to control insect pests of turfgrass that live above the ground and feed on the turfgrass leaves, including chinch bugs (such as southern chinch bugs, *Blissus insularis*), Bermudagrass mite (*Eriophyes cynodoniensis*), rhodesgrass mealybug (*Antonina graminis*), two-lined spittlebug (*Propsapia bicincta*), leafhoppers, cutworms (Noctuidae family), and greenbugs.

The present invention may also be used to control other pests of turfgrass such as red imported fire ants (*Solenopsis invicta*) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis, Periplaneta americana, Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Stemostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergatesspp., Demodexspp., Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus*, and also hymenopterans such as *Sirex juvencus, Urocerus gigas, Urocerus gigas taignus* and *Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharina*.

The compounds according to the invention can be used as pesticidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated. The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethyl-hexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, $10^{th}$ Edition, Southern Illinois University, 2010. The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):

Emulsifiable Concentrates:
    active ingredient: 1 to 95%, preferably 60 to 90%
    surface-active agent: 1 to 30%, preferably 5 to 20%
    liquid carrier: 1 to 80%, preferably 1 to 35%

Dusts:
    active ingredient: 0.1 to 10%, preferably 0.1 to 5%
    solid carrier: 99.9 to 90%, preferably 99.9 to 99%

Suspension Concentrates:
    active ingredient: 5 to 75%, preferably 10 to 50%
    water: 94 to 24%, preferably 88 to 30%
    surface-active agent: 1 to 40%, preferably 2 to 30%

Wettable Powders:
    active ingredient: 0.5 to 90%, preferably 1 to 80%
    surface-active agent: 0.5 to 20%, preferably 1 to 15%
    solid carrier: 5 to 95%, preferably 15 to 90%

Granules:
    active ingredient: 0.1 to 30%, preferably 0.1 to 15%
    solid carrier: 99.5 to 70%, preferably 97 to 85%

The following Examples further illustrate, but do not limit, the invention.

| Wettable powders | a) | b) | c) |
|---|---|---|---|
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The combination is thoroughly mixed with the adjuvants and the mixture is thoroughly ground in a suitable mill, affording powders that can be used directly for seed treatment.

| Emulsifiable concentrate | |
|---|---|
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder granules | |
|---|---|
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
|---|---|
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

| Suspension concentrate | |
|---|---|
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

Formulation types include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

PREPARATORY EXAMPLES

"Mp" means melting point in ° C. Free radicals represent methyl groups. $^1$H and $^{19}$F NMR measurements were recorded on Brucker 400 MHz or 300 MHz spectrometers, chemical shifts are given in ppm relevant to a TMS standard. Spectra measured in deuterated solvents as indicated.

LCMS Methods:

Method A—Standard:

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 □m, 30×2.1 mm, Temp: 60° C., DAD Wavelength range (nm): 210 to 500, Solvent Gradient: A=water+5% MeOH+0.05% HCOOH, B=Acetonitrile+0.05% HCOOH:gradient:gradient: 0 min 0% B, 100% A; 1.2-1.5 min 100% B; Flow (ml/min) 0.85.

Method B—Standard Long:

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 □m, 30×2.1 mm, Temp: 60° C., DAD Wavelength range (nm): 210 to 500, Solvent Gradient: A=water+5% MeOH+0.05% HCOOH, B=Acetonitrile+0.05% HCOOH:gradient:gradient: 0 min 0% B, 100% A; 2.7-3.0 min 100% B; Flow (ml/min) 0.85

Method C—Unpolar:

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 □m, 30×2.1 mm, Temp: 60° C., DAD Wavelength range (nm): 210 to 500, Solvent Gradient: A=water+5% MeOH+0.05% HCOOH, B=Acetonitrile+0.05% HCOOH:gradient:gradient: 0 min 40% B, 60% A; 1.2-1.5 min 100% B; Flow (ml/min) 0.85

Synthesis of Intermediates:

Intermediate 1: Synthesis of 3-ethylsulfanylquinoline-2-carboxylic acid

Step A: ethyl 3-ethylsulfanylquinoline-2-carboxylate

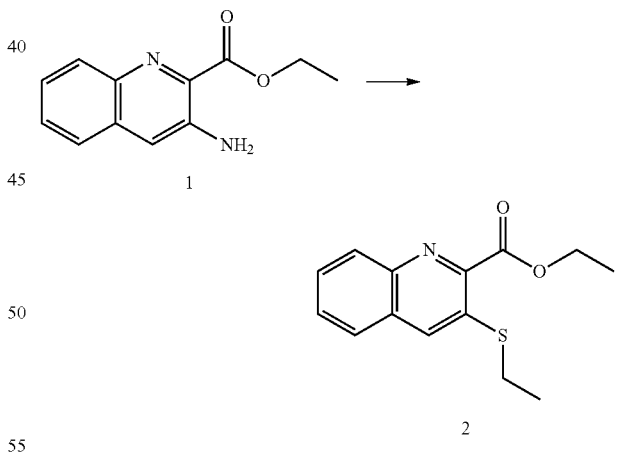

To stirred solution of compound 1 (3.6 g, 16.66 mmol) in DCE (30 ml) was added diethyldisulfide (4.51 ml, 36.6 mmol), t-butyl nitrite was then added dropwise at ambient temperature. The reaction mixture was heated to 40° C. for 2 hours. Reaction was monitored by TLC. After completion of the starting material, reaction mixture was diluted with CH$_2$Cl$_2$ and washed with water (2×10 mL). Organic layer was dried over Na$_2$SO$_4$. Filtered, concentrated and purified by column chromatography using hexane-ethyl acetate (100-200 silica gel) to give the desired compound as a yellow liquid (amount: 1.0 g; Yield=23%). $^1$H NMR (400

MHz, CDCl₃): δ (ppm) 8.14 (d, 1H), 8.06 (s, 1H), 7.75 (d, 1H), 7.68 (m, 1H), 7.58 (m, 1H), 4.54 (q, 2H), 3.03 (q, 2H), 1.48 (t, 3H), 1.40 (t, 3H).

Step B: 3-ethylsulfanylquinoline-2-carboxylic acid

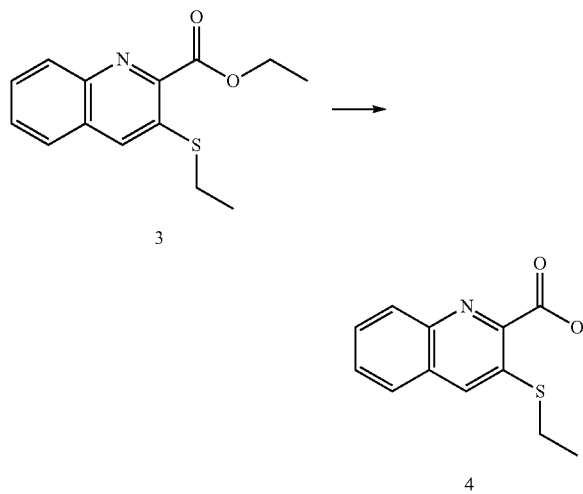

To as stirred solution of compound 3 (1 g, 3.8 mmol) in THF (8 ml) was added NaOH (2 N, 2.2 eq) at RT.

Reaction mixture was stirred for 16 hours at ambient temperature. Reaction was monitored by TLC. After completion of the starting material, reaction mixture was extracted with ethyl acetate (2×10 mL). Water part was then acidified to pH=4 by 10% citric acid solution and extracted with ethyl acetate (3×20 ml). Organic layer was dried over Na₂SO₄. Filtered, concentrated under reduced pressure to give the crude solid, which was triturated with ether to give the desired compound as yellow solid (amount: 613 mg; Yield=68%). ¹H NMR (400 MHz, DMSO-d₆): δ (ppm) 13.7 (s, 1H), 8.42 (s, 1H), 8.00 (m, 2H), 7.75 (m, 1H), 7.68 (m, 1H), 3.09 (q, 2H), 1.29 (t, 3H).

Intermediate 2: Synthesis of
3-ethylsulfanylnaphtalene-2-carboxylic acid

Step A: 3-sulfanylnaphthalene-2-carboxylic acid

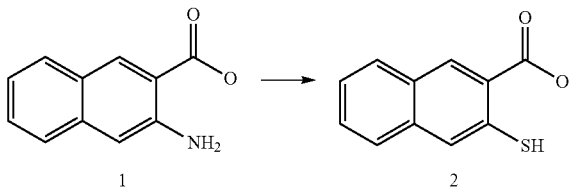 [SMILES: Nc1cc2ccccc2cc1C(=O)O ; O=C(O)c1cc2ccccc2cc1S]

To a stirred suspension of compound-1 (10 g, 53.47 mmol) in water (28 mL) and concentrate HCl (11.4 mL) at 5° C. was added dropwise a solution of NaNO₂ (3.69 g, 53.47 mmol) in water (14.6 mL) and the solution maintained at 5° C. Crushed ice was added to the reaction mixture periodically during addition to keep the temperature below 5° C. Meanwhile, Na₂S.9H₂O (13.7 g, 176.47 mmol) and sublimed sulfur (1.88 g, 58.82 mmol) were dissolved in water (15 mL) by heating and made alkaline by addition of NaOH (10 M, 5.5 mL), and the resulting alkaline disulfide solution was cooled to 5° C. in an ice bath. The cold diazo solution was added to the alkaline disulfide solution dropwise with crushed ice added periodically to maintain the temperature below 5° C. Following addition of the diazo solution, the mixture was stirred at ambient temperature until evolution of N₂ gas stopped. Concentrated HCl was added to the solution until precipitation of the crude product as a yellow solid was complete. The precipitate was collected and boiled in a saturated solution of NaHCO3 (130 mL). After being boiled for 15 min, the mixture was filtered to remove the insoluble material, and conc. HCl was added to the filtrate until the crude product precipitated out as a yellow solid. Excess conc. HCl was added to the mixture until precipitation was completed, and the precipitate was isolated by filtration. This material was boiled in absolute EtOH (50 mL) for 15 min and filtered and the filtrate concentrated under reduced pressure to yield the dithiosalicylic acid derivative The dithiosalicylic acid derivative was then mixed with Zn dust (3.2 g) in glacial CH₃COOH (50 mL) and refluxed for 48 hours. The mixture was then cooled and filtered. The solid collected in this manner was boiled in 5 M NaOH (100 mL). After being boiled for 30 min, the undissolved solid was removed by filtration and the clear filtrate acidified with concentrated HCl until the crude product precipitated out as a yellow solid. Concentrated HCl was added to the mixture until the precipitation was complete. The precipitate was collected and boiled in EtOH (40 mL) and filtered and the filtrate concentrated under reduced pressure to yield the thiosalicylic acid derivative 2. This material was directly carried on to the next step without extra purification (amount: 4 g; Yield=36%).

Step B: 3-ethylsulfanylnaphtalene-2-carboxylic acid

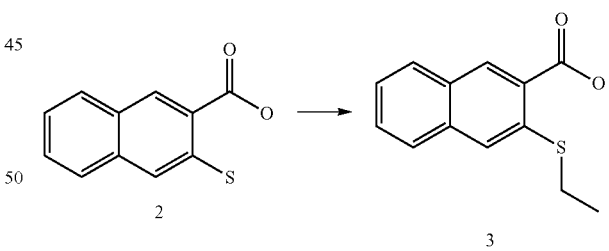

To a stirred solution of compound 2 (1.9 g, 9.36) in ethanol (10 ml) and NaOH (1 M, 10 mL) was added EtI (0.75 ml, 9.36 mmol) at ambient temperature. The reaction mixture was stirred for 48 hours. LC-MS showed desired product was formed. Solvent was evaporated and the crude was acidified to pH=2, extracted with ethyl acetate (2×30 ml). Ethyl acetate layer was dried over Na₂SO₄. Filtered, concentrated and purified by column chromatography using hexane-ethyl acetate (100-200 silica gel) to give the desired compound as a yellow solid. Yield=amount: 274 mg; 25%. ¹H NMR (400 MHz, DMSO-d₆): δ (ppm) 13.14 (s, 1H), 8.49 (s, 1H), 7.99 (d, 1H), 7.90 (d, 1H), 7.81 (s, 1H), 7.62 (t, 1H), 7.48 (t, 1H), 3.04 (q, 2H), 1.32 (t, 3H).

Intermediate 3: Synthesis of
7-ethylsulfanylisoquinoline-6-carboxylic acid

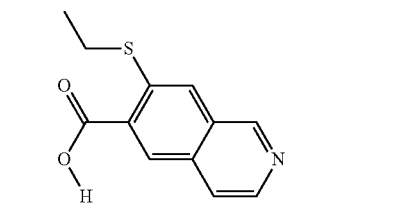 [SMILES: CCSc1cc2cnccc2cc1C(=O)O]

Step A: methyl 7-fluoroisoquinoline-6-carboxylate

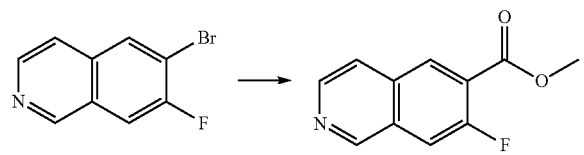

In an autoclave, 6-bromo-7-fluoroisoquinoline (commercially available or synthesized by analogy with WO08077553, 0.452 mg), Bis(triphenylphoshine) palladuim dichloride (71.0 mg) and triethylamine (404.8 mg) were added to methanol (40 mL). Then, the inert atmosphere of autoclave was replaced by CO and the pressure in the vessel was 20 bar. The autoclave was heated to 80° C. for 15 h. The solvent was evaporated and the residue was dissolved in ethyl acetate. The organic solution was washed with brine, dried and concentrated under vacuum. The residue was purified by column chromatography using i-hexane/ethyl 2:1 to give the desired compound (314 mg, 76.5% yield). $^1$H NMR (400 MHz, CDCl$_3$) δ ppm 9.27 (s, 1H); 8.60 (d, 1H); 8.50 (d, 1H); 7.73 (d, 1H); 7.68 (d, 1H); 4.02 (s, t).

Step B: methyl
7-ethylsulfanylisoquinoline-6-carboxylate

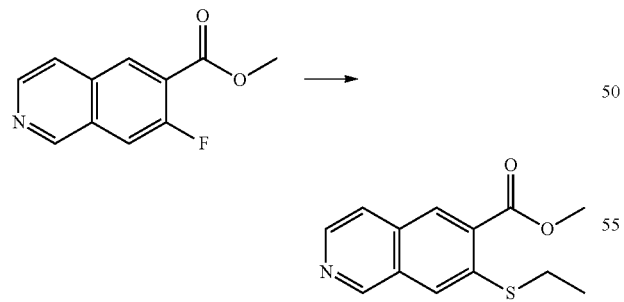

The mixture of methyl 7-fluoroisoquinoline-6-carboxylate (324.0 mg), sodium ethanethiolate (162.5 mg) and DMF (3 mL) was stirred at ambient temperature overnight. The solvent was evaporated after addition of toluene. The residue was dissolved in ethyl acetate and washed with water, dried and evaporated under vacuum. The crude product was purified column chromatography using hexane/ethyl 1:2 to give the desired compound (235 mg, 60.1% yield). $^1$H NMR (400 MHz, CDCl$_3$) δ ppm 9.21 (s, 1H); 8.52 (d, 1H); 8.42 (s, 1H); 7.76 (s, 1H); 7.64 (d, 1H); 4.00 (s, t); 3.10 (q, 2H); 1.46 (t, 3H).

Step C: 7-ethylsulfanylisoquinoline-6-carboxylic acid

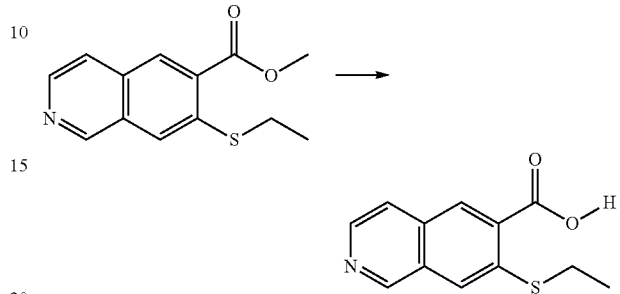

To a solution of methyl 7-ethylsulfanylisoquinoline-6-carboxylate (1115.41 mg), in a mixture of water (2 mL) and methanol (20 mL), was added sodium hydroxide (225.5 mg) at ambient temperature. The solution was stirred overnight at ambient temperature. The solvent was evaporated and, after addition of water, the organic phase was washed with ethyl acetate. The aqueous layer was acidified with diluted hydrochloric acid (pH 4-5) until precipitation of the desired product. The yellow precipitate was filtered off and dried under vacuum and used without extra purification for the next step.
$^1$H NMR (400 MHz, CDCl$_3$) δ ppm 9.69 (s, 1H); 8.68 (d, 1H); 8.61 (d, 1H); 8.36 (2d, 2H); 3.13 (q, 2H); 1.37 (t, 3H).

Intermediate 4: Synthesis of
5-chloro-3-ethylsulfanyl-quinoline-2-carboxylic acid

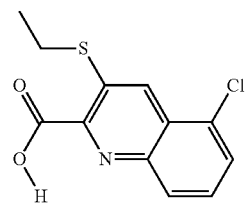 [SMILES: CCSc1cc2c(Cl)cccc2nc1C(=O)O]

Step A: methyl
3-amino-5-chloro-quinoline-2-carboxylate

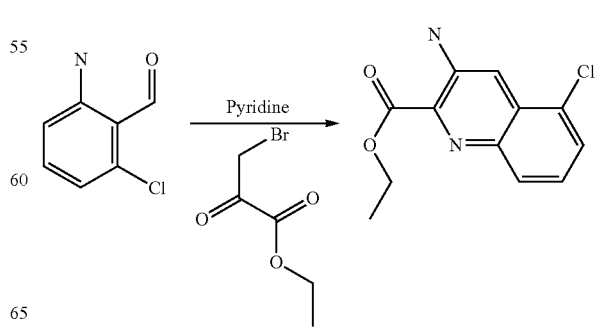

The methyl 3-amino-5-chloro-quinoline-2-carboxylate was synthesised using a similar protocol as described for the Intermediate 7 (Step A). $^1$H NMR (300 MHz, CDCl3) ppm 7.988 (dd, 1H); 7.725 (d, 1H); 7.546 (dd, 1H); 7.341 (dd, 1H); 5.752 (broad s, 2H); 4.556 (q, 2H); 1.534 (t, 3H).

Step B: methyl 5-chloro-3-ethylsulfanyl-quinoline-2-carboxylate

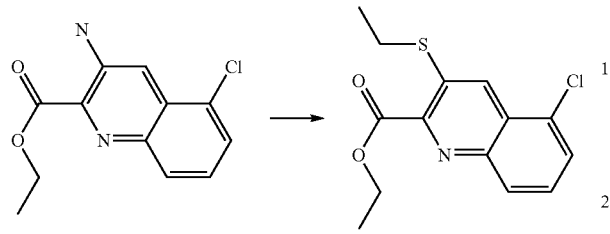

The ethyl 5-chloro-3-ethylsulfanyl-quinoline-2-carboxylate was synthesised using a similar protocol as described for the intermediate 1 (step A): $^1$H NMR (300 MHz, CDCl3) ppm 8.441 (s, 1H); 8.073 (dd, 1H); 7.663 (d, 1H); 7.590 (dd, 1H); 4.562 (q, 2H); 3.101 (q, 2H); 1.493 (t, 3H); 1.450 (t, 3H).

Step C: 5-chloro-3-ethylsulfanyl-quinoline-2-carboxylic acid

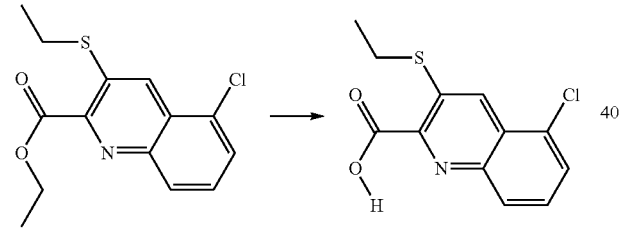

The 5-chloro-3-ethylsulfanyl-quinoline-2-carboxylic acid was synthesised using a similar protocol as described for the Intermediate 7 (Step C): $^1$H NMR (300 MHz, DMSO) ppm 8.376 (s, 1H); 8.040 (d, 1H); 7.895 (dd, 1H); 7.753 (dd, 1H); 3.157 (q, 2H); 1.333 (t, 3H).

Intermediate 5: Synthesis of 5-bromo-3-ethylsulfanyl-quinoline-2-carboxylic acid

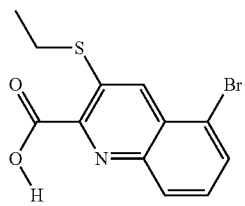 [SMILES: CCSc1cc2c(Br)cccc2nc1C(=O)O]

Step A: ethyl 3-amino-5-bromo-quinoline-2-carboxylate

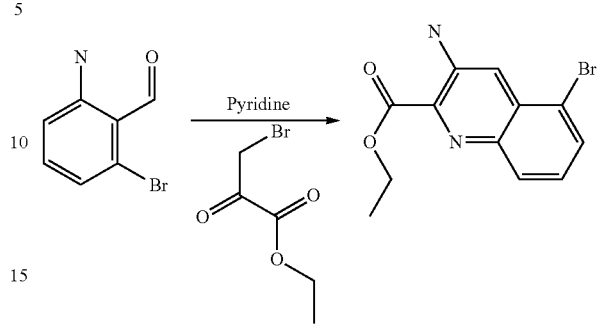

The ethyl 3-amino-5-bromo-quinoline-2-carboxylate was synthesised using a similar protocol as described for the Intermediate 7 (Step A). $^1$H NMR (300 MHz, CDCl$_3$) δ ppm 8.03 (dd, 1H); 7.75 (dd, 1H); 7.70 (d, 1H); 7.30 (dd, 1H); 5.76 (sb, 2H); 4.56 (q, 2H); 1.511 (t, 3H).

Step B: ethyl 5-bromo-3-ethylsulfanyl-quinoline-2-carboxylate

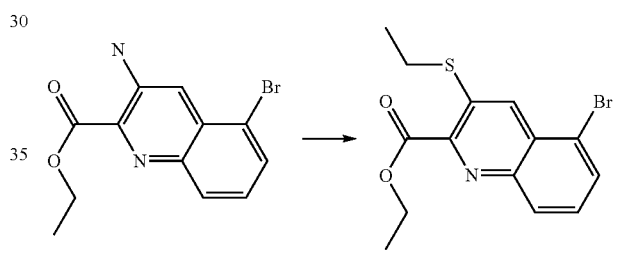

The ethyl 5-bromo-3-ethylsulfanyl-quinoline-2-carboxylate was synthesised using a similar protocol as described for the intermediate 1 (step A): $^1$H NMR (300 MHz, CDCl3) ppm 8.41 (s, 1H); 8.12 (dd, 1H); 7.88 (dd, 1H); 7.53 (dd, 1H); 4.56 (q, 2H), 4.56 (q, 2H); 1.51 (m, 6H).

Step C: 5-bromo-3-ethylsulfanyl-quinoline-2-carboxylic acid

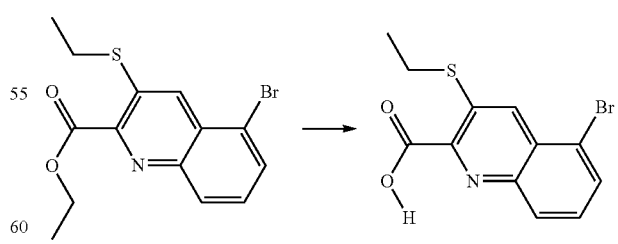

The 5-bromo-3-ethylsulfanyl-quinoline-2-carboxylic acid was synthesised using a similar protocol as described for the Intermediate 7 (Step C): $^1$H NMR (300 MHz, DMSO) ppm 8.324 (s, 1H); 8.077 (d, 1H); 8.054 (d, 1H); 7.690 (dd, 1H); 3.146 (q, 2H); 1.347 (t, 3H).

Intermediate 6: Synthesis of 6-chloro-3-ethylsulfanyl-quinoline-2-carboxylic acid

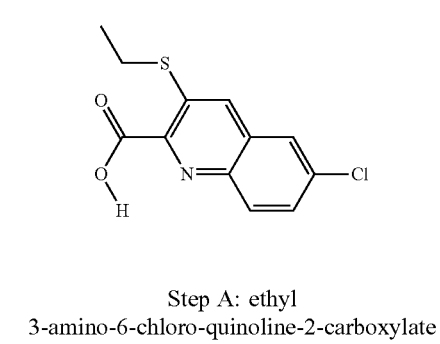

Step A: ethyl 3-amino-6-chloro-quinoline-2-carboxylate

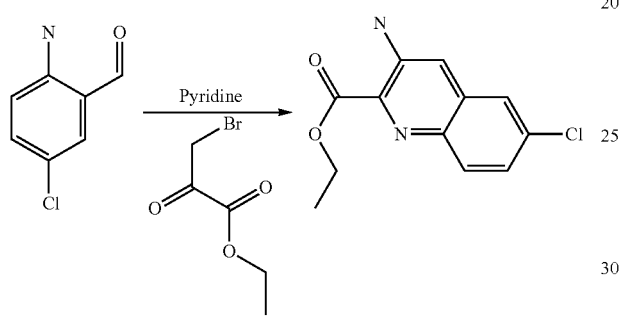

The ethyl 3-amino-6-chloro-quinoline-2-carboxylate was synthesised using a similar protocol as described for the Intermediate 7 (Step A). $^1$H NMR (300 MHz, CDCl$_3$) δ ppm 7.98 (d, 1H); 7.54 (d, 1H); 7.35 (dd, 1H); 7.24 (s, 1H); 5.67 (sb, 2H), 4.54 (q, 2H); 1.50 (t, 3H).

Step B: ethyl 6-chloro-3-ethylsulfanyl-quinoline-2-carboxylate

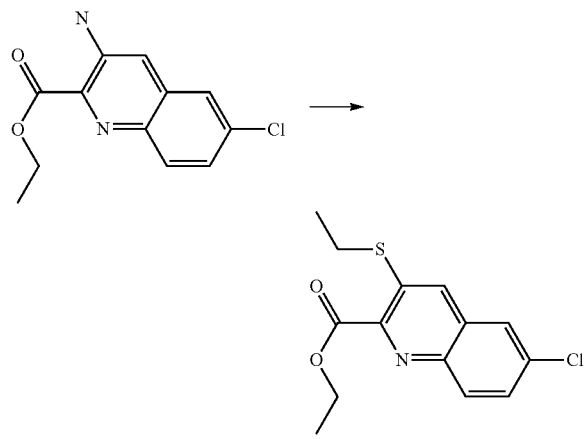

The ethyl 6-chloro-3-ethylsulfanyl-quinoline-2-carboxylate was synthesised using a similar protocol as described for the intermediate 1 (step A): $^1$H NMR (300 MHz, DMSO) ppm 8.45 (s, 1H); 8.14 (d, 1H); 8.05 (d, 1H); 8.77 (dd, 1H); 4.42 (q, 2H); 3.11 (q, 2H); 1.384-1.276 (m, 6H).

Step C: 6-Chloro-3-ethylsulfanyl-quinoline-2-carboxylic acid

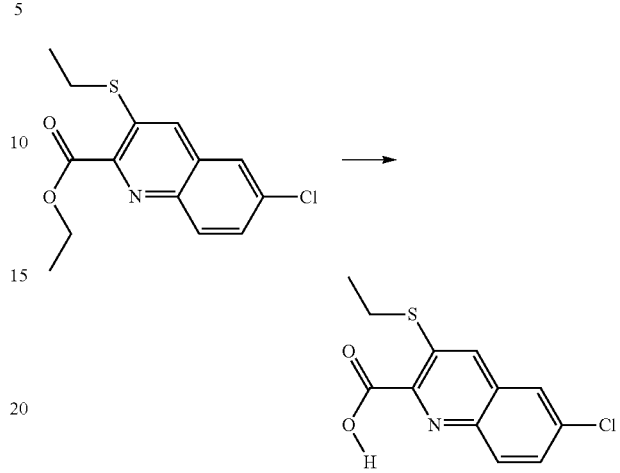

The 6-Chloro-3-ethylsulfanyl-quinoline-2-carboxylic acid was synthesised using a similar protocol as described for the Intermediate 7 (Step C): $^1$H NMR (300 MHz, DMSO) ppm 13.72 (broad s, 1H); 8.40 (s, 1H); 8.13 (d, 1H); 8.04 (d, 1H); 7.75 (dd, 1H); 3.09 (q, 2H); 1.31 (t, 3H).

Intermediate 7: Synthesis of 6-bromo-3-ethylsulfanyl-quinoline-2-carboxylic acid

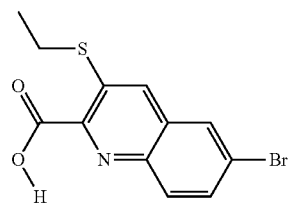 [SMILES: CCSc1cc2cc(Br)ccc2nc1C(=O)O]

Step A: ethyl 3-amino-6-bromo-quinoline-2-carboxylate

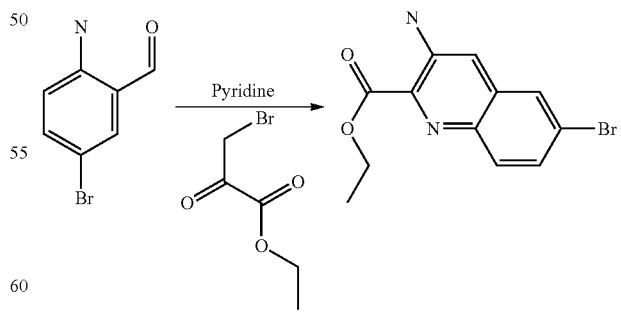

To a mixture of pyridine (415 mg, 0.40 mL, 5.25 mmol) in 14.5 mL of EtOH was slowly added ethyl bromopyruvate (1084 mg, 0.69 mL, 5 mmol) in EtOH (10 mL) dropwise over 30 min. The resulting mixture was heated at 60-70° C. for one hour and cooled to ambient temperature. 5-Bromo- 2-aminobenzaldehyde (990 mg, 4.95 mmol, 1 eq.) and pyridine (1 mL) were added and after heating at reflux for 5 h, pyrrolidine (838 mg, 1.0 mL, 11.78 mmol, 2.38 eq.) was added. The resulting mixture was heated for an additional 2 h at reflux. The reaction mixture was concentrated and the residue was chromatographed (ethyl acetate/hexanes 1:3) to give the desired product (719 mg, 49% yield). $^1$H NMR (300 MHz, CDCl3) ppm 7.91 (d, 1H); 774 (d, 1H); 7.48 (dd, 1H); 7.25 (d, 1H); 5.67 (broad s, 2H); 4.55 (q, 2H); 1.53 (t, 3H).

Step B: ethyl 6-bromo-3-ethylsulfanyl-quinoline-2-carboxylate

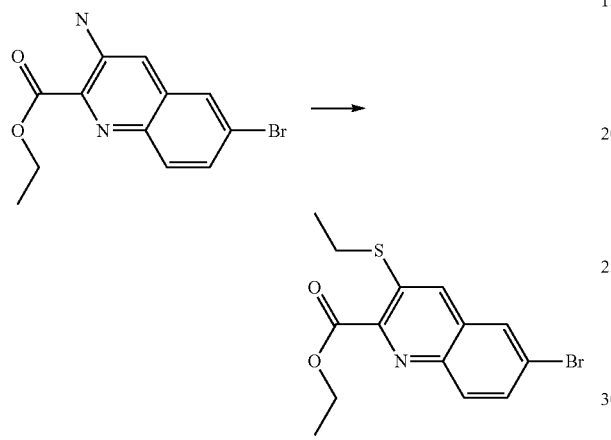

The ethyl 6-bromo-3-ethylsulfanyl-quinoline-2-carboxylate was synthesised using a similar protocol as described for the intermediate 1 (step A) and used without extra purification: $^1$H NMR (300 MHz, CDCl$_3$) ppm 8.01 (d, 1H), 7.93 (d, 1H), 7.73 (dd, 1H), 4.55 (q, 2H), 3.03 (q, 2H); 1.39-1.51 (m, 6H).

Step C: 6-bromo-3-ethylsulfanyl-quinoline-2-carboxylic acid

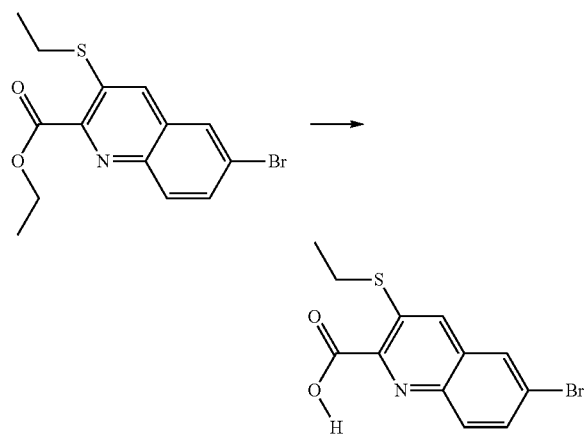

To stirred solution of compound ethyl 6-bromo-3-ethylsulfanyl-quinoline-2-carboxylate (351 mg, 1.03 mmol) in THF (6 ml) was added aqueous solution of NaOH (1 M, 2.1 mL; 2.1 eq.) and the reaction mixture was stirred at ambient temperature for 4 hours. After completion of the reaction, the reaction mixture was diluted with water (15 mL) and extracted with ethyl acetate (2×15 mL). The water phase was then acidified to pH=4 by 1 M HCl solution and extracted with ethyl acetate (3×20 ml). Organic layer was dried over sodium sulfate, filtered and concentrated under reduced pressure to give the title product (310 mg, 96% yield). $^1$H NMR (300 MHz, DMSO) ppm 13.75 (broad s, 1H); 8.40 (s, 1H); 8.29 (d, 1H); 7.96 (d, 1H); 7.86. (dd, 1H); 3.09 (q, 2H); 1.310 (t, 3H).

Intermediate 8: Synthesis of 6-ethylsulfanyl-1-methyl-2-(trifluoromethyl)benzimidazole-5-carboxylic acid

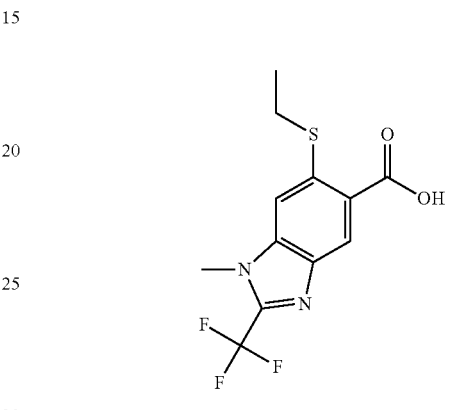

Step A: Synthesis of 4-chloro-2-ethylsulfanyl-5-nitro-benzoic acid

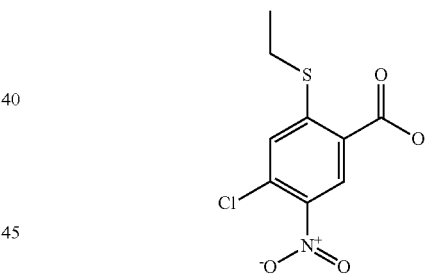

To a solution of 4-chloro-2-fluoro-5-nitro-benzoic acid (20 g, 91.095 mmol, commercially available) in 1-Methyl-2-pyrrolidone (250 mL) at 90° C. was added sodium t-butoxide (9.6302 g, 100.20 mmol). After 10 min ethylsulfanylsodium (9.366 g, 100.20 mmol) was added.

The reaction was stirred at 90° C. for two hours. The conversion is complete, two products were formed. The reaction mixture was poured into one liter of water and pH was acidified by addition of hydrochloride acid conc. (37%) and precipitate was formed. Filtration of the solid gave the mixture of two products. Filtrate was allowed to stand. The solid was suspended in ethyl ether and filtered. The solid (pure) was identified as the bis-ethylsulfanyl product. The filtrate was concentration under vacuum to give 4-chloro-2-ethylsulfanyl-5-nitro-benzoic acid (8.9 g, 34 mmol, 37% Yield). LC-MS (Method A): RT 1.00 (260, MH$^-$) (262, MH$^+$).

$^1$H NMR (300 MHz, CDCl$_3$) ppm 13.84 (s, 1H) 8.52 (s, 1H); 7.6 (s, 1H); 3.09 (q, 2H); 1.3 (t, 3H).

Step B: Synthesis of 2-ethylsulfanyl-4-(methylamino)-5-nitro-benzoic acid

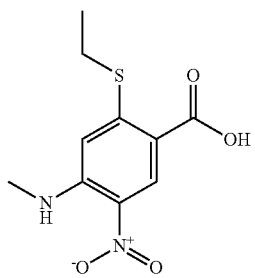

To a solution of 4-chloro-2-ethylsulfanyl-5-nitro-benzoic acid (8.9 g, 34 mmol) in tetrahydrofuran (20 mL, 244 mmol) was added gently methylamine (2 mol/L) in tetrahydrofuran (100 mL, 200 mmol). The mixture was stirred overnight at ambient temperature. Only a few conversions were observed. The suspension was transferred in an autoclave, 30 mL of methylamine 2N was added, and the reaction was stirred at 80° C. for five hours. The reaction is not complete and 20 mL more of 2N methylamine was added then the reaction was stirred in an autoclave over week end. Reaction is finished, and reaction mixture was concentrated under vacuum. Solids were taken up in water and basified with sodium hydroxide 1 N, then extracted with ethyl acetate. The water phase was acidified with hydrochloride acid conc. 37% and extracted with ethyl acetate. All organic layers are combined and were dried on magnesium sulfate, and concentrated on vacuum. The residue was then purified by Flash Chromatography to give 2-ethylsulfanyl-4-(methylamino)-5-nitro-benzoic acid (3.95 g, 15.4 mmol, 45% Yield) as a yellow-brownish solid. LC-MS (Method A): RT 1.04 (257, MH$^+$).

$^1$H NMR (300 MHz, CDCl$_3$) ppm 12.87 (s, 1H) 8.68 (s, 1H); 6.55 (s, 1H); 3.05 (s, 3H); 3.00 (q, 2H) 1.33 (t, 3H).

Step C: Synthesis of 6-ethylsulfanyl-1-methyl-2-(trifluoromethyl)benzimidazole-5-carboxylic acid

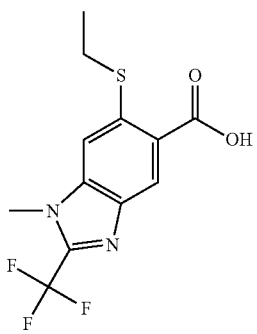 [SMILES: CCSc1cc2c(cc1C(=O)O)nc(C(F)(F)F)n2C]

To a solution of 2-ethylsulfanyl-4-(methylamino)-5-nitro-benzoic acid (0.300 g, 1.17 mmol) in 2,2,2-trifluoroacetic acid (10 mL, 129 mmol) at 0° C., zinc (0.260 g, 3.98 mmol) was added and cooling bath was removed. After 30 min, reduction is complete according to LC/MS; a few cyclized product was observed. The brown solution was then heated at 70° C. to cyclize the di-amino product. After one hour LC/MS showed completion of the cyclisation. Reaction mixture was concentrated to the half, poured into water and extracted with ethyl acetate. Organic phase was washed with water and brine, dried over magnesium sulfate and concentrated under vacuum.

Residue was purified by flash chromatography to give 6-ethylsulfanyl-1-methyl-2-(trifluoromethyl)benzimidazole-5-carboxylic acid (0.14 g, 0.46 mmol, 39.3% Yield).

LC-MS (Method A): RT 1.06 (303, MH$^-$) (305, MH$^+$).

$^1$H NMR (300 MHz, CDCl$_3$) ppm 13.03 (s, 1H) 8.30 (s, 1H); 7.64 (s, 1H); 4.00 (s, 3H); 3.06 (q, 2H) 1.32 (t, 3H).

Intermediate 9: Preparation of methyl 5-bromo-3-ethylsulfanyl-pyridine-2-carboxylate

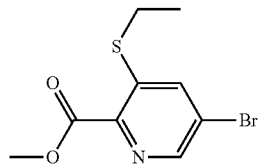

To a solution of methyl 5-bromo-3-chloro-pyridine-2-carboxylate (0.100 g, 0.399 mmol) (commercial product) in THF, stirred at 0° C., was added sodium ethanolate (0.034 g, 0.399 mmol). After 1 hour at that temperature, the ice bath was removed and stirring was continued for 20 hours. The reaction mixture was then poured onto water (15 ml) and extracted twice with EtOAc. The combined organic phases were dried over sodium sulfate and the solvent was removed in vacuo. The residue was submitted to flash chromatography over silica gel and the selected fractions evaporated to yield methyl 5-bromo-3-ethylsulfanyl-pyridine-2-carboxylate as a colorless solid.

LCMS (method 1): 276, 278 (M+H); retention time: 0.92 min.

$^1$H NMR (400 MHz, CDCl$_3$) δ ppm: 8.46 (s, 1H); 7.79 (s, 1H); 4.00 (s, 3H); 2.94 (q, 2H); 1.42 (t, 3H).

Intermediate 10: Synthesis of 6-ethylsulfonyl-1-methyl-2-(trifluoromethyl)imidazo[4,5-b]pyridine-5-carboxylic acid

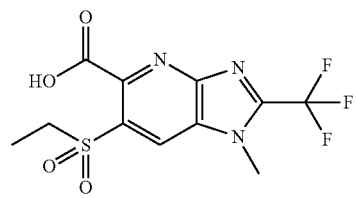 [SMILES: CCS(=O)(=O)c1cc2c(nc1C(=O)O)nc(C(F)(F)F)n2C]

Step A: Synthesis of methyl 5-[(2,4-dimethoxyphenyl)methylamino]-3-ethylsulfanyl-pyridine-2-carboxylate

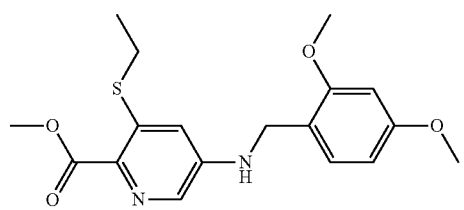

Methyl 5-bromo-3-ethylsulfanyl-pyridine-2-carboxylate (Intermediate 9, 5 mmol, 1380.75 mg) was dissolved in dried toluene (35 ml) and cesium carbonate (7.5 mmol) was then added. The mixture was degassed with argon and then tris(dibenzylideneacetone)dipalladium(0) (0.11 mmol), 2,2'-bis(diphénylphosphino)-1,1'-binaphtyle (0.2 mmol) and 2,4-Dimethoxybenzylamine (5 mmol) were added.

The mixture was stirred under argon at 105° C. (bath). The dark violet color of the mixture changed to pale yellow within a 15 min. After 20 h, the reaction was cooled and the solvent was removed under reduced pressure. The residue was purified on 50 g of silica gel, eluent 50% ethyl acetate in hexane, then ethyl acetate.

$^1$H NMR (300 MHz, CDCl$_3$) δ ppm 7.84 (d, 1H); 7.15 (d, 1H); 6.68 (d, 1H); 6.49-6.42 (m, 2H); 4.63 (t, 1H); 4.32 (d, 2H); 3.93 (s, 3H); 3.84 (s, 3H); 3.80 (s, 3H); 2.83 (q, 2H); 1.36 (t, 3H).

Step B: Synthesis of methyl 5-amino-3-ethylsulfanyl-pyridine-2-carboxylate

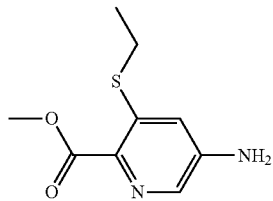

Methyl 5-[(2,4-dimethoxyphenyl)methylamino]-3-ethylsulfanyl-pyridine-2-carboxylate (3.31 mmol, 1.2 g) was dissolved in dichloromethane (20 ml) at ambient temperature and trifluoroacetic acid (3.31 mmol) was then added. The orange-red solution was stirred at ambient temperature for 5 h. The volatiles were removed under reduced pressure. The residue was alkalized with saturated solution of NaHCO3 and extracted with ethyl acetate. The organic phase was separated, dried and concentrated. The residue was purified on 50 g of silica gel, eluent ethyl acetate to give a pale orange solid. (530 mg, 75%)

$^1$H NMR (300 MHz, CDCl$_3$) δ ppm 7.88 (d, 1H); 6.8 (d, 1H); 4.2 (s, 2H); 3.9 (s, 3H); 2.83 (q, 2H); 1.36 (t, 3H).

Step C: Synthesis of methyl 5-amino-6-bromo-3-ethylsulfanyl-pyridine-2-carboxylate

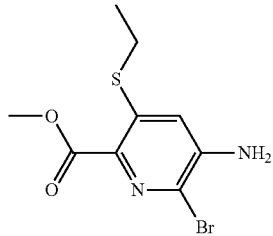

Methyl 5-amino-3-ethylsulfanyl-pyridine-2-carboxylate (0.93 mmol) was dissolved in acetic acid glacial (10 ml) and then anhydrous sodium acetate (1.22 mmol) was added. Then bromine (0.93 mmol) was added dropwise at ambient temperature. The orange mixture was stirred at ambient temperature for 2 hours. TLC showed no more starting material. The volatiles were removed under reduced pressure and the residue was dissolved in ethyl acetate. The organic phase was washed with sodium hydrogen carbonate solution followed by sodium thiosulfate solution and finally with water. The organic phase was dried and concentrated. The residue was purified on 25 g of silica gel, eluent 50% ethyl acetate in hexane to give white solid (250 mg, 92%).

$^1$H NMR (300 MHz, CDCl$_3$) ppm 6.83 (d, 1H); 4.57 (s, 2H); 3.93 (s, 3H); 2.85 (q, 2H); 1.39 (t, 3H).

Step D: Synthesis of methyl 6-bromo-3-ethylsulfanyl-5-[(2,2,2-trifluoroacetyl)amino]pyridine-2-carboxylate

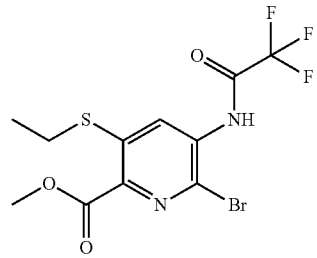 [SMILES: CCSc1cc(NC(=O)C(F)(F)F)c(Br)nc1C(=O)OC]

Methyl 5-amino-6-bromo-3-ethylsulfanyl-pyridine-2-carboxylate (0.82 mmol) was dissolved in dried tetrahydrofuran (10 ml) at ambient temperature under argon and sodium carbonate was then added followed by trifluoroacetic anhydride (0.82 mmol). The suspension was stirred at ambient temperature for 16 hours. The volatiles were removed under reduced pressure and the residue was dissolved in ethyl acetate. The solution was washed with water; the organic phase was dried and concentrated. The residue was purified on 40 g of silica gel, eluent hexane/ethyl acetate (2:1) to give a white solid.

$^1$H NMR (300 MHz, CDCl$_3$) ppm 8.76 (s, 1H); 8.60 (s, 1H); 3.99 (s, 3H); 3.00 (q, 2H); 1.42 (t, 3H).

Step E: Synthesis of methyl 6-bromo-3-ethylsulfanyl-5-[methyl-(2,2,2-trifluoroacetyl)amino]pyridine-2-carboxylate

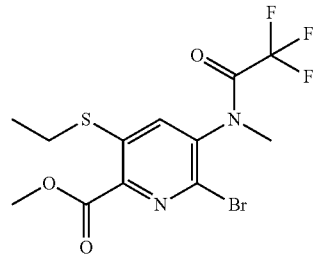 [SMILES: CCSc1cc(N(C)C(=O)C(F)(F)F)c(Br)nc1C(=O)OC]

Methyl 6-bromo-3-ethylsulfanyl-5-[(2,2,2-trifluoroacetyl)amino]pyridine-2-carboxylate (0.3 mmol, 116 mg) was dissolved in N,N-Dimethylformamide (1.2 ml) at ambient temperature under argon. Then potassium carbonate (0.72 mmol) was added followed by methyl iodine (0.3 mmol). The mixture was stirred at ambient temperature for 40 h, then diluted with water and extracted with ethyl acetate. The organic phase was washed with water, dried and concentrated. The residue was purified on 15 g of silica gel, eluent dichloromethane to give a white solid.

$^1$H NMR (300 MHz, CDCl$_3$) ppm 7.56 (s, 1H); 4.00 (s, 3H); 3.35 (s, 3H) 2.92 (q, 2H); 1.42 (t, 3H).

Step F: Synthesis of methyl 6-bromo-3-ethylsulfonyl-5-[methyl-(2,2,2-trifluoroacetyl)amino]pyridine-2-carboxylate

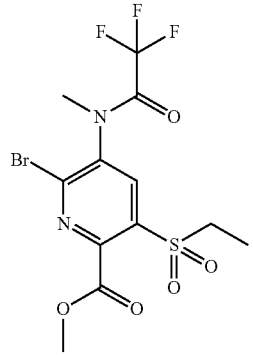 [SMILES: CCS(=O)(=O)c1cc(N(C)C(=O)C(F)(F)F)c(Br)nc1C(=O)OC]

To a solution of Methyl 6-bromo-3-ethylsulfanyl-5-[methyl-(2,2,2-trifluoroacetyl)amino]pyridine-2-carboxylate (200 mg) in dichloromethane (7 mL) was added meta-chloroperbenzoic acid (253 mg). The yellow solution was stirred at ambient temperature for an hour. After this time, the reaction mixture was diluted with aqueous sodium thiosulfate solution and extracted with dichloromethane, the combined organic fractions washed with sodium carbonate, dried over magnesium sulfate, and concentrated in vacuum. The crude product was purified with silica gel, eluent 50% of ethyl acetate in hexane to give colorless resin.

$^1$H NMR (300 MHz, CDCl$_3$) ppm 8.24 (d, 1H); 4.06 (s, 3H); 3.70 (q, 2H); 3.5 (s, 3H); 1.35 (t, 3H).

Step G: Synthesis of methyl 6-ethylsulfonyl-1-methyl-2-(trifluoromethyl)imidazo[4,5-b]pyridine-5-carboxylate

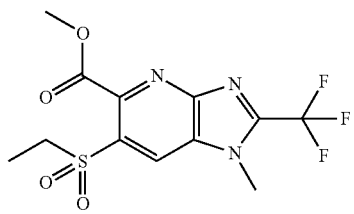 [SMILES: CCS(=O)(=O)c1cc2c(nc1C(=O)OC)nc(C(F)(F)F)n2C]

To a solution of methyl 6-bromo-3-ethylsulfonyl-5-[methyl-(2,2,2-trifluoroacetyl)amino]pyridine-2-carboxylate (160 mg, 0.37 mmol) in DMSO (8 ml) under argon, sodium trinitride (52 mg, 0.77 mmol) followed by copper Iodide (75 mg, 0.38 mmol) were added. The stirred mixture was degassed with argon and then N,N'-Dimethylethylenediamine (57.4 mg, 0.65 mmol) was added. The mixture was vigorously stirred while heated at 120° C. for 53 min. The cooled mixture was further stirred with saturated solution of ammonium chloride (25 ml) and 25 ml of ethyl acetate for 30 min. Then the mixture was diluted with ethyl acetate (100 ml). The organic phase was washed with brine. The organic phase was dried, concentrated and the residue was purified on 10 g of silica gel, eluent 50% of ethyl acetate in hexane to give a colorless resin (20 mg, 15.4%).

$^1$H NMR (300 MHz, CDCl$_3$) ppm 8.56 (s, 1H); 4.11 (s, 3H); 4.06 (s, 3H); 3.65 (q, 2H); 1.37 (t, 3H).

Step H: Synthesis of 6-ethylsulfonyl-1-methyl-2-(trifluoromethyl)imidazo[4,5-b]pyridine-5-carboxylic acid

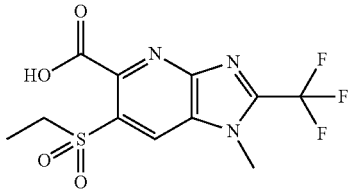 [SMILES: CCS(=O)(=O)c1cc2c(nc1C(=O)O)nc(C(F)(F)F)n2C]

To a solution of methyl 6-ethylsulfonyl-1-methyl-2-(trifluoromethyl)imidazo[4,5-b]pyridine-5-carboxylate in tetrahydrofuran (10 ml) at ambient temperature was added lithium hydroxide (26.46 mg, 0.63 mmol) followed by water (4 ml). The mixture was stirred at ambient temperature overnight. Evolution of reaction was followed by TLC, after a complete conversion of starting material the solvent was evaporated and the residue was dissolved in 30 ml of water. The solution was acidified with 1M hydrochloride acid to pH=3. The acid was extracted 3×50 ml of ethyl acetate. The collected extracts were dried and evaporated to dryness affording a pale solid.

$^1$H NMR (300 MHz, Acetone) ppm 8.86 (s, 1H); 4.31 (s, 3H); 3.63 (q, 2H); 1.29 (t, 3H).

Example P1: Preparation of 2-(3-ethylsulfanyl-2-naphthyl)-3-methyl-6-(trifluoromethyl)imidazo[4,5-b]pyridine (A1, 1.001)

(1.001)

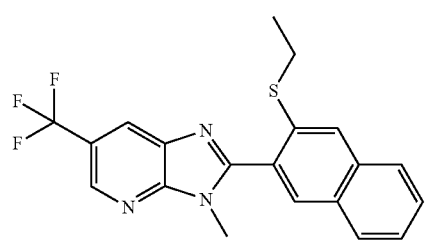

Step A: Preparation of 3-ethylsulfanyl-N-[2-(methylamino)-5-(trifluoromethyl)-3-pyridyl]naphthalene-2-carboxamide A1a

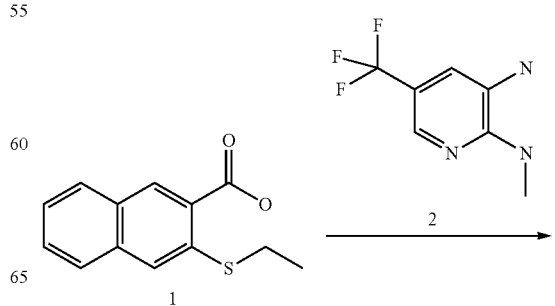

-continued

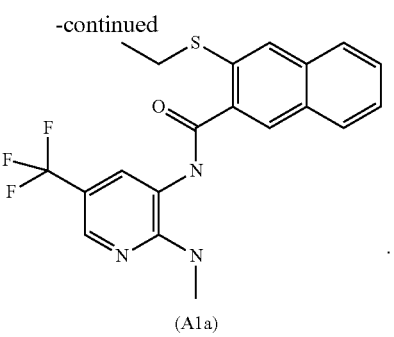

(A1a)

To a stirred solution of compound 1 (0.54 g, 2.96 mmol) in pyridine (7 ml) was added EDCI.HCl (0.68 g, 3.56 mmol) followed by the addition of compound 2 (0.68 g, 3.56 mmol). The total reaction mixture was stirred for 8 hours at 120° C. The reaction was monitored by TLC. After completion of the starting amine, reaction mixture was poured into water and extracted with ethyl acetate (25×2 mL). The combined organic layer was washed with water, brine and dried over $Na_2SO_4$. Filtered, concentrated and purified by column chromatography using hexane-ethyl acetate (100-200 silica gel) to give the desired compound as a white solid (amount: 360 mg; Yield=41%). $^1$H NMR (400 MHz, DMSO-$d_6$): δ (ppm) 9.87 (s, 1H), 8.29 (s, 2H), 7.96 (m, 4H), 7.59 (m, 2H), 6.87 (s, 1H), 3.08 (q, 2H), 2.85 (s, 3H), 1.29 (t, 3H).

Compound A4a 3-ethylsulfanyl-N-[2-(methylamino)-5-(trifluoromethyl)-3-pyridyl]quinoline-2-carboxamide) was prepared by the same method using 3-ethylsulfanylquinoline-2-carboxylic acid as starting material.

$^1$H NMR (400 MHz, CDCl$_3$): δ (ppm) 9.83 (s, 1H), 8.35 (s, 1H), 8.05 (m, 2H), 7.92 (s, 1H), 7.79 (d, 1H), 7.70 (m, 1H), 7.63 (m, 1H), 5.16 (s, 1H), 3.09-3.02 (m, 5H), 1.47 (t, 3H).

Step B: Preparation of 2-(3-ethylsulfanyl-2-naphthyl)-3-methyl-6-(trifluromethyl)imidazo[4,5-b]pyridine (A1, 1.001)

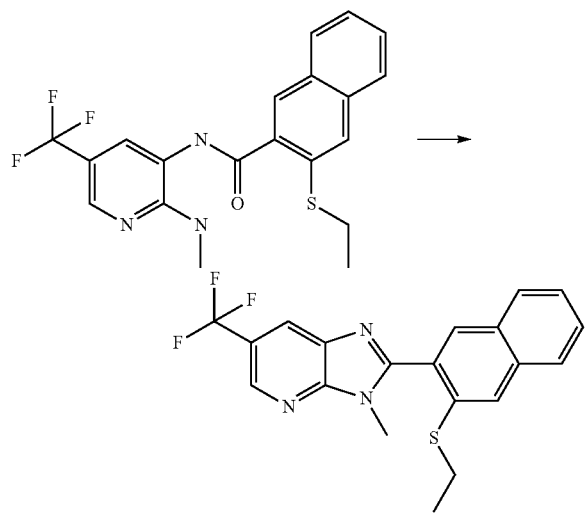

To a stirred solution of compound A1a (360 mg, 0.88 mmol) in xylene (5 ml) was added tosic acid (506 mg, 2.67 mmol) and the total reaction mixture was heated to 150° C. for 16 h. Reaction was monitored by TLC. After completion of the starting material, reaction mixture was diluted with ethyl acetate and washed with water (2×10 mL). Organic layer was dried over $Na_2SO_4$. Filtered, concentrated and purified by column chromatography using hexane-ethyl acetate (100-200 silica gel) to give the desired compound as a white solid (amount: 243 mg; Yield=71%). $^1$H NMR (400 MHz, CDCl$_3$): δ (ppm) 8.72 (s, 1H), 8.34 (s, 1H), 7.97 (s, 1H), 7.89 (s, 1H), 7.85 (m, 2H), 7.60 (m, 1H), 7.52 (m, 1H), 3.78 (s, 3H), 2.92 (q, 2H), 1.26 (t, 3H).

Compound A4 (1.004) from table A were prepared by the same method using A4a (Step A) as starting material. $^1$H NMR (400 MHz, CDCl$_3$): δ (ppm) 8.75 (s, 1H), 8.41 (s, 1H), 8.13-8.09 (m, 2H), 7.83 (d, 1H), 7.72 (m, 1H), 7.62 (m, 1H), 4.08 (s, 3H), 3.05 (q, 2H), 1.38 (t, 3H).

Example P2: Preparation of 2-(3-ethylsulfinyl-2-naphthyl)-3-methyl-6-(trifluoromethyl)imidazo[4,5-b]pyridine (A2, 1.002)

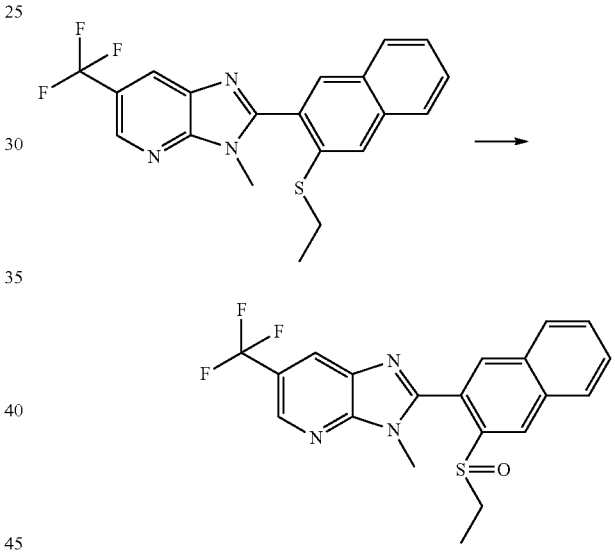

To a stirred solution of compound A1 (90 mg, 0.23 mmol) in CH$_2$Cl$_2$ (2 ml) was added m-CPBA (44 mg, 0.25 mmol) at RT. The reaction mixture was then stirred for 2 h. Reaction was monitored by TLC. After completion of the starting, the reaction mixture was quenched with saturated Na$_2$S2O3, NaHCO$_3$ and extracted with CH$_2$Cl$_2$ (10×2 mL). CH$_2$Cl$_2$ layer was dried over Na2SO4. Filtered, concentrated and the crude was triturated with pentane to give the desired compound as a white solid (amount: 71 mg; Yield=76%). $^1$H NMR (400 MHz, CDCl$_3$): δ (ppm) 8.80 (s, 1H), 8.70 (s, 1H), 8.32 (s, 1H), 8.11-8.08 (m, 2H), 7.99 (m, 1H), 7.71 (m, 2H), 3.92 (s, 3H), 3.37 (m, 1H), 2.91 (m, 1H), 1.27 (t, 3H).

Compound A5 (1.005) from table A were prepared by the same method using A4 (1.004) as starting material. $^1$H NMR (400 MHz, CDCl$_3$): δ (ppm) 9.11 (s, 1H), 8.78 (s, 1H), 8.37 (s, 1H), 8.25 (d, 1H), 8.07 (d, 1H), 7.90 (m, 1H), 7.74 (m, 1H), 4.5 (s, 3H), 3.73 (m, 1H), 3.07 (m, 1H), 1.47 (t, 3H).

Example P3: Preparation of 2-(3-ethylsulfonyl-2-naphthyl)-3-methyl-6-(trifluoromethyl)imidazo[4,5-b]pyridine (A3, 1.003)

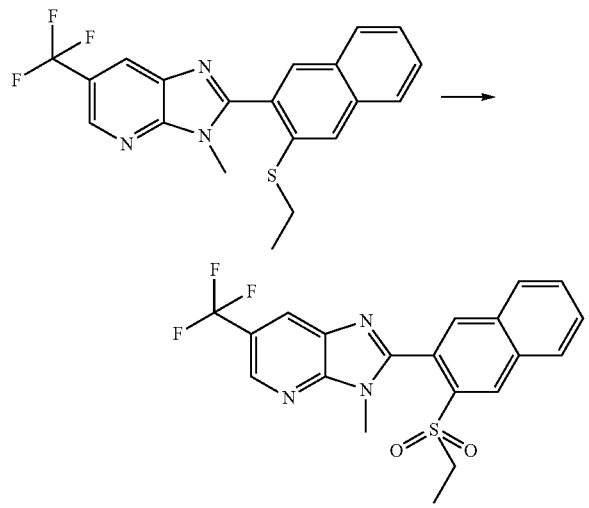

To a stirred solution of compound A1 (90 mg, 0.23 mmol) in CH$_2$Cl$_2$ (3 ml) was added m-CPBA (158 mg, 0.92 mmol) at ambient temperature. The reaction mixture was then stirred for 2 hours. Reaction was monitored by TLC. After completion of the starting, the reaction mixture was quenched with saturated Na$_2$S$_2$O$_3$ and NaHCO$_3$ and extracted with CH$_2$Cl$_2$ (20×2 ml). CH$_2$Cl$_2$ layer was dried over Na$_2$SO$_4$. Filtered, concentrated and the crude was triturated with pentane to give the desired compound as a white solid (amount: 80 mg; Yield=82%). $^1$H NMR (400 MHz, CDCl$_3$): δ (ppm) 8.75 (m, 2H), 8.29 (s, 1H), 8.14 (m, 1H), 8.03 (s, 1H), 7.98 (m, 1H), 7.79 (m, 2H), 3.74 (s, 3H), 3.45 (q, 2H), 1.26 (t, 3H).

In addition, compound A6 (1.006) from table A were prepared by the same method using A4 (1.004) as starting material. $^1$H NMR (400 MHz, CDCl$_3$): δ (ppm) 9.08 (s, 1H), 8.77 (s, 1H), 8.32 (s, 1H), 8.25 (d, 1H), 8.13 (d, 1H), 8.02 (t, 1H), 7.84 (t, 1H), 3.93 (s, 3H), 3.87 (q, 2H), 1.39 (t, 3H).

Example P4: Preparation of 2-[6-ethylsulfonyl-2-(trifluoromethyl)-3H-benzimidazol-5-yl]-3-methyl-6-(trifluoromethyl)imidazo[4,5-c]pyridine A7, 2-[6-ethylsulfonyl-3-methyl-2-(trifluoromethyl)benzimidazol-5-yl]-3-methyl-6-(trifluoromethyl)imidazo[4,5-c]pyridine A8 and 2-[6-ethylsulfonyl-1-methyl-2-(trifluoromethyl)benzimidazol-5-yl]-3-methyl-6-(trifluoromethyl)imidazo[4,5-c]pyridine A9

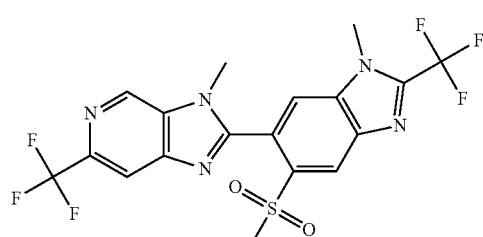
A7

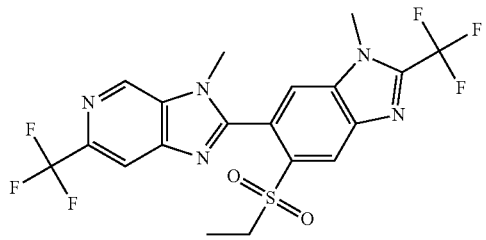
A8

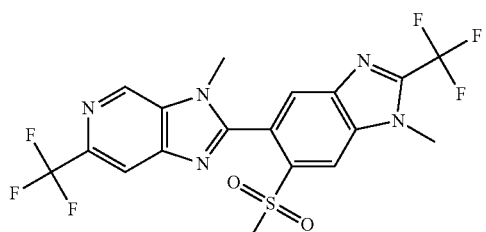
A9

Step A: Preparation of 3-ethylsulfonyl-4-[3-methyl-6-(trifluoromethyl)imidazo[4,5-c]pyridin-2-yl]aniline

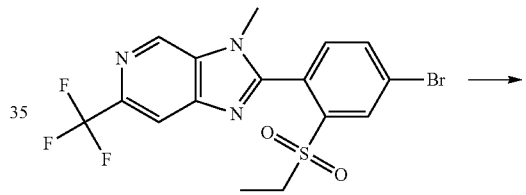

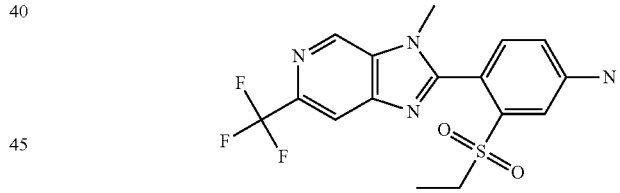

To a stirred solution of 2-(4-bromo-2-ethylsulfonyl-phenyl)-3-methyl-6-(trifluoromethyl)imidazo [4,5-c]pyridine (Prepared as described in WO 2015/000715, 471.71 mg) in dimethyl sulfoxide (12 mL) was added cooper iodine (220.0 mg) and sodium azide (140 mg). The stirred mixture was degassed with argon and then DMEDA (Dimethylethylenediamine, 164 mg) was added. The mixture was heated at 110° C. for 55 min., then cooled and stirred with a saturated solution of ammonium chloride for 30 min. Then the mixture was repeatedly extracted with ethyl acetate. The combined organic phases were washed with water, dried, concentrated under vacuum. The residue was subjected to column chromatography over silica gel (60 g), eluting with ethyl acetate. The selected fractions were evaporated to yield the title compound (49% yield): $^1$H NMR (300 MHz, acetone-D6) ppm 9.14 (s, 1H); 8.44 (d, 1H); 8.10 (d, 1H); 7.73 (d, 1H); 6.01 (brs, 2H); 3.93 (s, 3H); 3.79 (q, 2H); 1.27 (t, 3H).

Step B: Preparation of 5-ethylsulfonyl-2-iodo-4-[3-methyl-6-(trifluoromethyl)imidazo[4,5-c]pyridin-2-yl]aniline

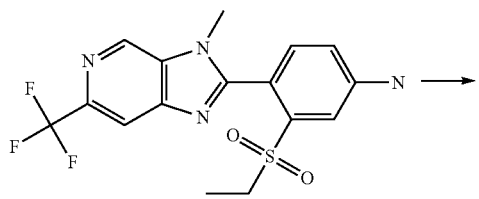

To a stirred solution of 3-ethylsulfonyl-4-[3-methyl-6-(trifluoromethyl)imidazo[4,5-c]pyridin-2-yl]aniline (99.94 mg) in acetic acid (3 mL) was added NIS (61.42 mg). The solution was stirred at ambient temperature overnight. Then, the solvent was removed under reduced pressure. The residue was dissolved in ethyl acetate, washed with Na₂CO₃ solution followed by water. The organic phase was dried, concentrated under vacuum. The residue was subjected to column chromatography over silica gel (15 g), eluting with ethyl acetate:hexane (1:1). The selected fractions were evaporated to yield the title compound (90.5% yield). $^1$H NMR (300 MHz, CDCl₃) ppm 8.91 (s, 1H); 8.06 (s, 1H); 7.79 (s, 1H); 7.43 (s, 1H); 4.79 (bs, 2H); 3.76 (s, 3H); 3.32 (q, 2H); 1.24 (t, 3H).

Step C: Preparation of N-[5-ethylsulfonyl-2-iodo-4-[3-methyl-6-(trifluoromethyl)imidazo[4,5-c]pyridin-2-yl]phenyl]-2,2,2-trifluoro-acetamide

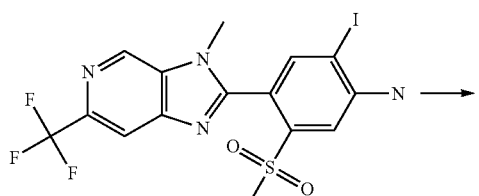

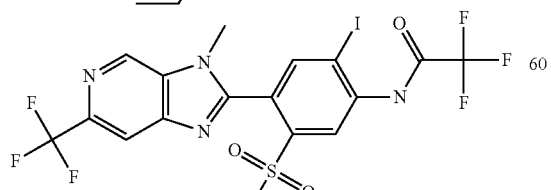

To a stirred solution of 5-ethylsulfonyl-2-iodo-4-[3-methyl-6-(trifluoromethyl)imidazo[4,5-c]pyridin-2-yl]aniline (387.8 mg) in dried THF (15 mL) was added Na2CO3 (128.1 mg) and trifluoroacetic anhydride (0.27 mL). The clear colorless solution was stirred at ambient temperature for 24 h. The volatiles were removed under reduced pressure. The residue was treated with a saturated solution of Na₂CO₃ and then extracted three times with ethyl acetate. The combinated organic phases were washed with water, dried and concentrated affording a white solid. The compound was used without extra purification in the next step. $^1$H NMR (300 MHz, CDCl₃) ppm 9.00 (s, 1H); 8.95 (s, 1H); 8.55 (bs, 1H); 8.09-8.07 (m, 2H); 3.78 (s, 3H); 3.26 (q, 2H); 1.27 (t, 3H).

Step D: Preparation of 2-[6-ethylsulfonyl-2-(trifluoromethyl)-3H-benzimidazol-5-yl]-3-methyl-6-(trifluoromethyl)imidazo[4,5-c]pyridine A7

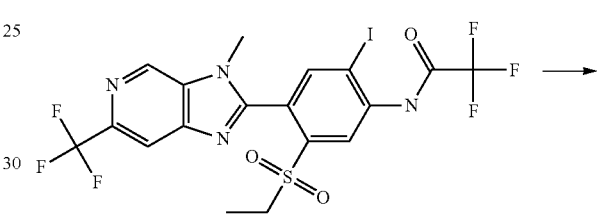

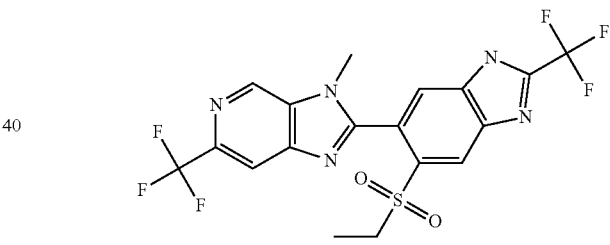

To a stirred solution of N-[5-ethylsulfonyl-2-iodo-4-[3-methyl-6-(trifluoromethyl)imidazo[4,5-c]pyridin-2-yl]phenyl]-2,2,2-trifluoro-acetamide (260.7 mg) in dimethyl sulfoxide (10 mL) was added cooper iodine (90 mg) and sodium azide (60.0 mg). The stirred mixture was degassed with argon and then DMEDA (Dimethylethylenediamine, 65.6 mg) was added. The mixture was heated at 110° C. for 55 min., then cooled and stirred with a saturated solution of ammonium chloride for 30 min. Then the mixture was repeatedly extracted with ethyl acetate. The combined organic phases were washed with water, dried, concentrated under vacuum. The residue was subjected to column chromatography over silica gel (60 g), eluting with ethyl acetate. The selected fractions were evaporated to yield the title compound (78% yield): $^1$H NMR (300 MHz, acetone d6) ppm 9.16 (s, 1H); 8.59 (s, 1H); 8.26 (s, 1H); 8.13 (s, 1H); 8.01 (s, 1H); 3.86 (s, 3H); 3.54 (m, 2H); 1.20 (t, 3H).

Step E: Preparation of 2-[6-ethylsulfonyl-3-methyl-2-(trifluoromethyl)benzimidazol-5-yl]-3-methyl-6-(trifluoromethyl)imidazo[4,5-c]pyridine A8 and 2-[6-ethylsulfonyl-1-methyl-2-(trifluoromethyl)benzimidazol-5-yl]-3-methyl-6-(trifluoromethyl)imidazo[4,5-c]pyridine A9

Example P4b: Alternative preparation of 2-[6-ethylsulfonyl-1-methyl-2-(trifluoromethyl)benzimidazol-5-yl]-3-methyl-6-(trifluoromethyl)imidazo[4,5-c]pyridine A9

Step A: Preparation of 6-ethylsulfanyl-1-methyl-N-[5-(methylamino)-2-(trifluoromethyl)-4-pyridyl]-2-(trifluoromethyl)benzimidazole-5-carboxamide and 6-ethylsulfanyl-1-methyl-N-[5-(methylamino)-2-(trifluoromethyl)-4-pyridyl]-2-(trifluoromethyl)benzimidazole-5-carboxamide

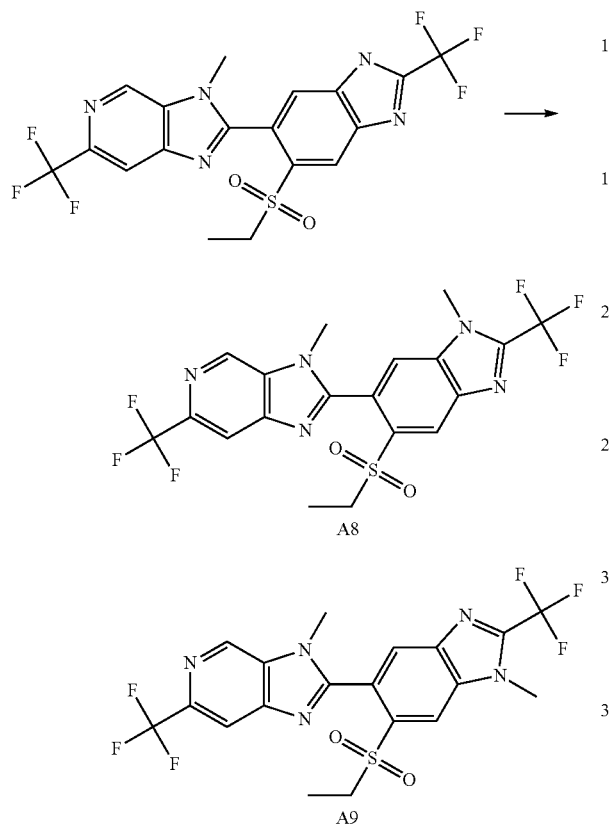

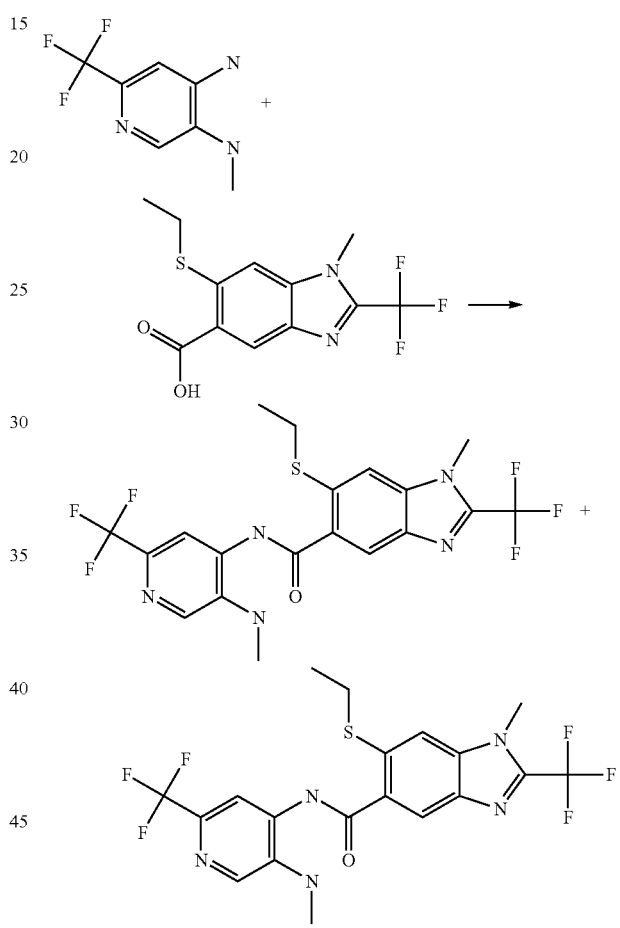

To a stirred solution of 2-[6-ethylsulfonyl-2-(trifluoromethyl)-3H-benzimidazol-5-yl]-3-methyl-6-(trifluoromethyl)imidazo[4,5-c]pyridine A7 (157.5 mg) in acetone (20 mL) was added K2CO3 (138 mg) and iodomethane (0.06 mL). The mixture was stirred at ambient temperature for 17 h. The volatiles were removed under reduced pressure. Then, the residue was dissolved in ethyl acetate, washed with water, dried and concentrated under vacuum. The residue was subjected to column chromatography over silica gel (60 g), eluting with ethyl acetate:hexane (1:1). The selected fractions were evaporated to yield 2-[6-ethylsulfonyl-3-methyl-2-(trifluoromethyl)benzimidazol-5-yl]-3-methyl-6-(trifluoromethyl)imidazo[4,5-c]pyridine A8 (43% yield) and 2-[6-ethylsulfonyl-1-methyl-2-(trifluoromethyl)benzimidazol-5-yl]-3-methyl-6-(trifluoromethyl)imidazo[4,5-c]pyridine A9 (40% yield). 2-[6-ethylsulfonyl-3-methyl-2-(trifluoromethyl)benzimidazol-5-yl]-3-methyl-6-(trifluoromethyl)imidazo[4,5-c]pyridine A9: $^1$H NMR (600 MHz, CDCl$_3$) δ ppm 1.28 (t, 3H) 3.51 (br s, 2H) 3.74 (s, 3H) 4.17 (s, 3H) 8.05 (s, 1H) 8.12 (s, 1H) 8.44 (s, 1H) 8.97 (s, 1H). 2-[6-ethylsulfonyl-1-methyl-2-(trifluoromethyl)benzimidazol-5-yl]-3-methyl-6-(trifluoromethyl)imidazo[4,5-c]pyridine A8: $^1$H NMR (600 MHz, CDCl$_3$) δ ppm 1.22 (t, 3H) 3.08-3.57 (m, 2H) 3.77 (s, 3H) 4.06 (s, 3H) 7.69 (s, 1H) 8.12 (s, 1H) 8.79 (s, 1H) 8.97 (s, 1H).

To a suspension of 6-ethylsulfanyl-1-methyl-2-(trifluoromethyl)benzimidazole-5-carboxylic acid (138 mg, Prepared previously) in dichloromethane (5 ml) was added one drop of N,N-dimethylformamide, followed by oxalyl chloride (1.8 equiv., 0.103 mL). After the end of gas evolution, the reaction mixture was in the form of a pale yellow solution. The latter was evaporated under reduced pressure at a bath temperature of 60° C. The residue formed dark red crystals of 5-bromo-5-bromo-3-ethylsulfanyl-benzothiophene-2-carboxylic chloride and the residue was redissolved in 6 ml of tetrahydrofuran. To a solution of N3-methyl-6-(trifluoromethyl)pyridine-3,4-diamine (85 mg, commercially available CAS 1643139-91-6) in ethyl acetate (5 ml) was added N,N-diethylethanamine (2.5 equiv., 0.157 mL) then the resulting solution was cooled with an ice bath, before slow addition of the previous acyl chloride solution. The resulting mixture was stirred 1 hour at ambient temperature. The solution was neutralized by addition of a saturated aqueous solution of sodium bicarbonate and the product was extracted twice with ethyl acetate. The organic solution was dried over sodium sulfate and evaporated under reduced pressure to yield the crude product. A mixture of 6-ethylsulfanyl-1-methyl-N-[5-(methylamino)-2-(trifluoromethyl)-4-pyridyl]-2-(trifluoromethyl)benzimidazole-5-carboxamide and 6-ethylsulfanyl-1-methyl-N-[5-(methylamino)-2-(trifluoromethyl)-4-pyridyl]-2-(trifluoromethyl)benzimidazole-5-carboxamide was obtained after column chromatography over silica gel, eluting with ethyl acetate/cyclohexane and used without extra purification. LC-MS (Method A): RT 0.95 (476, MH−) (478, MH+).

Step B: Preparation of 2-[6-ethylsulfanyl-1-methyl-2-(trifluoromethyl)benzimidazol-5-yl]-3-methyl-6-(trifluoromethyl)imidazo[4,5-c]pyridine A39

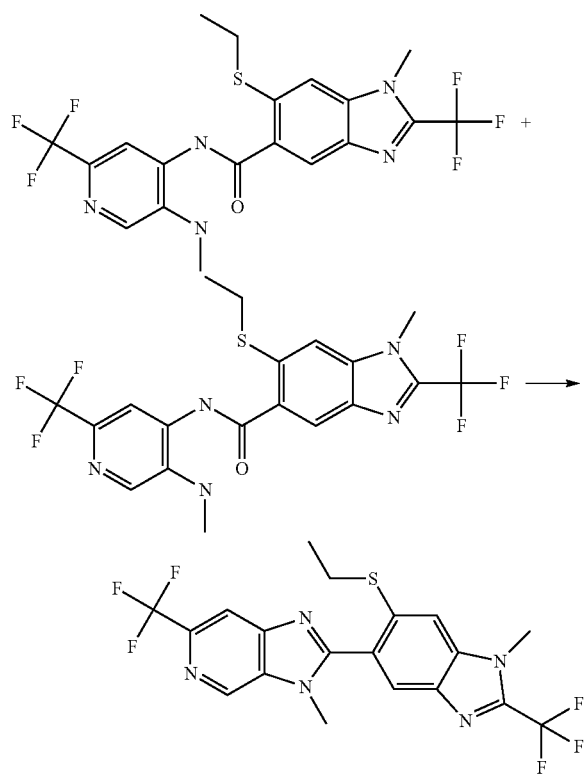

A mixture of 6-ethylsulfanyl-1-methyl-N-[5-(methylamino)-2-(trifluoromethyl)-4-pyridyl]-2-(trifluoromethyl)benzimidazole-5-carboxamide and 6-ethylsulfanyl-1-methyl-N-[5-(methylamino)-2-(trifluoromethyl)-4-pyridyl]-2-(trifluoromethyl)benzimidazole-5-carboxamide (0.16 g) in acetic acid (3.2 ml) was heated to 150° C. for 1 hour in a microwave. The reaction was monitored by TLC. After completion of the starting material, reaction mixture was diluted with ethyl acetate and washed with water. Organic layer was dried over sodium thiosulfate. Filtered, concentrated and purified by column chromatography using cyclohexane-ethyl acetate to give 2-[6-ethylsulfanyl-1-methyl-2-(trifluoromethyl)benzimidazol-5-yl]-3-methyl-6-(trifluoromethyl)imidazo[4,5-c]pyridine as a yellow solid (96 mg; Yield=62%).

$^1$H NMR (400 MHz, CDCl$_3$) δ ppm 1.22 (t, 3H) 2.86 (q, 2H) 3.76 (s, 3H) 4.03 (s, 3H) 7.60 (s, 1H) 7.98 (s, 1H) 8.16 (s, 1H) 8.94 (s, 1H) LC-MS (Method A): RT 1.04 (461, MH+).

Step C: Preparation of 2-[6-ethylsulfonyl-1-methyl-2-(trifluoromethyl)benzimidazol-5-yl]-3-methyl-6-(trifluoromethyl)imidazo[4,5-c]pyridine A9

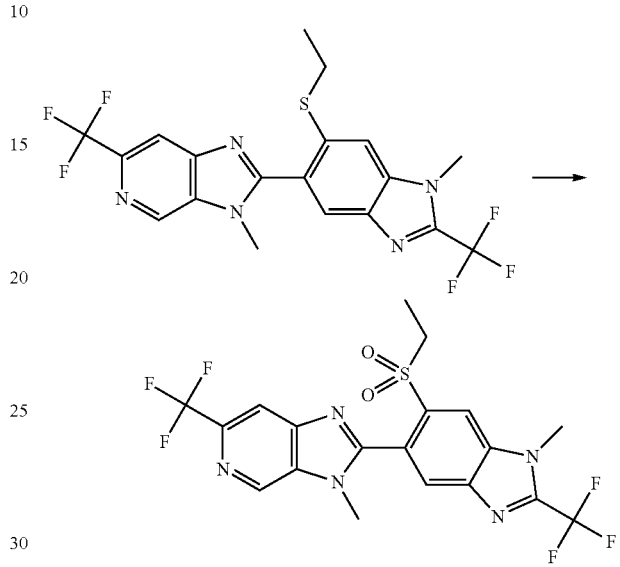

To a stirred solution of 2-[6-ethylsulfanyl-1-methyl-2-(trifluoromethyl)benzimidazol-5-yl]-3-methyl-6-(trifluoromethyl)imidazo[4,5-c]pyridine A39 (90 mg) in CH$_2$Cl$_2$ (10 ml) was added acid 3-chloroperoxybenzoique (2.05 equiv., 92 mg) at ambient temperature. The reaction mixture was then stirred for 1 hour. The reaction was monitored by TLC. After completion of the starting, the reaction mixture was quenched with saturated sodium thiosulfate, sodium hydrogen carbonate and extracted with dichloromethane (2 times). Organic layer was dried over magnesium sulphate. Filtered, concentrated and the crude was purified by column chromatography using cyclohexane-ethyl acetate to give the desired compound as a white solid (97 mg; Yield=100%).

$^1$H NMR (400 MHz, CDCl$_3$) δ ppm 1.28 (t, 3H) 3.51 (br s, 2H) 3.74 (s, 3H) 4.17 (s, 3H) 8.05 (s, 1H) 8.12 (s, 1H) 8.44 (s, 1H) 8.97 (s, 1H). LC-MS (Method A): RT 0.97 (492, MH+).

Example P5: Preparation of 2-(6-ethylsulfonyl-3-methyl-benzimidazol-5-yl)-3-methyl-6-(trifluoromethyl)imidazo[4,5-c]pyridine A11 and 2-(6-ethylsulfonyl-1-methyl-benzimidazol-5-yl)-3-methyl-6-(trifluoromethyl)imidazo[4,5-c]pyridine A12

A11

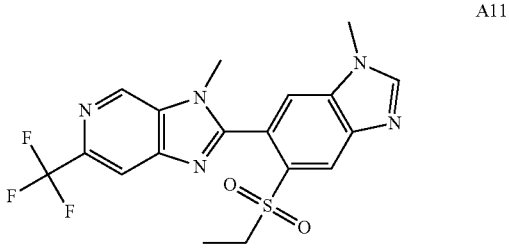

A12

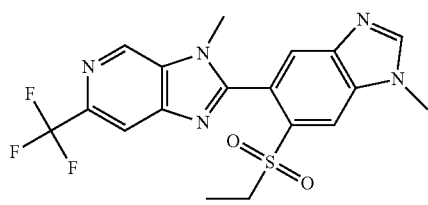

Step A: Preparation of N-[5-ethylsulfonyl-2-iodo-4-[3-methyl-6-(trifluoromethyl)imidazo[4,5-c]pyridin-2-yl]phenyl]formamide

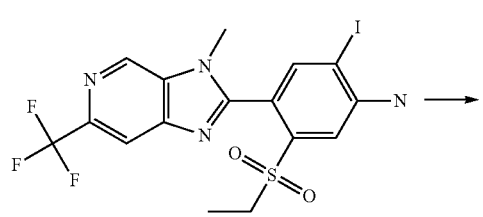

A stirred solution of 5-ethylsulfonyl-2-iodo-4-[3-methyl-6-(trifluoromethyl)imidazo[4,5-c]pyridin-2-yl]aniline (199 mg) in dried formic acid (5.89 mL) was refluxed for 17 hours. Then the solvent was removed under reduced pressure and the residue was dissolved in ethyl acetate and washed with a solution of Na₂CO₃. The organic phase was separated, washed with water and dried. Evaporation of the solvent afforded a solid (86% yield) used in the next step without extra-purification. ¹H NMR (300 MHz, acetone—D6) ppm 9.25 (bs, 1H); 9.15 (s, 1H); 9.10 (s, 1H); 8.70 (bs, 1H); 8.40 (s, 1H); 8.12 (s, 1 h); 3.89 (s, 3H); 3.49 (q, 2H); 1.22 (t, 3H).

Step B: Preparation of N-[2-amino-5-ethylsulfonyl-4-[3-methyl-6-(trifluoromethyl)imidazo[4,5-c]pyridin-2-yl]phenyl]formamide

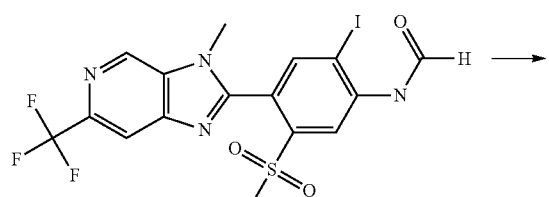

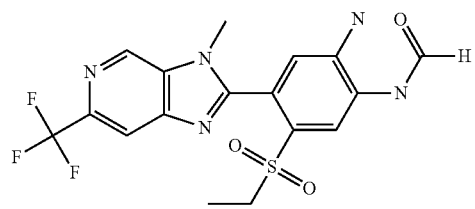

A similar protocol described in Example P4, step D was use but, the no cyclized compound was obtained (50% yield). N-[2-amino-5-ethylsulfonyl-4-[3-methyl-6-(trifluoromethyl)imidazo[4,5-c]pyridin-2-yl]phenyl]formamide. The compound was used without extra purification in the next step. ¹H NMR (300 MHz, CDCl3) ppm 8.93 (s, 1H); 8.45 (s, 1H); 8.08 (s, 1H); 7.92-7.86 (m, 1H); 7.68 (bs, 1H); 6.86 (s, 1H); 4.74 (bs, 2H); 3.77 (s, 3H); 3.27 (q, 2H); 1.23 (t, 3H).

Step C: 2-(6-ethylsulfonyl-1H-benzimidazol-5-yl)-3-methyl-6-(trifluoromethyl)imidazo[4,5-c]pyridine A10

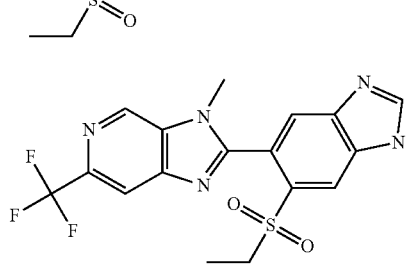

A stirred solution of N-[2-amino-5-ethylsulfonyl-4-[3-methyl-6-(trifluoromethyl)imidazo[4,5-c]pyridin-2-yl]phenyl]formamide (59.84 mg) in acetic acid (5 mL) was refluxed for 17 h. The solvent was then removed under reduced pressure. The residue was dissolved in ethyl acetate and washed with an excess of saturated solution of Na₂CO₃. The organic phase was separated, dried and concentrated under vacuum. The residue was subjected to column chromatography over silica gel (15 g), eluting with ethyl acetate: methanol (9:1). The selected fractions were evaporated to yield 2-(6-ethylsulfonyl-1H-benzimidazol-5-yl)-3-methyl-6-(trifluoromethyl)imidazo[4,5-c]pyridine A10. ¹H NMR (300 MHz, acetone d 6) ppm 9.14 (s, 1H); 8.60 (s, 1H); 8.48 (s, 1H); 8.12 (s, 1H); 8.08 (s, 1H); 3.84 (s, 3H); 3.50 (m, 2H); 1.17 (t, 3H).

Step D: Preparation of 2-(6-ethylsulfonyl-3-methyl-benzimidazol-5-yl)-3-methyl-6-(trifluoromethyl)imidazo[4,5-c]pyridine A11 and 2-(6-ethylsulfonyl-1-methyl-benzimidazol-5-yl)-3-methyl-6-(trifluoromethyl)imidazo[4,5-c]pyridine A12

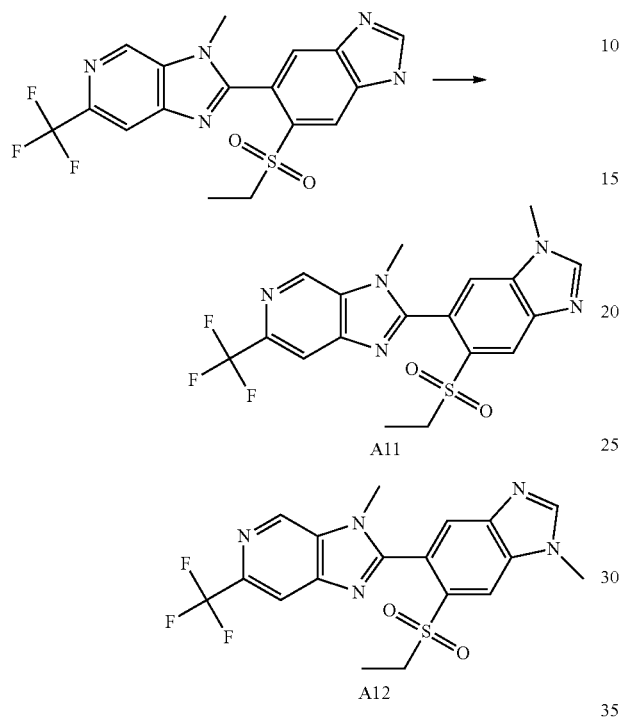

A similar protocol described in Example P4, step E. The compounds were not separable on silica gel but, were separable on HPLC chiral.

Preparative HPLC Method:
Auto purification System from Waters: 2767 sample Manager, 2489 UV/Visible Detector, 2545 Quaternary Gradient Module.
Column: Daicel CHIRALPAK® IC, 50 m, 1.0 cm×25 cm
Mobile phase: Hept/EtOAc/DEA 60/40/0.1%
Flow rate: 10 ml/min
Detection: UV 230 nm
Sample concentration: 23 mg/mL in EtOAc/DCM/MeOH
Injection: 200-600 µl

| First eluting Peak | Second eluting Peak |
|---|---|
| Retention time (min) ~0.89 | Retention time (min) ~1.39 |
| Quantity (mg) return fraction | Quantity (mg) return fraction |
| Chemical purity (area % at 265 nm) 99 | Chemical purity (area % at 265 nm) 99 |

2-(6-ethylsulfonyl-3-methyl-benzimidazol-5-yl)-3-methyl-6-(trifluoromethyl)imidazo[4,5-c]pyridine A11 (Peak 2): $^1$H NMR (400 MHz, CDCl$_3$) ppm 8.94 (s, 1H); 8.68 (s, 1H); 8.19 (s, 1H); 8.10 (s, 1H); 7.59 (s, 1H); 3.96 (s, 3H); 3.75 (s, 3H); 3.42-3.20 (m, 2H); 1.22 (t, 3H).

2-(6-ethylsulfonyl-1-methyl-benzimidazol-5-yl)-3-methyl-6-(trifluoromethyl)imidazo[4,5-c]pyridine A12 (peak 1): $^1$H NMR (400 MHz, CDCl$_3$) ppm 8.95 (s, 1H); 8.34 (s, 1H); 8.22 (s, 1H); 8.10 (s, 1H); 7.95 (s, 1H); 4.06 (s, 3H); 3.73 (s, 3H); 3.48 (m, 2H); 1.26 (t, 3H).

Example P6: Preparation of 2-(6-ethylsulfonyl-2-methyl-3H-benzimidazol-5-yl)-3-methyl-6-(trifluoromethyl)imidazo[4,5-c]pyridine A13, 2-(6-ethylsulfonyl-2,3-dimethyl-benzimidazol-5-yl)-3-methyl-6-(trifluoromethyl)imidazo[4,5-c]pyridine A14 and 2-(6-ethylsulfonyl-1,2-dimethyl-benzimidazol-5-yl)-3-methyl-6-(trifluoromethyl)imidazo[4,5-c]pyridine A15

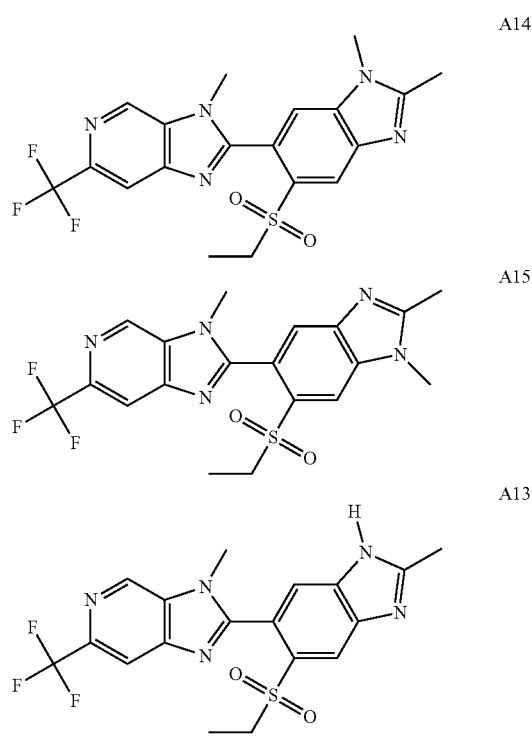

Step A: Preparation of N-[5-ethylsulfonyl-2-iodo-4-[3-methyl-6-(trifluoromethyl)imidazo[4,5-c]pyridin-2-yl]phenyl]acetamide

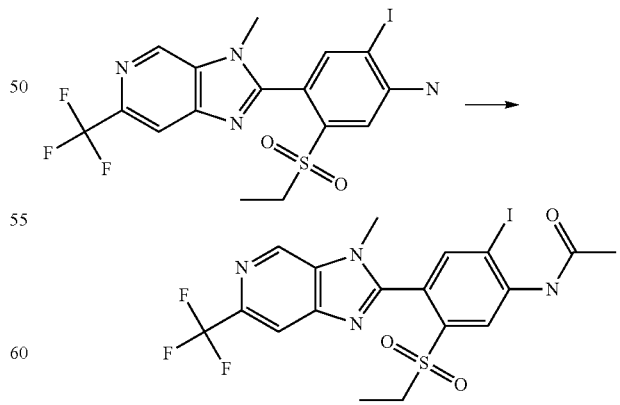

To a stirred solution of 5-ethylsulfonyl-2-iodo-4-[3-methyl-6-(trifluoromethyl)imidazo[4,5-c]pyridin-2-yl]aniline (209.1 mg) in toluene (5. mL) was added pyridine (0.07 mL), acetyl chloride (0.06 mL). The reaction was refluxed for 7 hours. Then the volatiles were removed under reduced pressure and the residue was dissolved in ethyl acetate and washed with 0.1.M HCl, then with water, dried and concentrated under vacuum. The residue was subjected to column chromatography over silica gel (25 g), eluting with ethyl acetate. The selected fractions were evaporated to yield the N-[5-ethylsulfonyl-2-iodo-4-[3-methyl-6-(trifluoromethyl)imidazo[4,5-c]pyridin-2-yl]phenyl]acetamide (82% yield). $^1$H NMR (300 MHz, CDCl$_3$) ppm 9.07 (s, 1H); 8.93 (s, 1H); 8.08 (s, 1H); 7.98 (s, 1H); 7.68 (bs, 1H); 3.77 (s, 3H); 3.30 (q, 2H); 2.35 (s, 3H); 1.26 (t, 3H).

Step B: Preparation of N-[2-amino-5-ethylsulfonyl-4-[3-methyl-6-(trifluoromethyl)imidazo[4,5-c]pyridin-2-yl]phenyl]acetamide

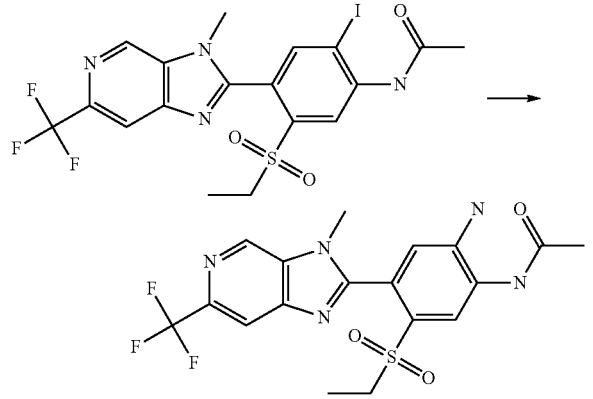

A protocol identical to example P5, step B was used. Analytic data of the title compound: $^1$H NMR (300 MHz, CDCl3) ppm 8.91 (s, 1H); 8.40 (s, 1H); 8.07 (s, 1H); 7.93 (s, 1H); 6.81 (s, 1H); 4.86 (bs, 2H); 3.75 (s, 3H); 3.24 (q, 2H); 2.28 (s, 3H); 1.24 (t, 3H).

Step C: Preparation of 2-(6-ethylsulfonyl-2-methyl-3H-benzimidazol-5-yl)-3-methyl-6-(trifluoromethyl)imidazo[4,5-c]pyridine A13

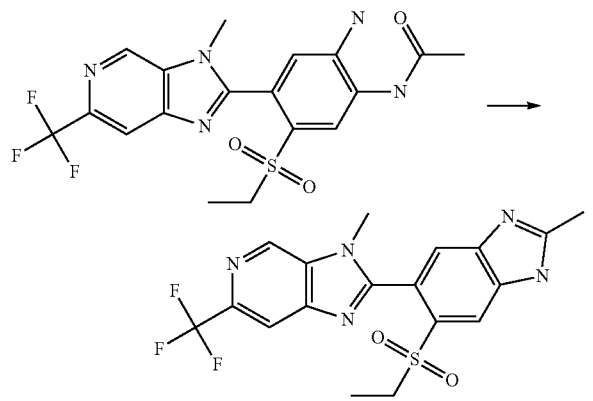

A protocol identical to example P5, step C was used. The compound obtained was used without extra purification in the next step.

Step D: Preparation of 2-(6-ethylsulfonyl-2,3-dimethyl-benzimidazol-5-yl)-3-methyl-6-(trifluoromethyl)imidazo[4,5-c]pyridine A14 and 2-(6-ethylsulfonyl-1,2-dimethyl-benzimidazol-5-yl)-3-methyl-6-(trifluoromethyl)imidazo[4,5-c]pyridine A15

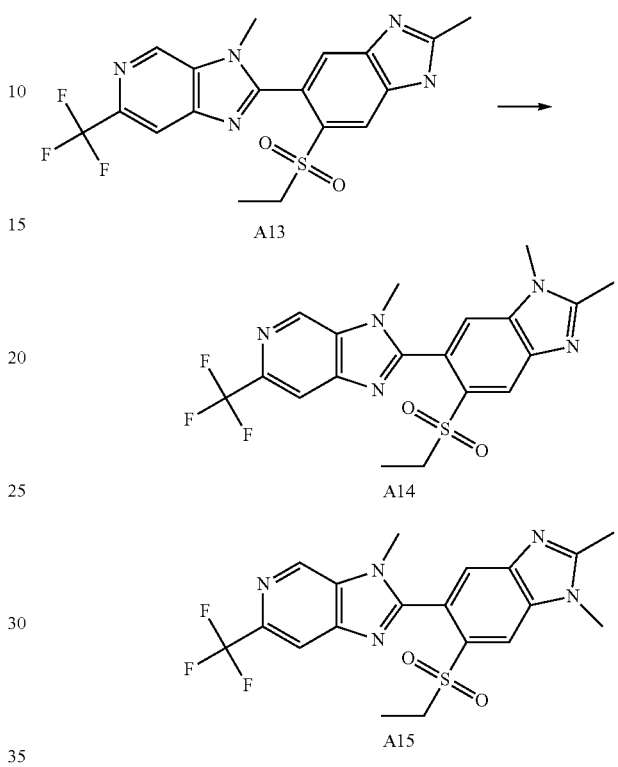

A similar protocol described in Example P4, step E. The compounds were not separable on silica gel. A mixture of 2-(6-ethylsulfonyl-2,3-dimethyl-benzimidazol-5-yl)-3-methyl-6-(trifluoromethyl)imidazo[4,5-c]pyridine A14 and 2-(6-ethylsulfonyl-1,2-dimethyl-benzimidazol-5-yl)-3-methyl-6-(trifluoromethyl)imidazo[4,5-c]pyridine A15 was obtained in 89% yield. Then, they were separable on HPLC chiral.

Preparative HPLC Method:
Auto purification System from Waters: 2767 sample Manager, 2489 UV/Visible Detector, 2545 Quaternary Gradient Module.
Column: Daicel CHIRALPAK® IC, 5 µm, 1.0 cm×25 cm
Mobile phase: Hept/EtOAc/DEA 50/50/0.1%
Flow rate: 10 ml/min
Detection: UV 230 nm
Sample concentration: 15 mg/mL in EtOAc/DCM/MeOH
Injection: 400-800 µl

| First eluting Peak | Second eluting Peak |
|---|---|
| Retention time (min) ~0.74 | Retention time (min) ~1.39 |
| Quantity (mg) return fraction | Quantity (mg) return fraction |
| Chemical purity (area % at 265 nm) 98 | Chemical purity (area % at 265 nm) 99 |

2-(6-ethylsulfonyl-2,3-dimethyl-benzimidazol-5-yl)-3-methyl-6-(trifluoromethyl)imidazo[4,5-c]pyridine A14 (peak 2): $^1$H NMR (400 MHz, CDCl$_3$) ppm 8.95 (s, 1H); 8.53 (s, 1H); 8.10 (s, 1H); 7.46 (s, 1H); 3.83 (s, 3H); 3.76 (s, 3H); 3.32 (m, 2H); 2.74 (s, 3H); 1.20 (t, 3H).

2-(6-ethylsulfonyl-1,2-dimethyl-benzimidazol-5-yl)-3-methyl-6-(trifluoromethyl)imidazo[4,5-c]pyridine A15 (peak 1): ¹H NMR (400 MHz, CDCl₃) ppm 8.95 (s, 1H); 8.21 (s, 1H); 8.10 (s, 1H); 7.79 (s, 1H); 3.93 (s, 3H); 3.72 (s, 3H); 3.46 (m, 2H); 2.75 (s, 3H); 1.25 (t, 3H).

2-(6-ethylsulfonyl-2-phenyl-3H-benzimidazol-5-yl)-3-methyl-6-(trifluoromethyl)imidazo[4,5-c]pyridine A16 was prepared using the same serial of step described in Example P6, step A to step C.

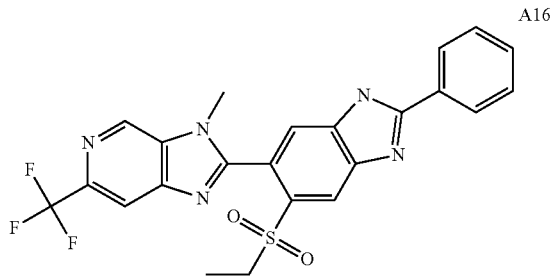 [SMILES: CCS(=O)(=O)c1cc2nc(-c3ccccc3)[nH]c2cc1-c1nc2cc(C(F)(F)F)ncc2n1C]

LC-MS (method A) RT 0.95, 486 (MH⁺), 484 (M–H⁺).

Example P7: Preparation of 2-(6-ethylsulfonyl-3H-benzotriazol-5-yl)-3-methyl-6-(trifluoromethyl)imidazo[4,5-c]pyridine A17

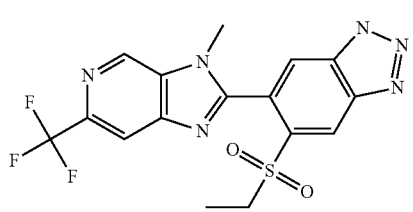

Step A: Preparation of 4-ethylsulfonyl-5-[3-methyl-6-(trifluoromethyl)imidazo[4,5-c]pyridin-2-yl]benzene-1,2-diamine

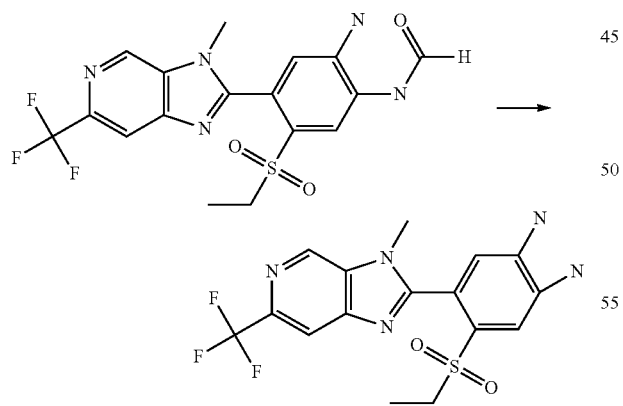

To a stirred solution of N-[2-amino-5-ethylsulfonyl-4-[3-methyl-6-(trifluoromethyl)imidazo[4,5-c]pyridin-2-yl]phenyl]formamide (Prepared in example P5, step B, 90 mg) in methanol (7 mL) was added water (1 mL) and sodium hydroxide (20 mg) at ambient temperature. The mixture was refluxed for 17 hours. The solvent was evaporated and the residue was dissolved in ethyl acetate. The organic phase was washed with water, dried and concentrated under vacuum. The residue was subjected to column chromatography over silica gel (10 g), eluting with 10% MeOH in ethyl acetate. The selected fractions were evaporated to yield the 4-ethylsulfonyl-5-[3-methyl-6-(trifluoromethyl)imidazo[4,5-c]pyridin-2-yl]benzene-1,2-diamine (60% yield). ¹H NMR (300 MHz, CDCl₃) ppm 8.89 (s, 1H); 8.06 (d, 1H); 7.45 (s, 1H); 6.74 (s, 1H); 3.97 (brs, 2H); 3.74 (s, 3H); 3.23 (q, 2H); 1.21 (t, 3H).

Step B: Preparation of 2-(6-ethylsulfonyl-3H-benzotriazol-5-yl)-3-methyl-6-(trifluoromethyl)imidazo[4,5-c]pyridine A17

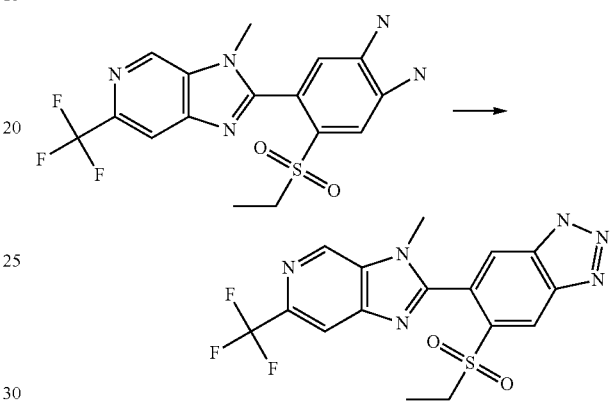

To a stirred solution of 4-ethylsulfonyl-5-[3-methyl-6-(trifluoromethyl)imidazo[4,5-c]pyridin-2-yl]benzene-1,2-diamine (80 mg) in acetic acid (3 mL) was added a solution of sodium nitrite (69 mg) in water (1 mL) at ambient temperature. The mixture was stirred at ambient temperature for 2 h. Then, the solvents were evaporated under reduced pressure and the residue was dissolved into ethyl acetate and water. The organic phase was separated and washed with a saturated solution of Na₂CO₃, dried and concentrated under vacuum. The residue was subjected to column chromatography over silica gel (30 g), eluting with 10% MeOH in ethyl acetate. The selected fractions were evaporated to yield the 2-(6-ethylsulfonyl-3H-benzotriazol-5-yl)-3-methyl-6-(trifluoromethyl)imidazo[4,5-c]pyridine A17 (73% yield). ¹H NMR (300 MHz, acetone-D6) ppm 9.18 (s, 1H); 8.82 (s, 1H); 8.47 (s, 1H); 8.15 (s, 1H); 3.88 (s, 3H); 3.59 (q, 2H); 1.21 (t, 3H).

Example P8: Preparation of 5-ethylsulfonyl-6-[3-methyl-6-(trifluoromethyl)imidazo[4,5-c]pyridin-2-yl]-2,1,3-benzothiadiazole A18

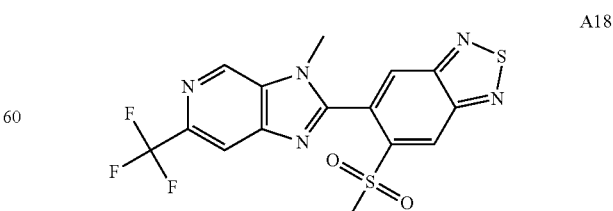

To a stirred solution of 4-ethylsulfonyl-5-[3-methyl-6-(trifluoromethyl)imidazo[4,5-c]pyridin-2-yl]benzene-1,2- diamine (prepared in example P7, step A, 99.85 mg) in dried toluene (10 mL) was added thionyl chloride (0.06 mL). The mixture refluxed under argon for 2 h. Then the solvent was evaporated and the residue was dissolved in ethyl acetate. The organic phase was washed with a saturated solution NaHCO$_3$, dried and concentrated under vacuum. The residue was subjected to column chromatography over silica gel (10 g), eluting with hexane: ethyl acetate (1:1). The selected fractions were evaporated to yield the 5-ethylsulfonyl-6-[3-methyl-6-(trifluoromethyl)imidazo[4,5-c]pyridin-2-yl]-2,1,3-benzothiadiazole A18 (47% yield). $^1$H NMR (300 MHz, CDCl$_3$) ppm 8.99 (s, 2H); 8.26 (s, 1H); 8.13 (s, 1H); 3.83 (s, 3H); 3.50 (q, 2H); 1.30 (t, 3H).

Example P9: Preparation of 5-ethylsulfonyl-2-methyl-6-[3-methyl-6-(trifluoromethyl)imidazo[4,5-c]pyridin-2-yl]-1,3-benzothiazole A19

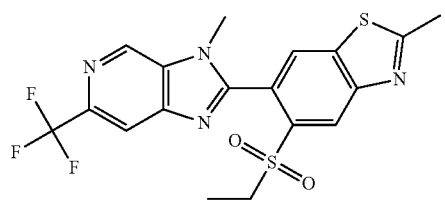

To a stirred solution of N-[5-ethylsulfonyl-2-iodo-4-[3-methyl-6-(trifluoromethyl)imidazo[4,5-c]pyridin-2-yl]phenyl]acetamide (prepared in example P6, step A, 171.22 mg) in dried toluene (7 mL) was added the lawesson reagent (76.85 mg). The mixture refluxed under argon for 17 h. Then the solvent was evaporated and The residue was subjected to column chromatography over silica gel (35 g), eluting with ethyl acetate. The selected fractions were evaporated to yield the 5-ethylsulfonyl-2-methyl-6-[3-methyl-6-(trifluoromethyl)imidazo[4,5-c]pyridin-2-yl]-1,3-benzothiazole A19 (80.5% yield). $^1$H NMR (300 MHz, CDCl3) ppm 8.96 (s, 1H); 8.77 (s, 1H); 8.10 (s, 1H); 8.02 (s, 1H); 3.77 (s, 3H); 3.37 (q, 2H); 2.98 (s, 3H); 1.25 (t, 3H).

Example P10: Preparation of 6-ethylsulfonyl-7-[3-methyl-6-(trifluoromethyl)imidazo[4,5-c]pyridin-2-yl]quinoxaline A20

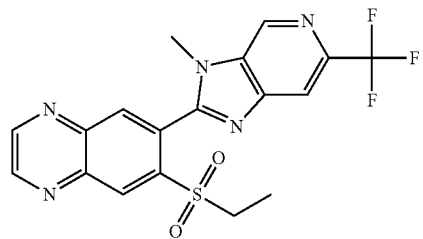

To a stirred solution of 4-ethylsulfonyl-5-[3-methyl-6-(trifluoromethyl)imidazo[4,5-c]pyridin-2-yl]benzene-1,2-diamine (prepared in example P7, step A, 171.22 mg) in ethanol (5 mL) was added of a solution of glyoxal (40% in aqueous water). The mixture refluxed under argon for 1 h. Then the solvent was evaporated and The residue was triturated with 5 mL of cold methanol. The solid was isolated by filtration, washed with a little cold methanol and dried to give 6-ethylsulfonyl-7-[3-methyl-6-(trifluoromethyl)imidazo[4,5-c]pyridin-2-yl]quinoxaline A20 (38% yield). $^1$H NMR (300 MHz, CDCl$_3$) ppm 9.15 (s, 1H); 9.12 (s, 1H); 9.05 (s, 1H); 9.00 (s, 1H); 8.34 (s, 1H); 8.13 (s, 1H); 3.83 (s, 3H); 3.53 (q, 2H); 1.31 (t, 3H).

Compounds A28 and A29 were prepared using the protocol described before, and with the Trifluoro methyl glyoxal (20% aq. soln). Compounds A28 and A29 were purified on 30 g of silica gel, eluent hexane:ethyl acetate 1:1.

A28: $^1$H NMR (600 MHz, CDCl$_3$) δ ppm 1.34 (t, 3H), 3.56 (m, 2H), 3.85 (s, 3H), 8.16 (s, 1H), 8.47 (s, 1H), 9.03 (s, 1H), 9.15 (s, 1H), 9.47 (s, 1H).

A29: $^1$H NMR (600 MHz, CDCl$_3$) δ ppm 1.33 (t, 3H), 3.53 (m, 2H), 3.85 (s, 3H), 8.16 (s, 1H), 8.46 (s, 1H), 9.03 (s, 1H), 9.18 (s, 1H), 9.44 (s, 1H).

Example P11: Preparation of 3-ethylsulfanyl-2-[3-methyl-6-(trifluoromethyl)imidazo[4,5-c]pyridin-2-yl]quinolone A21, 3-ethylsulfonyl-2-[3-methyl-6-(trifluoromethyl)imidazo[4,5-c]pyridin-2-yl]quinolone A22, 2-(3-ethylsulfanyl-2-naphthyl)-3-methyl-6-(trifluoromethyl)imidazo[4,5-c]pyridine A23 and 2-(3-ethylsulfonyl-2-naphthyl)-3-methyl-6-(trifluoromethyl)imidazo[4,5-c]pyridine A24

Compounds A21 and A23 were prepared using intermediate 1 or 2 with the protocol described in Example P1, and with the diamide A (see scheme, prepared in WO 2015/000715), then A22 and A24 were prepared via the oxidation of A21 and A23 via an identical method as described in Example P3.

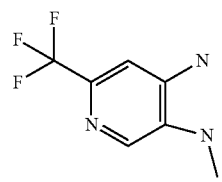

Compound A21:

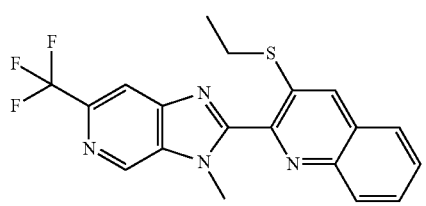 [SMILES: CCSc1cc2ccccc2nc1-c1nc2cc(C(F)(F)F)ncc2n1C]

$^1$H NMR (300 MHz, CDCl$_3$) ppm 9.05 (s, 1H), 8.28 (s, 1H), 8.20 (s, 1H), 8.16 (d, 1H), 7.89 (d, 1H), 7.79 (m, 1H), 7.70 (m, 1H), 4.14 (s, 3H), 3.10 (q, 2H), 1.42 (t, 3H).

Compound A22:

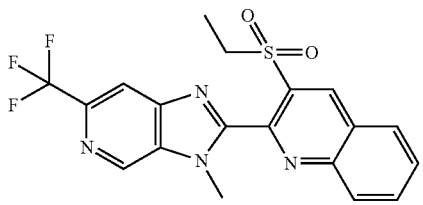

$^1$H NMR (300 MHz, CDCl$_3$) ppm 9.12 (s, 1H), 9.04 (s, 1H), 8.30 (d, 1H), 8.17 (m, 2H), 8.07 (t, 1H), 7.90 (t, 1H), 3.99 (s, 3H), 3.88 (q, 2H), 1.42 (t, 3H).

Compound A23:

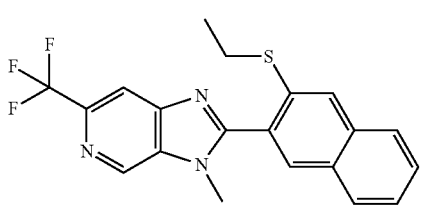 [SMILES: CCSc1cc2ccccc2cc1-c1nc2cc(C(F)(F)F)ncc2n1C]

$^1$H NMR (300 MHz, CDCl$_3$) ppm 8.95 (s, 1H), 8.16 (s, 1H), 8.00 (s, 1H), 7.92 (s, 1H), 7.87 (d, 1H), 7.63 (t, 1H), 7.55 (m, 1H), 7.70 (m, 1H), 3.82 (s, 3H), 2.92 (q, 2H), 1.26 (t, 3H).

Compound A24:

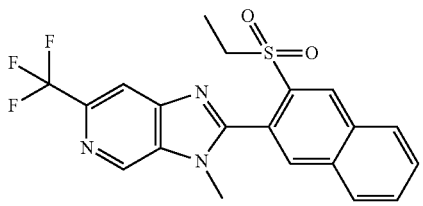

$^1$H NMR (300 MHz, CDCl$_3$) ppm 8.96 (s, 1H), 8.77 (s, 1H), 8.16 (m, 1H), 8.12 (s, 1H), 8.05 (s, 1H), 8.01 (m, 1H), 7.82 (m, 2H), 3.78 (s, 3H), 3.42 (m, 2H), 1.26 (t, 3H).

Example P12: Preparation of 7-ethylsulfanyl-6-[3-methyl-6-(trifluoromethyl)imidazo[4,5-c]pyridin-2-yl]isoquinoline A25, 7-ethylsulfonyl-6-[3-methyl-6-(trifluoromethyl)imidazo[4,5-c]pyridin-2-yl] isoquinoline A26, 7-ethylsulfonyl-6-[3-methyl-6-(trifluoromethyl)imidazo[4,5-c]pyridin-2-yl]-2-oxido-isoquinolin-2-ium A27

Compounds A25 was prepared using intermediate 3 with the protocol described in P1, then A26 and A27 were prepared via the oxidation of A25 via an identical method as described in Example P3, in the case of A27, 2.5 eq of m-CPBA were used.

Compound A25:

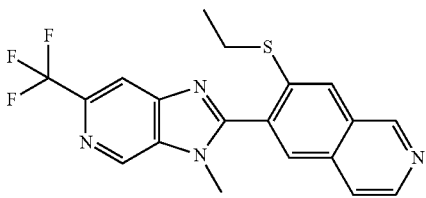 [SMILES: CCSc1cc2cnccc2cc1-c1nc2cc(C(F)(F)F)ncc2n1C]

$^1$H NMR (300 MHz, CDCl$_3$) ppm 9.32 (s, 1H), 8.98 (s, 1H), 8.61 (d, 1H), 8.17 (s, 1H), 7.99 (s, 2H), 7.68 (d, 1H), 3.84 (s, 3H), 3.00 (q, 2H), 1.32 (t, 3H).

Compound A26:

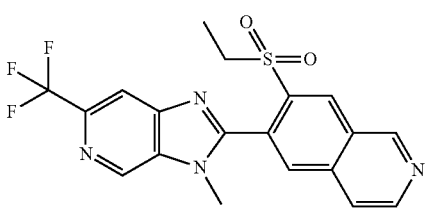 [SMILES: CCS(=O)(=O)c1cc2cnccc2cc1-c1nc2cc(C(F)(F)F)ncc2n1C]

$^1$H NMR (300 MHz, CDCl$_3$) ppm 9.60 (s, 1H), 8.98 (s, 1H), 8.93 (s, 1H), 8.89 (d, 1H), 8.12 (s, 1H), 8.06 (s, 1H), 7.83 (d, 1H), 3.80 (s, 3H), 3.44 (br. s., 2H), 1.28 (t, 3H).

Compound A27:

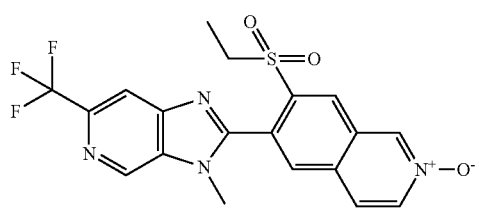 [SMILES: CCS(=O)(=O)c1cc2c[n+]([O-])ccc2cc1-c1nc2cc(C(F)(F)F)ncc2n1C]

$^1$H NMR (300 MHz, CDCl$_3$) ppm 8.97 (d, 2H), 8.59 (s, 1H), 8.36 (dd, 1H), 8.12 (s, 1H), 7.98 (s, 1H), 7.82 (d, 1H), 3.80 (s, 3H), 3.44 (m, 2H), 1.28 (t, 3H).

Example P13: Preparation of 5-ethylsulfonyl-6-[3-methyl-6-(trifluoromethyl)imidazo[4,5-c]pyridin-2-yl]-1,3-benzothiazole A30

A30

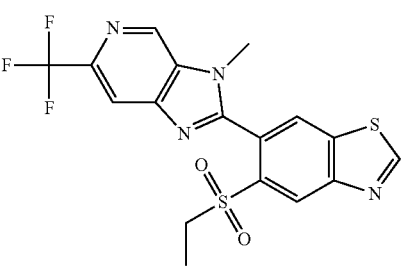

133

Step A: Preparation of N-[5-ethylsulfonyl-2-iodo-4-[3-methyl-6-(trifluoromethyl)imidazo[4,5-c]pyridin-2-yl]phenyl]thioformamide

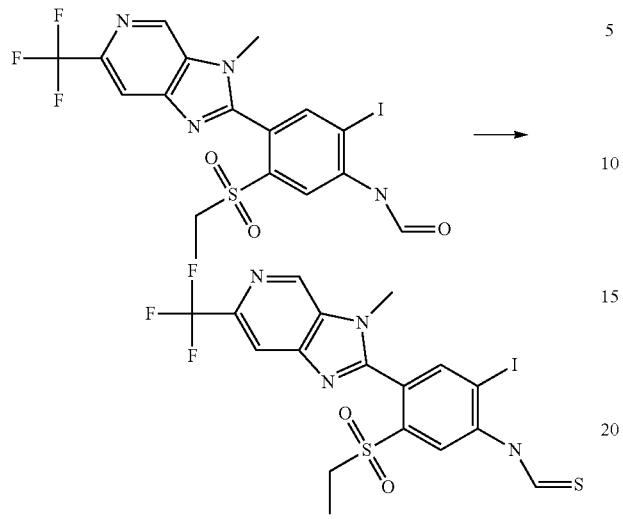

To a stirred solution of N-[5-ethylsulfonyl-2-iodo-4-[3-methyl-6-(trifluoromethyl)imidazo[4,5-c]pyridin-2-yl]phenyl]formamide (102.3 mg, prepared in example P5, Step A) in dried toluene (8 mL) was added the lawesson reagent (50 mg). The mixture refluxed under argon for 15 minutes. Then the solvent was concentrated to 2 ml solution and the residue was subjected to column chromatography over silica gel (20 g), eluting with hexane/ethyl acetate 1:1. The selected fractions were evaporated to yield the N-[5-ethylsulfonyl-2-iodo-4-[3-methyl-6-(trifluoromethyl)imidazo[4,5-c]pyridin-2-yl]phenyl]thioformamide (80 mg). H NMR (300 MHz, DMSO) δ ppm 12.02 (s, 1H); 9.85-9.77 (m, 1H); 9.26 (s, 1H); 8.55-7.92 (m, 3H); 3.77 (s, 3H); 3.51 (q, 2H); 1.17 (t, 3H).

Step B: Preparation of 5-ethylsulfonyl-6-[3-methyl-6-(trifluoromethyl)imidazo[4,5-c]pyridin-2-yl]-1,3-benzothiazole A30

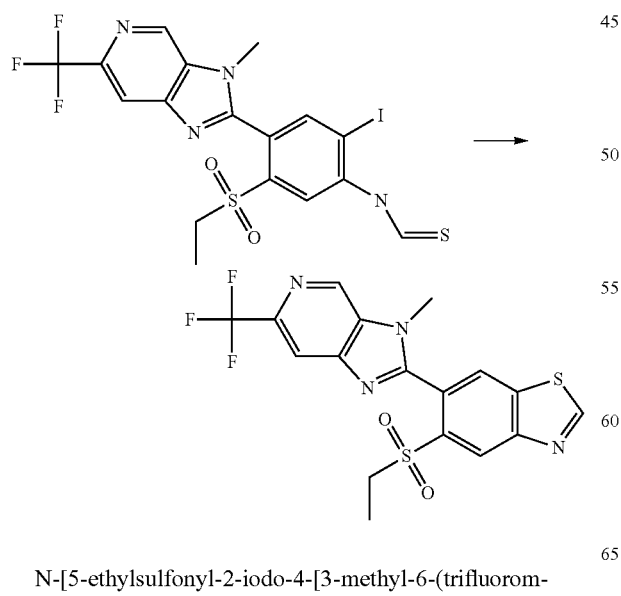

N-[5-ethylsulfonyl-2-iodo-4-[3-methyl-6-(trifluoromethyl)imidazo[4,5-c]pyridin-2-yl]phenyl]thioformamide (89 mg) was suspended in Dimethoxyethane (7 mL) under argon and cesium carbonate (78.24 mg), copper iodine (3.8 mg) and 1,10-Phenanthroline (7.2 mg) were added. The mixture was refluxed under argon for 17 h. The solvent was evaporated under reduced pressure and the residue was subjected to column chromatography over silica gel (25 g), eluting with ethyl acetate. The selected fractions were evaporated to yield the 5-ethylsulfonyl-6-[3-methyl-6-(trifluoromethyl)imidazo[4,5-c]pyridin-2-yl]-1,3-benzothiazole A30 (68 mg). $^1$H NMR (300 MHz, CDCl$_3$) δ ppm 9.35 (s, 1H); 8.99 (s, 1H); 8.97 (s, 1H); 8.19 (s, 1H); 8.11 (s, 1H); 3.78 (s, 3H); 3.39 (m, 2H); 1.27 (t, 3H).

Example P14: Preparation of 5-ethylsulfonyl-6-[3-methyl-6-(trifluoromethyl)imidazo[4,5-c]pyridin-2-yl]-2-(trifluoromethyl)-1,3-benzothiazole A31

A31

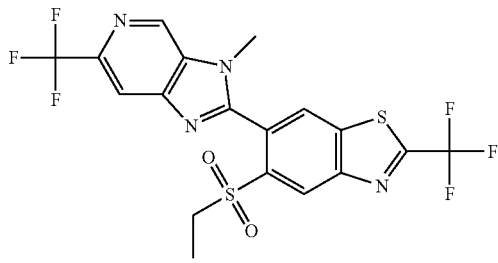

Compound A31 was prepared using the protocol described in Example P9, using as starting material N-[5-ethylsulfonyl-2-iodo-4-[3-methyl-6-(trifluoromethyl)imidazo[4,5-c]pyridin-2-yl]phenyl]-2,2,2-trifluoro-acetamide (Example P4, Step C). $^1$H NMR (300 MHz, CDCl$_3$) δ ppm 9.07 (s, 1H); 8.98 (s, 1H); 8.24 (s, 1H); 8.12 (s, 1H); 3.78 (s, 3H); 3.41 (q, 2H); 1.26 (t, 3H).

Example P15: Preparation of 6-ethylsulfonyl-5-[3-methyl-6-(trifluoromethyl)imidazo[4,5-c]pyridin-2-yl]-2-(trifluoromethyl)-1H-imidazo[4,5-b]pyridine A34, 6-ethylsulfonyl-1-methyl-5-[3-methyl-6-(trifluoromethyl)imidazo[4,5-c]pyridin-2-yl]-2-(trifluoromethyl)imidazo[4,5-b]pyridine A33 and 6-ethylsulfonyl-3-methyl-5-[3-methyl-6-(trifluoromethyl)imidazo[4,5-c]pyridin-2-yl]-2-(trifluoromethyl)imidazo[4,5-b]pyridine A32

A34

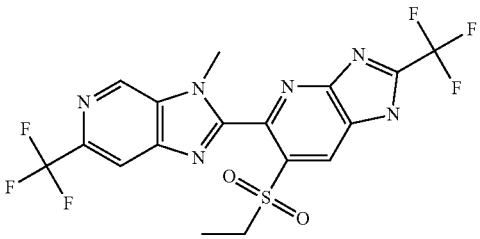

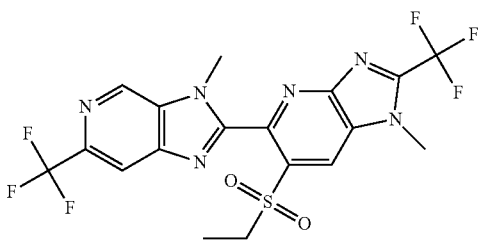

A33

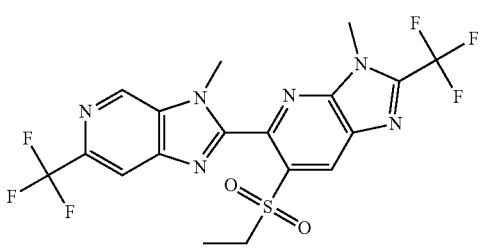

A32

Compounds A34, A33 and A32 were prepared as described in Example P4 using same conditions with, as starting material, the 2-(5-bromo-3-ethylsulfonyl-2-pyridyl)-3-methyl-6-(trifluoromethyl)imidazo[4,5-c]pyridine (C1, prepared as described in WO 2015/000715) and replacing NIS by NBS in step B as described in the following scheme

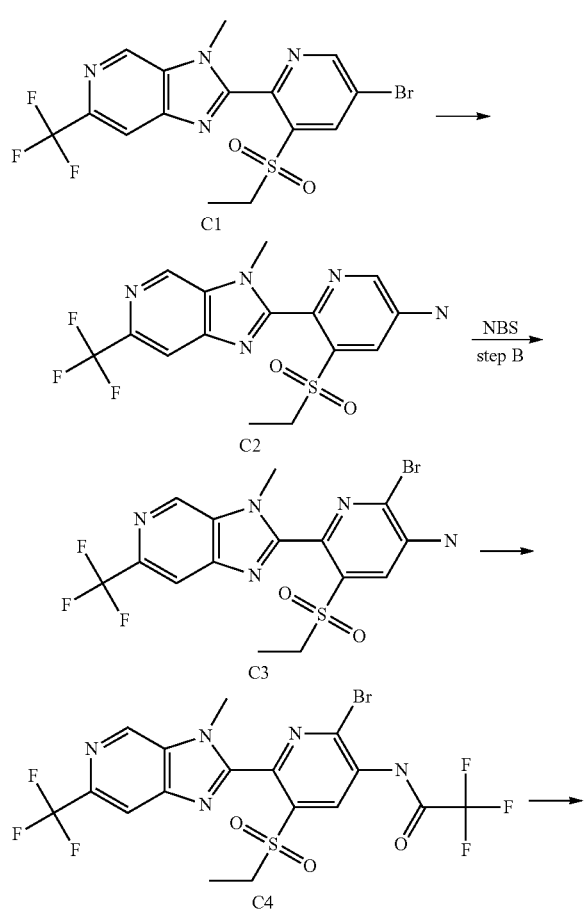

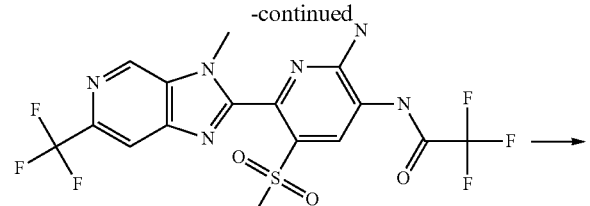

C5

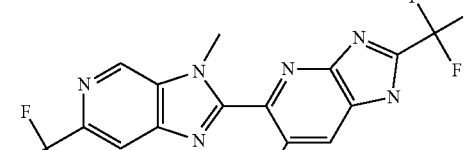

A34

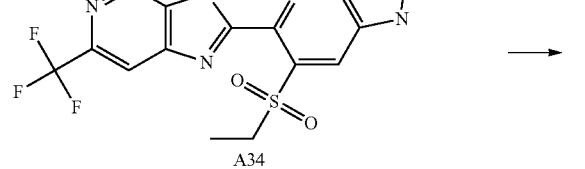

A34

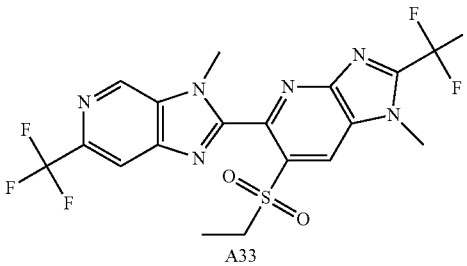

A33

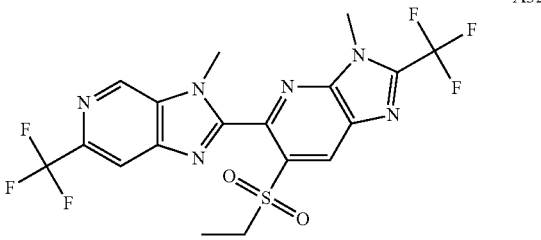

A32

C2: $^1$H NMR (300 MHz, acetone-d6) δ ppm 9.14 (s, 1H); 8.44 (d, 1H); 8.10 (d, 1H); 7.73 (d, 1H); 6.01 (brs, 2H); 3.93 (s, 3H); 3.79 (q, 2H); 1.27 (t, 3H).

C3: $^1$H NMR (300 MHz, CDCl$_3$) δ ppm 8.94 (s, 1H); 8.07 (d, 1H); 7.71 (s, 1H) 3.90 (s, 3H); 3.78 (q, 2H); 1.36 (t, 3H).

C4: $^1$H NMR (300 MHz, acetone-d6) δ ppm 9.18 (s, 1H); 9.13 (s, 1H); 8.13 (d, 1H); 3.99 (s, 3H); 3.76 (q, 2H); 1.29 (t, 3H).

C5: $^1$H NMR (300 MHz, acetone-d6) δ ppm 10.10 (bs, 1H); 9.18 (s, 1H); 8.27 (s, 1H); 8.14 (s, 1H); 6.98 (bs, 2H); 3.98 (s, 3H); 3.65 (q, 2H); 1.25 (t, 3H).

A34: $^1$H NMR (300 MHz, acetone-d6) δ ppm 9.15 (s, 1H); 8.54 (s, 1H); 8.11 (s, 1H); 3.88 (s, 3H); 3.69 (q, 2H); 1.24 (t, 3H).

A33: $^1$H NMR (300 MHz, CDCl$_3$) δ ppm 9.00 (s, 1H); 8.77 (s, 1H); 8.11 (s, 1H); 4.19 (s, 3H); 3.94 (m, 5H); 1.40 (t, 3H).

A32: ¹H NMR (300 MHz, CDCl₃) δ ppm 9.02 (s, 2H); 8.13 (s, 1H); 4.12 (s, 3H); 3.87 (s, 3H); 3.70 (q, 2H); 1.35 (t, 3H).

Example P16: Preparation of 5-ethylsulfonyl-1-methyl-6-[3-methyl-6-(trifluoromethyl)imidazo[4,5-c]pyridin-2-yl]benzotriazole A35, 6-ethylsulfonyl-1-methyl-5-[3-methyl-6-(trifluoromethyl)imidazo[4,5-c]pyridin-2-yl]benzotriazole A36 and 5-ethylsulfonyl-2-methyl-6-[3-methyl-6-(trifluoromethyl)imidazo[4,5-c]pyridin-2-yl]benzotriazole A37

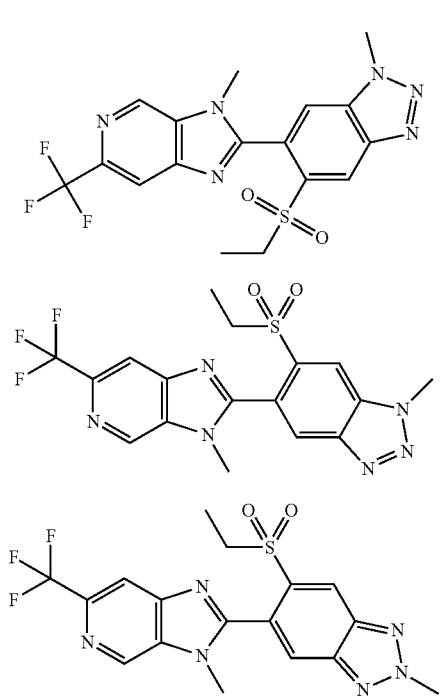

A similar protocol described in Example P4, step E starting from 2-(6-ethylsulfonyl-3H-benzotriazol-5-yl)-3-methyl-6-(trifluoromethyl)imidazo[4,5-c]pyridine A17. The compounds A36 and A37 were not separable on silica gel and were separate by HPLC on reverse phase using the following method:

Autopurification System from Waters: 2767 sample Manager, 2489 UV/Visible Detector, 2545 Quaternary Gradient Module. Column: Phenomenex Gemini NX C18, 4 micron particle size, 80 Angström, 75×30.00 mm, DAD Wavelength (nm): 220 and 254. Solvent Gradient: Reversed Phase, A=water (in House-HPLC quality) and B=Acetonitrile for prep. HPLC.

| Time | A % | B % | Flow (ml/min) |
|---|---|---|---|
| 0.00 | 70 | 30 | 50.00 |
| 0.01 | 70 | 30 | 50.00 |
| 6.00 | 30 | 70 | 50.00 |
| 7.90 | 30 | 70 | 50.00 |
| 8.00 | 0 | 100 | 50.00 |
| 8.90 | 0 | 100 | 50.00 |
| 9.00 | 70 | 30 | 50.00 |
| 10.0 | 70 | 30 | 50.00 |

A35: ¹H NMR (300 MHz, acetone-d6) δ ppm 9.18 (s, 1H); 8.83 (s, 1H); 8.38 (s, 1H); 8.15 (s, 1H); 4.52 (s, 3H); 3.88 (s, 3H); 3.57 (m, 2H); 1.21 (t, 3H).

A36: ¹H NMR (600 MHz, CDCl₃) δ ppm 1.29 (t, J=7.4 Hz, 3H) 3.53 (br s, 2H) 3.77 (s, 3H) 4.53 (s, 3H) 8.13 (s, 1H) 8.28 (s, 1H) 8.54 (s, 1H) 8.99 (s, 1H).

A37: ¹H NMR (600 MHz, CDCl₃) δ ppm 1.27 (t, J=7.3 Hz, 3H) 3.46 (br s, 2H) 3.78 (s, 3H) 4.69 (s, 3H) 8.09 (s, 1H) 8.12 (s, 1H) 8.87 (s, 1H) 8.98 (s, 1H)

Example P17: Preparation of 5-ethylsulfonyl-6-[3-methyl-6-(trifluoromethyl)imidazo[4,5-c]pyridin-2-yl]-3H-1,3-benzothiazole-2-thione A38

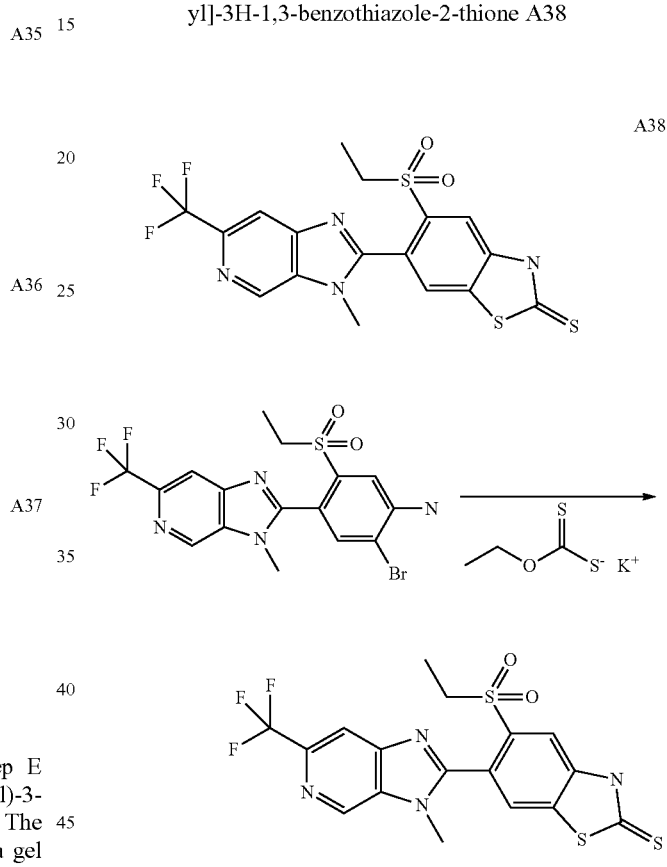

2-bromo-5-ethylsulfonyl-4-[3-methyl-6-(trifluoromethyl)imidazo[4,5-c]pyridin-2-yl]aniline (C3, see example P15, 139 mg) was heated with potassium xantoghenate (commercially available, 105.8 mg) in dried DMF at 120° C. for 1 h under argon. The solution was treated with saturated solution of ammonium chloride and extracted with ethyl acetate. The organic phase and aqueous phase were separated and the organic phase was dried and concentrated under vacuum. The residue was subjected to column chromatography over silica gel (25 g), eluting with ethyl acetate. The selected fractions were evaporated to yield 5-ethylsulfonyl-6-[3-methyl-6-(trifluoromethyl)imidazo[4,5-c]pyridin-2-yl]-3H-1,3-benzothiazole-2-thione A38 (95% purity, 60 mg). LC-MS (Method A) RT 0.91 (459, MH⁺). ¹H NMR (400 MHz, DMSO-d6) δ ppm 9.25 (s, 1H), 8.26 (s, 1H), 8.16 (s, 1H), 7.88 (s, 1H), 3.74 (s, 3H), 3.54 (q, 2H), 1.12 (t, 3H).

Example P18: Preparation of 5-cyclopropyl-3-ethyl-sulfonyl-2-[3-methyl-6-(trifluoromethyl)imidazo[4,5-c]pyridin-2-yl]quinoline A43

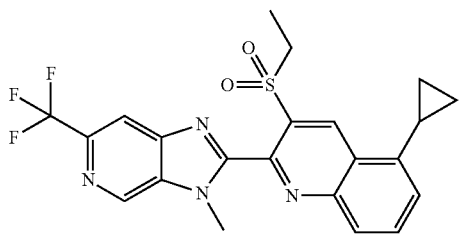 [SMILES: CCS(=O)(=O)c1cc2c(C3CC3)cccc2nc1-c1nc2cc(C(F)(F)F)ncc2n1C]

To a solution of 5-bromo-3-ethylsulfonyl-2-[3-methyl-6-(trifluoromethyl)imidazo[4,5-c]pyridin-2-yl]quinolone A42 (See table 8, 0.1 mmol) in toluene (2 mL) was added cyclopropylboronic acid (15 mg, 0.17 mmol) and $K_3PO_4$ (75 mg, 0.35 mmol) and tricyclohexylphosphine (4 mg, 0.01 mmol). The mixture was degassed for 10 min and $Pd(OAc)_2$ (2 mg, 0.007 mmol) was added. The mixture was heated at 100° C. for 2 h. The mixture was filtered through a plug of Celite and concentrated under vacuum. The residue was purified by column chromatography (CombiFlash Rf150; 10 g $SiO_2$; iHEX:EA=4:1) to give the desired product (26 mg; 56.5%). $^1$H NMR: See table 8.

Example P19: Preparation of 3-ethylsulfonyl-2-[3-methyl-6-(trifluoromethyl)imidazo[4,5-c]pyridin-2-yl]quinoline-6-carbonitrile A50

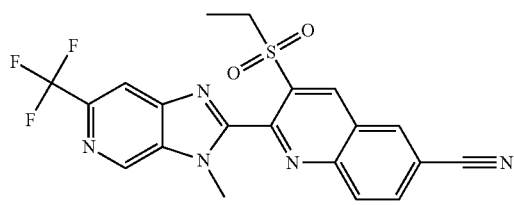 [SMILES: CCS(=O)(=O)c1cc2cc(C#N)ccc2nc1-c1nc2cc(C(F)(F)F)ncc2n1C]

A solution of 6-chloro-3-ethylsulfonyl-2-[3-methyl-6-(trifluoromethyl)imidazo[4,5-b]pyridin-2-yl]quinolone A49 (See table 8, 86 mg, 0.19 mmol), $Pd_2dba_3$ (27 mg, 0.03 mmol), S-Phos (32 mg, 0.08 mmol) and $Zn(CN)_2$ (45 mg, 0.38 mmol) in 4 mL of a mixture of DMF:water (99:1) was heated to 170° C. for 30 min in the microwave reactor. The solution was diluted with water and extracted with ethylacetate (2.times). The combined organic layers were combinated, dried over MgSO4, filtered and concentrated to give an oil. The oil was purified on silica gel, FCC (CombiFlash Rf150; 10 g SiO2; iHEX:EA=3:1→2:1) to afford the title compound (42 mg; 49.6% yield). $^1$H NMR: See table 8.

Example P20: Preparation of 3-ethylsulfonyl-2-[3-methyl-6-(trifluoromethyl)imidazo[4,5-c]pyridin-2-yl]-6-(1,1,2,2,2-pentafluoroethyl)quinoline A52

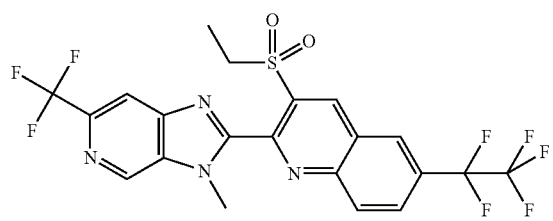 [SMILES: CCS(=O)(=O)c1cc2cc(C(F)(F)C(F)(F)F)ccc2nc1-c1nc2cc(C(F)(F)F)ncc2n1C]

A 5 mL MW vial under argon was charged with A45 (see table 8, 24 mg, 0.48 mmol), NMP (3972 mg, 3.845 mL, 39.7 mmol, 82.5) and pentafluoroethylator (369.2 mg, 0.96 mmol). The mixture was stirred at 90° C. for 3 hour and 1 eq. of pentafluoroethylator was added and MW Vial was put 1 hour more at 90° C. The reaction mixture was diluted with water (30 ml) and extracted twice with ethyl acetate (3×30 mL). The combined organic phases were dried over sodium sulfate and concentrated under reduced pressure. The residue was subjected to column chromatography over silica gel, eluting with ethyl acetate/cyclohexane. The selected fractions were evaporated to yield the title compound (118 mg). $^1$H NMR: See table 8.

Example P20: Preparation of 2-[6-ethylsulfanyl-1-methyl-2-(trifluoromethyl)benzimidazol-5-yl]-3-methyl-6-(trifluoromethyl)imidazo[4,5-b]pyridine A53, 2-[6-ethylsulfanyl-1-methyl-2-(trifluoromethyl)benzimidazol-5-yl]-3-methyl-6-(trifluoromethylsulfanyl)imidazo[4,5-b]pyridine A54, 2-[6-ethylsulfonyl-1-methyl-2-(trifluoromethyl)benzimidazol-5-yl]-3-methyl-6-(trifluoromethyl)imidazo[4,5-b]pyridine A55, 2-[6-ethylsulfonyl-1-methyl-2-(trifluoromethyl)benzimidazol-5-yl]-3-methyl-6-(trifluoromethylsulfanyl)imidazo[4,5-b]pyridine A56 and 2-[6-ethylsulfonyl-1-methyl-2-(trifluoromethyl)benzimidazol-5-yl]-3-methyl-6-(trifluoromethylsulfinyl)imidazo[4,5-b]pyridine A57

A53

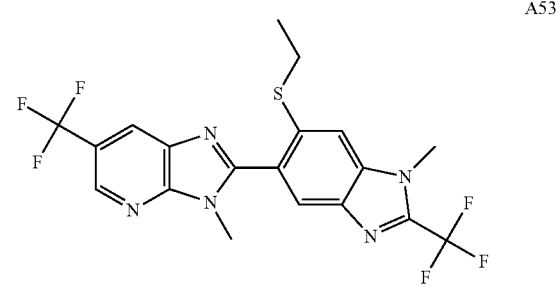

A54

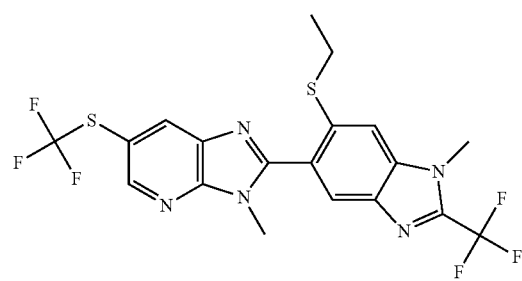

A53 and A54 were synthesized by the same protocol using N2-methyl-5-(trifluoromethyl)pyridine-2,3-diamine (cas: 1643139-91-6) and N2-methyl-5-(trifluoromethylsulfanyl)pyridine-2,3-diamine (cas: 1383840-73-0) with the intermediate 8.

A55

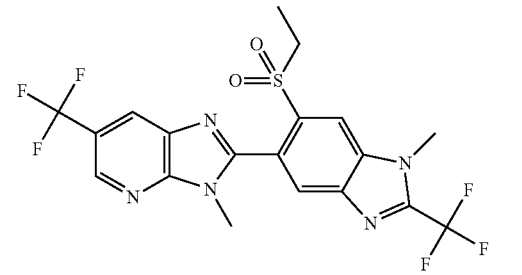

A56

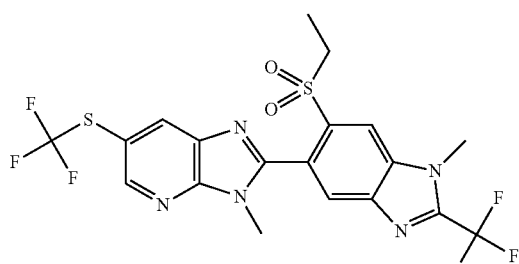

A55 and A56 were synthesized by the same protocol for A3 using 2-[6-ethylsulfanyl-1-methyl-2-(trifluoromethyl)benzimidazol-5-yl]-3-methyl-6-(trifluoromethyl)imidazo[4,5-b]pyridine A53 and 2-[6-ethylsulfanyl-1-methyl-2-(trifluoromethyl)benzimidazol-5-yl]-3-methyl-6-(trifluoromethylsulfanyl)imidazo[4,5-b]pyridine A54.

A57

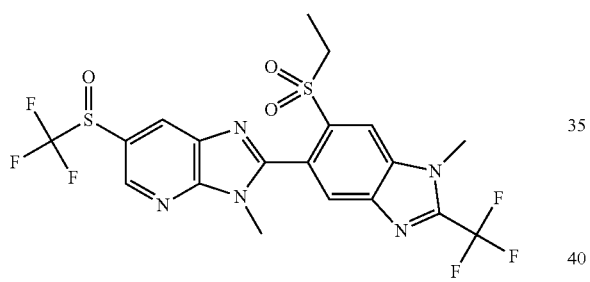

A57 was isolated as a byproduct with the compound A56.

Example P20: Preparation of 6-ethylsulfanyl-2,2-dimethyl-5-[3-methyl-6-(trifluoromethyl)imidazo[4,5-c]pyridin-2-yl]-3H-furo[3,2-b]pyridine A58 and 6-ethylsulfonyl-2,2-dimethyl-5-[3-methyl-6-(trifluoromethyl)imidazo[4,5-c]pyridin-2-yl]-3H-furo[3,2-b]pyridine A59

A58

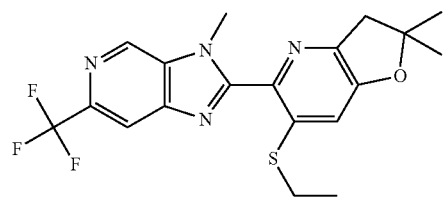

A59

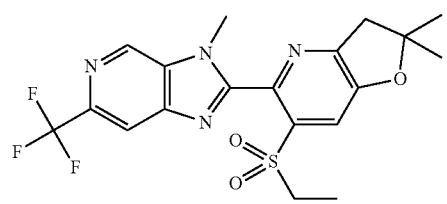

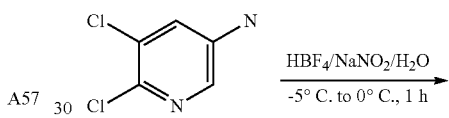

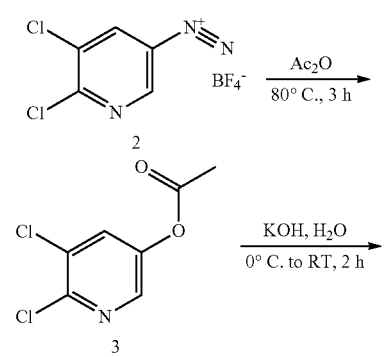

| | NMR | LC/MS |
|---|---|---|
| A53 | ¹H NMR (400 MHz, CDCl₃) δ ppm 1.23 (t, 3 H), 2.88 (q, 2 H), 3.74 (s, 3 H), 4.03 (s, 3 H), 7.59 (s, 1 H), 7.97 (s, 1 H), 8.35 (d, 1 H), 8.74 (d, 1 H). | LC-MS (Method A): RT 1.12 (461, MH⁺). |
| A54 | ¹H NMR (400 MHz, CDCl₃) δ ppm 1.24 (t, 4 H), 2.89 (q, 2 H), 3.72 (s, 3 H), 4.03 (s, 3 H) 7.58 (s, 1 H) 7.96 (s, 1 H) 8.42 (d, 1 H) 8.68 (d, 1 H). | LC-MS (Method A): RT 1.18 (492, MH⁺). |
| A55 | ¹H NMR (400 MHz, CDCl₃) δ ppm 1.28 (t, 3 H), 3.56 (q, 2 H), 3.70 (s, 3 H), 4.16 (s, 3 H), 8.04 (s, 1 H), 8.30 (d, 1 H), 8.43 (s, 1 H), 8.76 (d, 1 H). | LC-MS (Method A): RT 1.03 (492, MH⁺). |
| A56 | ¹H NMR (400 MHz, CDCl₃) δ ppm 1.28 (m, 3 H), 3.56 (q, 2 H), 3.69 (s, 3 H), 4.16 (s, 3 H), 8.04 (s, 1 H), 8.37 (d, 1 H), 8.43 (s, 1 H), 8.70 (d, 1 H). | LC-MS (Method A): RT 1.09 (525, MH⁺). |
| A57 | ¹H NMR (400 MHz, CDCl₃) δ ppm 1.28 (m, 3 H), 3.56 (q, 2 H,) 3.73 (s, 3 H), 4.16 (s, 3 H), 8.06 (s, 1 H), 8.44 (s, 1 H), 8.57 (s, 1 H), 8.77 (d, 1 H). | LC-MS (Method A): RT 0.96 (540, MH⁺). |

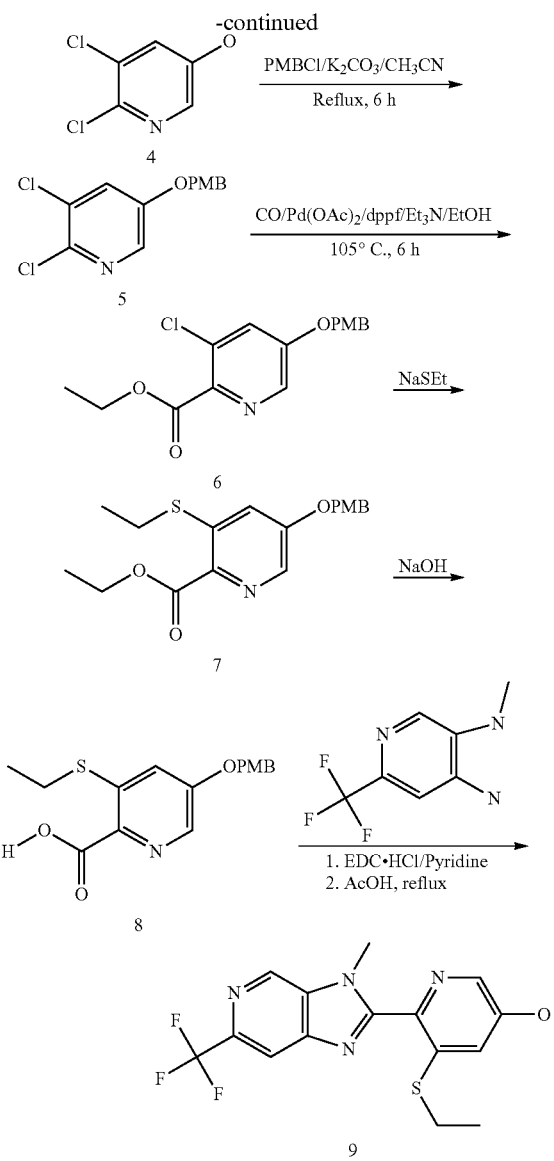

Step A: Preparation of Compound 2

A solution of NaNO$_2$ (7.21 g, 126 mmol) in 100 ml of water was added to a mixture of compound 1 (16.3 g, 100 mmol) in 200 ml of HBF$_4$ (40%) when the temperature was dropped to −5~0° C. After stirring at 0° C. for 1 h the reaction mixture was filtered. The filter residue was washed with water two times and with ether at 0° C. two times. The crude product (24.6 g, y: 93%) was used for the next step.

Step A: Preparation of Compound 3

The compound 2 (24.6 g) was added slowly to 250 ml of acetic acid when the temperature was heated to 70° C.~90° C. Then the mixture solution was stirred for 2 h at 80~90° C.

The reaction mixture was concentrated and poured into water, extracted with ethyl acetate three times. The combined organic layers were dried over sodium sulfate, filtered and concentrated under vacuum.

The crude product was purified by column chromatography on silica gel to provide product 3 (7.7 g, y: 37%). $^1$H NMR (400 MHz, DMSO-d6) δ (ppm): 2.32 (s, 3H), 8.17 (d, 1H), 8.33 (d, 1H).

Step C: Preparation of Compound 4

A solution of KOH (728 mg, 13 mmol) in 7 ml of water was added to a solution of compound 3 (1 g, 4.8 mmol) in 10 ml of THF at 0° C. After addition, the mixture was stirred at ambient temperature for 2 h. Then the mixture added dilute hydrochloric acid to adjust the pH value to weak alkaline and filtered. The filter residue was purified by recrystallization to give compound 4 (517 mg, y: 65%). $^1$H NMR (400 MHz, DMSO-d6) δ (ppm): 7.47 (d, 1H), 7.93 (d, 1H), 10.72 (s, 1H).

Step D: Preparation of Compound 5

A mixture of compound 4 (8.15 g, 0.05 mmol), PMBCl (11.78 g, 0.075 mmol) and K$_2$CO$_3$ (13.8 g, 0.1 mmol) in 130 ml of CH$_3$CN was refluxed under nitrogen for 6 h. Then, the reaction mixture was filtered. The filtrate was concentrated and purified by recrystallization to give compound 5 (8.8 g, y: 67%). $^1$H NMR (400 Mz, CDCl$_3$) δ (ppm): 3.81 (s, 3H), 5.00 (s, 2H), 6.91 (d, 2H), 7.30 (d, 2H), 7.37 (s, 1H), 8.03 (s, 1H).

Step E: Preparation of Compound 6

A mixture of compound 5 (10 g, 35 mmol), Pd(OAc)$_2$ (158 mg, 0.7 mmol), dppf (975 mg, 1.8 mmol) and Et$_3$N (10.2 g, 70 mmol) in 120 ml of ethanol was placed in a high pressure vessel and added CO gas. The press was controlled at 20 bar. Then the reaction mixture was stirred at 100-120° C. for 6 h. After reaction, the mixture was filtered. The filtrate was concentrated and purified by column chromatography on silica gel to provide product 6 (6 g, y: 53%). $^1$H NMR (400 MHz, DMSO-d6) δ (ppm): 1.31 (t, 3H), 3.76 (s, 3H), 4.33 (q, 2H), 5.20 (s, 2H), 6.95 (d, 2H), 7.41 (d, 2H), 7.78 (d, 1H), 8.36 (d, 1H).

Step F: Preparation of Compound 7

Compound 6 (11 g, 34.2 mmol) was dissolved in DMF (60 ml) and EtSNa (5.75 g, 68.4 mmol) was added when the temperature was dropped to 0° C. After the mixture was stirred at r.t for 0.5 h, it was poured into the water and extracted with ethyl acetate three times. The combined organic layers were dried over sodium sulfate, filtered and concentrated under vacuum. The crude product was purified by recrystallization to give compound 7 (4.77 g, y: 61%) $^1$H NMR (400 Mz, CDCl$_3$) δ (ppm): 1.33 (t, 3H), 1.40 (t, 3H), 2.83 (q, 2H), 3.79 (s, 3H), 4.42 (q, 2H), 5.09 (s, 3H), 6.90 (d, 2H), 7.11 (s, 1H), 7.32 (d, 2H), 8.16 (s, 1H).

Step G: Preparation of Compound 8

A mixture of compound 7 (10.64 g, 30.66 mmol) and NaOH (3.67 g, 92 mmol) in 90 ml of water and 90 ml of THF was stirred at ambient temperature for 16 h. Then, the reaction mixture was poured into diluted hydrochloric acid and extracted with ethyl acetate three times. The combined organic layers were dried over sodium sulfate, filtered and concentrated under vacuum. The crude product was purified by recrystallization to provide product 8 (9 g, y: 92%). $^1$H NMR (400 MHz, CDCl$_3$) δ (ppm): 1.36 (t, 3H), 2.85 (q, 2H), 3.80 (s, 3H), 5.12 (s, 2H), 6.92 (d, 2H), 7.14 (s, 1H), 7.33 (d, 2H), 7.99 (s, 1H), 10.98 (s, 1H).

Step H: Preparation of Compound 9

A mixture of N3-methyl-6-(trifluoromethyl)pyridine-3,4-diamine (Prepared in WO 2015000715, 2.5 g, 15.6 mmol), compound 8 (5 g, 15.6 mmol) and EDC.HCl (3.3 g, 17.2 mmol) in 50 ml of pyridine was refluxed for 16 h. Then, the mixture was concentrated, diluted with ethyl acetate and washed with NaHCO$_3$ saturated solution three times. The combined organic layers were dried over sodium sulfate, filtered and concentrated under vacuum. The crude product in 100 ml of acetic acid was refluxed overnight. Then the mixture was concentrated and added Na$_2$CO$_3$ saturated solution to adjust the PH value to weak alkaline.

The mixture solution was diluted with ethyl acetate three times, dried over sodium sulfate, filtered and concentrated under vacuum. The crude product was purified by column chromatography on silica gel to provide product 9 (1.93 g, y: 35%). $^1$H NMR (400 MHz, DMSO-d6) δ (ppm): 1.18 (t, 3H), 2.91 (q, 2H), 3.93 (s, 3H), 7.30 (s, 1H), 8.08 (s, 1H), 8.19 (s, 1H), 9.15 (s, 1H), 10.70 (s, 1H). $^{19}$F-NMR (300 Mz, CDCl$_3$) δ: −64.35 (s, 3F).

Step I: Preparation of Compound 10

Compound 9 (1 mmol, 354 mg), Methylallyl chloride (109 mg, 1.2 mmol), K$_2$CO$_3$ (0.8 mmol, 110 mg), and KI(0.012 mmol, 2 mg) in 4 ml of Acetone and 1 ml of DMF were refluxed for 8 h. Then the mixture was poured into water, and extracted with ethyl acetate three times. The combined organic layers were dried over sodium sulfate, filtered and concentrated under vacuum. The crude product was purified by column chromatography on silica gel to give product 10 (240 mg, y: 58%). $^1$H NMR (400 MHz, CDCl$_3$) δ (ppm): 1.33 (t, 3H), 1.85 (s, 3H), 2.91 (q, 2H), 4.02 (s, 3H), 4.59 (s, 2H), 5.10 (d, 2H), 5.27 (s, 1H), 7.25 (d, 1H), 8.15 (s, 1H), 8.19 (d, 19), 8.90 (s, 1H). $^{19}$F-NMR (300 Mz, CDCl$_3$) δ: −66.33 (s, 3F).

Step J: Preparation of Compound A58

Compound 10 (3.1 mmol, 0.83 g) in 10 ml of NMP was stirred under nitrogen at 185° C. for 24 h. Then the mixture

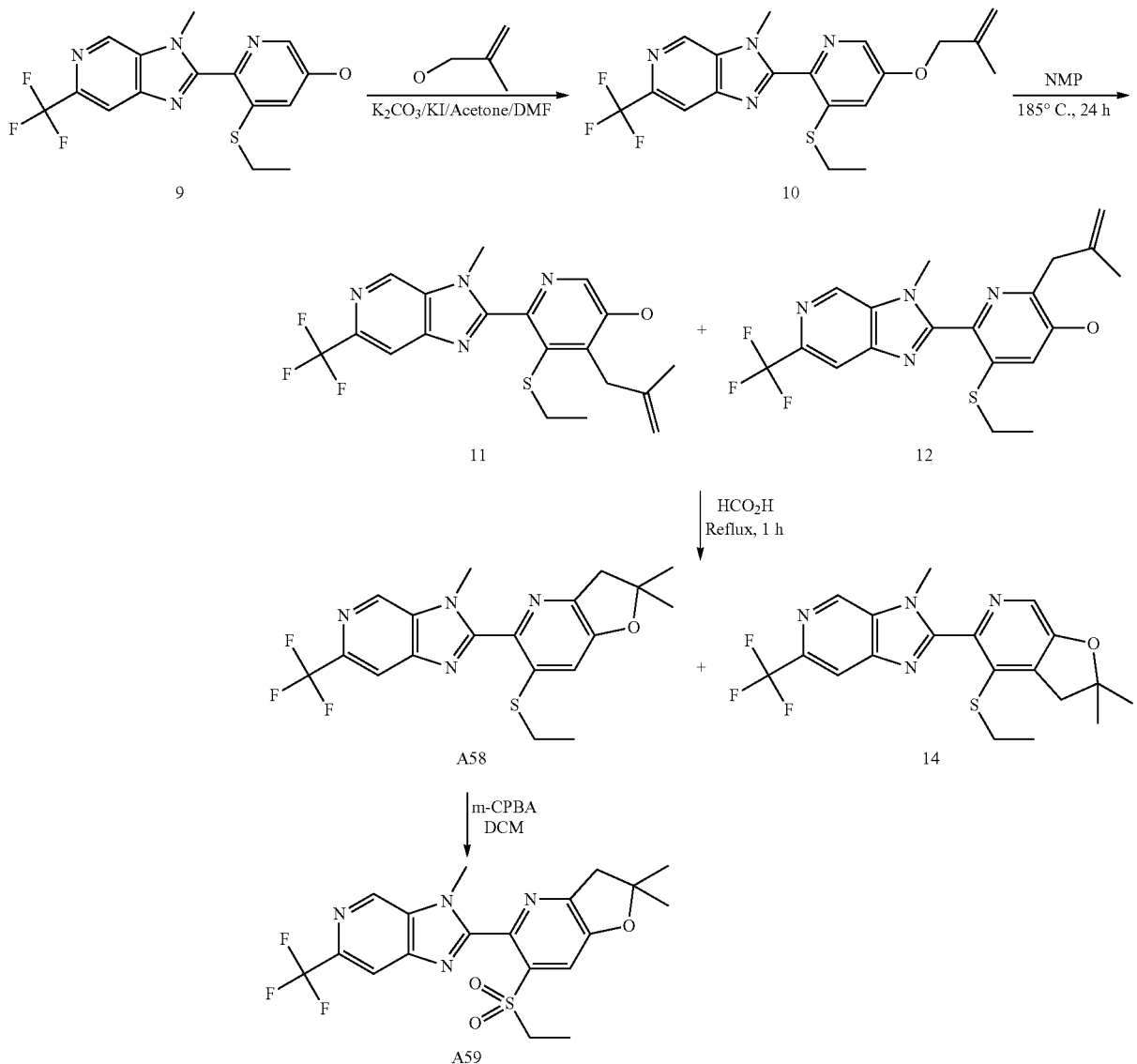

was poured into water, and extracted with ethyl acetate three times. The combined organic layers were dried over sodium sulfate, filtered and concentrated under vacuum. The crude product in 10 ml of HCO₂H was refluxed for 1 h. Then, the mixture solution was poured into water and extracted with ethyl acetate three times. The combined organic layers were dried over sodium sulfate, filtered and concentrated under vacuum. The crude product was purified by column chromatography on silica gel to provide product A58 (100 mg, y: 12%) and the by-product 14 (41 mg, y: 5%).

Compound A58: $^1$H NMR (400 MHz, CDCl₃) δ (ppm): 1.27 (t, 3H), 1.57 (s, 6H), 2.85 (q, 2H), 3.15 (s, 2H), 3.94 (s, 3H), 7.08 (s, 1H), 8.14 (s, 1H), 8.90 (s, 1H). $^{19}$F-NMR (300 Mz, CDCl₃) δ: −70.7 (s, 3F). The compound 13 was isolated with 91% of purity and used, for the next step, without extra purification.

Compound 14 (by-product): $^1$H NMR (400 MHz, CDCl₃) δ (ppm): 1.10 (t, 3H), 1.57 (s, 6H), 2.68 (q, 2H), 3.19 (s, 2H), 3.88 (s, 3H), 8.12 (s, 1H), 8.13 (s, 1H), 8.90 (s, 1H). $^{19}$F-NMR (300 Mz, CDCl₃) δ: −70.7 (s, 3F).

Step J: Preparation of Compound A59

Compound A58 (0.24 mmol, 100 mg) and m-CPBA (0.87 mmol, 150 mg) in 10 ml of DCM was stirred at ambient temperature for 4 h. Then the mixture was poured into a saturated solution of NaHCO₃ and Na₂SO₃ in water, and extracted with ethyl acetate three times. The combined organic layers were dried over sodium sulfate, filtered and concentrated under vacuum. The crude product was purified by column chromatography on silica gel to give tittle product (70 mg, y: 66%) $^1$H NMR (400 MHz, CDCl₃) δ (ppm): 1.31 (t, 3H), 1.62 (s, 6H), 3.26 (s, 2H), 3.60 (q, 2H), 3.83 (s, 3H), 7.66 (s, 1H), 8.08 (s, 1H), 8.94 (s, 1H); $^{19}$F-NMR (300 Mz, CDCl₃) δ: −71.61 (s, 3F).

TABLE 5

This table discloses compounds of formula I-1a:

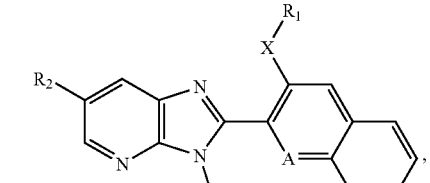

(I-1a)

| Comp. No. | X | R₁ | R₂ | A | R₆ |
|---|---|---|---|---|---|
| A1 (1.001) | S | —CH₂CH₃ | CF₃ | CH | CH₃ |
| A2 (1.002) | SO | —CH₂CH₃ | CF₃ | CH | CH₃ |
| A3 (1.003) | SO2 | —CH₂CH₃ | CF₃ | CH | CH₃ |
| A4 (1.004) | S | —CH₂CH₃ | CF₃ | N | CH₃ |
| A5 (1.005) | SO | —CH₂CH₃ | CF₃ | N | CH₃ |
| A6 (1.006) | SO2 | —CH₂CH₃ | CF₃ | N | CH₃ |

TABLE 6

This table discloses compounds of formula I-1a1:

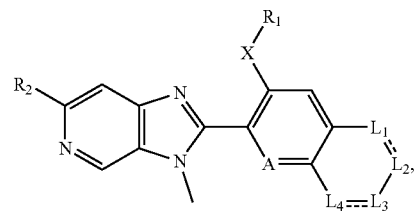

(I-1a1)

| Comp. No. | X | R₁ | R₂ | A | L₁ | L₂ | L₃ | L₄ |
|---|---|---|---|---|---|---|---|---|
| A7 (2.094) | SO₂ | —CH₂CH₃ | CF₃ | CH | NH | C—CF₃ | N | — |
| A8 (2.126) | SO2 | —CH₂CH₃ | CF₃ | CH | N | C—CF₃ | N—CH₃ | — |
| A9 (2.114) | SO₂ | —CH₂CH₃ | CF₃ | CH | N-CH₃ | C—CF₃ | N | - |
| A10 (2.102) | SO₂ | —CH₂CH₃ | CF₃ | CH | NH | C—H | N | — |
| A11 (2.118) | SO₂ | —CH₂CH₃ | CF₃ | CH | N | C—H | N—CH₃ | — |
| A12 (2.106) | SO₂ | —CH₂CH₃ | CF₃ | CH | N-CH₃ | C—H | N | — |
| A13 (2.098) | SO₂ | —CH₂CH₃ | CF₃ | CH | NH | C—CH₃ | N | — |
| A14 (2.122) | SO₂ | —CH₂CH₃ | CF₃ | CH | N | C—CH₃ | N—CH₃ | — |
| A15 (2.110) | SO₂ | —CH₂CH₃ | CF₃ | CH | N-CH3 | C—CH₃ | N | — |
| A16 | SO₂ | —CH₂CH₃ | CF₃ | CH | NH | C—Ph | N | — |
| A17 (2.046) | SO₂ | —CH₂CH₃ | CF₃ | CH | NH | N | N | — |
| A18 (2.042) | SO₂ | —CH₂CH₃ | CF₃ | CH | N | S | N | — |

TABLE 6-continued

This table discloses compounds of formula I-1a1:

(I-1a1)

[Structure of formula I-1a1]

| Comp. No. | X | R₁ | R₂ | A | L₁ | L₂ | L₃ | L₄ |
|---|---|---|---|---|---|---|---|---|
| A19 (2.086) | SO₂ | —CH₂CH₃ | CF₃ | CH | S | C—CH₃ | N | — |
| A20 | SO₂ | —CH₂CH₃ | CF₃ | CH | N | CH | CH | N |
| A25 (2.021) | S | —CH₂CH₃ | CF₃ | CH | CH | N | CH | CH |
| A26 (2.022) | SO₂ | —CH₂CH₃ | CF₃ | CH | CH | N | CH | CH |
| A27 | SO₂ | —CH₂CH₃ | CF₃ | CH | CH | N⁺—O⁻ | CH | CH |
| A28 | SO₂ | —CH₂CH₃ | CF₃ | CH | N | CH | C—CF₃ | N |
| A29 | SO₂ | —CH₂CH₃ | CF₃ | CH | N | C—CF₃ | CH | N |
| A30 (2.070) | SO₂ | —CH₂CH₃ | CF₃ | CH | N | CH | S | — |
| A31 (2.078) | SO₂ | —CH₂CH₃ | CF₃ | CH | N | C—CF₃ | S | — |
| A32 (2.128) | SO₂ | —CH₂CH₃ | CF₃ | N | N | C—CF₃ | N—CH₃ | — |
| A33 (2.116) | SO₂ | —CH₂CH₃ | CF₃ | N | N-CH₃ | C—CF₃ | N | — |
| A34 (2.096) | SO₂ | —CH₂CH₃ | CF₃ | N | NH | C—CF₃ | N | — |
| A35 (2.054) | SO₂ | —CH₂CH₃ | CF₃ | CH | N | N | N—CH₃ | — |
| A36 (2.058) | SO₂ | —CH₂CH₃ | CF₃ | CH | N-CH₃ | N | N | — |
| A37 (2.050) | SO₂ | —CH₂CH₃ | CF₃ | CH | N | N—CH₃ | N | — |
| A38 | SO₂ | —CH₂CH₃ | CF₃ | CH | N | C—SH | S | — |
| A39 (2.113) | S | —CH₂CH₃ | CF₃ | CH | N-CH₃ | C—CF₃ | N | — |
| A58 | S | —CH₂CH₃ | CF₃ | N | O | C(CH3)2 | CH₂ | — |
| A59 | SO₂ | —CH₂CH₃ | CF₃ | N | O | C(CH3)2 | CH₂ | — |

TABLE 7

This table discloses compounds of formula I-1a3:

(I-1a3)

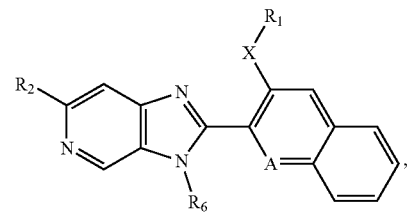

| Comp. No. | X | R₁ | R₂ | A | R₆ |
|---|---|---|---|---|---|
| A21 (2.004) | S | —CH₂CH₃ | CF₃ | N | CH₃ |
| A22 (2.006) | SO₂ | —CH₂CH₃ | CF₃ | N | CH₃ |

TABLE 7-continued

This table discloses compounds of formula I-1a3:

(I-1a3)

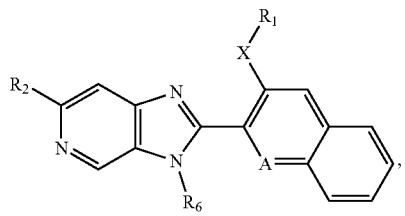

| Comp. No. | X | R₁ | R₂ | A | R₆ |
|---|---|---|---|---|---|
| A23 (2.001) | S | —CH₂CH₃ | CF₃ | CH | CH₃ |
| A24 (2.003) | SO₂ | —CH₂CH₃ | CF₃ | CH | CH₃ |

TABLE 8

This table discloses compounds of formula I-1a4:

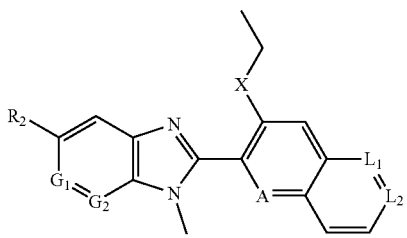

I-1a4

| Comp. No. | X | $G_1$ | $G_2$ | $R_2$ | A | $L_1$ | $L_2$ | Analytic data/information |
|---|---|---|---|---|---|---|---|---|
| A39 | S | N | CH | $CF_3$ | N | CCl | CH | Prepared from intermediate 4, using a similar protocol as described in Example P1. LC-MS (Method 1) RT 1.21, 423 (MH). $^1$H NMR (300 MHz, DMSO) ppm 9.309 (s, 1 H); 8.505 (s, 1 H); 8.341 (s, 1 H); 8.124 (d, 1 H); 7.955. (d, 1 H); 7.813 (dd, 1 H); 4.061 (s, 3 H); 3.183 (q, 2 H); 1.306 (t, 3 H). |
| A40 | $SO_2$ | N | CH | $CF_3$ | N | CCl | CH | Prepared from A39, using a similar protocol as described in Example P3. LC-MS (Method 1) RT 1.10 455 (MH$^+$). $^1$H NMR (300 MHz, DMSO) ppm 9.328 (s, 1 H); 9.248 (d, 1 H); 8.349 (d, 1 H); 8.306 (m, 1 H); 8.193-8.117 (m, 2 H); 3.941 (s, 3 H); 3.915 (q, 2 H); 1.249 (t, 3 H). |
| A41 | S | N | CH | $CF_3$ | N | CBr | CH | Prepared from intermediate 5, using a similar protocol as described in Example P1. LC-MS (Method 1) RT 1.21, 469(MH$^+$). $^1$H NMR (300 MHz, DMSO) ppm 9.309 (s, 1 H); 8.452 (s, 1 H); 8.342 (d, 1 H); 8.174-8.112 (m, 2 H); 7.750 (dd, 1 H); 4.066 (s, 3 H); 3.173 (q, 2 H); 1.320 (t, 3 H). |
| A42 | $SO_2$ | N | CH | $CF_3$ | N | CBr | CH | Prepared from A41, using a similar protocol as described in Example P3. LC-MS (Method 1) RT 1.09 501 (MH$^+$). $^1$H NMR (300 MHz, DMSO) ppm 9.327 (s, 1 H); 9.215 (s, 1 H); 8.331 (m, 3 H); 8.075 (dd, 1 H); 3.939 (s, 3 H); 3.917 (q, 2 H); 1.248 (t, 3 H). |
| A43 | $SO_2$ | N | CH | $CF_3$ | N | C-Cyclopropyl | CH | Example P18: $^1$H NMR (300 MHz, DMSO) ppm 9.570 (d, 1 H); 9.004 (s, 1 H); 8.137 (s, 1 H); 8.088 (dd, 1 H); 7.912 (dd; 1 H); 7.599 (d; 1 H); 3.943 (s, 3 H); 3.848 (q, 2 H); 2.497 (m; 1 H); 1.402 (t, 3 H); 1.241 (m; 2 H); 0.895 (m; 2 H). |
| A44 | S | N | CH | $CF_3$ | N | CH | CBr | Prepared from intermediate 7, using a similar protocol as described in Example P1. LC-MS (Method 1) RT 1.19, 469 (MH$^+$). $^1$H NMR (300 MHz, DMSO) ppm 9.294 (s, 1 H); 8.541 (s, 1 H); 8.383 (d, 1 H); 8.321 (d, 1 H); 8.041 (d, 1 H); 7.922 (dd; 1 H); 4.040 (s, 3 H); 3.112 (q, 2 H); 1.282 (t, 3 H). |
| A45 | $SO_2$ | N | CH | $CF_3$ | N | CH | CBr | Prepared from A44, using a similar protocol as described in Example P3. LC-MS (Method 1) RT 1.11, 501(MH$^+$). $^1$H NMR (300 MHz, DMSO) ppm 9.320 (s, 2 H); 8.825 (d, 1 H); 8.331 (d, 1 H); 8.30-8.20 (m, 2 H); 3.925 (s, 3 H); 3.844 (q, 2 H); 1.228(t, 3 H). |

TABLE 8-continued

This table discloses compounds of formula I-1a4:

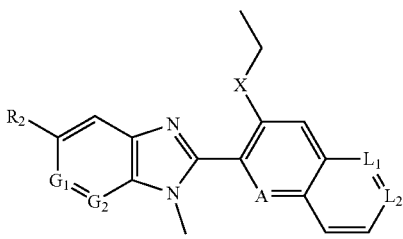

I-1a4

| Comp. No. | X | $G_1$ | $G_2$ | $R_2$ | A | $L_1$ | $L_2$ | Analytic data/information |
|---|---|---|---|---|---|---|---|---|
| A46 | S | N | CH | $CF_3$ | N | CH | CCl | Prepared from intermediate 6, using a similar protocol as described in Example P1. LC-MS (Method 1) RT 1.18, 423 (MH$^+$). $^1$H NMR (300 MHz, DMSO) ppm 9.295 (s, 1 H); 8.546 (s, 1 H); 8.324 (s, 1 H); 8.219 (d, 1 H); 8.118 (d, 1 H); 7.815 (dd, 1 H); 4.043 (s, 3 H); 3.114 (q, 2 H); 1.284 (t, 3 H). |
| A47 | $SO_2$ | N | CH | $CF_3$ | N | CH | CCl | Prepared from A46, using a similar protocol as described in Example P3. LC-MS (Method 1) RT 1.10, 455 (MH$^+$). $^1$H NMR (300 MHz, DMSO) ppm 9.328 (s, 1 H); 9.324 (d, 1 H); 8.670 (d, 1 H); 8.331 (d, 1 H); 8.300 (d, 1 H); 8.158 (dd, 1 H); 3.927 (s, 3 H); 3.847 (q, 2 H); 1.230 (t, 3 H). |
| A48 | S | CH | N | $CF_3$ | N | CH | CCl | Prepared from intermediate 6, using a similar protocol as described in Example P1. LC-MS (Method 1) RT 1.28, 423 (MH$^+$). $^1$H NMR (300 MHz, DMSO) ppm 8.900 (dd, 1 H); 8.707 (dd, 1 H); 8.531 (s, 1 H); 8.212 (d, 1 H); 8.120 (d, 1 H); 8.707 (d, 1 H); 3.998 (s, 3 H; ) 3.120 (q, 2 H); 1.297 (t, 3 H). |
| A49 | $SO_2$ | CH | N | $CF_3$ | N | CH | CCl | Prepared from A48, using a similar protocol as described in Example P3. LC-MS (Method 1) RT 1.17, 455(MH$^+$). $^1$H NMR (300 MHz, DMSO) ppm9.331 (s, 1 H); 8.925 (dd, 1 H); 8.717 (dd, 1 H); 8.668 (d, 1 H); 8.309 (d, 1 H); 8.156 (dd, 1 H); 3.888 (q, 2 H); 3.834 (s, 3 H); 1.244 (t, 3 H). |
| A50 | $SO_2$ | N | CH | $CF_3$ | N | CH | CCN | $^1$H NMR (300 MHz, DMSO) ppm 9.452 (s, 1 H); 9.332 (s, 1 H); 9.151 (s, 1 H); 8.433 (s, 1 H); 8.429 (s, 1 H); 8.48 (d, 1 H); 3.951 (s, 3 H; ) 3.880 (q, 2 H); 1.245(t, 3 H). |
| A51 | $SO_2$ | N | CH | $CF_3$ | N | CH | C-cyclopropyl | Prepared as described for A43: $^1$H NMR (300 MHz, DMSO) ppm 9.306 (s, 1 H); 9.152 (s, 1 H); 8.315 (d, 1 H); 8.171 (s, 1 H); 8.154 (d, 1 H); 7.882 (dd, 1 H); 3.904 (s, 3 H; ) 3.818 (q, 2 H); 2.254 (m; 1 H(; 1.242-0.80 (m; 7 H). |
| A52 | $SO_2$ | N | CH | $CF_3$ | N | CH | $CC_2F_5$ | $^1$H NMR (400 MHz, CDCl$_3$) ☐ ppm 1.39-1.42 (m, 3 H) 3.90 (q, J = 7.34 Hz, 2 H) 3.95-4.01 (m, 3 H) 8.11-8.23 (m, 2 H) 8.37-8.50 (m, 2 H) 9.04 (s, 1 H) 9.21 (s, 1 H). |

TABLE 9

This table discloses compounds of formula I-1a5:

(I-1a5)

| Comp. No. | X | $R_1$ | $R_2$ | A | $L_1$ | $L_2$ | $L_3$ | $L_4$ |
|---|---|---|---|---|---|---|---|---|
| A53 | S | —CH$_2$CH$_3$ | CF$_3$ | CH | N—CH$_3$ | C—CF$_3$ | N | — |
| A54 | S | —CH$_2$CH$_3$ | CF$_3$S | CH | N—CH$_3$ | C—CF$_3$ | N | — |
| A55 | SO$_2$ | —CH$_2$CH$_3$ | CF$_3$ | CH | N—CH$_3$ | C—CF$_3$ | N | — |
| A56 | SO$_2$ | —CH$_2$CH$_3$ | CF$_3$S | CH | N—CH$_3$ | C—CF$_3$ | N | — |
| A57 | SO$_2$ | —CH$_2$CH$_3$ | CF$_3$S(O) | CH | N—CH$_3$ | C—CF$_3$ | N | — |

TABLE 10

This table discloses compounds of formula I-1a6:

(I-1a6)

| Comp. No. | X | $R_1$ | $R_2$ | A | $L_1$ | $L_2$ | $L_3$ | $L_4$ | Analytic data/information |
|---|---|---|---|---|---|---|---|---|---|
| A60 | S | —CH$_2$CH$_3$ | CF$_3$ | CH | N—CH$_3$ | C—CF$_3$ | N | — | Prepared as described for A39 (example P4b) with N1-methyl-4-(trifluoromethyl)benzene-1,2-diamine (commercially available) and intermediate 8: $^1$H NMR (400 MHz,CDCl$_3$) δ ppm 8.14 (s, 1H), 7.96 (S, 1H), 7.62 (dd, 1 H), 7.56 (s, 1 H), 7.51 (d, 1 H), 4.02 (s, 3 H), 3.65 (s, 3 H), 2.85 (q, 2 H), 1.22 (t, 3 H). |
| A61 | SO2 | —CH$_2$CH$_3$ | CF3 | CH | N—CH$_3$ | C—CF$_3$ | N | — | Prepared from A60 as described for A9 (example P3, Step C): $^1$H NMR (400 MHz,CDCl$_3$) δ ppm 8.42 (s, 1 H), 8.08 (s, 1 H), 8.03 (s, 1 H), 7.64 (dd, 1 H), 7.53 (d, 1 H), 4.15 (s, 3 H), 3.61 (s, 3 H), 3.55 (br. s., 2 H), 1.26 (t, 3 H). |

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds described in Table 1 to 10 of the present invention"):

an adjuvant selected from the group of substances consisting of petroleum oils (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel [CCN]+TX, coumaphos (174)+TX, crotamiton [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos+TX, dicofol (242)+TX, dicrotophos (243)+TX, dienochlor (1071)+TX, dimefox (1081)+TX, dimethoate (262)+TX, dinactin (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram [CCN]+TX, disulfoton (278)+TX, DNOC (282)+TX, dofenapyn (1113)+TX, doramectin [CCN]+TX, endosulfan (294)+TX, endothion (1121)+TX, EPN (297)+TX, eprinomectin [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (473)+TX, isopropyl O-(methoxyaminothiophosphoryl)salicylate (IUPAC name) (473)+TX, ivermectin [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime [CCN]+TX, mipafox (1293)+TX, monocrotophos (561)+TX, morphothion (1300)+TX, moxidectin [CCN]+TX, naled (567)+TX, NC-184 (compound code)+TX, NC-512 (compound code)+TX, nifluridide (1309)+TX, nikkomycins [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos+TX, selamectin [CCN]+TX, SI-0009 (compound code)+TX, sophamide (1402)+TX, spirodiclofen (738)+TX, spiromesifen (739)+TX, SSI-121 (development code) (1404)+TX, sulfiram [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam+TX, tetrachlorvinphos (777)+TX, tetradifon (786)+TX, tetranactin (653)+TX, tetrasul (1425)+TX, thiafenox+TX, thiocarboxime (1431)+TX, thiofanox (800)+TX, thiometon (801)+TX, thioquinox (1436)+TX, thuringiensin [CCN]+TX, triamiphos (1441)+TX, triarathene (1443)+TX, triazophos (820)+TX, triazuron+TX, trichlorfon (824)+TX, trifenofos (1455)+TX, trinactin (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin [CCN]+TX, emamectin (291)+TX, emamectin benzoate (291)+TX, eprinomectin [CCN]+TX, ivermectin [CCN]+TX, milbemycin oxime [CCN]+TX, moxidectin [CCN]+TX, piperazine [CCN]+TX, selamectin [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal [CCN]+TX, a biological agent selected from the group of substances consisting of *Adoxophyes orana* GV (12)+TX, *Agrobacterium radiobacter* (13)+TX, *Amblyseius* spp. (19)+TX, *Anagrapha falcifera* NPV (28)+TX, *Anagrus atomus* (29)+TX, *Aphelinus abdominalis* (33)+TX, *Aphidius colemani* (34)+TX, *Aphidoletes aphidimyza* (35)+TX, *Autographa californica* NPV (38)+TX, *Bacillus firmus* (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (53)+TX, *Beauveria brongniartii* (54)+TX, *Chrysoperla carnea* (151)+TX, *Cryptolaemus montrouzieri* (178)+TX, *Cydia pomonella* GV (191)+TX, *Dacnusa sibirica* (212)+TX, *Diglyphus isaea* (254)+TX, *Encarsia formosa* (scientific name) (293)+TX, *Eretmocerus eremicus* (300)+TX, *Helicoverpa zea* NPV (431)+TX, *Heterorhabditis bacteriophora* and *H. megidis* (433)+TX, *Hippodamia convergens* (442)+TX, *Leptomastix dactylopii* (488)+TX, *Macrolophus caliginosus* (491)+TX, *Mamestra brassicae* NPV (494)+TX, *Metaphycus helvolus* (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (575)+TX, *Orius* spp. (596)+TX, *Paecilomyces fumosoroseus* (613)+TX, *Phytoseiulus persimilis* (644)+TX, *Spodoptera exigua* multicapsid nuclear polyhedrosis virus (scientific name) (741)+TX, *Steinernema bibionis* (742)+TX, *Steinernema carpocapsae* (742)+TX, *Steinernema feltiae* (742)+TX, *Steinernema glaseri* (742)+TX, *Steinernema riobrave* (742)+TX, *Steinernema riobravis* (742)+TX, *Steinernema scapterisci* (742)+TX, *Steinernema* spp. (742)+TX, *Trichogramma* spp. (826)+TX, *Typhlodromus occidentalis* (844) and *Verticillium lecanii* (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir [CCN]+TX, busulfan [CCN]+TX, diflubenzuron (250)+TX, dimatif [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron [CCN]+TX, tepa [CCN]+TX, thiohempa [CCN]+TX, thiotepa [CCN]+TX, tretamine [CCN] and uredepa [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin [CCN]+TX, brevicomin [CCN]+TX, codlelure [CCN]+TX, codlemone (167)+TX, cuelure (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure [CCN]+TX, ethyl 4-methyloctanoate (IUPAC name) (317)+TX, eugenol [CCN]+TX, frontalin [CCN]+TX, gossyplure (420)+TX, grandlure (421)+TX, grandlure I (421)+TX, grandlure II (421)+TX, grandlure III (421)+TX, grandlure IV (421)+TX, hexalure [CCN]+TX, ipsdienol [CCN]+TX, ipsenol [CCN]+TX, japonilure (481)+TX, lineatin [CCN]+TX, litlure [CCN]+TX, looplure [CCN]+TX, medlure [CCN]+TX, megatomoic acid [CCN]+TX, methyl eugenol (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure [CCN]+TX, oryctalure (317)+TX, ostramone [CCN]+TX, siglure [CCN]+TX, sordidin (736)+TX, sulcatol [CCN]+TX, tetradec-11-en-1-yl acetate (IUPAC name) (785)+TX, trimedlure (839)+TX, trimedlure A (839)+TX, trimedlure $B_1$ (839)+TX, trimedlure $B_2$ (839)+TX, trimedlure C (839) and trunc-call [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3, 4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy) ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin

[CCN]+TX, allyxycarb (866)+TX, alpha-cypermethrin (202)+TX, alpha-ecdysone [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (41)+TX, azamethiphos (42)+TX, azinphos-ethyl (44)+TX, azinphos-methyl (45)+TX, azothoate (889)+TX, *Bacillus thuringiensis* delta endotoxins (52)+TX, barium hexafluorosilicate [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate+TX, bromfenvinfos (914)+TX, bromocyclen (918)+TX, bromo-DDT [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin+TX, cismethrin (80)+TX, clocythrin+TX, cloethocarb (999)+TX, closantel [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton [CCN]+TX, crotoxyphos (1010)+TX, crufomate (1011)+TX, cryolite (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate [CCN]+TX, d-limonene [CCN]+TX, d-tetramethrin (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos+TX, dicresyl [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin [CCN]+TX, DSP (1115)+TX, ecdysterone [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin [CCN]+TX, esfenvalerate (302)+TX, etaphos [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (473)+TX, isodrin (1235)+TX, isofenphos (1236)+TX, isolane (1237)+TX, isoprocarb (472)+TX, isopropyl O-(methoxy-aminothiophosphoryl)salicylate (IUPAC name) (473)+TX, isoprothiolane (474)+TX, isothioate (1244)+TX, isoxathion (480)+TX, ivermectin [CCN]+TX, jasmolin I (696)+TX, jasmolin II (696)+TX, jodfenphos (1248)+TX, juvenile hormone I [CCN]+TX, juvenile hormone II [CCN]+TX, juvenile hormone III [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquinbutyl (1276)+TX, methothrin (533)+TX, methoxychlor (534)+TX, methoxyfenozide (535)+TX, methyl bromide (537)+TX, methyl isothiocyanate (543)+TX, methylchloroform [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime [CCN]+TX, mipafox (1293)+TX, mirex (1294)+TX, monocrotophos (561)+TX, morphothion (1300)+TX, moxidectin [CCN]+TX, naftalofos [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron [CCN]+TX, pentachlorophenol (623)+TX, pentachlorophenyl laurate (IUPAC name) (623)+TX, permethrin (626)+TX, petroleum oils (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I [CCN]+TX, precocene II [CCN]+TX, precocene III [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin 1 (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia [CCN]+TX, quinalphos (711)+TX, quinalphos-methyl (1376)+TX, quinothion (1380)+TX, quintiofos (1381)+TX, R-1492 (development code) (1382)+TX, rafoxanide [CCN]+TX, resmethrin (719)+TX, rotenone (722)+TX, RU 15525 (development code) (723)+TX, RU 25475 (development code) (1386)+TX, ryania (1387)+TX, ryanodine (traditional name) (1387)+TX, sabadilla (725)+TX, schradan (1389)+TX, sebufos+TX, selamectin [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron+TX, trichlorfon (824)+TX, trichlormetaphos-3 [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (725)+TX, veratrine (725)+TX, XMC (853)+TX, xylylcarb (854)+TX, YI-5302 (compound code)+TX, zeta-cypermethrin (205)+TX, zetamethrin+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, fluxametamide (WO 2007/026965)+TX, epsilon-metofluthrin [240494-71-7]+TX, epsilon-momfluorothrin [1065124-65-3]+TX, fluazaindolizine [1254304-22-7]+TX, chloropralethrin [399572-87-3]+TX, fluxametamide [928783-29-3]+TX, cyhalodiamide [1262605-53-7]+TX, tioxazafen [330459-31-9]+TX, broflanilide [1207727-04-5]+TX, flufiprole [704886-18-0]+TX, cyclaniliprole [1031756-98-5]+TX, tetraniliprole [1229654-66-3]+TX, guadipyr (described in WO2010/060231)+TX, cycloxaprid (described in WO2005/077934)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (210)+TX, dazomet (216)+TX, DBCP (1045)+TX, DCIP (218)+TX, diamidafos (1044)+TX, dichlofenthion (1051)+TX, dicliphos+TX, dimethoate (262)+TX, doramectin [CCN]+TX, emamectin (291)+TX, emamectin benzoate (291)+TX, eprinomectin [CCN]+TX, ethoprophos (312)+TX, ethylene dibromide (316)+TX, fenamiphos (326)+TX, fenpyrad+TX, fensulfothion (1158)+TX, fosthiazate (408)+TX, fosthietan (1196)+TX, furfural [CCN]+TX, GY-81 (development code) (423)+TX, heterophos [CCN]+TX, iodomethane (IUPAC name) (542)+TX, isamidofos (1230)+TX, isazofos (1231)+TX, ivermectin [CCN]+TX, kinetin (210)+TX, mecarphon (1258)+TX, metam (519)+TX, metam-potassium (519)+TX, metam-sodium (519)+TX, methyl bromide (537)+TX, methyl isothiocyanate (543)+TX, milbemycin oxime [CCN]+TX, moxidectin [CCN]+TX, *Myrothecium verrucaria* composition (565)+TX, NC-184 (compound code)+TX, oxamyl (602)+TX, phorate (636)+TX, phosphamidon (639)+TX, phosphocarb [CCN]+TX, sebufos+TX, selamectin [CCN]+TX, spinosad (737)+TX, terbam+TX, terbufos (773)+TX, tetrachlorothiophene (IUPAC/Chemical Abstracts name) (1422)+TX, thiafenox+TX, thionazin (1434)+TX, triazophos (820)+TX, triazuron+TX, xylenols [CCN]+TX, YI-5302 (compound code) and zeatin (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoro-acetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin [CCN] and ribavirin [CCN]+TX, a wound protectant selected from the group of substances consisting of mercuric oxide (512)+TX, octhilinone (590) and thiophanate-methyl (802)+TX, and biologically active compounds selected from the group consisting of azaconazole [60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl

[77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoximmethyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-LI90 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (dislosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-11-oxo-9-(3-pyridinyl)-2H,11Hnaphtho[2,1-b]pyrano[3,4-e]pyran-4-yl] methyl-cyclopropanecarboxylate [915972-17-7]+TX and 1,3,5-trimethyl-N-(2-methyl-1-oxopropyl)-N-[3-(2-methylpropyl)-4-[2,2,2-trifluoro-1-methoxy-1-(trifluoromethyl) ethyl]phenyl]-1H-pyrazole-4-carboxamide [926914-55-8]+TX; and microbials including: *Acinetobacter lwoffii*+TX, *Acremonium alternatum*+TX+TX, *Acremonium cephalosporium*+TX+TX, *Acremonium diospyri*+TX, *Acremonium obclavatum*+TX, *Adoxophyes orana granulovirus* (AdoxGV) (Capex®)+TX, *Agrobacterium radiobacter* strain K84 (Galltrol-A®)+TX, *Alternaria alternate*+TX, *Alternaria cassia*+TX, *Alternaria destruens* (Smolder®)+TX, *Ampelomyces quisqualis* (AQ10®)+TX, *Aspergillus flavus* AF36 (AF36®)+TX, *Aspergillus flavus* NRRL 21882 (Aflaguard®)+TX, *Aspergillus* spp.+TX, *Aureobasidium pullulans*+TX, *Azospirillum*+TX, (MicroAZ®+TX, TAZO B®)+TX, *Azotobacter*+TX, *Azotobacter chroocuccum* (Azotomeal®)+TX, *Azotobacter* cysts (Bionatural Blooming Blossoms®)+TX, *Bacillus amyloliquefaciens*+TX, *Bacillus cereus*+TX, *Bacillus chitinosporus* strain CM-1+TX, *Bacillus chitinosporus* strain AQ746+TX, *Bacillus licheniformis* strain HB-2 (Biostart™ Rhizoboost®)+TX, *Bacillus licheniformis* strain 3086 (EcoGuard®+TX, Green Releaf®)+TX, *Bacillus circulans*+TX, *Bacillus firmus* (BioSafe®+TX, BioNem-WP®+TX, VOTiVO®)+TX, *Bacillus firmus* strain 1-1582+TX, *Bacillus macerans*+TX, *Bacillus marismortui*+TX, *Bacillus megaterium*+TX, *Bacillus mycoides* strain AQ726+TX, *Bacillus papillae* (Milky Spore Powder®)+TX, *Bacillus pumilus* spp.+TX, *Bacillus pumilus* strain GB34 (Yield Shield®)+TX, *Bacillus pumilus* strain AQ717+TX, *Bacillus pumilus* strain QST 2808 (Sonata®+TX, Ballad Plus®)+TX, *Bacillus spahericus* (VectoLex®)+TX, *Bacillus* spp.+TX, *Bacillus* spp. strain AQ175+TX, *Bacillus* spp. strain AQ177+TX, *Bacillus* spp. strain AQ178+TX, *Bacillus subtilis* strain QST 713 (CEASE®+TX, Serenade®+TX, Rhapsody®)+TX, *Bacillus subtilis* strain QST 714 (JAZZ®)+TX, *Bacillus subtilis* strain AQ153+TX, *Bacillus subtilis* strain AQ743+TX, *Bacillus subtilis* strain QST3002+TX, *Bacillus subtilis* strain QST3004+TX, *Bacillus subtilis* var. *amyloliquefaciens* strain FZB24 (Taegro®+TX, Rhizopro®)+TX, *Bacillus thuringiensis* Cry 2Ae+TX, *Bacillus thuringiensis* Cry1 Ab+TX, *Bacillus thuringiensis aizawai* GC 91 (Agree®)+TX, *Bacillus thuringiensis israelensis* (BMP123®+TX, Aquabac®+TX, VectoBac®)+TX, *Bacillus thuringiensis kurstaki* (Javelin®+TX, Deliver®+TX, CryMax®+TX, Bonide®+TX, Scutella WP®+TX, Turilav WP®+TX, Astuto®+TX, Dipel WP®+TX, Biobit®+TX, Foray®)+TX, *Bacillus thuringiensis kurstaki* BMP 123 (Baritone®)+TX, *Bacillus thuringiensis kurstaki* HD-1 (Bioprotec-CAF/ 3P®)+TX, *Bacillus thuringiensis* strain BD#32+TX, *Bacillus thuringiensis* strain AQ52+TX, *Bacillus thuringiensis* var. *aizawai* (XenTari®+TX, DiPel®)+TX, bacteria spp. (GROWMEND®+TX, GROWSWEET®+TX, Shootup®)+TX, bacteriophage of *Clavipacter michiganensis* (AgriPhage®)+TX, Bakflor®+TX, *Beauveria bassiana* (Beaugenic®+TX, Brocaril WP®)+TX, *Beauveria bassiana* GHA (Mycotrol ES®+TX, Mycotrol O®+TX, BotaniGuard®)+TX, *Beauveria brongniartii* (Engerlingspilz®+TX, Schweizer *Beauveria*®+TX, Melocont®)+TX, *Beauveria* spp.+

TX, *Botrytis cineria*+TX, *Bradyrhizobium japonicum* (TerraMax®)+TX, *Brevibacillus brevis*+TX, *Bacillus thuringiensis tenebrionis* (Novodor®)+TX, BtBooster+TX, *Burkholderia cepacia* (Deny®+TX, Intercept®+TX, Blue Circle®)+TX, *Burkholderia gladii*+TX, *Burkholderia gladioli*+TX, *Burkholderia* spp.+TX, Canadian thistle fungus (CBH Canadian Bioherbicide®)+TX, *Candida butyri*+TX, *Candida famata*+TX, *Candida fructus*+TX, *Candida glabrata*+TX, *Candida guilliermondii*+TX, *Candida melibiosica*+TX, *Candida oleophila* strain O+TX, *Candida parapsilosis*+TX, *Candida pelliculosa*+TX, *Candida pulcherrima*+TX, *Candida reukaufii*+TX, *Candida saitoana* (Bio-Coat®+TX, Biocure®)+TX, *Candida sake*+TX, *Candida* spp.+TX, *Candida tenius*+TX, *Cedecea dravisae*+TX, *Cellulomonas flavigena*+TX, *Chaetomium cochliodes* (Nova-Cide®)+TX, *Chaetomium globosum* (Nova-Cide®)+TX, Chromobacterium subtsugae strain PRAA4-1T (Grandevo®)+TX, *Cladosporium cladosporioides*+TX, *Cladosporium oxysporum*+TX, *Cladosporium chlorocephalum*+TX, *Cladosporium* spp.+TX, *Cladosporium tenuissimum*+TX, *Clonostachys rosea* (EndoFine®)+TX, *Colletotrichum acutatum*+TX, *Coniothyrium minitans* (Cotans WG®)+TX, *Coniothyrium* spp.+TX, *Cryptococcus albidus* (YIELDPLUS®)+TX, *Cryptococcus humicola*+TX, *Cryptococcus infirmo-miniatus*+TX, *Cryptococcus laurentii*+TX, *Cryptophlebia leucotreta granulovirus* (Cryptex®)+TX, *Cupriavidus campinensis*+TX, *Cydia pomonella granulovirus* (CYD-X®)+TX, *Cydia pomonella granulovirus* (Madex®+TX, Madex Plus®+TX, Madex Max/Carpovirusine®)+TX, *Cylindrobasidium laeve* (Stumpout®)+TX, Cylindrocladium+TX, *Debaryomyces hansenii*+TX, *Drechslera hawaiinensis*+TX, *Enterobacter cloacae*+TX, Enterobacteriaceae+TX, *Entomophtora virulenta* (Vektor®)+TX, *Epicoccum nigrum*+TX, *Epicoccum purpurascens*+TX, *Epicoccum* spp.+TX, *Filobasidium floriforme*+TX, *Fusarium acuminatum*+TX, *Fusarium chlamydosporum*+TX, *Fusarium oxysporum* (Fusaclean®/Biofox C®)+TX, *Fusarium proliferatum*+TX, *Fusarium* spp.+TX, *Galactomyces geotrichum*+TX, *Gliocladium catenulatum* (Primastop®+TX, Prestop®)+TX, *Gliocladium roseum*+TX, *Gliocladium* spp. (SoilGard®)+TX, *Gliocladium virens* (Soilgard®)+TX, Granulovirus (Granupom®)+TX, *Halobacillus halophilus*+TX, *Halobacillus litoralis*+TX, *Halobacillus trueperi*+TX, *Halomonas* spp.+TX, *Halomonas subglaciescola*+TX, *Halovibrio variabilis*+TX, *Hanseniaspora uvarum*+TX, *Helicoverpa armigera nucleopolyhedrovirus* (Helicovex®)+TX, *Helicoverpa zea* nuclear polyhedrosis virus (Gemstar®)+TX, Isoflavone—formononetin (Myconate®)+TX, *Kloeckera apiculata*+TX, *Kloeckera* spp.+TX, *Lagenidium giganteum* (Laginex®)+TX, *Lecanicillium longisporum* (Vertiblast®)+TX, *Lecanicillium muscarium* (Vertikil®)+TX, *Lymantria Dispar* nucleopolyhedrosis virus (Disparvirus®)+TX, *Marinococcus halophilus*+TX, *Meira geulakonigi*+TX, *Metarhizium anisopliae* (Met52®)+TX, *Metarhizium anisopliae* (Destruxin WP®)+TX, *Metschnikowia fruticola* (Shemer®)+TX, *Metschnikowia pulcherrima*+TX, *Microdochium dimerum* (Antibot®)+TX, *Micromonospora coerulea*+TX, *Microsphaeropsis ochracea*+TX, *Muscodor albus* 620 (Muscudor®)+TX, *Muscodor roseus* strain A3-5+TX, Mycorrhizae spp. (AMykor®+TX, Root Maximizer®)+TX, *Myrothecium verrucaria* strain AARC-0255 (DiTera®)+TX, BROS PLUS®+TX, *Ophiostoma piliferum* strain D97 (Sylvanex®)+TX, *Paecilomyces farinosus*+TX, *Paecilomyces fumosoroseus* (PFR-97®+TX, PreFeRal®)+TX, *Paecilomyces linacinus* (Biostat WP®)+TX, *Paecilomyces lilacinus* strain 251 (MeloCon WG®)+TX, *Paenibacillus polymyxa*+TX, *Pantoea agglomerans* (BlightBan C9-1®)+TX, *Pantoea* spp.+TX, *Pasteuria* spp. (Econem®)+TX, *Pasteuria nishizawae*+TX, *Penicillium aurantiogriseum*+TX, *Penicillium billai* (Jumpstart®+TX, TagTeam®)+TX, *Penicillium brevicompactum*+TX, *Penicillium frequentans*+TX, *Penicillium griseofulvum*+TX, *Penicillium purpurogenum*+TX, *Penicillium* spp.+TX, *Penicillium viridicatum*+TX, *Phlebiopsis gigantean* (Rotstop®)+TX, phosphate solubilizing bacteria (Phosphomeal®)+TX, *Phytophthora cryptogea*+TX, *Phytophthora palmivora* (Devine®)+TX, *Pichia anomala*+TX, *Pichia guilermondii*+TX, *Pichia membranaefaciens*+TX, *Pichia onychis*+TX, *Pichia stipites*+TX, *Pseudomonas aeruginosa*+TX, *Pseudomonas aureofasciens* (Spot-Less Biofungicide®)+TX, *Pseudomonas cepacia*+TX, *Pseudomonas chlororaphis* (AtEze®)+TX, *Pseudomonas corrugate*+TX, *Pseudomonas fluorescens* strain A506 (BlightBan A506®)+TX, *Pseudomonas putida*+TX, *Pseudomonas reactans*+TX, *Pseudomonas* spp.+TX, *Pseudomonas syringae* (Bio-Save®)+TX, *Pseudomonas viridiflava*+TX, Pseudomons *fluorescens* (Zequanox)+TX, *Pseudozyma flocculosa* strain PF-A22 UL (Sporodex L®)+TX, *Puccinia canaliculata*+TX, *Puccinia thlaspeos* (Wood Warrior®)+TX, *Pythium paroecandrum*+TX, *Pythium oligandrum* (Polygandron®+TX, Polyversum®)+TX, *Pythium periplocum*+TX, *Rhanella aquatilis*+TX, *Rhanella* spp.+TX, Rhizobia (Dormal®+TX, Vault®)+TX, Rhizoctonia+TX, *Rhodococcus globerulus* strain AQ719+TX, *Rhodosporidium diobovatum*+TX, *Rhodosporidium toruloides*+TX, *Rhodotorula* spp.+TX, *Rhodotorula glutinis*+TX, *Rhodotorula graminis*+TX, *Rhodotorula mucilagnosa*+TX, *Rhodotorula rubra*+TX, *Saccharomyces cerevisiae*+TX, *Salinococcus roseus*+TX, *Sclerotinia minor*+TX, *Sclerotinia minor* (SARRITOR®)+TX, *Scytalidium* spp.+TX, *Scytalidium uredinicola*+TX, *Spodoptera exigua* nuclear polyhedrosis virus (Spod-X®+TX, Spexit®)+TX, *Serratia marcescens*+TX, *Serratia plymuthica*+TX, *Serratia* spp.+TX, *Sordaria fimicola*+TX, *Spodoptera littoralis nucleopolyhedrovirus* (Littovir®)+TX, *Sporobolomyces roseus*+TX, *Stenotrophomonas maltophilia*+TX, *Streptomyces ahygroscopicus*+TX, *Streptomyces albaduncus*+TX, *Streptomyces exfoliates*+TX, *Streptomyces galbus*+TX, *Streptomyces griseoplanus*+TX, *Streptomyces griseoviridis* (Mycostop®)+TX, *Streptomyces lydicus* (Actinovate®)+TX, *Streptomyces lydicus* WYEC-108 (ActinoGrow®)+TX, *Streptomyces violaceus*+TX, *Tilletiopsis minor*+TX, *Tilletiopsis* spp.+TX, *Trichoderma asperellum* (T34 Biocontrol®)+TX, *Trichoderma gamsii* (Tenet®)+TX, *Trichoderma atroviride* (Plantmate®)+TX, *Trichoderma hamatum* TH 382+TX, *Trichoderma harzianum rifai* (Mycostar®)+TX, *Trichoderma harzianum* T-22 (Trianum-P®+TX, PlantShield HC®+TX, RootShield®+TX, Trianum-G®)+TX, *Trichoderma harzianum* T-39 (Trichodex®)+TX, *Trichoderma inhamatum*+TX, *Trichoderma koningii*+TX, *Trichoderma* spp. LC 52 (Sentinel®)+TX, *Trichoderma lignorum*+TX, *Trichoderma longibrachiatum*+TX, *Trichoderma polysporum* (Binab T®)+TX, *Trichoderma taxi*+TX, *Trichoderma virens*+TX, *Trichoderma virens* (formerly *Gliocladium virens* GL-21) (SoilGuard®)+TX, *Trichoderma viride*+TX, *Trichoderma viride* strain ICC 080 (Remedier®)+TX, *Trichosporon pullulans*+TX, *Trichosporon* spp.+TX, *Trichothecium* spp.+TX, *Trichothecium roseum*+TX, *Typhula phacorrhiza* strain 94670+TX, *Typhula phacorrhiza* strain 94671+TX, *Ulocladium atrum*+TX, *Ulocladium oudemansii* (Botry-Zen®)+TX, *Ustilago maydis*+TX, various bacteria and supplementary micronutrients (Natural II®)+TX, various fungi (Millennium Microbes®)+TX, *Verticillium chlamydosporium*+TX, *Verticillium lecanii (Mycotal®+TX, Vertalec®)+TX, Vip3Aa20 (VIPtera®)+TX, *Virgibaclillus marismortui*+TX, *Xanthomonas campestris* pv. *Poae* (Camperico®)+TX, *Xenorhabdus bovienii*+TX, *Xenorhabdus nematophilus*; and Plant extracts including: pine oil (Retenol®)+TX, azadirachtin (Plasma Neem Oil®+TX, AzaGuard®+TX, MeemAzal®+TX, Molt-X®+TX, Botanical IGR (Neemazad®+TX, Neemix®)+TX, canola oil (Lilly Miller Vegol®)+TX, *Chenopodium ambrosioides* near *ambrosioides* (Requiem®)+TX, *Chrysanthemum* extract (Crisant®)+TX, extract of neem oil (Trilogy®)+TX, essentials oils of Labiatae (Botania®)+TX, extracts of clove rosemary peppermint and thyme oil (Garden insect Killer®)+TX, Glycinebetaine (Greenstim®)+TX, garlic+TX, lemongrass oil (GreenMatch®)+TX, neem oil+TX, *Nepeta cataria* (Catnip oil)+TX, *Nepeta catarina*+TX, nicotine+TX, oregano oil (MossBuster®)+TX, Pedaliaceae oil (Nematon®)+TX, pyrethrum+TX, *Quillaja saponaria* (NemaQ®)+TX, *Reynoutria sachalinensis* (Regalia®+TX, Sakalia®)+TX, rotenone (Eco Roten®)+TX, Rutaceae plant extract (Soleo®)+TX, soybean oil (Ortho Ecosense®)+TX, tea tree oil (Timorex Gold®)+TX, thymus oil+TX, AGNIQUE® MMF+TX, BugOil®+TX, mixture of rosemary sesame peppermint thyme and cinnamon extracts (EF 300®)+TX, mixture of clove rosemary and peppermint extract (EF 400®)+TX, mixture of clove pepermint garlic oil and mint (Soil Shot®)+TX, kaolin (Screen®)+TX, storage glucam of brown algae (Laminarin®); and pheromones including: blackheaded fireworm pheromone (3M Sprayable Blackheaded Fireworm Pheromone®)+TX, Codling Moth Pheromone (Paramount dispenser-(CM)/Isomate C-Plus®)+TX, Grape Berry Moth Pheromone (3M MEC-GBM Sprayable Pheromone®)+TX, Leafroller pheromone (3M MEC—LR Sprayable Pheromone®)+TX, Muscamone (Snip7 Fly Bait®+TX, Starbar Premium Fly Bait®)+TX, Oriental Fruit Moth Pheromone (3M oriental fruit moth sprayable Pheromone®)+TX, Peachtree Borer Pheromone (Isomate-P®)+TX, Tomato Pinworm Pheromone (3M Sprayable Pheromone®)+TX, Entostat powder (extract from palm tree) (Exosex CM®)+TX, (E+TX,Z+TX, Z)-3+TX,8+TX,11 Tetradecatrienyl acetate+TX, (Z+TX,Z+TX,E)-7+TX,11+TX,13-Hexadecatrienal+TX, (E+TX,Z)-7+TX,9-Dodecadien-1-yl acetate+TX, 2-Methyl-1-butanol+TX, Calcium acetate+TX, Scenturion®+TX, Biolure®+TX, Check-Mate®+TX, Lavandulyl senecioate; and Macrobials including: *Aphelinus abdominalis*+TX, *Aphidius ervi* (*Aphelinus*-System®)+TX, *Acerophagus papaya*+TX, *Adalia bipunctata* (*Adalia*-System®)+TX, *Adalia bipunctata* (Adaline®)+TX, *Adalia bipunctata* (Aphidalia®)+TX, *Ageniaspis citricola*+TX, *Ageniaspis fuscicollis*+TX, *Amblyseius andersoni* (Anderline®+TX, Andersoni-System®)+TX, *Amblyseius californicus* (Amblyline®+TX, Spical®)+TX, *Amblyseius cucumeris* (Thripex®+TX, Bugline Cucumeris®)+TX, *Amblyseius fallacis* (Fallacis®)+TX, *Amblyseius swirskii* (Bugline Swirskii®+TX, Swirskii-Mite®)+TX, *Amblyseius womersleyi* (WomerMite®)+TX, *Amitus hesperidum*+TX, *Anagrus atomus*+TX, *Anagyrus fusciventris*+TX, *Anagyrus kamali*+TX, *Anagyrus loecki*+TX, *Anagyrus pseudococci* (Citripar®)+TX, *Anicetus benefices*+TX, *Anisopteromalus calandrae*+TX, *Anthocoris nemoralis* (*Anthocoris*-System®)+TX, *Aphelinus abdominalis* (Apheline®+TX, Aphiline®)+TX, *Aphelinus asychis*+TX, *Aphidius colemani* (Aphipar®)+TX, *Aphidius ervi* (Ervipar®)+TX, *Aphidius gifuensis*+TX, *Aphidius matricariae* (Aphipar-M®)+TX, *Aphidoletes aphidimyza* (Aphidend®)+TX, *Aphidoletes aphidimyza* (Aphidoline®)+TX, *Aphytis lingnanensis*+TX, *Aphytis melinus*+TX, *Aprostocetus hagenowii*+TX, *Atheta coriaria* (Staphyline®)+TX, *Bombus* spp.+TX, *Bombus terrestris* (Natupol Beehive®)+TX, *Bombus terrestris* (Beeline®+TX, Tripol®)+TX, *Cephalonomia stephanoderis*+TX, *Chilocorus nigritus*+TX, *Chrysoperla camea* (Chrysoline®)+TX, *Chrysoperla carnea* (Chrysopa®)+TX, *Chrysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, *Cryptolaemus montrouzieri* (Cryptobug®+TX, Cryptoline®)+TX, *Cybocephalus nipponicus*+TX, *Dacnusa sibirica*+TX, *Dacnusa sibirica* (Minusa®)+TX, *Diglyphus isaea* (Diminex®)+TX, *Delphastus catalinae* (*Delphastus*®)+TX, *Delphastus pusillus*+TX, *Diachasmimorpha krausii*+TX, *Diachasmimorpha longicaudata*+TX, *Diaparsis jucunda*+TX, *Diaphorencyrtus aligarhensis*+TX, *Diglyphus isaea*+TX, *Diglyphus isaea* (Miglyphus®+TX, Digline®)+TX, *Dacnusa sibirica* (DacDigline®+TX, Minex®)+TX, *Diversinervus* spp.+TX, *Encarsia citrina*+TX, *Encarsia formosa* (*Encarsia* Max®+TX, Encarline®+TX, En-Strip®)+TX, *Eretmocerus eremicus* (Enermix®)+TX, *Encarsia guadeloupae*+TX, *Encarsia haitiensis*+TX, *Episyrphus balteatus* (Syrphidend®)+TX, *Eretmoceris siphonini*+TX, *Eretmocerus californicus*+TX, *Eretmocerus eremicus* (Ercal®+TX, Eretline e®)+TX, *Eretmocerus eremicus* (Bemimix®)+TX, *Eretmocerus hayati*+TX, *Eretmocerus mundus* (Bemipar®+TX, Eretline m®)+TX, *Eretmocerus siphonini*+TX, *Exochomus quadripustulatus*+TX, *Feltiella acarisuga* (Spidend®)+TX, *Feltiella acarisuga* (Feltiline®)+TX, *Fopius arisanus*+TX, *Fopius ceratitivorus*+TX, Formononetin (Wirless Beehome®)+TX, *Franklinothrips vespiformis* (Vespop®)+TX, *Galendromus occidentalis*+TX, *Goniozus legneri*+TX, *Habrobracon hebetor*+TX, *Harmonia axyridis* (HarmoBeetle®)+TX, *Heterorhabditis* spp. (Lawn Patrol®)+TX, *Heterorhabditis bacteriophora* (NemaShield HB®+TX, Nemaseek®+TX, Terranem-Nam®+TX, Terranem®+TX, Larvanem®+TX, B-Green®+TX, NemAttack®+TX, Nematop®)+TX, *Heterorhabditis megidis* (Nemasys H®+TX, BioNem H®+TX, Exhibitline hm®+TX, Larvanem-M®)+TX, *Hippodamia convergens*+TX, *Hypoaspis aculeifer* (Aculeifer-System®+TX, Entomite-A®)+TX, *Hypoaspis miles* (Hypoline m®+TX, Entomite-M®)+TX, *Lbalia leucospoides*+TX, *Lecanoideus floccissimus*+TX, *Lemophagus errabundus*+TX, *Leptomastidea abnormis*+TX, *Leptomastix dactylopii* (Leptopar®)+TX, *Leptomastix epona*+TX, *Lindorus lophanthae*+TX, *Lipolexis oregmae*+TX, *Lucilia caesar* (Natufly®)+TX, *Lysiphlebus testaceipes*+TX, *Macrolophus caliginosus* (Mirical-N®+TX, Macroline c®®+TX, Mirical®)+TX, *Mesoseiulus longipes*+TX, *Metaphycus flavus*+TX, *Metaphycus lounsburyi*+TX, *Micromus angulatus* (Milacewing®)+TX, *Microterys flavus*+TX, *Muscidifurax raptorellus* and *Spalangia cameroni* (Biopar®)+TX, *Neodryinus typhlocybae*+TX, *Neoseiulus californicus*+TX, *Neoseiulus cucumeris* (THRYPEX®)+TX, *Neoseiulus fallacis*+TX, *Nesideocoris tenuis* (NesidioBug®+TX, Nesibug®)+TX, *Ophyra aenescens* (Biofly®)+TX, *Orius insidiosus* (Thripor-I®+TX, Oriline i®)+TX, *Orius laevigatus* (Thripor-L®+TX, Oriline I®)+TX, *Orius majusculus* (Oriline m®)+TX, *Orius strigicollis* (Thripor-S®)+TX, *Pauesia juniperorum*+TX, *Pediobius foveolatus*+TX, *Phasmarhabditis hermaphrodita* (Nemaslug®)+TX, *Phymastichus coffea*+TX, *Phytoseiulus macropilus*+TX, *Phytoseiulus persimilis* (Spidex®+TX, Phytoline p®)+TX, *Podisus maculiventris* (*Podisus*®)+TX, *Pseudacteon curvatus*+TX,

*Pseudacteon obtusus*+TX, *Pseudacteon tricuspis*+TX, *Pseudaphycus maculipennis*+TX, *Pseudleptomastix mexicana*+TX, *Psyllaephagus pilosus*+TX, *Psyttalia concolor* (complex)+TX, *Quadrastichus* spp.+TX, *Rhyzobius lophanthae*+TX, *Rodolia cardinalis*+TX, *Rumina decollate*+TX, *Semielacher petiolatus*+TX, *Sitobion avenae* (Ervibank®)+TX, *Steinernema carpocapsae* (Nematac C®+TX, Millenium®+TX, BioNem C®+TX, NemAttack®+TX, Nemastar®+TX, Capsanem®)+TX, *Steinernema feltiae* (NemaShield®+TX, Nemasys F®+TX, BioNem F®+TX, *Steinernema*-System®+TX, NemAttack®+TX, Nemaplus®+TX, Exhibitline sf®+TX, Scia-rid®+TX, Entonem®)+TX, *Steinernema* kraussei (Nemasys L®+TX, BioNem L®+TX, Exhibitline srb®)+TX, *Steinernema riobrave* (BioVector®+TX, BioVektor®)+TX, *Steinernema scapterisci* (Nematac S®)+TX, *Steinernema* spp.+TX, *Steinernematid* spp. (Guardian Nematodes®)+TX, *Stethorus punctillum* (Stethorus®)+TX, *Tamarixia radiate*+TX, *Tetrastichus setifer*+TX, *Thripobius semiluteus*+TX, *Torymus sinensis*+TX, *Trichogramma brassicae* (Tricholine b®)+TX, *Trichogramma brassicae* (Tricho-Strip®)+TX, *Trichogramma evanescens*+TX, *Trichogramma minutum*+TX, *Trichogramma ostriniae*+TX, *Trichogramma platneri*+TX, *Trichogramma pretiosum*+TX, *Xanthopimpla stemmator*; and other biologicals including: abscisic acid+TX, bioSea®+TX, *Chondrostereum purpureum* (Chontrol Paste®)+TX, *Colletotrichum gloeosporioides* (Collego®)+TX, Copper Octanoate (Cueva®)+TX, Delta traps (Trapline d®)+TX, *Erwinia amylovora* (Harpin) (ProAct®+TX, Ni-HIBIT Gold CST®)+TX, Ferri-phosphate (Ferramol®)+TX, Funnel traps (Trapline y®)+TX, Gallex®+TX, Grower's Secret®+TX, Homo-brassonolide+TX, Iron Phosphate (Lilly Miller Worry Free Ferramol Slug & Snail Bait®)+TX, MCP hail trap (Trapline f®)+TX, *Microctonus hyperodae*+TX, *Mycoleptodiscus terrestris* (Des-X®)+TX, BioGain®+TX, Aminomite®+TX, Zenox®+TX, Pheromone trap (Thripline ams®)+TX, potassium bicarbonate (MilStop®)+TX, potassium salts of fatty acids (Sanova®)+TX, potassium silicate solution (Sil-Matrix®)+TX, potassium iodide+potassium-thiocyanate (Enzicur®)+TX, SuffOil-X®+TX, Spider venom+TX, *Nosema locustae* (Semaspore Organic Grasshopper Control®)+TX, Sticky traps (Trapline YF®+TX, Rebell Amarillo®)+TX and Traps (Takitrapline y+b®)+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright © 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "develoment code" is used or, if neither one of those designations nor a "common name" is used, an "alternative name" is employed. "CAS Reg. No" means the Chemical Abstracts Registry Number.

The active ingredient mixture of the compounds of formula I selected from Table 1 to 10 with active ingredients described above comprises a compound selected from Table 1 to 10 and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from Table 1 to 10 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Table 1 to 10 and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted at the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula I. Further, it is hereby made available, a composition comprising a plant propagation material treated with a compound of formula I.

Seed treatment comprises all suitable seed treatment techniques known in the art, such as seed dressing, seed coating, seed dusting, seed soaking and seed pelleting. The seed treatment application of the compound formula I can be carried out by any known methods, such as spraying or by dusting the seeds before sowing or during the sowing/planting of the seeds.

BIOLOGICAL EXAMPLES

Example B1: Activity Against *Bemisia tabaci* (Cotton White Fly): Feeding/Contact Activity Cotton leaf discs were placed on agar in 24-well microtiter plates and sprayed with aqueous test solutions prepared from 10,000 ppm DMSO stock solutions. After drying the leaf discs were infested with adult white flies. The samples were checked for mortality 6 days after incubation.

The following compounds resulted in at least 80% mortality at an application rate of 200 ppm:
A8, A9, A27, A28, A29, A31, A32, A33, A45, A47, A49, A50, A58 and A59.

Example B2: Activity Against *Diabrotica balteata* (Corn Root Worm)

Maize sprouts placed onto an agar layer in 24-well microtiter plates were treated with aqueous test solutions prepared from 10,000 ppm DMSO stock solutions by spraying. After drying, the plates were infested with L2 larvae (6 to 10 per well). The samples were assessed for mortality and growth inhibition in comparison to untreated samples 4 days after infestation.

The following compounds gave an effect of at least 80% in at least one of the two categories (mortality or growth inhibition) at an application rate of 200 ppm:
A1, A2, A3, A4, A5, A6, A8, A9, A11, A19, A20, A21, A22, A23, A24, A25, A28, A29, A30, A31, A32, A33, A34, A35, A36, A37, A39, A40, A41, A42, A43, A44, A45, A46, A47, A48, A49, A50, A51, A52, A58 and A59.

Example B3: Activity Against *Euschistus heros* (Neotropical Brown Stink Bug)

Soybean leaves on agar in 24-well microtiter plates were sprayed with aqueous test solutions prepared from 10,000 ppm DMSO stock solutions. After drying the leaves were infested with N2 nymphs. The samples were assessed for mortality and growth inhibition in comparison to untreated samples 5 days after infestation.

The following compounds gave an effect of at least 80% in at least one of the two categories (mortality or growth inhibition) at an application rate of 200 ppm:
A1, A2, A3, A6, A8, A9, A11, A12, A14, A15, A17, A19, A21, A22, A23, A24, A25, A26, A27, A28, A29, A30, A31, A32, A33, A34, A36, A37, A40, A42, A43, A44, A45, A46, A47, A48, A49, A50, A51, A52, A58 and A59.

Example B4: Activity Against *Frankliniella occidentalis* (Western Flower *Thrips*): Feeding/Contact Activity Sunflower leaf discs were placed on agar in 24-well microtiter plates and sprayed with aqueous test solutions prepared from 10,000 DMSO stock solutions. After drying the leaf discs were infested with a *Frankliniella* population of mixed ages. The samples were assessed for mortality 7 days after infestation.

The following compounds resulted in at least 80% mortality at an application rate of 200 ppm:
A9, A29, A31, A33, A37 and A51.

Example B5: Activity Against *Myzus persicae* (Green Peach Aphid): Feeding/Contact Activity Sunflower leaf discs were placed onto agar in a 24-well microtiter plate and sprayed with aqueous test solutions prepared from 10,000 ppm DMSO stock solutions. After drying, the leaf discs were infested with an aphid population of mixed ages. The samples were assessed for mortality 6 days after infestation.

The following compounds resulted in at least 80% mortality at an application rate of 200 ppm:
A3, A5, A6, A8, A9, A11, A12, A14, A15, A19, A21, A22, A23, A24, A27, A28, A29, A31, A32, A33, A35, A36, A37, A40, A42, A43, A45, A47, A49, A50, A51, A58 and A59.

Example B6: Activity Against *Myzus persicae* (Green Peach Aphid). Systemic Activity Roots of pea seedlings infested with an aphid population of mixed ages were placed directly into aqueous test solutions prepared from 10,000 DMSO stock solutions. The samples were assessed for mortality 6 days after placing seedlings into test solutions.

The following compounds resulted in at least 80% mortality at a test rate of 24 ppm:
A8, A9, A11, A12, A15, A19, A20, A22, A27, A32, A33, A34, A35, A36, A37 and A59.

Example B7: Activity Against *Myzus persicae* (Green Peach Aphid). Intrinsic Activity Test compounds prepared from 10,000 ppm DMSO stock solutions were applied by pipette into 24-well microtiter plates and mixed with sucrose solution. The plates were closed with a stretched Parafilm. A plastic stencil with 24 holes was placed onto the plate and infested pea seedlings were placed directly on the Parafilm. The infested plate was closed with a gel blotting paper and another plastic stencil and then turned upside down. The samples were assessed for mortality 5 days after infestation.

The following compounds resulted in at least 80% mortality at a test rate of 12 ppm:
A3, A21, A22, A23, A24 and A58.

Example B8: Activity Against *Plutella xylostella* (Diamond Back Moth)

24-well microtiter plates with artificial diet were treated with aqueous test solutions prepared from 10,000 ppm DMSO stock solutions by pipetting. After drying, the plates were infested with L2 larvae (10 to 15 per well). The samples were assessed for mortality and growth inhibition in comparison to untreated samples 5 days after infestation.

The following compounds gave an effect of at least 80% in at least one of the two categories (mortality or growth inhibition) at an application rate of 200 ppm:
A3, A4, A5, A6, A8, A9, A12, A15, A16, A21, A22, A23, A24, A28, A29, A30, A31, A32, A33, A36, A37, A39, A40, A41, A42, A43, A44, A45, A46, A47, A48, A49, A50, A51, A52, A58 and A59.

Example B9: Activity Against *Spodoptera littoralis* (Egyptian Cotton Leaf Worm)

Cotton leaf discs were placed onto agar in 24-well microtiter plates and sprayed with aqueous test solutions prepared from 10,000 ppm DMSO stock solutions. After drying the leaf discs were infested with five L1 larvae. The samples were assessed for mortality, anti-feeding effect, and growth inhibition in comparison to untreated samples 3 days after infestation. Control of *Spodoptera littoralis* by a test sample is given when at least one of the categories mortality, anti-feedant effect, and growth inhibition is higher than the untreated sample.

The following compounds resulted in at least 80% control at an application rate of 200 ppm:
A3, A5, A6, A7, A9, A19, A21, A22, A24, A28, A29, A31, A32, A33, A37, A40, A41, A42, A43, A44, A45, A46, A47, A48, A49, A50, A51, A52, A58 and A59.

Example B10: Activity Against *Spodoptera littoralis* (Egyptian Cotton Leaf Worm)

Test compounds were applied by pipette from 10,000 ppm DMSO stock solutions into 24-well plates and mixed with agar. Lettuce seeds were placed onto the agar and the multi well plate was closed by another plate which contained also agar. After 7 days the compound was absorbed by the roots and the lettuce grew into the lid plate. The lettuce leaves were then cut off into the lid plate. *Spodoptera* eggs were pipetted through a plastic stencil onto a humid gel blotting paper and the lid plate was closed with it. The samples were assessed for mortality, anti-feedant effect and growth inhibition in comparison to untreated samples 6 days after infestation.

The following compounds gave an effect of at least 80% in at least one of the three categories (mortality, anti-feeding, or growth inhibition) at a test rate of 12.5 ppm:
A6, A9, A19, A22, A24, A29, A31, A32, A40, A42, A43, A45, A47, A49, A50 and A59.

Example B11: Activity Against *Tetranychus urticae* (Two-Spotted Spider Mite): Feeding/Contact Activity Bean leaf discs on agar in 24-well microtiter plates were sprayed with aqueous test solutions prepared from 10,000 ppm DMSO stock solutions. After drying the leaf discs were infested with a mite population of mixed ages. The samples were assessed for mortality on mixed population (mobile stages) 8 days after infestation.

The following compounds resulted in at least 80% mortality at an application rate of 200 ppm:
A4, A5, A6, A7, A24, A43 and A45.

Example B12: Activity Against *Thrips tabaci* (Onion *Thrips*) Feeding/Contact Activity Sunflower leaf discs were placed on agar in 24-well microtiter plates and sprayed with aqueous test solutions prepared from 10,000 ppm DMSO stock solutions. After drying the leaf discs were infested with a *thrips* population of mixed ages. The samples were assessed for mortality 6 days after infestation.

The following compounds resulted in at least 80% mortality at an application rate of 200 ppm: A9, A29, A32, A51 and A59.

Example B13: Activity Against *Aedes aegypti* (Yellow Fever Mosquito)

Test solutions, at an application rate of 200 ppm in ethanol, were applied to 12 well tissue culture plates. Once the deposits were dry, five, two to five day old adult female *Aedes aegypti* were added to each well, and sustained with a 10% sucrose solution in a cotton wool plug. Assessment of knockdown was made one hour after introduction, and mortality was assessed at 24 and 48 hours after introduction.

The following compounds gave at least 80% control of *Aedes aegypti* after 48 h and/or 24 h:
A6, A8, A9, A22, A24, A28, A29, A31, A32, A39, A40, A41, A42, A45, A46, A47, A49, A51 and A52.

Example B14: Activity Against *Anopheles stephensi* (Indian Malaria Mosquito)

Test solutions, at an application rate of 200 ppm in ethanol, were applied to 12 well tissue culture plates. Once the deposits were dry, five, two to five day old adult female *Anopheles stephensi* were added to each well, and sustained with a 10% sucrose solution in a cotton wool plug. Assessment of knockdown was made one hour after introduction, and mortality was assessed at 24 and 48 hours after introduction.

The following compounds gave at least 80% control of *Anopheles stephensi* after 48 h and/or 24 h:

A6, A9, A22, A24, A40, A45, A46, A47, A49, A51 and A52.

The invention claimed is:
1. A compound of formula I,

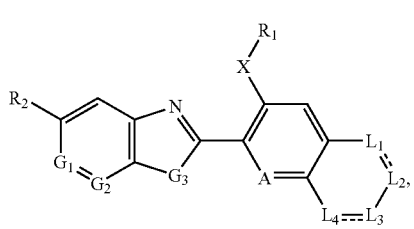

(I)

wherein
A is CH or N;
X is S, SO or $SO_2$;
$R_1$ is $C_1$-$C_4$alkyl, $C_2$-$C_6$alkenyl, $C_2$-$C_6$haloalkenyl, $C_2$-$C_6$alkynyl, $C_1$-$C_4$haloalkyl, $C_3$-$C_6$cycloalkyl, $C_3$-$C_6$cycloalkyl-$C_1$-$C_4$alkyl; or is $C_3$-$C_6$cycloalkyl mono- or polysubstituted by substituents selected from the group consisting of halogen, cyano, $C_1$-$C_4$haloalkyl and $C_1$-$C_4$alkyl; or is $C_3$-$C_6$cycloalkyl-$C_1$-$C_4$alkyl mono- or polysubstituted by substituents selected from the group consisting of halogen, cyano, $C_1$-$C_4$haloalkyl and $C_1$-$C_4$alkyl;
$R_2$ is hydrogen, halogen, $C_1$-$C_4$haloalkylsulfanyl, $C_1$-$C_4$haloalkylsulfinyl, $C_1$-$C_4$haloalkylsulfonyl, O($C_1$-$C_4$haloalkyl), —$SF_5$, —C(O)$C_1$-$C_4$haloalkyl, cyano, $C_1$-$C_6$haloalkyl or is $C_1$-$C_6$haloalkyl substituted by one or two substituents selected from the group consisting of hydroxyl, methoxy and cyano; or is $C_3$-$C_6$cycloalkyl which can be mono- or polysubstituted by substituents selected from the group consisting of halogen, cyano, $C_1$-$C_4$haloalkyl and $C_1$-$C_4$alkyl;
$G_1$ is N or $CR_4$;
$G_2$ is N or $CR_5$;
$G_3$ is O, S or $NR_6$;
$R_6$ is $C_1$-$C_4$alkyl which can be mono- or polysubstituted by substituents selected from the group consisting of halogen and $C_1$-$C_2$alkylsulfinyl;
$R_4$ and $R_5$, independently from each other, are hydrogen, halogen, cyano, nitro, $C_1$-$C_6$alkyl, $C_1$-$C_6$haloalkyl, or are $C_3$-$C_6$cycloalkyl which can be mono- or polysubstituted by $R_8$; or are $C_3$-$C_6$cycloalkyl-$C_1$-$C_4$alkyl which can be mono- or polysubstituted by $R_9$; or
$R_4$ and $R_5$, independently from each other, are $C_2$-$C_6$alkenyl, $C_2$-$C_6$haloalkenyl, $C_2$-$C_6$alkynyl, $C_2$-$C_6$haloalkynyl, $C_1$-$C_6$haloalkoxy, $C_1$-$C_6$alkoxy, $C_1$-$C_6$alkylsulfanyl, $C_1$-$C_4$alkylsulfonyl, $C_1$-$C_6$alkylsulfinyl $C_1$-$C_6$haloalkylsulfanyl, $C_1$-$C_4$haloalkylsulfonyl, $C_1$-$C_6$haloalkylsulfinyl or hydroxyl;
$R_8$ and $R_9$, independently from each other, are halogen, nitro, cyano, $C_1$-$C_4$haloalkoxy, $C_1$-$C_4$alkoxy, $C_1$-$C_4$alkyl or $C_1$-$C_4$haloalkyl;
$L_1$, $L_2$, $L_3$ and $L_4$ form together with the two carbon atoms to which $L_1$ and $L_4$ are attached, an aromatic or partially saturated carbocyclic or heterocyclic ring system;
wherein
$L_1$ is nitrogen, S(O)n, oxygen, N—$R_{10a}$ or $C(R_{10a})_m$;
$L_2$ is nitrogen, S(O)n, oxygen, N—$R_{10b}$ or $C(R_{10b})_m$;
$L_3$ is nitrogen, S(O)n, oxygen, N—$R_{10c}$ or $C(R_{10c})_m$;
$L_4$ is nitrogen, S(O)n, oxygen, a direct bond, N—$R_{10d}$ or $C(R_{10d})_m$; with the provisos that no more than 2 substituents selected from $L_1$, $L_2$, $L_3$ and $L_4$ can be oxygen or sulfur;
and if two L groups are oxygen, they are not adjacent to each other; and no more than three L groups can be nitrogen;
n is 0 to 2;
m is 1 or 2;
$R_{10a}$, $R_{10b}$, $R_{10c}$, and $R_{10d}$, independently from each other, are hydrogen, halogen, nitro, cyano, amino, hydroxyl, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_6$alkoxy, $C_1$-$C_4$alkoxy $C_1$-$C_4$alkyl, $C_1$-$C_6$haloalkoxy, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, $C_2$-$C_6$alkylcarbonyl, $C_2$-$C_6$alkoxycarbonyl, $C_2$-$C_6$ haloalkylcarbonyl, $C_2$-$C_6$haloalkoxycarbonyl, ($C_1$-$C_6$alkyl)NH, ($C_1$-$C_6$ alkyl)$_2$N, ($C_1$-$C_6$ cycloalkyl)NH, ($C_1$-$C_6$cycloalkyl)$_2$N, $C_1$-$C_6$alkylcarbonylamino, $C_1$-$C_6$cycloalkylcarbonylamino or —$SF_5$;
additionally one of $R_{10a}$, $R_{10b}$, $R_{10c}$ and $R_{10d}$ can be oxo; or
$R_{10a}$, $R_{10b}$, $R_{10c}$, and $R_{10d}$, independently from each other, are $C_3$-$C_6$cycloalkyl mono- or polysubstituted by substituents selected from the group consisting of $C_1$-$C_4$haloalkyl, $C_1$-$C_4$alkyl and cyano; or
$R_{10a}$, $R_{10b}$, $R_{10c}$, and $R_{10d}$, independently from each other, are phenyl which can be mono- or polysubstituted by substituents selected from the group consisting of halogen, $C_1$-$C_4$ haloalkyl, $C_1$-$C_4$alkyl, $C_1$-$C_4$alkoxy and cyano; and agrochemically acceptable salts, stereoisomers, enantiomers, tautomers and N-oxides of those compounds.

2. The compound of claim 1, represented by the compounds of formula I-1

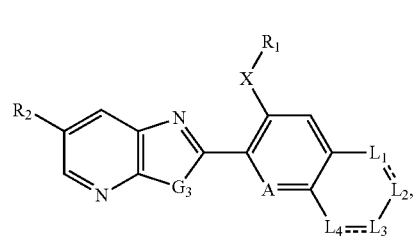

(I-1)

wherein the substituents X, A, $R_1$, $R_2$, $R_6$, $G_3$, $L_1$, $L_2$, $L_3$ and $L_4$ are as defined under formula I in claim 1.

3. The compound of claim 1, represented by the compounds of formula I-2

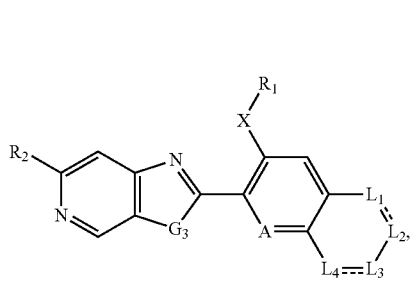
(I-2)

wherein the substituents X, A, $R_1$, $R_2$, $R_6$, $G_3$, $L_1$, $L_2$, $L_3$ and $L_4$ are as defined under formula I in claim 1.

4. The compound of claim 1, represented by the compounds of formula I-3

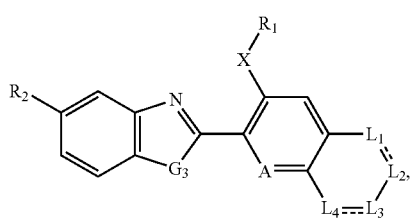
(I-3)

wherein the substituents X, A, $R_1$, $R_2$, $R_6$, $G_3$, $L_1$, $L_2$, $L_3$ and $L_4$ are as defined under formula I in claim 1.

5. The compound of claim 1, represented by the compounds of formula I-4

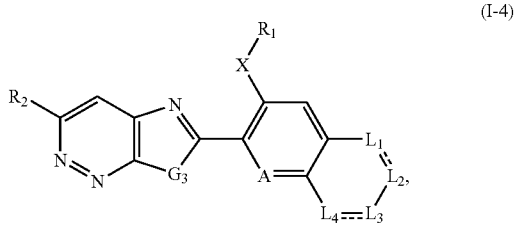
(I-4)

wherein the substituents X, A, $R_1$, $R_2$, $R_6$, $G_3$, $L_1$, $L_2$, $L_3$ and $L_4$ are as defined under formula I in claim 1.

6. The compound of claim 1, represented by the compounds of formula I-5a

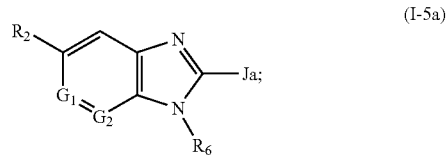
(I-5a)

wherein
$G_1$ is N or CH;
$G_2$ is N or CH;
$R_2$ is $C_1$-$C_4$haloalkyl, $C_1$-$C_4$halosulfanyl or $C_1$-$C_4$halosulfinyl;
A is N or CH;
$R_6$ is $C_1$-$C_4$alkyl;
X is S or $SO_2$;
$R_1$ is $C_1$-$C_4$alkyl; and
Ja is selected from the group consisting of

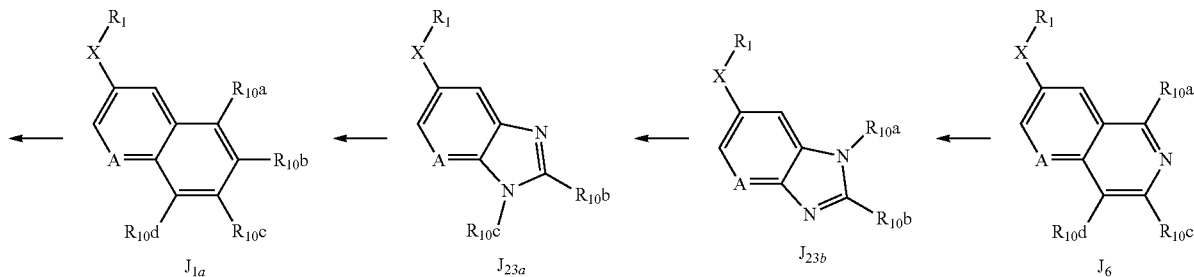

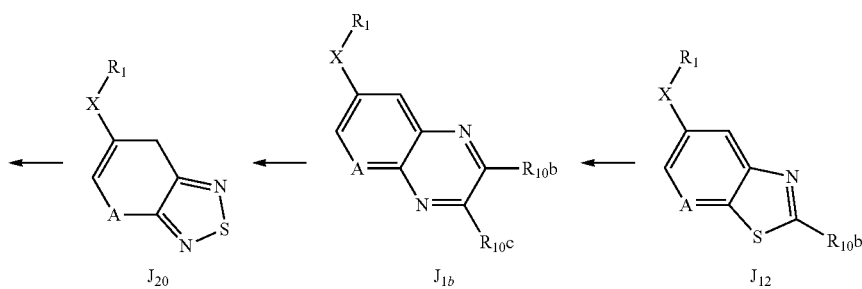

-continued

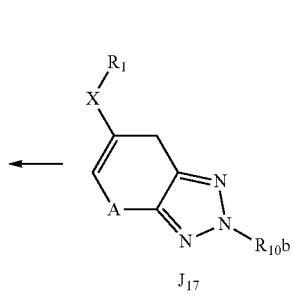

J₁₇

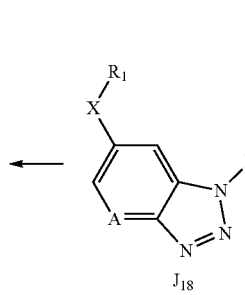

J₁₈

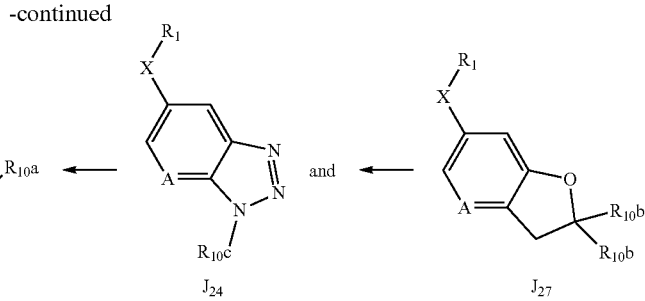

J₂₄ and J₂₇ wherein $R_{10a}$, $R_{10b}$, $R_{10c}$, and $R_{10d}$, independently from each other, are selected from the group consisting of hydrogen, halogen, cyano, cyclopropyl, $C_1$-$C_4$ alkyl and $C_1$-$C_4$ haloalkyl.

7. A pesticidal composition, which comprises at least one compound of formula I according to claim 1 or a tautomer thereof, in each case in free form or in agrochemically utilizable salt form, as active ingredient and at least one auxiliary.

8. A method for controlling pests, which comprises applying the composition according to claim 7 to the pests or their environment with the exception of a method for treatment of the human or animal body by surgery or therapy and diagnostic methods practised on the human or animal body.

9. A method for protection of plant propagation material from the attack by pests, which comprises treating the propagation material or the site, where the propagation material is planted, with a composition according to claim 7.

10. The plant propagation material treated in accordance with the method described in claim 9.

* * * * *